(12) United States Patent
Desai et al.

(10) Patent No.: US 12,357,695 B2
(45) Date of Patent: Jul. 15, 2025

(54) PEPTIDES AND NANOPARTICLES FOR INTRACELLULAR DELIVERY OF MOLECULES

(71) Applicant: AADIGEN, LLC, Pacific Palisades, CA (US)

(72) Inventors: Neil P. Desai, Pacific Palisades, CA (US); Gilles Divita, Saint-Andre-de-Sangonis (FR)

(73) Assignee: AADIGEN, LLC, Pacific Palisades, CA (US)

( * ) Notice: Subject to any disclaimer, the term of this patent is extended or adjusted under 35 U.S.C. 154(b) by 404 days.

(21) Appl. No.: 17/594,454

(22) PCT Filed: Apr. 16, 2020

(86) PCT No.: PCT/US2020/028572
§ 371 (c)(1),
(2) Date: Oct. 15, 2021

(87) PCT Pub. No.: WO2020/214846
PCT Pub. Date: Oct. 22, 2020

(65) Prior Publication Data
US 2022/0313825 A1    Oct. 6, 2022

(30) Foreign Application Priority Data
Apr. 17, 2019  (FR) ...................................... 1904115

(51) Int. Cl.
| A61K 47/10 | (2017.01) |
| A61K 9/51 | (2006.01) |
| A61K 47/60 | (2017.01) |
| A61K 47/64 | (2017.01) |
| A61K 47/69 | (2017.01) |
| C07K 5/062 | (2006.01) |
| C07K 7/08 | (2006.01) |

(52) U.S. Cl.
CPC ............ *A61K 47/10* (2013.01); *A61K 9/5169* (2013.01); *A61K 47/60* (2017.08); *A61K 47/64* (2017.08); *A61K 47/6929* (2017.08); *C07K 5/06026* (2013.01); *C07K 7/08* (2013.01); *C07K 2319/10* (2013.01)

(58) Field of Classification Search
None
See application file for complete search history.

(56) References Cited

U.S. PATENT DOCUMENTS

| 7,507,811 B2 | 3/2009 | Khvorova et al. |
| 7,514,530 B2 | 4/2009 | Divita |
| 7,576,197 B2 | 8/2009 | Khvorova et al. |
| 7,745,611 B2 | 6/2010 | Khvorova et al. |
| 8,008,474 B2 | 8/2011 | Khvorova et al. |
| 8,822,647 B2 | 9/2014 | Jensen |
| 9,061,059 B2 | 6/2015 | Chakraborty |
| 9,221,891 B2 | 12/2015 | Bancel et al. |
| 9,376,468 B2 | 6/2016 | Divita et al. |
| 9,579,395 B2 | 2/2017 | Divita et al. |
| 9,598,465 B2 | 3/2017 | Divita et al. |
| 9,834,581 B2 | 12/2017 | Divita et al. |
| 10,111,965 B2 | 10/2018 | Divita et al. |
| 10,118,944 B2 | 11/2018 | Divita et al. |
| 10,189,876 B2 | 1/2019 | Divita et al. |
| 10,287,581 B2 | 5/2019 | Divita et al. |
| 10,421,784 B2 | 9/2019 | Divita et al. |
| 10,688,194 B2 | 6/2020 | Divita et al. |
| 10,745,440 B2 | 8/2020 | Divita et al. |
| 11,713,336 B2 | 8/2023 | Divita et al. |
| 2010/0099626 A2 | 4/2010 | Divita |
| 2011/0059502 A1 | 3/2011 | Chalasani |
| 2014/0227344 A1 | 8/2014 | Divita et al. |
| 2015/0051266 A1 | 2/2015 | Kochenderfer |
| 2016/0060296 A1 | 3/2016 | Divita et al. |

(Continued)

FOREIGN PATENT DOCUMENTS

| CN | 104487450 A | 4/2015 |
| CN | 104822698 A | 8/2015 |

(Continued)

OTHER PUBLICATIONS

Vaissière et al. ("A retro-inverso cell-penetrating peptide for siRNA delivery," J Nanobiotechnol (2017) 15:34, pp. 1-18) (Year: 2017).*
Gao et al. ("Angiopep 2 and Activatable Cell-Penetrating Peptide Dual Functionalized Nanoparticles for Systemic Glioma-Targeting Delivery," Mol. Pharmaceutics 2014, 11, 2755-2763) (Year: 2014).*
Aldrian et al. ("PEGylation rate influences peptide-based nanoparticles mediated siRNA delivery in vitro and in vivo," Journal of Controlled Release 256 (2017) 79-91) (Year: 2017).*
Sarfati et al. ("Targeting of polymeric nanoparticles to lung metastases by surface-attachment of YIGSR peptide from laminin," Biomaterials 32 (2011) 152-161) (Year: 2011).*
Acunzo, M. et al. (May 23, 2017, e-pub. May 8, 2017). "Selective Targeting of Point-Mutated KRAS Through Artificial MicroRNAs," Proc. Natl. Acad. Sci USA 114(2):E4203-E4212.

(Continued)

*Primary Examiner* — Christina Bradley
(74) *Attorney, Agent, or Firm* — MORRISON & FOERSTER LLP

(57) ABSTRACT

The present application is directed to cargo delivery complexes for intracellular delivery of a cargo molecule comprising: a first peptide comprising a cell-penetrating peptide (CPP), a second peptide comprising a cell-penetrating peptide, and a cargo molecule. The second peptide comprises a polyethylene glycol (PEG) moiety linked to the second CPP, and the first peptide does not have a PEG moiety. The present application is also directed to a cargo delivery complex comprising a CPP and a cargo molecule wherein the CPP is a retro-inverso peptide. The present application is also directed to a cargo delivery complex comprising a CPP and a cargo molecule wherein the peptide further comprises a targeting sequence selected from the group consisting of GYVSK, GYVS, YIGS and YIGSR. Methods of making and using the cargo delivery complexes are also disclosed.

25 Claims, 25 Drawing Sheets
Specification includes a Sequence Listing.

(56) References Cited

U.S. PATENT DOCUMENTS

| | | | |
|---|---|---|---|
| 2016/0089447 | A1 | 3/2016 | Divita et al. |
| 2016/0115199 | A1 | 4/2016 | Divita et al. |
| 2016/0145299 | A1 | 5/2016 | Divita |
| 2017/0081661 | A1 | 3/2017 | Divita |
| 2017/0258928 | A1 | 9/2017 | Divita et al. |
| 2018/0179253 | A1 | 6/2018 | Divita et al. |
| 2019/0002499 | A1 | 1/2019 | Divita |
| 2019/0046652 | A1 | 2/2019 | Divita |
| 2019/0077833 | A1 | 3/2019 | Divita |
| 2019/0211317 | A1 | 7/2019 | Divita et al. |
| 2020/0172913 | A1 | 6/2020 | Desai et al. |
| 2020/0323964 | A1 | 10/2020 | Desai et al. |
| 2021/0032290 | A1 | 2/2021 | Divita et al. |
| 2022/0313825 | A1 | 10/2022 | Desai et al. |
| 2023/0167437 | A1 | 6/2023 | Desai et al. |

FOREIGN PATENT DOCUMENTS

| | | | |
|---|---|---|---|
| CN | 107548401 A | 1/2018 | |
| EP | 2694529 B1 | 11/2020 | |
| JP | 2013212052 A | 10/2013 | |
| JP | 2013544505 | 12/2013 | |
| WO | 2012129352 A1 | 9/2012 | |
| WO | 2012137150 A2 | 10/2012 | |
| WO | 2012137150 A3 | 12/2012 | |
| WO | 2013150338 A1 | 10/2013 | |
| WO | 2014013995 A1 | 1/2014 | |
| WO | 2014053622 A1 | 4/2014 | |
| WO | 2014053624 A1 | 4/2014 | |
| WO | 2014053628 A1 | 4/2014 | |
| WO | 2014053629 A1 | 4/2014 | |
| WO | 2014053879 A1 | 4/2014 | |
| WO | 2014053880 A1 | 4/2014 | |
| WO | 2014053881 A1 | 4/2014 | |
| WO | 2014053882 A1 | 4/2014 | |
| WO | 2014099671 A1 | 6/2014 | |
| WO | 2014118817 A2 | 8/2014 | |
| WO | 2014127261 A1 | 8/2014 | |
| WO | 2014118817 A3 | 10/2014 | |
| WO | WO-2016102687 A1 * | 6/2016 | ........... A61K 31/713 |
| WO | 2017179660 A1 | 10/2017 | |
| WO | 2017205846 A1 | 11/2017 | |
| WO | 2019032917 A1 | 2/2019 | |
| WO | 2019079215 A1 | 4/2019 | |
| WO | 2020214846 A1 | 10/2020 | |
| WO | 2021217100 A1 | 10/2021 | |
| WO | 2022020782 A1 | 1/2022 | |

OTHER PUBLICATIONS

Aldrian G, et al. (2017, e-pub. Apr. 12, 2017). "PEGylation rate influences peptide-based nanoparticles mediated siRNA delivery in vitro and in vivo," Journal of Controlled Release 256:79-91.

Anzalone, A. et al. (Dec. 5, 2019, e-pub. Oct. 21, 2019). "Search-and-Replace Genome Editing Without Double-Strand Breaks or Donor DNA," Nature 576(7785):149-157, 30 pages.

Batzer, M.A. et al. (Sep. 25, 1991). "Enhanced Evolutionary PCR Using Oligonucleotides With Inosine at the 3'-Terminus," Nucleic Acid Res. 19(18):5081.

Bikard, D. et al. (2013, e-pub. Jun. 12, 2013). "Programmable Repression and Activation of Bacterial Gene Expression Using an Engineered CRISPR-Cas System," Nucleic Acids Research 41(15):7429-7437.

Calegari, F. et al., (Oct. 29, 2002) "Tissue-Specific RNA Interference in Postimplantation Mouse Embryos with Endoribonuclease-Prepared Short Interfering RNA," Proc. Natl. Acad. Sci. USA 99:14236-14240.

Carr, P.A. et al. (2009, e-pub. Dec. 9, 2009). "Genome Engineering," Nature Biotechnology 27(12):1151-1162.

Crommelin, D.J.A. et al. (2021, e-pub. Dec. 13, 2020). "Addressing the Cold Reality of mRNA Vaccine Stability," Journal of Pharmaceutical Sciences 110:997-1001.

Dominguez, A.A. et al. (Jan. 2016, e-pub. Dec. 16, 2015). "Beyond Editing: Repurposing CRISPR-Cas9 for Precision Genome Regulation and Interrogation," Nature Reviews Molecular Cell Biology 17(1):5-15.

Dow, L.E .et al. (Apr. 2015). "Inducible in vivo Genome Editing with CRISPR/Cas9," Nature Biotechnology 33(4):390-394, (includes Supplemental Material), 24 pages.

Gump, J.M. et al. (Oct. 2007). "TAT Transduction: The Molecular Mechanism and Therapeutic Prospects," Trends Mol. Med. 13(10):443-448.

Heitz, F. et al. (2009, e-pub. Mar. 20, 2009). "Themed Section: Vector Design and Drug Delivery Review. Twenty Years of Cell-Penetrating Peptides: From Molecular Mechanisms to Therapeutics," British Journal of Pharmacology 157:195-206.

Helmenstine, A.M. (Feb. 2, 2020). "The Differences Between DNA and RNA," located at https://www.thoughtco.com/dna-versus-rna-608191?, 4 pages.

Holm T, et al. (2011, e-pub. Nov. 9, 2010). 'Retro-Inversion of Certain Cell-Penetrating Peptides Causes Severe Cellular Toxicity,' Biochimica et Biophysica Acta 1808:1544-1551.

Ibraheem, D. et al. (Jan. 1, 2014; e-pub. Nov. 25, 2013). "Gene Therapy and DNA Delivery Systems," Int J Pharm 459(1-2):70-83.

International Preliminary Report on Patentability mailed on Oct. 28, 2021, for PCT Application No. PCT/US2020/028572, filed on Apr. 16, 2020, 12 pages.

International Search Report and Written Opinion mailed Jun. 12, 2020, for Patent Application No. PCT/US2020/028572, filed Apr. 16, 2020, 18 pages.

Kawasaki, H. et al. (2003). "siRNAs generated by recombinant human Dicer induce specific and significant but target site-independent gene silencing in human cells," Nucleic Acids Res. 31(3):981-987.

Kleinstiver, B.P. et al. (Jul. 23, 2015). "Engineered CRISPR-Cas9 Nucleases With Altered PAM Specificities," Nature 523(7561):481-485, 27 pages.

Knight, S.W. et al. (Sep. 21, 2001). "A Role for the Rnase III Enzyme DCR-1 in RNA Interference and Germ Line Development in Caenorhabditis elegans," Science 293:2269-2271.

Komatsu, K.R. et al. (2020). "RNA Structure-Wide Discovery of Functional Interactions With Multiplexed RNA Motif Libra," Nature Communications 11:6275, 14 pages.

Kowalski, P.S. et al. (Apr. 2019). "Delivering the Messenger: Advances in Technologies for Therapeutic mRNA Delivery," Molecular Therapy 27(4):710-728.

Leppek, K. et al. (2022). "Combinatorial Optimization of mRNA Structure, Stability, and Translation for RNA-Based Therapeutics," Nature Communication 1:1536, 22 pages.

Mickan, A. et al. (2014). "Rational Design of CPP-based Drug Delivery Systems: Considerations from Pharmacokinetics," Current Pharmaceutical Biotechnology 15(3):200-209, 10 pages.

Morris, M.C. et al. (1997). "A New Peptide Vector for Efficient Delivery of Oligonucleotides Into Mammalian Cells," Nucleic Acids Res. 25(14):2730-2736.

Morris, M.C. et al. (Dec. 2001). "A Peptide Carrier for the Delivery of Biologically Active Proteins Into Mammalian Cells," Nat. Biotechnol. 19:1173-1176.

Nakamura, Y. et al. (2000). "Codon Usage Tabulated From the International DNA Sequence Databases: Status for the Year 2000," Nucl. Acids Res. 28(1):292, 1 page.

Nakase, I. et al. (Dec. 2004). "Cellular Uptake of Arginine-Rich Peptides: Roles for Macropinocytosis and Actin Rearrangement," Molecular Therapy 10(6):1011-1022.

Ohtsuka, E. et al. (Mar. 10, 1985). "An Alternative Approach to Deoxyoligonucleotides as Hybridization Probes by Insertion of Deoxyinosine at Ambiguous Codon Positions," J. Biol. Chem. 260(5):2605-2608.

Polstein, L.R. et al. (Mar. 2015). "A Light-Inducible CRISPR/Cas9 System for Control of Endogenous Gene Activation," Nature Chemical Biology 11(3):198-200, 10 pages.

Qi L.S. et al. (Feb. 28, 2013). "Repurposing CRISPR as an RNA-Guided Platform for Sequence-Specific Control of Gene Expression," Cell 152(5):1173-1183.

(56) References Cited

OTHER PUBLICATIONS

Robertson, H.G. et al. (Jan. 10, 1968). "Purification and Properties of Ribnuclease III from *Escherichia coli*," J. Biol. Chem. 243:82-91.

Rosa, S. S. et al. (Apr. 15, 2021, e-pub. Mar. 24, 2021). "mRNA Vaccines Manufacturing: Challenges and Bottlenecks," Vaccine 39(16):2190-2200.

Rossolini, G.M. et al. (1994). "Use of Deoxyinosine-containing Primers vs Degenerate Primers for Polymerase Chain Reaction Based on Ambiguous Sequence Information," Molecular and Cellular Probes 8:91-98.

Rothbard, J.B. et al. (2004; e-pub. Jul. 20, 2004). "Role of Membrane Potential and Hydrogen Bonding in the Mechanism of Translocation of Guanidinium-Rich Peptides into Cells," Journal of American Chemical Society 126(31):9506-9507.

Sahin, U. et al. (Oct. 2014). "mRNA-Based Therapeutics—Developing a New Class of Drugs," Nature Reviews Drug Discovery 13:759-780.

Shukla, R.S. et al. (2014; Aug. 26, 2014). "Peptides Used in the Delivery of Small Noncoding RNA," Molecular Pharmaceuticals 11(10):3395-3408.

Yang, D. et al. (Jul. 23, 2002, e-pub. Jul. 2, 2002). "Short RNA Duplexes Produced By Hydrolysis With *Escherichia Coli* RNase III Mediate Effective RNA Interference in Mammalian Cells," PNAS USA 99(15):9942-9947.

Yin, H. et al. (Aug. 2014). "Non-Viral Vectors for Gene-Based Therapy," Nature Reviews Genetics 15:541-555.

Zetsche, B. et al. (Feb. 2015). "A Split-Cas9 Architecture for Inducible Genome Editing and Transcription Modulation," Nature biotechnology 33(2):139-142.

Zuker, M. et al. (1981). "Optimal Computer Folding of Large RNA Sequences Using Thermodynamics and Auxiliary Information," Nucleic Acids Res. 9(1):133-148.

Hatakeyama, H. et al. (2011, e-pub. Sep. 15, 2010). "A Multifunctional Envelope Type Nano Device (MEND) for Gene Delivery to Tumours Based on the EPR Effect: A Strategy for Overcoming the PEG Dilemma," Advanced Drug Delivery Reviews 63(3):152-160.

\* cited by examiner

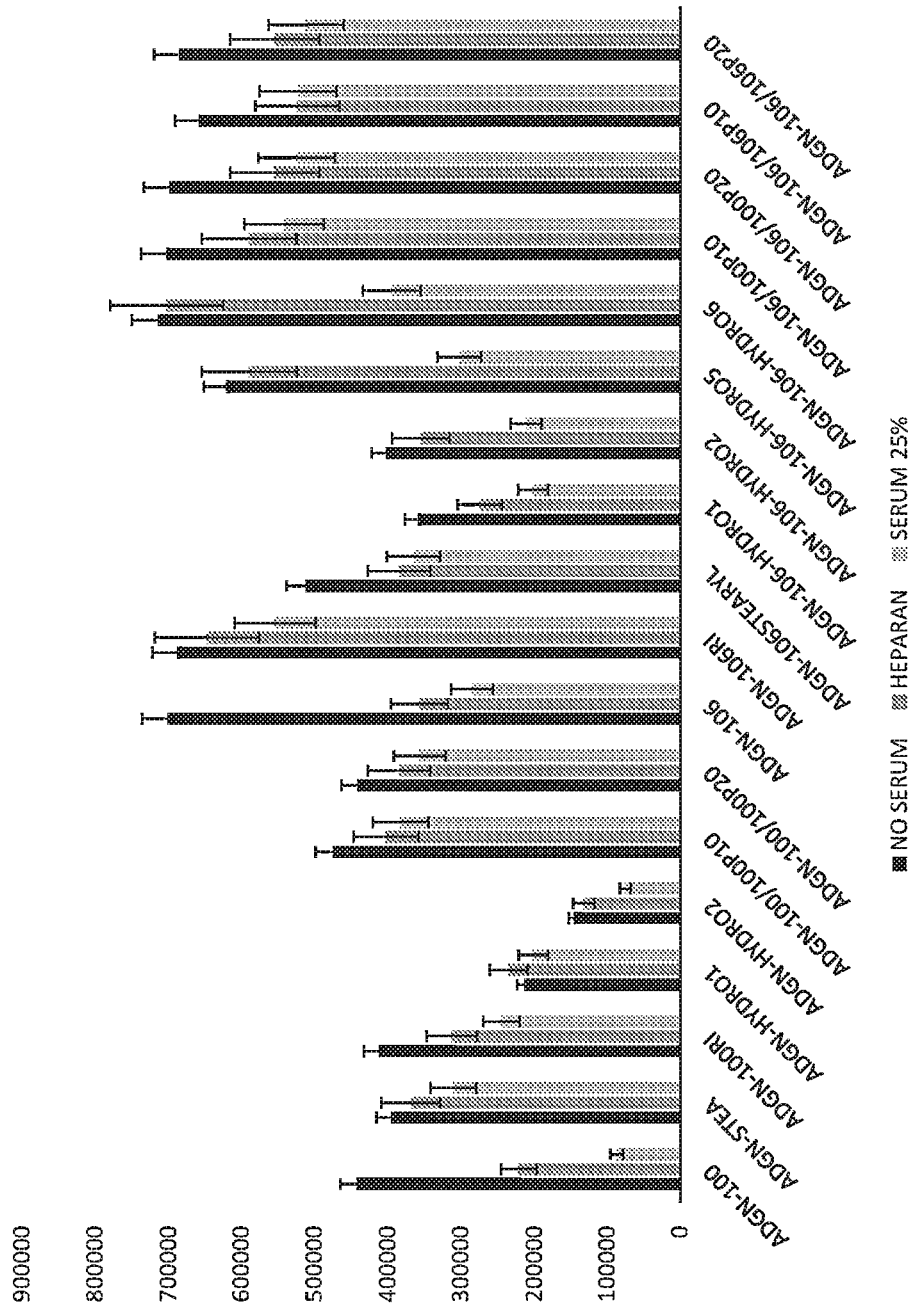

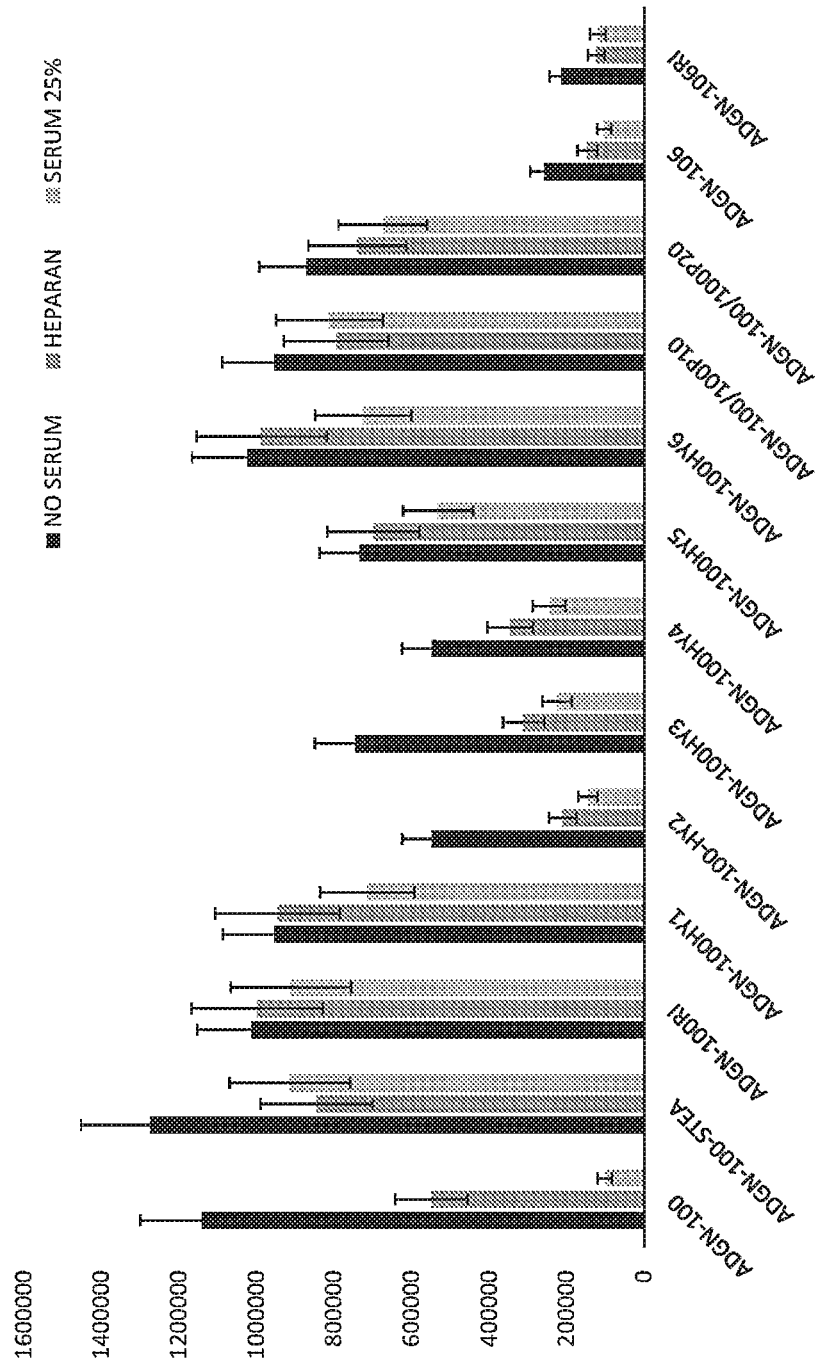

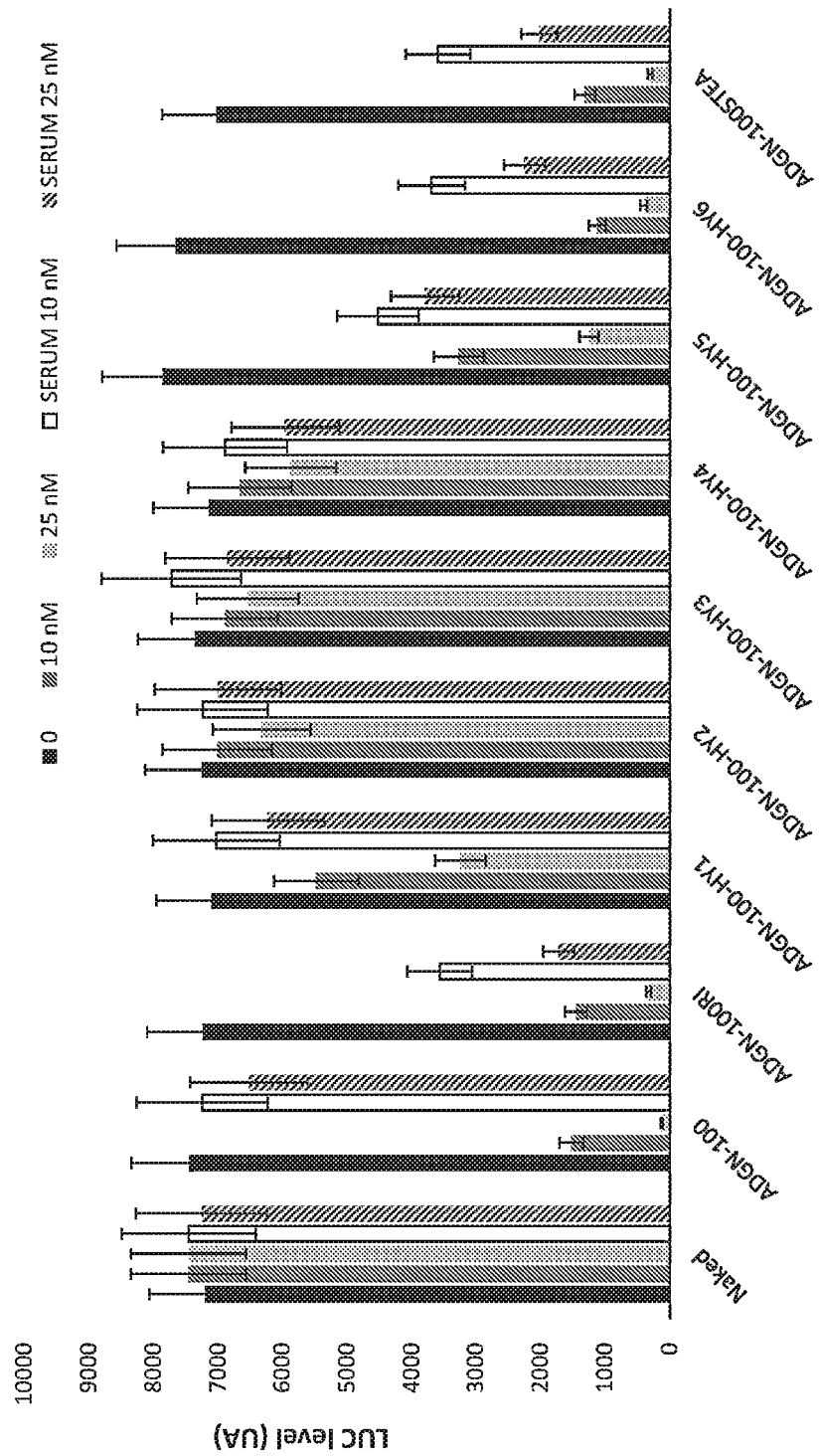

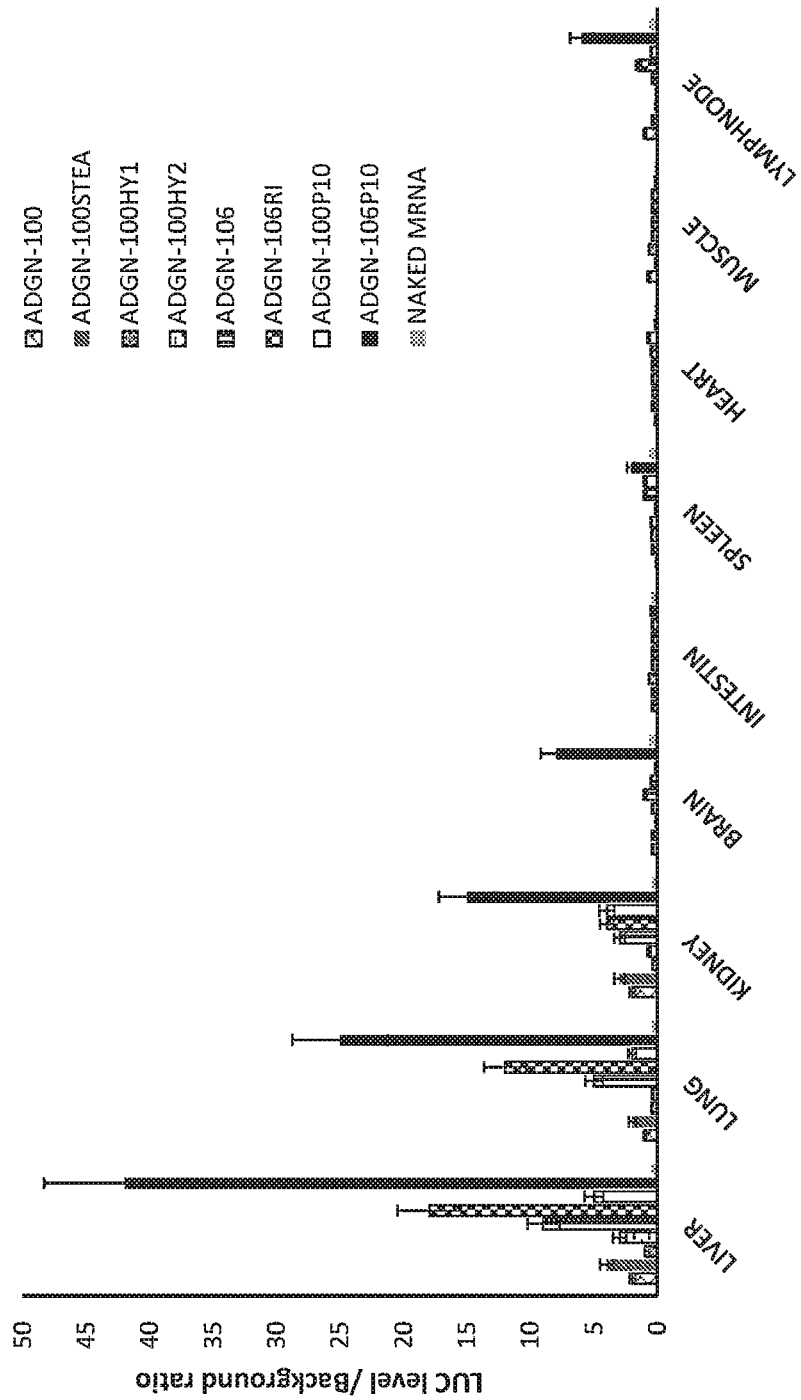

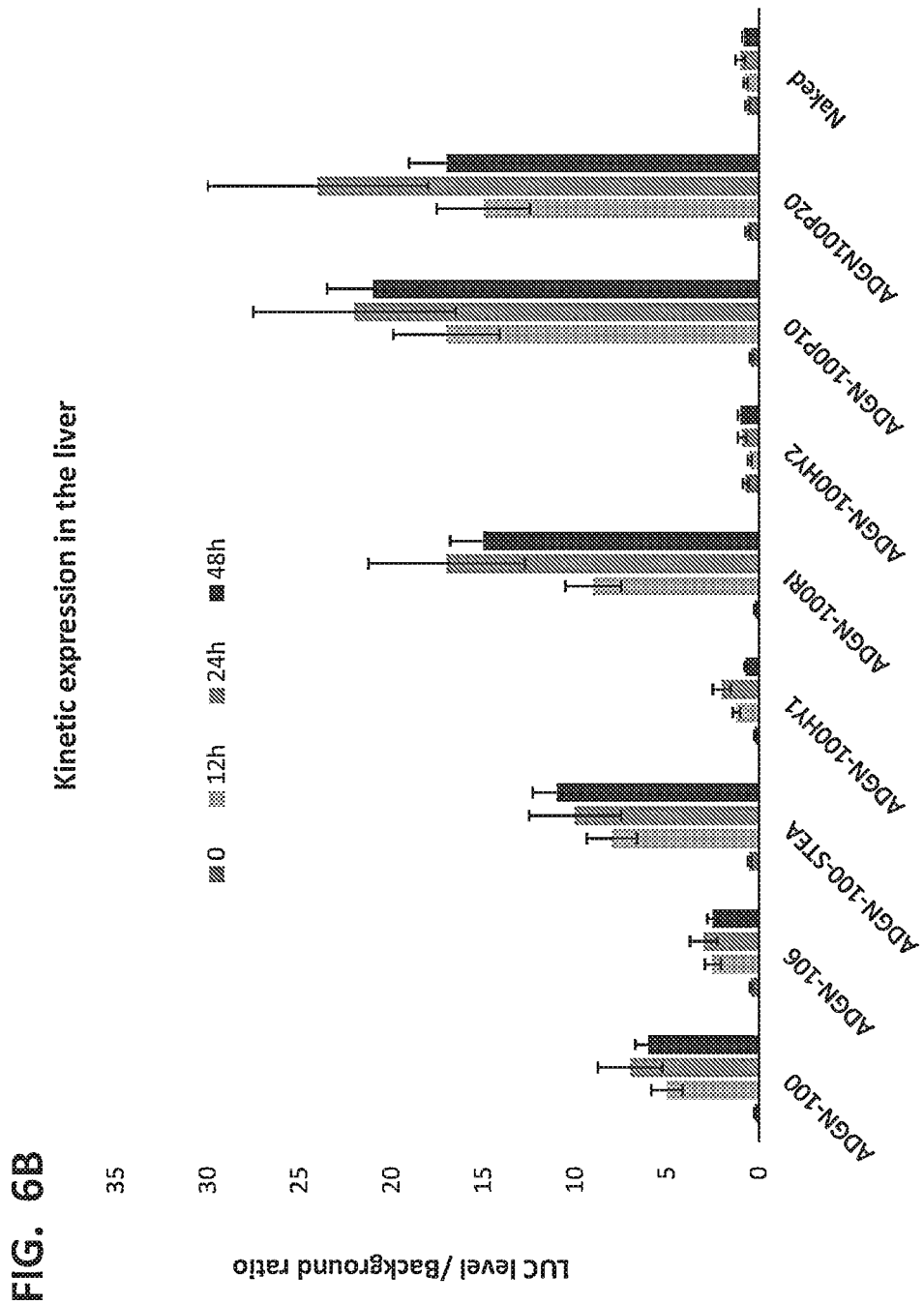

FIG. 8

| PEPTIDES | NO FILTRATION | | | FILTRATION 0.45 PES | | | FILTRATION 0.45 PVDF | | |
|---|---|---|---|---|---|---|---|---|---|
| | Number Particle Size Distribution | % | Number Particle Size Distribution | % | Number Particle Size Distribution | RATIO NF/F | AGGREGAT % | RATIO NF/F | AGGREGAT % |
| ADGN-100 | 127,2 | 94,5 | 545,4 | 5,5 | 128,1 | 0,78 | 22 | 127,8 | 0,75 | 25 |
| ADGN-100 RI | 107,2 | 95,7 | 601,4 | 3,2 | 101,4 | 0,84 | 16 | 115,2 | 0,74 | 26 |
| ADGN-100 STEARYL | 117,2 | 95,2 | 442,1 | 4,8 | 115,4 | 0,74 | 26 | 124,1 | 0,74 | 26 |
| ADGN-100 HYDRO1 | 102,6 | 88,5 | 652,1 | 10,2 | 107,2 | 0,81 | 19 | 110,4 | 0,68 | 32 |
| ADGN-100 HYDRO2 | 168,5 | 93,7 | 853,1 | 6,5 | 154,7 | 0,79 | 21 | 171,2 | 0,71 | 29 |
| ADGN-100 HYDRO3 | 137,2 | 85,4 | 985,2 | 12,5 | 135,4 | 0,78 | 22 | 137,8 | 0,65 | 35 |
| ADGN-100 HYDRO4 | 154,5 | 87,2 | 1036 | 11,4 | 147,2 | 0,8 | 20 | 144,8 | 0,71 | 29 |
| ADGN-100 HYDRO5 | 145,2 | 98,2 | 1045 | 1 | 144,7 | 0,85 | 15 | 141,5 | 0,74 | 26 |
| ADGN-100 HYDRO6 | 168,5 | 95,7 | 1024,8 | 3,4 | 158,6 | 0,85 | 15 | 138,5 | 0,75 | 25 |
| ADGN-100/ ADGN-100P10% | 135,4 | 84,5 | 778,2 | 5,2 | 130,4 | 0,75 | 25 | 127,8 | 0,69 | 31 |
| ADGN-100/ ADGN-100P 20% | 151,4 | 87,1 | 569,2 | 12,9 | 144,2 | 0,76 | 24 | 147,5 | 0,7 | 30 |

FIG. 9

| PEPTIDES | NO FILTRATION | | | | FILTRATION 0.45 PES | | | FILTRATION 0.45 PVDF | | |
|---|---|---|---|---|---|---|---|---|---|---|
| | Number Particle Size Distribution | % | Number Particle Size Distribution | % | Number Particle Size Distribution | RATIO NF/F | AGGREGAT % | Number Particle Size Distribution | RATIO NF/F | AGGREGAT % |
| ADGN-106 | 124,5 | 91,5 | 501,2 | 8,8 | 121,8 | 0,81 | 19 | 121,4 | 0,71 | 29 |
| ADGN-106RI | 112,7 | 97,5 | 1022 | 2 | 107,5 | 0,87 | 13 | 114,8 | 0,75 | 25 |
| ADGN-106 STEARYL | 221,5 | 95,2 | 767,5 | 7 | 127,4 | 0,74 | 26 | 118,4 | 0,71 | 29 |
| ADGN-106 HYDRO1 | 131,6 | 87,5 | 981,2 | 12,5 | 121,4 | 0,8 | 20 | 124,7 | 0,65 | 35 |
| ADGN-106 HYDRO2 | 157,4 | 94 | 958,7 | 6 | 144,8 | 0,8 | 20 | 124,7 | 0,65 | 35 |
| ADGN-106 HYDRO3 | 174,7 | 91,2 | 841,4 | 8 | 171,1 | 0,78 | 22 | 167,1 | 0,62 | 38 |
| ADGN-106 HYDRO4 | 148,5 | 87,4 | 1075,1 | 12,1 | 149,7 | 0,81 | 19 | 144,1 | 0,68 | 32 |
| ADGN-106 HYDRO5 | 129,4 | 94,2 | 948,2 | 5,5 | 127,1 | 0,85 | 15 | 131,1 | 0,71 | 29 |
| ADGN-106 HYDRO6 | 117,2 | 9 | 1450 | 1 | 118,1 | 0,87 | 13 | 119,7 | 0,75 | 25 |
| ADGN-100P10% ADGN-106 | 148,5 | 94,1 | 985,2 | 5,4 | 149,5 | 0,79 | 22 | 144,7 | 0,72 | 28 |
| ADGN-100P20% ADGN-106 | 125,7 | 92,5 | 753,8 | 7,5 | 117,9 | 0,78 | 22 | 121,7 | 0,64 | 36 |

FIG. 10

| PEPTIDES | NO FILTRATION | | | FILTRATION 0.45 PES | | | FILTRATION 0.45 PVDF | | |
|---|---|---|---|---|---|---|---|---|---|
| | Number Particle Size Distribution | % | Number Particle Size Distribution | Number Particle Size Distribution | RATIO NF/F | AGGREGAT % | Number Particle Size Distribution | RATIO NF/F | AGGREGAT % |
| ADGN-100 | 107,2 | 92,1 | 784,1 | 102,4 | 0,71 | 29 | 108,7 | 0,69 | 31 |
| ADGN-100Ri | 114,2 | 96 | 894,4 | 115,4 | 0,85 | 15 | 114,7 | 0,75 | 25 |
| ADGN-100 STEARYL | 112,5 | 91,4 | >1000 | 102,4 | 0,72 | 28 | 100,2 | 0,55 | 55 |
| ADGN-100 HYDRO 1 | 124,5 | 91,0 | 972,2 | 110,7 | 0,79 | 22 | 110,8 | 0,58 | 42 |
| ADGN-100 HYDRO 2 | 157,5 | 71,2 | >1000 | 237,4 | 0,41 | 59 | 254,5 | 0,28 | 72 |
| ADGN-100 HYDRO 3 | 210,4 | 81 | 873 | 257,1 | 0,65 | 35 | 255 | 0,37 | 63 |
| ADGN-100 HYDRO 4 | 185,2 | 85 | 749,2 | 177,5 | 0,71 | 29 | 158,7 | 0,65 | 35 |
| ADGN-100 HYDRO 5 | 115,2 | 98,1 | >1000 | 111 | 0,81 | 19 | 113,2 | 0,75 | 25 |
| ADGN-100 HYDRO 6 | 157,4 | 97,2 | >1000 | 152,3 | 0,85 | 15 | 154,3 | 0,75 | 25 |
| ADGN100/ADGN100P10% | 118,5 | 91,2 | 865,2 | 115 | 0,74 | 26 | 119,5 | 0,61 | 39 |
| ADGN100/ADGN100P20% | 124,7 | 86 | >1000 | 117,8 | 0,76 | 24 | 123,4 | 0,65 | 35 |
| ADGN-106 | 314,2 | 85,4 | 914,7 | 246,5 | 0,34 | 76 | 269,1 | 0,21 | 79 |
| ADGN-106Ri | 358,2 | 91,7 | >1000 | 286,1 | 0,55 | 45 | 275,3 | 0,34 | 66 |
| ADGN106/ADGN100P10% | 307,4 | 84 | >1000 | 234,2 | 0,28 | 71 | 269,4 | 0,21 | 79 |
| ADGN106/ADGN100P20% | 347,2 | 81,4 | >1000 | 278,5 | 0,31 | 69 | 301,2 | 0,22 | 78 |

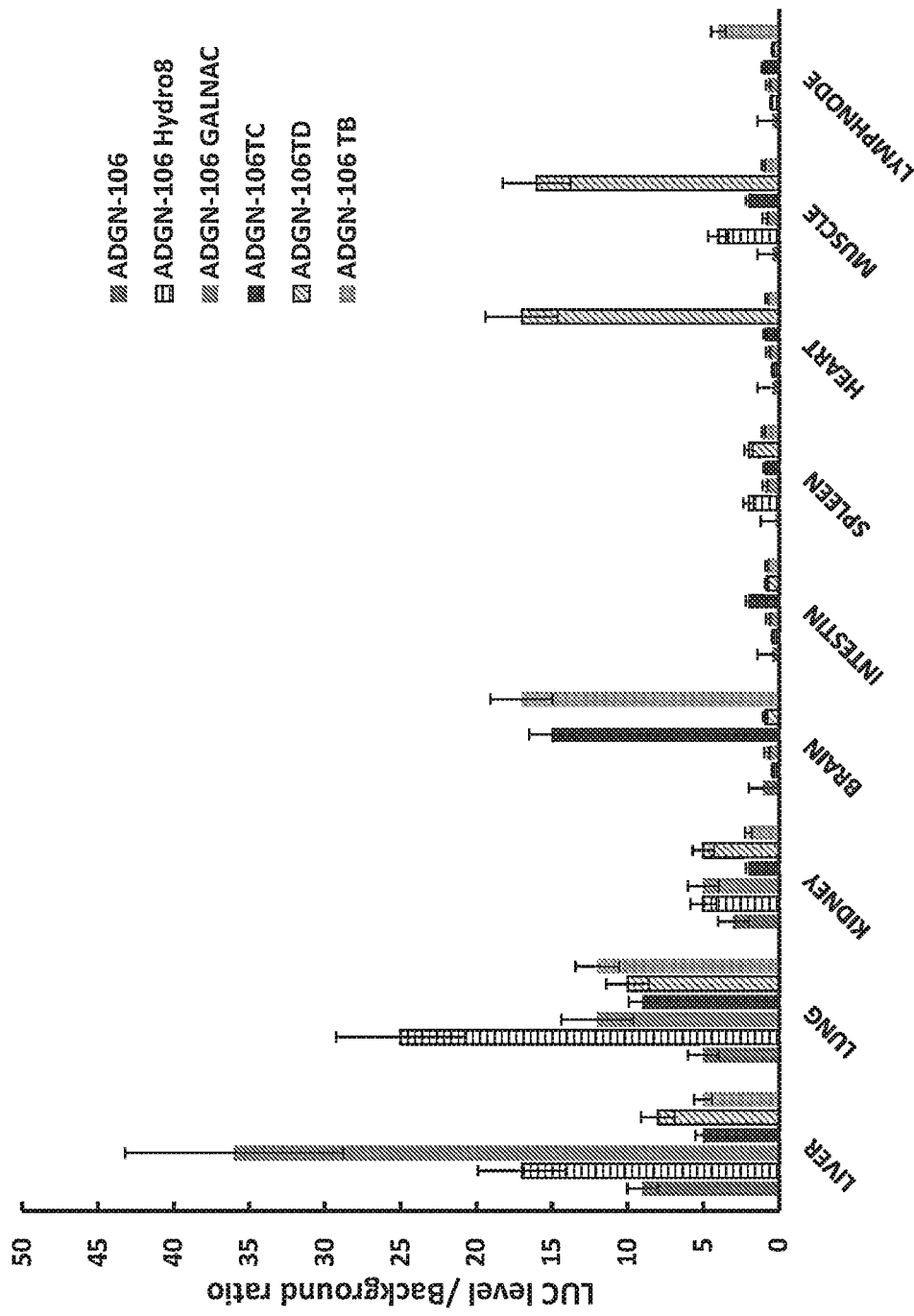

SEQUENCE LISTING

<160> NUMBER OF SEQ ID NOS: 210

<210> SEQ ID NO 1
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2, 6
<223> OTHER INFORMATION: Xaa = K, R or L
<220> FEATURE:
<221> NAME/KEY: VARIANT
<222> LOCATION: 3, 7, 11
<223> OTHER INFORMATION: Xaa = F or W
<220> FEATURE:
<221> NAME/KEY: VARIANT
<222> LOCATION: 4, 8
<223> OTHER INFORMATION: Xaa = F, W or Y
<220> FEATURE:
<221> NAME/KEY: VARIANT
<222> LOCATION: 5
<223> OTHER INFORMATION: Xaa = E, R or S
<220> FEATURE:
<221> NAME/KEY: VARIANT
<222> LOCATION: 9
<223> OTHER INFORMATION: Xaa = R, T or S
<220> FEATURE:
<221> NAME/KEY: VARIANT
<222> LOCATION: 10
<223> OTHER INFORMATION: Xaa = E, R, or S
<220> FEATURE:
<221> NAME/KEY: VARIANT
<222> LOCATION: 12
<223> OTHER INFORMATION: Xaa = none, F or W
<220> FEATURE:
<221> NAME/KEY: VARIANT
<222> LOCATION: 13
<223> OTHER INFORMATION: Xaa = P or R
<220> FEATURE:
<221> NAME/KEY: VARIANT
<222> LOCATION: 14
<223> OTHER INFORMATION: Xaa = R or L
<220> FEATURE:
<221> NAME/KEY: VARIANT
<222> LOCATION: 15
<223> OTHER INFORMATION: Xaa = K, W or R
<220> FEATURE:
<221> NAME/KEY: VARIANT
<222> LOCATION: 16
<223> OTHER INFORMATION: Xaa = R or F
<220> FEATURE:
<221> NAME/KEY: VARIANT
<222> LOCATION: 17
<223> OTHER INFORMATION: Xaa = R or K

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1

```
<223> OTHER INFORMATION: Xaa = beta-A or S
<220> FEATURE:
<221> NAME/KEY: VARIANT
<222> LOCATION: 2, 6
<223> OTHER INFORMATION: Xaa = R or K
<220> FEATURE:
<221> NAME/KEY: VARIANT
<222> LOCATION: 4, 8
<223> OTHER INFORMATION: Xaa = F, W, or Y
<220> FEATURE:
<221> NAME/KEY: VARIANT
<222> LOCATION: 9
<223> OTHER INFORMATION: Xaa = T or R
<220> FEATURE:
<221> NAME/KEY: VARIANT
<222> LOCATION: 10
<223> OTHER INFORMATION: Xaa = E or R
<220> FEATURE:
<221> NAME/KEY: VARIANT
<222> LOCATION: 11
<223> OTHER INFORMATION: Xaa = W or F
<220> FEATURE:
<221> NAME/KEY: VARIANT
<222> LOCATION: 14
<223> OTHER INFORMATION: Xaa = R or K
<220> FEATURE:
<221> NAME/KEY: VARIANT
<222> LOCATION: 16
<223> OTHER INFORMATION: Xaa = R or K

<400> SEQUENCE: 2

Xaa Xaa Trp Xaa Glu Xaa Trp Xaa Xaa Xaa Xaa Pro Arg Xaa Arg Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 3

Xaa Lys Trp Phe Glu Arg Trp Phe Arg Glu Trp Pro Arg Lys Arg Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 4

Xaa Lys Trp Trp Glu Arg Trp Trp Arg Glu Trp Pro Arg Lys Arg Arg
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

<223> OTHER INFORMATION: Xaa = beta-A or S

<400> SEQUENCE: 5

Xaa Lys Trp Trp Glu Arg Trp Trp Arg Glu Trp Pro Arg Lys Arg Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 6

Xaa Arg Trp Trp Glu Lys Trp Trp Thr Arg Trp Pro Arg Lys Arg Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 7

Xaa Arg Trp Tyr Glu Lys Trp Tyr Thr Glu Phe Pro Arg Arg Arg Arg
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3, 11
<223> OTHER INFORMATION: Xaa = Any non-natural amino acid
<220> FEATURE:
<221> NAME/KEY: VARIANT
<222> LOCATION: 3, 11
<223> OTHER INFORMATION: Xaa = Linked by a hydrocarbon linkage

<400> SEQUENCE: 8

Xaa Lys Xaa Trp Trp Glu Arg Trp Trp Arg Xaa Trp Pro Arg Lys Arg
1               5                   10                  15

Lys

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

```
<220> FEATURE:
<221> NAME/KEY: VARIANT
<222> LOCATION: 2
<223> OTHER INFORMATION: Xaa = K, R or L
<220> FEATURE:
<221> NAME/KEY: VARIANT
<222> LOCATION: 3, 7
<223> OTHER INFORMATION: Xaa = F or W
<220> FEATURE:
<221> NAME/KEY: VARIANT
<222> LOCATION: 5
<223> OTHER INFORMATION: Xaa = R or S
<220> FEATURE:
<221> NAME/KEY: VARIANT
<222> LOCATION: 6, 14
<223> OTHER INFORMATION: Xaa = L or R
<220> FEATURE:
<221> NAME/KEY: VARIANT
<222> LOCATION: 9
<223> OTHER INFORMATION: Xaa = R or S
<220> FEATURE:
<221> NAME/KEY: VARIANT
<222> LOCATION: 10
<223> OTHER INFORMATION: Xaa = R or S
<220> FEATURE:
<221> NAME/KEY: VARIANT
<222> LOCATION: 12
<223> OTHER INFORMATION: Xaa = F or W
<220> FEATURE:
<221> NAME/KEY: VARIANT
<222> LOCATION: 13
<223> OTHER INFORMATION: Xaa = R or P
<220> FEATURE:
<221> NAME/KEY: VARIANT
<222> LOCATION: 16
<223> OTHER INFORMATION: Xaa = R or F

<400> SEQUENCE: 9

Xaa Xaa Xaa Trp Xaa Xaa Xaa Trp Xaa Xaa Trp Xaa Xaa Xaa Trp Xaa
1               5                   10                  15

Arg

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 10

Xaa Arg Trp Trp Arg Leu Trp Trp Arg Ser Trp Phe Arg Leu Trp Arg
1               5                   10                  15

Arg

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 11

Xaa Leu Trp Trp Arg Arg Trp Trp Ser Arg Trp Trp Pro Arg Trp Arg
1               5                   10                  15
```

Arg

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 12

Xaa Leu Trp Trp Ser Arg Trp Trp Arg Ser Trp Phe Arg Leu Trp Phe
1               5                   10                  15

Arg

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 13

Xaa Lys Phe Trp Ser Arg Phe Trp Arg Ser Trp Phe Arg Leu Trp Arg
1               5                   10                  15

Arg

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 5, 12
<223> OTHER INFORMATION: Xaa = Any non-natural amino acid
<220> FEATURE:
<221> NAME/KEY: VARIANT
<222> LOCATION: 5, 12
<223> OTHER INFORMATION: Xaa = Linked by a hydrocarbon linkage

<400> SEQUENCE: 14

Xaa Arg Trp Trp Xaa Leu Trp Trp Arg Ser Trp Xaa Arg Leu Trp Arg
1               5                   10                  15

Arg

<210> SEQ ID NO 15
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

```
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8, 11, 15
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 15

Xaa Leu Xaa Arg Ala Leu Trp Xaa Leu Xaa Xaa Xaa Leu Trp Xaa Leu
1               5                   10                  15

Xaa Xaa Xaa Xaa
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8, 11, 15
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
```

<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 16

Xaa Leu Xaa Leu Ala Arg Trp Xaa Leu Xaa Xaa Xaa Leu Trp Xaa Leu
1               5                   10                  15

Xaa Xaa Xaa Xaa
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 8, 11, 15
<223> OTHER INFORMATION: Xaa = R or S
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 17

Xaa Leu Xaa Ala Arg Leu Trp Xaa Leu Xaa Xaa Xaa Leu Trp Xaa Leu
1               5                   10                  15

Xaa Xaa Xaa Xaa
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT

```
<222> LOCATION: 3
<223> OTHER INFORMATION: Xaa = F or W
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 19
<223> OTHER INFORMATION: Xaa = K or R
<220> FEATURE:
<221> NAME/KEY: VARIANT
<222> LOCATION: 20
<223> OTHER INFORMATION: Xaa = A or none

<400> SEQUENCE: 18

Xaa Leu Xaa Arg Ala Leu Trp Arg Leu Xaa Arg Xaa Leu Trp Arg Leu
1               5                   10                  15

Xaa Xaa Xaa Xaa
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3
<223> OTHER INFORMATION: Xaa = F or W
<220> FEATURE:
<221> NAME/KEY: VARIANT
<222> LOCATION: 10
<223> OTHER INFORMATION: Xaa = L, W, C or I
<220> FEATURE:
<221> NAME/KEY: VARIANT
<222> LOCATION: 12
<223> OTHER INFORMATION: Xaa = S, A, N or T
<220> FEATURE:
<221> NAME/KEY: VARIANT
<222> LOCATION: 17
<223> OTHER INFORMATION: Xaa = L or W
<220> FEATURE:
<221> NAME/KEY: VARIANT
<222> LOCATION: 18
<223> OTHER INFORMATION: Xaa = W or R
<220> FEATURE:
<221> NAME/KEY: VARIANT
<222> LOCATION: 20
<223> OTHER INFORMATION: Xaa = K or R

<400> SEQUENCE: 19

Xaa Leu Xaa Arg Ala Leu Trp Arg Leu Xaa Arg Xaa Leu Trp Arg Leu
1               5                   10                  15

Xaa Xaa Lys Xaa
            20
```

```
<210> SEQ ID NO 20
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 20

Xaa Leu Phe Arg Ala Leu Trp Arg Leu Leu Arg Xaa Leu Trp Arg Leu
1               5                   10                  15

Leu Trp Xaa

<210> SEQ ID NO 21
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 21

Xaa Leu Trp Arg Ala Leu Trp Arg Leu Trp Arg Xaa Leu Trp Arg Leu
1               5                   10                  15

Leu Trp Xaa Ala
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L, C or I
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R
```

```
<400> SEQUENCE: 22

Xaa Leu Trp Arg Ala Leu Trp Arg Leu Xaa Arg Xaa Leu Trp Arg Leu
1               5                   10                  15

Trp Arg Xaa Ala
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 12
<223> OTHER INFORMATION: Xaa = S or T
<220> FEATURE:
<221> NAME/KEY: VARIANT
<222> LOCATION: 19
<223> OTHER INFORMATION: Xaa = K or R

<400> SEQUENCE: 23

Xaa Leu Trp Arg Ala Leu Trp Arg Leu Trp Arg Xaa Leu Trp Arg Leu
1               5                   10                  15

Trp Arg Xaa Ala
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L or I
<220> FEATURE:
<221> NAME/KEY: VARIANT
<222> LOCATION: 19
<223> OTHER INFORMATION: Xaa = K or R

<400> SEQUENCE: 24

Xaa Leu Trp Arg Ala Leu Trp Arg Leu Xaa Arg Ala Leu Trp Arg Leu
1               5                   10                  15

Leu Trp Xaa Ala
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 10
<223> OTHER INFORMATION: Xaa = L, C or I
```

```
<220> FEATURE:
<221> NAME/KEY: VARIANT
<222> LOCATION: 19
<223> OTHER INFORMATION: Xaa = K or R

<400> SEQUENCE: 25

Xaa Leu Trp Arg Ala Leu Trp Arg Leu Xaa Arg Asn Leu Trp Arg Leu
1               5                   10                  15

Leu Trp Xaa Ala
            20

<210> SEQ ID NO 26
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation

<400> SEQUENCE: 26

Xaa Leu Phe Arg Ala Leu Trp Arg Leu Leu Arg Ser Leu Trp Arg Leu
1               5                   10                  15

Leu Trp Lys

<210> SEQ ID NO 27
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 27

Xaa Leu Trp Arg Ala Leu Trp Arg Leu Trp Arg Ser Leu Trp Arg Leu
1               5                   10                  15

Leu Trp Lys Ala
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
```

-continued

```
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 28

Xaa Leu Trp Arg Ala Leu Trp Arg Leu Leu Arg Ser Leu Trp Arg Leu
1               5                   10                  15

Trp Arg Lys Ala
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 29

Xaa Leu Trp Arg Ala Leu Trp Arg Leu Trp Arg Ser Leu Trp Arg Leu
1               5                   10                  15

Trp Arg Lys Ala
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 30

Xaa Leu Trp Arg Ala Leu Trp Arg Leu Leu Arg Ala Leu Trp Arg Leu
1               5                   10                  15

Leu Trp Lys Ala
            20

<210> SEQ ID NO 31
<211> LENGTH: 20
<212> TYPE: PRT
<213> ORGANISM: Artificial Sequence
<220> FEATURE:
```

<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 31

Xaa Leu Trp Arg Ala Leu Trp Arg Leu Leu Arg Asn Leu Trp Arg Leu
1               5                   10                  15

Leu Trp Lys Ala
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 8, 12
<223> OTHER INFORMATION: Linked by a hydrocarbon linkage

<400> SEQUENCE: 32

Xaa Leu Phe Arg Ala Leu Trp Arg Leu Leu Arg Ser Leu Trp Arg Leu
1               5                   10                  15

Leu Trp Lys

<210> SEQ ID NO 33
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 8, 12
<223> OTHER INFORMATION: Linked by a hydrocarbon linkage

<400> SEQUENCE: 33

```
Xaa Leu Phe Leu Ala Arg Trp Arg Leu Leu Arg Ser Leu Trp Arg Leu
1               5                   10                  15

Leu Trp Lys

<210> SEQ ID NO 34
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 8, 12
<223> OTHER INFORMATION: Linked by a hydrocarbon linkage

<400> SEQUENCE: 34

Xaa Leu Phe Arg Ala Leu Trp Ser Leu Leu Arg Ser Leu Trp Arg Leu
1               5                   10                  15

Leu Trp Lys

<210> SEQ ID NO 35
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 8, 12
<223> OTHER INFORMATION: Linked by a hydrocarbon linkage

<400> SEQUENCE: 35

Xaa Leu Phe Leu Ala Arg Trp Ser Leu Leu Arg Ser Leu Trp Arg Leu
1               5                   10                  15

Leu Trp Lys

<210> SEQ ID NO 36
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
```

```
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 11, 15
<223> OTHER INFORMATION: Linked by a hydrocarbon linkage

<400> SEQUENCE: 36

Xaa Leu Phe Arg Ala Leu Trp Arg Leu Leu Arg Ser Leu Trp Ser Leu
1               5                   10                  15

Leu Trp Lys

<210> SEQ ID NO 37
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 11, 15
<223> OTHER INFORMATION: Linked by a hydrocarbon linkage

<400> SEQUENCE: 37

Xaa Leu Phe Leu Ala Arg Trp Arg Leu Leu Arg Ser Leu Trp Ser Leu
1               5                   10                  15

Leu Trp Lys

<210> SEQ ID NO 38
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 11, 15
<223> OTHER INFORMATION: Linked by a hydrocarbon linkage

<400> SEQUENCE: 38

Xaa Leu Phe Arg Ala Leu Trp Arg Leu Leu Ser Ser Leu Trp Ser Leu
1               5                   10                  15
```

Leu Trp Lys

<210> SEQ ID NO 39
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 11, 15
<223> OTHER INFORMATION: Linked by a hydrocarbon linkage

<400> SEQUENCE: 39

Xaa Leu Phe Leu Ala Arg Trp Arg Leu Leu Ser Ser Leu Trp Ser Leu
1               5                   10                  15

Leu Trp Lys

<210> SEQ ID NO 40
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 5, 12
<223> OTHER INFORMATION: Linked by a hydrocarbon linkage

<400> SEQUENCE: 40

Xaa Leu Phe Ala Arg Leu Trp Arg Leu Leu Arg Ser Leu Trp Arg Leu
1               5                   10                  15

Leu Trp Lys

<210> SEQ ID NO 41
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2
<223> OTHER INFORMATION: Xaa = L or none

```
<220> FEATURE:
<221> NAME/KEY: VARIANT
<222> LOCATION: 3, 11
<223> OTHER INFORMATION: Xaa = R or none, wherein if none, positions 2,
      16 and 17 are none as well
<220> FEATURE:
<221> NAME/KEY: VARIANT
<222> LOCATION: 6
<223> OTHER INFORMATION: Xaa = L, R or G
<220> FEATURE:
<221> NAME/KEY: VARIANT
<222> LOCATION: 7
<223> OTHER INFORMATION: Xaa = R, W or S
<220> FEATURE:
<221> NAME/KEY: VARIANT
<222> LOCATION: 10
<223> OTHER INFORMATION: Xaa = S, P or T
<220> FEATURE:
<221> NAME/KEY: VARIANT
<222> LOCATION: 12
<223> OTHER INFORMATION: Xaa = W or P
<220> FEATURE:
<221> NAME/KEY: VARIANT
<222> LOCATION: 13
<223> OTHER INFORMATION: Xaa = F, A or R
<220> FEATURE:
<221> NAME/KEY: VARIANT
<222> LOCATION: 14
<223> OTHER INFORMATION: Xaa = S, L, P or R
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 16
<223> OTHER INFORMATION: Xaa = W or none
<220> FEATURE:
<221> NAME/KEY: VARIANT
<222> LOCATION: 17
<223> OTHER INFORMATION: Xaa = A, R or none
<220> FEATURE:
<221> NAME/KEY: VARIANT
<222> LOCATION: 19
<223> OTHER INFORMATION: Xaa = W or F

<400> SEQUENCE: 41

Xaa Xaa Xaa Trp Trp Xaa Xaa Trp Ala Xaa Xaa Xaa Xaa Xaa Xaa Xaa
1               5                   10                  15

Xaa Trp Xaa Arg
        20

<210> SEQ ID NO 42
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 2
<223> OTHER INFORMATION: Xaa = L or none
<220> FEATURE:
<221> NAME/KEY: VARIANT
<222> LOCATION: 10
<223> OTHER INFORMATION: Xaa = S or P
<220> FEATURE:
<221> NAME/KEY: VARIANT
<222> LOCATION: 13
<223> OTHER INFORMATION: Xaa = F or A
<220> FEATURE:
<221> NAME/KEY: VARIANT
```

```
<222> LOCATION: 14
<223> OTHER INFORMATION: Xaa = S, L or P
<220> FEATURE:
<221> NAME/KEY: VARIANT
<222> LOCATION: 15
<223> OTHER INFORMATION: Xaa = R or S
<220> FEATURE:
<221> NAME/KEY: VARIANT
<222> LOCATION: 17
<223> OTHER INFORMATION: Xaa = A or R
<220> FEATURE:
<221> NAME/KEY: VARIANT
<222> LOCATION: 19
<223> OTHER INFORMATION: Xaa = W or F

<400> SEQUENCE: 42

Xaa Xaa Arg Trp Trp Leu Arg Trp Ala Xaa Arg Trp Xaa Xaa Xaa Trp
1               5                   10                  15

Xaa Trp Xaa Arg
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 43

Xaa Leu Arg Trp Trp Leu Arg Trp Ala Ser Arg Trp Phe Ser Arg Trp
1               5                   10                  15

Ala Trp Trp Arg
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 44

Xaa Leu Arg Trp Trp Leu Arg Trp Ala Ser Arg Trp Ala Ser Arg Trp
1               5                   10                  15

Ala Trp Phe Arg
            20

<210> SEQ ID NO 45
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 45

Xaa Arg Trp Trp Leu Arg Trp Ala Ser Arg Trp Ala Leu Ser Trp Arg
1               5                   10                  15
```

Trp Trp Arg

<210> SEQ ID NO 46
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Any Amino Acid

<400> SEQUENCE: 46

Xaa Arg Trp Trp Leu Arg Trp Ala Ser Arg Trp Phe Leu Ser Trp Arg
1               5                   10                  15

Trp Trp Arg

<210> SEQ ID NO 47
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 47

Xaa Arg Trp Trp Leu Arg Trp Ala Pro Arg Trp Phe Pro Ser Trp Arg
1               5                   10                  15

Trp Trp Arg

<210> SEQ ID NO 48
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 48

Xaa Arg Trp Trp Leu Arg Trp Ala Ser Arg Trp Ala Pro Ser Trp Arg
1               5                   10                  15

Trp Trp Arg

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 4
<223> OTHER INFORMATION: Xaa = R or G
<220> FEATURE:
<221> NAME/KEY: VARIANT
<222> LOCATION: 5
<223> OTHER INFORMATION: Xaa = W or S

```
<220> FEATURE:
<221> NAME/KEY: VARIANT
<222> LOCATION: 8
<223> OTHER INFORMATION: Xaa = S, T or P
<220> FEATURE:
<221> NAME/KEY: VARIANT
<222> LOCATION: 9
<223> OTHER INFORMATION: Xaa = W or P
<220> FEATURE:
<221> NAME/KEY: VARIANT
<222> LOCATION: 10
<223> OTHER INFORMATION: Xaa = A or R
<220> FEATURE:
<221> NAME/KEY: VARIANT
<222> LOCATION: 12
<223> OTHER INFORMATION: Xaa = S or R

<400> SEQUENCE: 49

Xaa Trp Trp Xaa Xaa Trp Ala Xaa Xaa Xaa Arg Xaa Trp Trp Arg
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 50

Xaa Trp Trp Arg Trp Trp Ala Ser Trp Ala Arg Ser Trp Trp Arg
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 51

Xaa Trp Trp Gly Ser Trp Ala Thr Pro Arg Arg Arg Trp Trp Arg
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 52

Xaa Trp Trp Arg Trp Trp Ala Pro Trp Ala Arg Ser Trp Trp Arg
1               5                   10                  15

<210> SEQ ID NO 53
<211> LENGTH: 20
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 1
<223> OTHER INFORMATION: Xaa = Any Amino Acid or none
<220> FEATURE:
<221> NAME/KEY: VARIANT
<222> LOCATION: 6, 7, 8, 15, 16, 17, 18
<223> OTHER INFORMATION: Xaa = Any Amino Acid

<400> SEQUENCE: 53

Xaa Lys Trp Arg Ser Xaa Xaa Xaa Arg Trp Arg Leu Trp Arg Xaa Xaa
1               5                   10                  15

Xaa Xaa Ser Arg
        20

<210> SEQ ID NO 54
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A, S, or none
<220> FEATURE:
<221> NAME/KEY: VARIANT
<222> LOCATION: 6
<223> OTHER INFORMATION: Xaa = A or V
<220> FEATURE:
<221> NAME/KEY: VARIANT
<222> LOCATION: 7
<223> OTHER INFORMATION: Xaa = G or L
<220> FEATURE:
<221> NAME/KEY: VARIANT
<222> LOCATION: 8
<223> OTHER INFORMATION: Xaa = W or Y
<220> FEATURE:
<221> NAME/KEY: VARIANT
<222> LOCATION: 15
<223> OTHER INFORMATION: Xaa = V or S
<220> FEATURE:
<221> NAME/KEY: VARIANT
<222> LOCATION: 16
<223> OTHER INFORMATION: Xaa = R, V, or A
<220> FEATURE:
<221> NAME/KEY: VARIANT
<222> LOCATION: 17
<223> OTHER INFORMATION: Xaa = S or L
<220> FEATURE:
<221> NAME/KEY: VARIANT
<222> LOCATION: 18
<223> OTHER INFORMATION: Xaa = W or Y

<400> SEQUENCE: 54

Xaa Lys Trp Arg Ser Xaa Xaa Xaa Arg Trp Arg Leu Trp Arg Xaa Xaa
1               5                   10                  15

Xaa Xaa Ser Arg
        20

<210> SEQ ID NO 55
<211> LENGTH: 19
<212> TYPE: PRT
<213> ORGANISM: Artificial Sequence
<220> FEATURE:
<223> OTHER INFORMATION: Synthetic Construct

<400> SEQUENCE: 55

Lys Trp Arg Ser Ala Gly Trp Arg Trp Arg Leu Trp Arg Val Arg Ser
1               5                   10                  15
```

Trp Ser Arg

<210> SEQ ID NO 56
<211> LENGTH: 19
<212> TYPE: PRT
<213> ORGANISM: Artificial Sequence
<220> FEATURE:
<223> OTHER INFORMATION: Synthetic Construct

<400> SEQUENCE: 56

Lys Trp Arg Ser Ala Leu Tyr Arg Trp Arg Leu Trp Arg Val Arg Ser
1               5                   10                  15

Trp Ser Arg

<210> SEQ ID NO 57
<211> LENGTH: 19
<212> TYPE: PRT
<213> ORGANISM: Artificial Sequence
<220> FEATURE:
<223> OTHER INFORMATION: Synthetic Construct

<400> SEQUENCE: 57

Lys Trp Arg Ser Ala Leu Tyr Arg Trp Arg Leu Trp Arg Ser Arg Ser
1               5                   10                  15

Trp Ser Arg

<210> SEQ ID NO 58
<211> LENGTH: 19
<212> TYPE: PRT
<213> ORGANISM: Artificial Sequence
<220> FEATURE:
<223> OTHER INFORMATION: Synthetic Construct

<400> SEQUENCE: 58

Lys Trp Arg Ser Ala Leu Tyr Arg Trp Arg Leu Trp Arg Ser Ala Leu
1               5                   10                  15

Tyr Ser Arg

<210> SEQ ID NO 59
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by a hydrocarbon linkage

<400> SEQUENCE: 59

Lys Trp Arg Ser Ala Gly Trp Arg Trp Arg Leu Trp Arg Val Arg Ser
1               5                   10                  15

Trp Ser Arg

<210> SEQ ID NO 60
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by a hydrocarbon linkage

<400> SEQUENCE: 60

Lys Trp Arg Ser Ala Gly Trp Arg Trp Arg Leu Trp Arg Val Arg Ser
1               5                   10                  15

Trp Ser Arg

<210> SEQ ID NO 61
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8, 15
<223> OTHER INFORMATION: Linked by a hydrocarbon linkage

<400> SEQUENCE: 61

Lys Trp Arg Ser Ala Gly Trp Arg Trp Arg Leu Trp Arg Val Arg Ser
1               5                   10                  15

Trp Ser Arg

<210> SEQ ID NO 62
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by a hydrocarbon linkage

<400> SEQUENCE: 62

Lys Trp Arg Ser Ala Leu Tyr Arg Trp Arg Leu Trp Arg Ser Arg Ser
1               5                   10                  15

Trp Ser Arg

<210> SEQ ID NO 63
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by a hydrocarbon linkage

<400> SEQUENCE: 63

Lys Trp Arg Ser Ala Leu Tyr Arg Trp Arg Leu Trp Arg Ser Arg Ser
1               5                   10                  15

Trp Ser Arg

<210> SEQ ID NO 64
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8, 15
<223> OTHER INFORMATION: Linked by a hydrocarbon linkage

<400> SEQUENCE: 64

Lys Trp Arg Ser Ala Leu Tyr Arg Trp Arg Leu Trp Arg Ser Arg Ser
1               5                   10                  15

Trp Ser Arg

<210> SEQ ID NO 65
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10, 14
<223> OTHER INFORMATION: Linked by a hydrocarbon linkage

<400> SEQUENCE: 65

Lys Trp Arg Ser Ala Leu Tyr Arg Trp Arg Leu Trp Arg Ser Arg Ser
1               5                   10                  15

Trp Ser Arg

<210> SEQ ID NO 66
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14, 18
<223> OTHER INFORMATION: Linked by a hydrocarbon linkage

<400> SEQUENCE: 66

Lys Trp Arg Ser Ala Leu Tyr Arg Trp Arg Leu Trp Arg Ser Arg Ser
1               5                   10                  15

Trp Ser Arg

<210> SEQ ID NO 67
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 10
<223> OTHER INFORMATION: Linked by a hydrocarbon linkage

<400> SEQUENCE: 67

Lys Trp Arg Ser Ala Leu Tyr Arg Trp Arg Leu Trp Arg Ser Ala Leu
1               5                   10                  15

Tyr Ser Arg

<210> SEQ ID NO 68
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 8
<223> OTHER INFORMATION: Linked by a hydrocarbon linkage

<400> SEQUENCE: 68

Lys Trp Arg Ser Ala Leu Tyr Arg Trp Arg Leu Trp Arg Ser Ala Leu
1               5                   10                  15

Tyr Ser Arg

```
<210> SEQ ID NO 69
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10, 14
<223> OTHER INFORMATION: Linked by a hydrocarbon linkage

<400> SEQUENCE: 69

Lys Trp Arg Ser Ala Leu Tyr Arg Trp Arg Leu Trp Arg Ser Ala Leu
1               5                   10                  15

Tyr Ser Arg

<210> SEQ ID NO 70
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14, 18
<223> OTHER INFORMATION: Linked by a hydrocarbon linkage

<400> SEQUENCE: 70

Lys Trp Arg Ser Ala Leu Tyr Arg Trp Arg Leu Trp Arg Ser Ala Leu
1               5                   10                  15

Tyr Ser Arg

<210> SEQ ID NO 71
<211> LENGTH: 21
<212> TYPE: PRT
<213> ORGANISM: Artificial Sequence
<220> FEATURE:
<223> OTHER INFORMATION: Synthetic Construct

<400> SEQUENCE: 71

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 72
<211> LENGTH: 21
<212> TYPE: PRT
<213> ORGANISM: Artificial Sequence
<220> FEATURE:
<223> OTHER INFORMATION: Synthetic Construct

<400> SEQUENCE: 72

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

<400> SEQUENCE: 73
```

```
Lys Trp Phe Glu Thr Trp Phe Thr Glu Trp Pro Lys Lys Arg Lys
1               5                   10                  15

<210> SEQ ID NO 74
<211> LENGTH: 27
<212> TYPE: PRT
<213> ORGANISM: Artificial Sequence
<220> FEATURE:
<223> OTHER INFORMATION: Synthetic Construct

<400> SEQUENCE: 74

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 75
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 75

Ala Lys Trp Phe Glu Arg Trp Phe Arg Glu Trp Pro Arg Lys Arg Arg
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 76

Ala Lys Trp Trp Glu Arg Trp Arg Glu Trp Pro Arg Lys Arg Arg
1               5                   10                  15

<210> SEQ ID NO 77
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 77

Ala Leu Trp Arg Ala Leu Trp Arg Leu Trp Arg Ser Leu Trp Arg Leu
1               5                   10                  15

Leu Trp Lys Ala
            20

<210> SEQ ID NO 78
<211> LENGTH: 20
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 78

Ala Leu Arg Trp Trp Leu Arg Trp Ala Ser Arg Trp Phe Ser Arg Trp
1               5                   10                  15

Ala Trp Trp Arg
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 79

Ala Lys Trp Arg Ser Ala Gly Trp Arg Trp Arg Leu Trp Arg Val Arg
1               5                   10                  15

Ser Trp Ser Arg
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A

<400> SEQUENCE: 80

Ala Lys Trp Arg Ser Ala Leu Tyr Arg Trp Arg Leu Trp Arg Val Arg
1               5                   10                  15

Ser Trp Ser Arg
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic Construct

<400> SEQUENCE: 81

Gly Leu Trp Arg Ala Leu Trp Arg Leu Leu Arg Ser Leu Trp Arg Leu
1               5                   10                  15

Leu Trp Lys Val
            20

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 82

Arg Gln Ile Lys Ile Trp Phe Gln Asn Arg Arg Met Lys Trp Lys Lys
1               5                   10                  15

Cys

<210> SEQ ID NO 83
<211> LENGTH: 31
<212> TYPE: PRT
<213> ORGANISM: Artificial Sequence
<220> FEATURE:
<223> OTHER INFORMATION: Synthetic Construct

<400> SEQUENCE: 83

Cys Arg Arg Arg Gln Arg Arg Lys Lys Arg Gly Gly Asp Ile Met Gly
1               5                   10                  15

Glu Trp Gly Asn Glu Ile Phe Gly Ala Ile Ala Gly Phe Leu Gly
            20                  25                  30

<210> SEQ ID NO 84
<211> LENGTH: 27
<212> TYPE: PRT
<213> ORGANISM: Artificial Sequence
<220> FEATURE:
<223> OTHER INFORMATION: Synthetic Construct

<400> SEQUENCE: 84

Lys Lys Ala Leu Leu Ala Leu Ala Leu His His Leu Ala His Leu Ala
1               5                   10                  15

Leu His Leu Ala Leu Ala Leu Lys Lys Ala Cys
            20                  25

<210> SEQ ID NO 85
<211> LENGTH: 20
<212> TYPE: PRT
<213> ORGANISM: Artificial Sequence
<220> FEATURE:
<223> OTHER INFORMATION: Synthetic Construct

<400> SEQUENCE: 85

Ala Lys Trp Leu Leu Arg Trp Leu Ser Arg Trp Leu Arg Trp Leu Ala
1               5                   10                  15

Arg Trp Leu Arg
            20

<210> SEQ ID NO 86
<211> LENGTH: 19
<212> TYPE: PRT
<213> ORGANISM: Artificial Sequence
<220> FEATURE:
<223> OTHER INFORMATION: Synthetic Construct

<400> SEQUENCE: 86

Arg Ser Trp Ser Arg Val Arg Trp Leu Arg Trp Arg Trp Gly Ala Ser
1               5                   10                  15

Arg Trp Lys

<210> SEQ ID NO 87
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
```

```
<222> LOCATION: 1
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 1
<223> OTHER INFORMATION: Linked to a (PEG)7 moiety

<400> SEQUENCE: 87

Ala Lys Trp Arg Ser Ala Leu Trp Arg Trp Arg Leu Trp Arg Val Arg
1               5                   10                  15

Ser Trp Ser Arg
            20

<210> SEQ ID NO 88
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 28
<223> OTHER INFORMATION: C-terminal amidation

<400> SEQUENCE: 88

Tyr Ile Gly Ser Arg Gly Gly Gly Lys Trp Arg Ser Ala Leu Trp
1               5                   10                  15

Arg Trp Arg Leu Trp Arg Val Arg Ser Trp Ser Arg
            20                  25

<210> SEQ ID NO 89
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation

<400> SEQUENCE: 89

Gly Tyr Val Ser Gly Gly Gly Lys Trp Arg Ser Ala Leu Trp Arg
1               5                   10                  15

Trp Arg Leu Trp Arg Val Arg Ser Trp Ser Arg
            20                  25

<210> SEQ ID NO 90
<211> LENGTH: 20
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 1
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 1
<223> OTHER INFORMATION: Linked to a Stearyl group

<400> SEQUENCE: 90

Ala Lys Trp Arg Ser Ala Leu Trp Arg Trp Arg Leu Trp Arg Val Arg
1               5                   10                  15

Ser Trp Ser Arg
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 1
<223> OTHER INFORMATION: Linked to a (PEG)2 moiety

<400> SEQUENCE: 91

Ala Lys Trp Arg Ser Ala Leu Trp Arg Trp Arg Leu Trp Arg Val Arg
1               5                   10                  15

Ser Trp Ser Arg
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 1
<223> OTHER INFORMATION: Linked to a (PEG)7 moiety
```

<400> SEQUENCE: 92

Ala Leu Trp Arg Ala Leu Trp Arg Leu Trp Arg Ser Leu Trp Arg Leu
1               5                   10                  15

Leu Trp Lys Ala
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 1
<223> OTHER INFORMATION: Linked to a (PEG)2 moiety

<400> SEQUENCE: 93

Ala Leu Trp Arg Ala Leu Trp Arg Leu Trp Arg Ser Leu Trp Arg Leu
1               5                   10                  15

Leu Trp Lys Ala
            20

<210> SEQ ID NO 94
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 29
<223> OTHER INFORMATION: C-terminal amidation

<400> SEQUENCE: 94

Tyr Ile Gly Ser Arg Gly Gly Gly Ala Leu Trp Arg Ala Leu Trp
1               5                   10                  15

Arg Leu Trp Arg Ser Leu Trp Arg Leu Leu Trp Lys Ala
                20                  25

<210> SEQ ID NO 95
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 28

<223> OTHER INFORMATION: C-terminal amidation

<400> SEQUENCE: 95

Gly Tyr Val Ser Gly Gly Gly Gly Ala Leu Trp Arg Ala Leu Trp Arg
1               5                   10                  15

Leu Trp Arg Ser Leu Trp Arg Leu Leu Trp Lys Ala
            20                  25

<210> SEQ ID NO 96
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a 5-amino pentanoic acid

<400> SEQUENCE: 96

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 97
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 4, 5
<223> OTHER INFORMATION: Linked by a 5-amino pentanoic acid

<400> SEQUENCE: 97

Gly Tyr Val Ser Ala Leu Trp Arg Ala Leu Trp Arg Leu Trp Arg Ser
1               5                   10                  15

Leu Trp Arg Leu Leu Trp Lys Ala
            20

<210> SEQ ID NO 98
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT

```
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a 11-amino-undecanoic acid

<400> SEQUENCE: 98

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 99
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 4, 5
<223> OTHER INFORMATION: Linked by a 11-amino-undecanoic acid

<400> SEQUENCE: 99

Gly Tyr Val Ser Ala Leu Trp Arg Ala Leu Trp Arg Leu Trp Arg Ser
1               5                   10                  15

Leu Trp Arg Leu Leu Trp Lys Ala
            20

<210> SEQ ID NO 100
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A
<220> FEATURE:
<221> NAME/KEY: VARIANT
<222> LOCATION: 21
<223> OTHER INFORMATION: C-terminal amidation
<220> FEATURE:
<221> NAME/KEY: VARIANT
<222> LOCATION: 1
<223> OTHER INFORMATION: Linked to a stearyl moiety

<400> SEQUENCE: 100

Ala Ala Leu Trp Arg Ala Leu Trp Arg Leu Trp Arg Ser Leu Trp Arg
1               5                   10                  15

Leu Leu Trp Lys Ala
            20

<210> SEQ ID NO 101
<211> LENGTH: 24
<212> TYPE: PRT
<213> ORGANISM: Artificial Sequence
<220> FEATURE:
<223> OTHER INFORMATION: Synthetic Construct
<220> FEATURE:
```

-continued

```
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 5, 6
<223> OTHER INFORMATION: Linked by a 5-amino pentanoic acid

<400> SEQUENCE: 101

Tyr Ile Gly Ser Arg Lys Trp Arg Ser Ala Leu Trp Arg Trp Arg Leu
1               5                   10                  15

Trp Arg Val Arg Ser Trp Ser Arg
            20

<210> SEQ ID NO 102
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 23
<223> OTHER INFORMATION: C-terminal amidation
<220> FEATURE:
<221> NAME/KEY: VARIANT
<222> LOCATION: 4, 5
<223> OTHER INFORMATION: Linked by a 5-amino pentanoic acid

<400> SEQUENCE: 102

Gly Tyr Val Ser Lys Trp Arg Ser Ala Leu Trp Arg Trp Arg Leu Trp
1               5                   10                  15

Arg Val Arg Ser Trp Ser Arg
            20

<210> SEQ ID NO 103
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 5, 6
<223> OTHER INFORMATION: Linked by a 11-amino-undecanoic acid

<400> SEQUENCE: 103

Tyr Ile Gly Ser Arg Lys Trp Arg Ser Ala Leu Trp Arg Trp Arg Leu
1               5                   10                  15

Trp Arg Val Arg Ser Trp Ser Arg
            20

<210> SEQ ID NO 104
<211> LENGTH: 23
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 23
<223> OTHER INFORMATION: C-terminal amidation
<220> FEATURE:
<221> NAME/KEY: VARIANT
<222> LOCATION: 4, 5
<223> OTHER INFORMATION: Linked by a 11-amino-undecanoic acid

<400> SEQUENCE: 104

Gly Tyr Val Ser Lys Trp Arg Ser Ala Leu Trp Arg Trp Arg Leu Trp
1               5                   10                  15

Arg Val Arg Ser Trp Ser Arg
            20

<210> SEQ ID NO 105
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation

<400> SEQUENCE: 105

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 106
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation

<400> SEQUENCE: 106

Tyr Ile Gly Ser Arg Ala Lys Trp Arg Ser Ala Leu Trp Arg Trp Arg
1               5                   10                  15

Leu Trp Arg Val Arg Ser Trp Ser Arg
```

```
                    20                  25

<210> SEQ ID NO 107
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)2 moiety

<400> SEQUENCE: 107

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 108
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)4 moiety

<400> SEQUENCE: 108

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 109
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
```

```
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)7 moiety

<400> SEQUENCE: 109

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 110
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)2 moiety

<400> SEQUENCE: 110

Tyr Ile Gly Ser Arg Ala Lys Trp Arg Ser Ala Leu Trp Arg Trp Arg
1               5                   10                  15

Leu Trp Arg Val Arg Ser Trp Ser Arg
            20                  25

<210> SEQ ID NO 111
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)4 moiety

<400> SEQUENCE: 111

Tyr Ile Gly Ser Arg Ala Lys Trp Arg Ser Ala Leu Trp Arg Trp Arg
1               5                   10                  15
```

Leu Trp Arg Val Arg Ser Trp Ser Arg
            20                  25

<210> SEQ ID NO 112
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a (PEG)7 moiety

<400> SEQUENCE: 112

Tyr Ile Gly Ser Arg Ala Lys Trp Arg Ser Ala Leu Trp Arg Trp Arg
1               5                   10                  15

Leu Trp Arg Val Arg Ser Trp Ser Arg
            20                  25

<210> SEQ ID NO 113
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7, 8
<223> OTHER INFORMATION: Linked by a 5-amino pentanoic acid

<400> SEQUENCE: 113

Ala Ser Ser Leu Asn Ile Ala Lys Trp Trp Glu Arg Trp Trp Arg Glu
1               5                   10                  15

Trp Pro Arg Lys Arg Arg
            20

<210> SEQ ID NO 114
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7, 8
<223> OTHER INFORMATION: Linked by a 5-amino pentanoic acid

<400> SEQUENCE: 114

Leu Ser Ser Arg Leu Asp Ala Lys Trp Trp Glu Arg Trp Trp Arg Glu
1               5                   10                  15

Trp Pro Arg Lys Arg Arg
            20

<210> SEQ ID NO 115
<211> LENGTH: 22

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 7, 8
<223> OTHER INFORMATION: Linked by a 5-amino pentanoic acid

<400> SEQUENCE: 115

Ser Tyr Thr Ser Ser Thr Met Lys Trp Trp Glu Arg Trp Trp Arg Glu
1               5                   10                  15

Trp Pro Arg Lys Arg Arg
            20

<210> SEQ ID NO 116
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7
<223> OTHER INFORMATION: Linked by a 5-amino pentanoic acid

<400> SEQUENCE: 116

Lys Ser Tyr Asp Thr Tyr Ala Leu Arg Trp Leu Arg Trp Ala Ser Arg
1               5                   10                  15

Trp Phe Ser Arg Trp Ala Trp Arg
            20

<210> SEQ ID NO 117
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation

<400> SEQUENCE: 117

Cys Lys Arg Ala Val Arg Trp Trp Leu Arg Trp Ala Ser Arg Trp Phe
1               5                   10                  15

Ser Arg Trp Ala Trp Trp Arg
            20

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-R

<400> SEQUENCE: 118

Arg Trp Trp Leu Arg Trp Ala Ser Arg Trp Phe Ser Arg Trp Ala Trp
1               5                   10                  15

Arg
```

<210> SEQ ID NO 119
<211> LENGTH: 25
<212> TYPE: PRT
<213> ORGANISM: Artificial Sequence
<220> FEATURE:
<223> OTHER INFORMATION: Synthetic Construct

<400> SEQUENCE: 119

Lys Ser Tyr Asp Thr Tyr Ala Ala Glu Thr Arg Arg Trp Ala Ser Arg
1               5                   10                  15

Trp Phe Ser Arg Trp Ala Trp Trp Arg
            20                  25

<210> SEQ ID NO 120
<211> LENGTH: 15
<212> TYPE: PRT
<213> ORGANISM: Artificial Sequence
<220> FEATURE:
<223> OTHER INFORMATION: Synthetic Construct

<400> SEQUENCE: 120

Lys Trp Trp Glu Arg Trp Trp Arg Glu Trp Pro Arg Lys Arg Arg
1               5                   10                  15

<210> SEQ ID NO 121
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation

<400> SEQUENCE: 121

Cys Ala Arg Pro Ala Arg Trp Arg Ser Ala Gly Trp Arg Trp Arg Leu
1               5                   10                  15

Trp Arg Val Arg Ser Trp Ser Arg
            20

<210> SEQ ID NO 122
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 27
<223> OTHER INFORMATION: C-terminal amidation

<400> SEQUENCE: 122

Thr Gly Asn Tyr Lys Ala Leu His Pro Asp His Asn Gly Trp Arg Ser
1               5                   10                  15

Ala Leu Arg Trp Arg Leu Trp Arg Trp Ser Arg
            20                  25

<210> SEQ ID NO 123
<211> LENGTH: 27
<212> TYPE: PRT
<213> ORGANISM: Artificial Sequence

```
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation
<220> FEATURE:
<221> NAME/KEY: VARIANT
<222> LOCATION: 13, 14
<223> OTHER INFORMATION: Linked by a 5-amino pentanoic acid

<400> SEQUENCE: 123

Thr Gly Asn Tyr Lys Ala Leu His Pro Asp His Asn Gly Trp Arg Ser
1               5                   10                  15

Ala Leu Arg Trp Arg Leu Trp Arg Trp Ser Arg
            20                  25

<210> SEQ ID NO 124
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 19
<223> OTHER INFORMATION: C-terminal amidation
<220> FEATURE:
<221> NAME/KEY: VARIANT
<222> LOCATION: 5, 6
<223> OTHER INFORMATION: Linked by a GalNAc moiety

<400> SEQUENCE: 124

Lys Trp Arg Ser Ala Leu Trp Arg Trp Arg Leu Trp Arg Val Arg Ser
1               5                   10                  15

Trp Ser Arg

<210> SEQ ID NO 125
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 5, 6
<223> OTHER INFORMATION: Linked by a aminocaproic acid

<400> SEQUENCE: 125

Tyr Ile Gly Ser Arg Lys Trp Arg Ser Ala Leu Trp Arg Trp Arg Leu
1               5                   10                  15

Trp Arg Val Arg Ser Trp Ser Arg
            20
```

```
<210> SEQ ID NO 126
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 5, 6
<223> OTHER INFORMATION: Linked by a aminocaproic acid

<400> SEQUENCE: 126

Tyr Ile Gly Ser Arg Lys Trp Arg Ser Ala Leu Trp Arg Trp Arg Leu
1               5                   10                  15

Trp Arg Val Arg Ser Trp Ser Arg
            20

<210> SEQ ID NO 127
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 23
<223> OTHER INFORMATION: C-terminal amidation
<220> FEATURE:
<221> NAME/KEY: VARIANT
<222> LOCATION: 4, 5
<223> OTHER INFORMATION: Linked by a aminocaproic acid

<400> SEQUENCE: 127

Gly Tyr Val Ser Lys Trp Arg Ser Ala Leu Trp Arg Trp Arg Leu Trp
1               5                   10                  15

Arg Val Arg Ser Trp Ser Arg
            20

<210> SEQ ID NO 128
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 26
<223> OTHER INFORMATION: C-terminal amidation
<220> FEATURE:
<221> NAME/KEY: VARIANT
<222> LOCATION: 7, 8
<223> OTHER INFORMATION: Linked by a 5-amino pentanoic acid

<400> SEQUENCE: 128

Ser Tyr Thr Ser Ser Thr Met Lys Trp Arg Ser Ala Leu Trp Arg Trp
1               5                   10                  15
```

```
Arg Leu Trp Arg Val Arg Ser Trp Ser Arg
            20                  25

<210> SEQ ID NO 129
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 20
<223> OTHER INFORMATION: C-terminal amidation
<220> FEATURE:
<221> NAME/KEY: VARIANT
<222> LOCATION: 5, 6
<223> OTHER INFORMATION: Linked by a GalNAc moiety

<400> SEQUENCE: 129

Ala Leu Trp Arg Ala Leu Trp Arg Leu Trp Arg Ser Leu Trp Arg Leu
1               5                   10                  15

Leu Trp Lys Ala
            20

<210> SEQ ID NO 130
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a aminocaproic acid

<400> SEQUENCE: 130

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 131
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation
<220> FEATURE:
<221> NAME/KEY: VARIANT
<222> LOCATION: 7, 8
<223> OTHER INFORMATION: Linked by a 5-amino pentanoic acid
```

<400> SEQUENCE: 131

Ser Tyr Thr Ser Ser Thr Met Ala Leu Trp Arg Ala Leu Trp Arg Leu
1               5                   10                  15

Trp Arg Ser Leu Trp Arg Leu Leu Trp Lys Ala
            20                  25

<210> SEQ ID NO 132
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: beta-A
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 26
<223> OTHER INFORMATION: C-terminal amidation
<220> FEATURE:
<221> NAME/KEY: VARIANT
<222> LOCATION: 7, 8
<223> OTHER INFORMATION: Linked by a 5-amino pentanoic acid

<400> SEQUENCE: 132

Ser Tyr Thr Ser Ser Thr Met Ala Leu Trp Arg Ala Leu Trp Arg Leu
1               5                   10                  15

Trp Arg Ser Leu Trp Arg Leu Leu Trp Lys
            20                  25

<210> SEQ ID NO 133
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 29
<223> OTHER INFORMATION: C-terminal amidation

<400> SEQUENCE: 133

Thr His Arg Pro Pro Asn Trp Ser Pro Val Trp Pro Arg Ala Leu Trp
1               5                   10                  15

Arg Leu Trp Arg Ser Leu Trp Arg Leu Arg Trp Lys Ala
            20                  25

<210> SEQ ID NO 134
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25

<223> OTHER INFORMATION: C-terminal amidation

<400> SEQUENCE: 134

Cys Lys Thr Arg Arg Val Pro Trp Arg Ala Leu Trp Arg Leu Trp Arg
1               5                   10                  15

Ser Leu Trp Arg Leu Leu Trp Lys Ala
            20                  25

<210> SEQ ID NO 135
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a aminocaproic acid

<400> SEQUENCE: 135

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 136
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 4, 5
<223> OTHER INFORMATION: Linked by a aminocaproic acid

<400> SEQUENCE: 136

Gly Tyr Val Ser Ala Leu Trp Arg Ala Leu Trp Arg Leu Trp Arg Ser
1               5                   10                  15

Leu Trp Arg Leu Leu Trp Lys Ala
            20

<210> SEQ ID NO 137
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT

```
<222> LOCATION: 25
<223> OTHER INFORMATION: C-terminal amidation
<220> FEATURE:
<221> NAME/KEY: VARIANT
<222> LOCATION: 7, 8
<223> OTHER INFORMATION: Linked by a 5-amino pentanoic acid

<400> SEQUENCE: 137

Cys Lys Thr Arg Arg Val Pro Trp Arg Ala Leu Trp Arg Leu Trp Arg
1               5                   10                  15

Ser Leu Trp Arg Leu Leu Trp Lys Ala
            20                  25

<210> SEQ ID NO 138
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation
<220> FEATURE:
<221> NAME/KEY: VARIANT
<222> LOCATION: 10, 11
<223> OTHER INFORMATION: Linked by a 5-amino pentanoic acid

<400> SEQUENCE: 138

Thr His Arg Pro Pro Asn Trp Ser Pro Val Trp Arg Ala Leu Trp Arg
1               5                   10                  15

Leu Trp Arg Ser Leu Trp Arg Leu Arg Trp Lys
            20                  25

<210> SEQ ID NO 139
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 23
<223> OTHER INFORMATION: C-terminal amidation
<220> FEATURE:
<221> NAME/KEY: VARIANT
<222> LOCATION: 6, 7
<223> OTHER INFORMATION: Linked by a 5-amino pentanoic acid

<400> SEQUENCE: 139

Cys Ala Arg Pro Ala Arg Trp Arg Ala Leu Trp Arg Leu Trp Arg Ser
1               5                   10                  15

Leu Trp Arg Leu Leu Trp Lys
            20

<210> SEQ ID NO 140
<211> LENGTH: 11
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 1
<223> OTHER INFORMATION: Xaa = beta-A or S
<220> FEATURE:
<221> NAME/KEY: VARIANT
<222> LOCATION: 3, 9, 10
<223> OTHER INFORMATION: Xaa = W or F
<220> FEATURE:
<221> NAME/KEY: VARIANT
<222> LOCATION: 6
<223> OTHER INFORMATION: Xaa = R when position 8 is S, or S when
      position 8 is R
<220> FEATURE:
<221> NAME/KEY: VARIANT
<222> LOCATION: 7
<223> OTHER INFORMATION: Xaa = none, or L when position 11 is none
<220> FEATURE:
<221> NAME/KEY: VARIANT
<222> LOCATION: 8
<223> OTHER INFORMATION: Xaa = S when position 6 is R, or R when
      position 6 is S
<220> FEATURE:
<221> NAME/KEY: VARIANT
<222> LOCATION: 11
<223> OTHER INFORMATION: Xaa = R or none

<400> SEQUENCE: 140

Xaa Trp Xaa Arg Leu Xaa Xaa Xaa Xaa Xaa Xaa
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 141

Xaa Trp Trp Arg Leu Ser Leu Arg Trp Trp
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 142

Xaa Trp Phe Arg Leu Ser Leu Arg Phe Trp Arg
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 143
```

```
Xaa Trp Trp Arg Leu Arg Ser Trp Phe Arg
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 144

Xaa Trp Phe Arg Leu Ser Leu Arg Phe Trp
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = R or S
<220> FEATURE:
<221> NAME/KEY: VARIANT
<222> LOCATION: 4, 8
<223> OTHER INFORMATION: Xaa = W or F

<400> SEQUENCE: 145

Arg Xaa Trp Xaa Arg Leu Trp Xaa Arg Leu Arg
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 146

Xaa Trp Trp Arg Leu Trp Trp Arg Leu Arg
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 147

Xaa Trp Phe Arg Leu Trp Phe Arg Leu Arg
1               5                   10

<210> SEQ ID NO 148
<211> LENGTH: 10
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 148

Xaa Trp Phe Arg Leu Trp Trp Arg Leu Arg
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 149

Xaa Trp Trp Arg Leu Trp Phe Arg Leu Arg
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 150

Xaa Arg Trp Trp Arg Leu Trp Trp Arg Leu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta-A or S

<400> SEQUENCE: 151

Xaa Arg Ser Trp Phe Arg Leu Trp Phe Arg
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 152

Ser Tyr Thr Ser Ser Thr Met
1               5

<210> SEQ ID NO 153
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 153

Cys Lys Thr Arg Arg Val Pro
1               5

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct

<400> SEQUENCE: 154

Thr His Arg Pro Pro Asn Trp Ser Pro Val
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Synthetic Construct

<400> SEQUENCE: 155

Thr Gly Asn Tyr Lys Ala Leu His Pro Asp His Asn Gly
1               5                   10

<210> SEQ ID NO 156
<211> LENGTH: 6
<212> TYPE: PRT
<213> ORGANISM: Artificial Sequence
<220> FEATURE:
<223> OTHER INFORMATION: Synthetic Construct

<400> SEQUENCE: 156

Cys Ala Arg Pro Ala Arg
1               5

<210> SEQ ID NO 157
<211> LENGTH: 5
<212> TYPE: PRT
<213> ORGANISM: Artificial Sequence
<220> FEATURE:
<223> OTHER INFORMATION: Synthetic Construct

<400> SEQUENCE: 157

Tyr Ile Gly Ser Arg
1               5

<210> SEQ ID NO 158
<211> LENGTH: 4
<212> TYPE: PRT
<213> ORGANISM: Artificial Sequence
<220> FEATURE:
<223> OTHER INFORMATION: Synthetic Construct

<400> SEQUENCE: 158

Gly Tyr Val Ser
1

<210> SEQ ID NO 159
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 159

Ala Ser Ser Leu Asn Ile Ala
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 160

Leu Ser Ser Arg Leu Asp Ala
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic Construct

<400> SEQUENCE: 161

Lys Ser Tyr Asp Thr Tyr
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic Construct

<400> SEQUENCE: 162

Cys Lys Arg Ala Val
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic Construct

<400> SEQUENCE: 163

Pro Lys Lys Lys Arg Lys Val
1               5

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Lys Arg Pro Ala Ala Thr Lys Lys Ala Gly Gln Ala Lys Lys Lys Lys
1               5                   10                  15

<210> SEQ ID NO 165
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 165

Pro Ala Ala Lys Arg Val Lys Leu Asp
1               5

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Arg Gln Arg Arg Asn Glu Leu Lys Arg Ser Pro
1               5                   10

<210> SEQ ID NO 167
<211> LENGTH: 38
<212> TYPE: PRT
<213> ORGANISM: Artificial Sequence
<220> FEATURE:
<223> OTHER INFORMATION: Synthetic Construct

<400> SEQUENCE: 167

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 168
<211> LENGTH: 42
<212> TYPE: PRT
<213> ORGANISM: Artificial Sequence
<220> FEATURE:
<223> OTHER INFORMATION: Synthetic Construct

<400> SEQUENCE: 168

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct

<400> SEQUENCE: 169

Val Ser Arg Lys Arg Pro Arg Pro
1               5

<210> SEQ ID NO 170
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 170

Pro Pro Lys Lys Ala Arg Glu Asp
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic Construct

<400> SEQUENCE: 171

Pro Gln Pro Lys Lys Lys Pro Leu
1               5

<210> SEQ ID NO 172
<211> LENGTH: 12
<212> TYPE: PRT
<213> ORGANISM: Artificial Sequence
<220> FEATURE:
<223> OTHER INFORMATION: Synthetic Construct

<400> SEQUENCE: 172

Ser Ala Leu Ile Lys Lys Lys Lys Lys Met Ala Pro
1               5                   10

<210> SEQ ID NO 173
<211> LENGTH: 5
<212> TYPE: PRT
<213> ORGANISM: Artificial Sequence
<220> FEATURE:
<223> OTHER INFORMATION: Synthetic Construct

<400> SEQUENCE: 173

Asp Arg Leu Arg Arg
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic Construct

<400> SEQUENCE: 174

Pro Lys Gln Lys Lys Arg Lys
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Arg Lys Leu Lys Lys Lys Ile Lys Lys Leu
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic Construct

<400> SEQUENCE: 176

Arg Glu Lys Lys Lys Phe Leu Lys Arg Arg
1               5                   10

<210> SEQ ID NO 177
<211> LENGTH: 20
<212> TYPE: PRT
<213> ORGANISM: Artificial Sequence
<220> FEATURE:
<223> OTHER INFORMATION: Synthetic Construct

<400> SEQUENCE: 177

Lys Arg Lys Gly Asp Glu Val Asp Gly Val Asp Glu Val Ala Lys Lys
1               5                   10                  15

Lys Ser Lys Lys
            20

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Arg Lys Cys Leu Gln Ala Gly Met Asn Leu Glu Ala Arg Lys Thr Lys
1               5                   10                  15

Lys

<210> SEQ ID NO 179
<211> LENGTH: 21
<212> TYPE: RNA
<213> ORGANISM: Artificial Sequence
<220> FEATURE:
<223> OTHER INFORMATION: Synthetic Construct

<400> SEQUENCE: 179
guuggagcuu guggcguagt t                                          21

<210> SEQ ID NO 180
<211> LENGTH: 21
<212> TYPE: RNA
<213> ORGANISM: Artificial Sequence
<220> FEATURE:
<223> OTHER INFORMATION: Synthetic Construct

<400> SEQUENCE: 180
cuacgccacc agcuccaact t                                          21

<210> SEQ ID NO 181
<211> LENGTH: 22
<212> TYPE: RNA
<213> ORGANISM: Artificial Sequence
<220> FEATURE:
<223> OTHER INFORMATION: Synthetic Construct

<400> SEQUENCE: 181
gatgaggcta ttcatgatga tt                                         22

<210> SEQ ID NO 182
<211> LENGTH: 21
<212> TYPE: RNA
<213> ORGANISM: Artificial Sequence
<220> FEATURE:

<223> OTHER INFORMATION: Synthetic Construct

<400> SEQUENCE: 182
gaagugcaua caccgagact t                                    21

<210> SEQ ID NO 183
<211> LENGTH: 20
<212> TYPE: RNA
<213> ORGANISM: Artificial Sequence
<220> FEATURE:
<223> OTHER INFORMATION: Synthetic Construct

<400> SEQUENCE: 183
gucucggugu agcacuuctt                                      20

<210> SEQ ID NO 184
<211> LENGTH: 21
<212> TYPE: RNA
<213> ORGANISM: Artificial Sequence
<220> FEATURE:
<223> OTHER INFORMATION: Synthetic Construct

<400> SEQUENCE: 184
guuggagcug uuggcguagt t                                    21

<210> SEQ ID NO 185
<211> LENGTH: 21
<212> TYPE: RNA
<213> ORGANISM: Artificial Sequence
<220> FEATURE:
<223> OTHER INFORMATION: Synthetic Construct

<400> SEQUENCE: 185
cuacgccaac agcuccaact t                                    21

<210> SEQ ID NO 186
<211> LENGTH: 4
<212> TYPE: PRT
<213> ORGANISM: Artificial Sequence
<220> FEATURE:
<223> OTHER INFORMATION: Synthetic Construct

<400> SEQUENCE: 186

Tyr Val Ser Lys
1

<210> SEQ ID NO 187
<211> LENGTH: 4
<212> TYPE: PRT
<213> ORGANISM: Artificial Sequence
<220> FEATURE:
<223> OTHER INFORMATION: Synthetic Construct

<400> SEQUENCE: 187

Tyr Ile Gly Ser
1

<210> SEQ ID NO 188
<211> LENGTH: 4
<212> TYPE: PRT
<213> ORGANISM: Artificial Sequence
<220> FEATURE:
<223> OTHER INFORMATION: Synthetic Construct

<400> SEQUENCE: 188

Ile Gly Ser Arg

```
1

<210> SEQ ID NO 189
<211> LENGTH: 5
<212> TYPE: PRT
<213> ORGANISM: Artificial Sequence
<220> FEATURE:
<223> OTHER INFORMATION: Synthetic Construct

<400> SEQUENCE: 189

Gly Tyr Val Ser Lys
1               5

<210> SEQ ID NO 190
<211> LENGTH: 5
<212> TYPE: PRT
<213> ORGANISM: Artificial Sequence
<220> FEATURE:
<223> OTHER INFORMATION: Synthetic Construct

<400> SEQUENCE: 190

Gly Gly Gly Gly Ser
1               5

<210> SEQ ID NO 191
<211> LENGTH: 5
<212> TYPE: PRT
<213> ORGANISM: Artificial Sequence
<220> FEATURE:
<223> OTHER INFORMATION: Synthetic Construct

<400> SEQUENCE: 191

Ser Gly Gly Gly Gly
1               5

<210> SEQ ID NO 192
<211> LENGTH: 21
<212> TYPE: RNA
<213> ORGANISM: Artificial Sequence
<220> FEATURE:
<223> OTHER INFORMATION: Synthetic Construct

<400> SEQUENCE: 192
cuuacgcuga guacuucgat t                                              21

<210> SEQ ID NO 193
<211> LENGTH: 21
<212> TYPE: RNA
<213> ORGANISM: Artificial Sequence
<220> FEATURE:
<223> OTHER INFORMATION: Synthetic Construct

<400> SEQUENCE: 193
ucgaaguacu cagcguaagt t                                              21

<210> SEQ ID NO 194
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: beta-A
<220> FEATURE:
<221> NAME/KEY: VARIANT
<222> LOCATION: 1
```

```
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 194

Ala Leu Trp Arg Ala Leu Trp Arg Leu Trp Arg Ser Leu Trp Arg Leu
1               5                   10                  15

Leu Trp Lys Ala
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Linked to a stearyl moiety
<220> FEATURE:
<221> NAME/KEY: VARIANT
<222> LOCATION: 20
<223> OTHER INFORMATION: C-terminal amidation

<400> SEQUENCE: 195

Ala Lys Trp Arg Ser Ala Leu Trp Arg Trp Arg Leu Trp Arg Val Arg
1               5                   10                  15

Ser Trp Ser Arg
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Linked to a (PEG)2 moiety
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 20
<223> OTHER INFORMATION: C-terminal amidation

<400> SEQUENCE: 196

Ala Lys Trp Arg Ser Ala Leu Trp Arg Trp Arg Leu Trp Arg Val Arg
1               5                   10                  15

Ser Trp Ser Arg
            20

<210> SEQ ID NO 197
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
```

```
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a 5-amino pentanoic acid further
      comprising (CH2)2

<400> SEQUENCE: 197

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 198
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 4, 5
<223> OTHER INFORMATION: Linked by a 5-amino pentanoic acid further
      comprising (CH2)2

<400> SEQUENCE: 198

Gly Tyr Val Ser Ala Leu Trp Arg Ala Leu Trp Arg Leu Trp Arg Ser
1               5                   10                  15

Leu Trp Arg Leu Leu Trp Lys Ala
            20

<210> SEQ ID NO 199
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation
<220> FEATURE:
<221> NAME/KEY: VARIANT
<222> LOCATION: 5, 6
<223> OTHER INFORMATION: Linked by a 11-amino-undecanoic acid further
      comprising (CH2)6

<400> SEQUENCE: 199

Tyr Ile Gly Ser Arg Ala Leu Trp Arg Ala Leu Trp Arg Leu Trp Arg
1               5                   10                  15

Ser Leu Trp Arg Leu Leu Trp Lys Ala
            20                  25

<210> SEQ ID NO 200
<211> LENGTH: 24
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 4, 5
<223> OTHER INFORMATION: Linked by a 11-amino-undecanoic acid further
      comprising (CH2)6

<400> SEQUENCE: 200

Gly Tyr Val Ser Ala Leu Trp Arg Ala Leu Trp Arg Leu Trp Arg Ser
1               5                   10                  15

Leu Trp Arg Leu Leu Trp Lys Ala
            20

<210> SEQ ID NO 201
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation

<400> SEQUENCE: 201

Tyr Ile Gly Ser Arg Ala Lys Trp Arg Ser Ala Leu Trp Arg Trp Arg
1               5                   10                  15

Leu Trp Arg Val Arg Ser Trp Ser Arg
            20                  25

<210> SEQ ID NO 202
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 22
<223> OTHER INFORMATION: C-terminal amidation
<220> FEATURE:
<221> NAME/KEY: VARIANT
<222> LOCATION: 7, 8
<223> OTHER INFORMATION: Linked by a 5-amino pentanoic acid

<400> SEQUENCE: 202

Ala Ser Ser Leu Asn Ile Ala Lys Trp Trp Glu Arg Trp Trp Arg Glu
1               5                   10                  15

Trp Pro Arg Lys Arg Arg
            20

<210> SEQ ID NO 203
<211> LENGTH: 22
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 7, 8
<223> OTHER INFORMATION: Linked by a 5-amino pentanoic acid

<400> SEQUENCE: 203

Leu Ser Ser Arg Leu Asp Ala Lys Trp Trp Glu Arg Trp Trp Arg Glu
1               5                   10                  15

Trp Pro Arg Lys Arg Arg
            20

<210> SEQ ID NO 204
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 7, 8
<223> OTHER INFORMATION: Linked by a 5-amino pentanoic acid

<400> SEQUENCE: 204

Ser Tyr Thr Ser Ser Thr Met Lys Trp Trp Glu Arg Trp Trp Arg Glu
1               5                   10                  15

Trp Pro Arg Lys Arg Arg
            20

<210> SEQ ID NO 205
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 24
<223> OTHER INFORMATION: C-terminal amidation
<220> FEATURE:
<221> NAME/KEY: VARIANT
<222> LOCATION: 6, 7
<223> OTHER INFORMATION: Linked by a 5-amino pentanoic acid

<400> SEQUENCE: 205

Lys Ser Tyr Asp Thr Tyr Ala Leu Arg Trp Leu Arg Trp Ala Ser Arg
1               5                   10                  15

Trp Phe Ser Arg Trp Ala Trp Arg
            20

<210> SEQ ID NO 206
<211> LENGTH: 23
<212> TYPE: PRT
<213> ORGANISM: Artificial Sequence
<220> FEATURE:
```

<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 23
<223> OTHER INFORMATION: C-terminal amidation

<400> SEQUENCE: 206

Cys Lys Arg Ala Val Arg Trp Trp Leu Arg Trp Ala Ser Arg Trp Phe
1               5                   10                  15
Ser Arg Trp Ala Trp Trp Arg
            20

<210> SEQ ID NO 207
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 25
<223> OTHER INFORMATION: C-terminal amidation

<400> SEQUENCE: 207

Lys Ser Tyr Asp Thr Tyr Ala Ala Glu Thr Arg Trp Ala Ser Arg
1               5                   10                  15
Trp Phe Ser Arg Trp Ala Trp Trp Arg
            20                  25

<210> SEQ ID NO 208
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation

<400> SEQUENCE: 208

Thr Gly Asn Tyr Lys Ala Leu His Pro Asp His Asn Gly Trp Arg Ser
1               5                   10                  15
Ala Leu Arg Trp Arg Leu Trp Arg Trp Ser Arg
            20                  25

<210> SEQ ID NO 209
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT

```
<222> LOCATION: 20
<223> OTHER INFORMATION: C-terminal amidation
<220> FEATURE:
<221> NAME/KEY: VARIANT
<222> LOCATION: 5, 6
<223> OTHER INFORMATION: Linked by a GalNAc moiety

<400> SEQUENCE: 209

Ala Leu Trp Arg Ala Leu Trp Arg Leu Trp Arg Ser Leu Trp Arg Leu
1               5                   10                  15

Leu Trp Lys Ala
            20

<210> SEQ ID NO 210
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: N-terminal acetylation
<220> FEATURE:
<221> NAME/KEY: VARIANT
<222> LOCATION: 27
<223> OTHER INFORMATION: C-terminal amidation

<400> SEQUENCE: 210

Tyr Ile Gly Ser Arg Gly Gly Ala Leu Trp Arg Ala Leu Trp Arg Leu
1               5                   10                  15

Trp Arg Ser Leu Trp Arg Leu Leu Trp Lys Ala
            20                  25
```

PEPTIDES AND NANOPARTICLES FOR INTRACELLULAR DELIVERY OF MOLECULES

RELATED APPLICATIONS

This application is a national stage application under 35 U.S.C. § 371 of International Application No. PCT/US2020/028572, filed internationally on Apr. 16, 2020, which claims priority benefit to French Application No. FR1904115, filed Apr. 17, 2019, the content of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737372001100SEQLIST.TXT, date recorded: Oct. 15, 2021, size: 83,435 bytes).

FIELD OF THE INVENTION

The present invention pertains to peptide-containing complexes/nanoparticles that are useful for delivering cargo molecules into a cell.

BACKGROUND

The disclosures of all publications, patents, patent applications and published patent applications referred to herein are hereby incorporated herein by reference in their entirety.

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications, (d) rapid endosomal release, and (e) ability to reach the target. Although viral delivery strategies had given much hope for gene and cellular therapies, their clinical application has suffered from side- and toxicity-effects (Ibraheem et al. (2014) *Int J Pharm* 459, 70-83). Researches were mainly focused on the development of non-viral strategies, and different methods have been proposed including lipid, polycationic nanoparticles and peptide-based formulations, but only few of these technologies have been efficient in vivo and have reached the clinic (Yin et al. (2014) *Nat Rev Genet* 15, 541-555). Thus, there is a need for improved methods for efficient delivery of mRNA or RNAi inside target cells.

BRIEF SUMMARY OF THE INVENTION

The present application provides cargo delivery complexes and nanoparticles that are useful for intracellular delivery of a cargo molecule. In some embodiments, the cargo delivery complexes for intracellular delivery of a cargo molecule comprises a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety. In some embodiments, the cargo delivery complexes for intracellular delivery of a cargo molecule comprise a cell-penetrating peptide and a cargo molecule, wherein the cell-penetrating peptide is a retro-inverso peptide. In some embodiments, the cargo delivery complexes for intracellular delivery of a cargo molecule comprise a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157). In some embodiments, the cargo molecule is selected from the group consisting of a nucleic acid, a virus, a polypeptide, a protein/nucleic complex, virus like particles, and a protein complex. In some embodiments, the cargo molecule does not comprise a virus. In some embodiments, the cell-penetrating peptide such as (first or second cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides.

In some embodiments, there is provided cargo delivery complexes for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and the second cell-penetrating peptides are selected from the group consisting of VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. In some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the cargo molecule is selected from the group consisting of a nucleic acid, a virus, a polypeptide, a protein/nucleic complex, virus like particles, and a protein complex. In some embodiments, the cargo molecule is a nucleic acid. In some embodiments, the nucleic acid is selected from the group consisting of an siRNA, an miRNA, a shRNA, a gRNA, an mRNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1. In some embodiments, the average diameter of the cargo delivery complex is between about 20 nm and about 1000 nm. In some embodiments, the ratio of the first cell-penetrating peptide to the second cell-penetrating peptide is about 50 to 1. In some embodiments, the PEG moiety is a linear PEG. In some embodiments, the PEG moiety is a branched PEG. In some embodiments, the molecular weight of the PEG moiety is about 5 kDa to about 10 kDa. In some embodiments, the PEG moiety consist of about one to ten ethylene glycol units. In some embodiments, the PEG moiety is conjugated to the N-terminus of the second cell-penetrating peptide. In some embodiments, the PEG moiety is conjugated to the C-terminus of the second cell-penetrating peptide. In some embodiments, the first and/or second peptide further comprises one or more moieties selected from the group consisting of an acetyl group, a stearyl group, a fatty acid, a cholesterol, a nuclear localization signal, a nuclear export signal, an antibody or antibody fragment thereof, a peptide, a polysaccharide, and a targeting sequence, wherein the one or more moieties are covalently linked to the N-terminus of the first or the second cell-penetrating peptide, or the PEG moiety. In some embodiments, the one or more moiety comprises a targeting sequence. In some embodiments, the targeting sequence is selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), and IGSR (SEQ ID NO: 188). In some embodiments, the targeting sequence is selected from the group consisting of GYVSK (SEQ ID NO: 189), GYVS (SEQ ID NO: 158), YIGS (SEQ ID NO: 187), and YIGSR (SEQ ID NO: 157). In some embodiments, the targeting sequence is covalently linked to the first or the second cell-penetrating peptide via a linker. In some embodiments, the one or more moiety comprises an acetyl group and/or a stearyl group. In some embodiments, the first and/or second peptide further comprises one or more moieties selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a nuclear localization signal, nuclear export signal, an antibody, a polysaccharide and a targeting sequence, wherein the one or more moieties are covalently linked to the C-terminus of the first cell-penetrating peptide, the second cell-penetrating peptide or the PEG moiety. In some embodiments, the first and/or second cell-penetrating peptide is a retro-inverso peptide.

In some embodiments, there is provided a cargo delivery complex for intracellular delivery of a cargo molecule comprising a cell-penetrating peptide and a cargo molecule, wherein the cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides, and wherein the cell-penetrating peptide is a retro-inverso peptide. In some embodiments, the retro-inverso peptide comprises a sequence of SEQ ID NO: 85 or 86. In some embodiments, the cargo molecule is selected from the group consisting of a nucleic acid, a polypeptide, and a protein complex. In some embodiments, the cargo molecule comprises a nucleic acid selected from the group consisting of an siRNA, an miRNA, a shRNA, a gRNA, an mRNA, a DNA, a DNA plasmid, an oligonucleotide and an analogue thereof. In some embodiments, the cargo molecule comprises an mRNA. In some embodiments, the cargo molecule comprises an RNAi. In some embodiments, the cargo molecule does not comprise a virus.

In some embodiments, there is provided a cargo delivery complex for intracellular delivery of a cargo molecule comprising a) a peptide comprising a cell-penetrating peptide and b) a cargo molecule, wherein the cell-penetrating peptide is selected from the group consisting of VEPEP-3 peptides, VEPEP-6 peptides, VEPEP-9 peptides, and ADGN-100 peptides, and wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157). In some embodiments, the targeting sequence is covalently linked to N-terminus of the cell-penetrating peptide via a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a polypeptide, and a protein complex. In some embodiments, the cargo molecule comprises a nucleic acid selected from the group consisting of an siRNA, an miRNA, a shRNA, a gRNA, an mRNA, a DNA, a DNA plasmid, an oligonucleotide and an analogue thereof. In some embodiments, the cargo molecule comprises an mRNA. In some embodiments, the cargo molecule comprises an RNAi. In some embodiments, the cargo molecule does not comprise a virus.

The present application also provides nanoparticles comprising a core comprising the cargo delivery complex described above. In some embodiments, the core is coated by a shell comprising a peripheral cell-penetrating peptide. In some embodiments, the peripheral cell-penetrating peptide is selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides.

The present application also provides pharmaceutical compositions comprising any one of the cargo delivery complex or nanoparticles described above and a pharmaceutically acceptable carrier.

The present application also provides methods of preparing the cargo delivery complex described above that comprise a) combining the first peptide and the second peptide, thereby forming a peptide mixture; b) combining the peptide mixture with the cargo, thereby forming the cargo delivery complex.

The present application also provides methods of preparing the cargo delivery complex described above that comprise combining the peptide with the cargo molecule, thereby forming the cargo delivery complex.

In some embodiments according to any of the methods of preparing the cargo delivery complexes described above, the peptide or the peptide mixture and the cargo molecule are combined at a molar ratio from about 1:1 to about 100:1, respectively. In some embodiments, the method comprises mixing a first solution comprising the cargo molecule with a second solution comprising the peptide or peptide mixture to form a third solution, wherein the third solution comprises or is adjusted to comprise i) about 0-5% sucrose, ii) about 0-5% glucose, iii) about 0-50% DMEM, iv) about 0-80 mM NaCl, or v) about 0-20% PBS, and wherein the third solution is incubated to allow formation of the cargo delivery complex. In some embodiments, the first solution comprises the cargo in sterile water and/or wherein the second solution comprises the peptide or peptide mixture in sterile water. In some embodiments, the third solution is adjusted to comprise i) about 0-5% sucrose, ii) about 0-5% glucose, iii) about 0-50% DMEM, iv) about 0-80 mM NaCl, or v) about 0-20% PBS after incubating to form the cargo delivery complex. In some embodiments, the method further comprises a filtration process, wherein the cargo delivery complex is filtered through a pore-sized membrane. In some embodiments, the pore has a diameter of at least about 0.1 μm.

The present application also provides methods of delivering one or more cargo into a cell, comprising contacting the cell with the cargo delivery complex or nanoparticle described above, wherein the cargo delivery complex comprises one or more cargo.

The present application also provides methods of delivering one or more cargo into a tissue or organ of an individual, comprising administering into the individual an effective amount of the cargo delivery complex, the nanoparticle, or the pharmaceutical composition described above, wherein the tissue or organ is selected from the group consisting of liver, lung, kidney, brain, intestine, spleen, heart, muscle, and lymph node. In some embodiments, the cargo delivery complex is administered intravenously. In some embodiments, the individual is a human.

The present application also provides methods of treating a disease or condition in an individual, comprising administering into the individual an effective amount of the cargo delivery complex, the nanoparticle, or the pharmaceutical composition described above. In some embodiments, the disease or condition is associated with a pathological cell in an organ or tissue selected from the group consisting of liver, lung, kidney, brain, intestine, spleen, heart, muscle, and lymph node. In some embodiments, the disease or condition is selected from the group consisting of cancer, diabetes, autoimmune diseases, hematological diseases, cardiac diseases, vascular diseases, inflammatory diseases, fibrotic diseases, viral infectious diseases, hereditary diseases, ocular diseases, liver diseases, lung diseases, muscle diseases, protein deficiency diseases, lysosomal storage diseases, neurological diseases, kidney diseases, aging and degenerative diseases, and diseases characterized by cholesterol level abnormality. In some embodiments, the cargo delivery complex is administered intravenously. In some embodiments, the individual is a human.

The present application also provides kits comprising the cargo delivery complex, the nanoparticle, or the pharmaceutical composition described above.

BRIEF DESCRIPTION OF THE FIGURES

FIGS. 1A-1C show luciferase expression in 293T cells treated with ADGN-peptide/mRNA complexes. 293T cells cultured in 48 well plates were transfected with ADGN-peptide nanoparticles. ADGN-100, ADGN-106, ADGN-100RI, ADGN-106RI, ADGN-100 Stearyl, ADGN-Hydro1, ADGN-Hydro2, ADGN-Hydro3, ADGN-Hydro4, ADGN-Hydro5, ADGN-Hydro6 and ADGN-peptide/ADGN-100PEG 10% nanoparticles containing 0.25 μg mRNA were formed in sterile water, diluted in sterile water containing 5% Sucrose and filtered with 0.45 μm PES filters. ADGN/mRNA complexes were incubated for 3 hrs in the presence of either 25% serum or heparan sulfate prior transfection. Luciferase expression was monitored 72 hours post transfection and results were reported as RLU (luminescence):mg of protein.

FIGS. 2A-2C show luciferase expression in 293T cells treated with ADGN-peptide/pGL4 plasmid DNA complexes. 293T cells cultured in 48 well plates were transfected with ADGN-peptide nanoparticles. ADGN-100, ADGN-106, ADGN-100RI, ADGN-106RI, ADGN-100 Stearyl, ADGN-Hydro1, ADGN-Hydro2, ADGN-Hydro3, ADGN-Hydro4, ADGN-Hydro5, and ADGN-Hydro6 containing 0.17 μg pGL4 plasmid DNA were formed in sterile water, diluted in sterile water containing 5% Sucrose. ADGN-peptide nanoparticles were evaluated prior (FIG. 2A) and after filtration with 0.45 μm PES filters (FIG. 2B). FIG. 2C impact of peGylated ADGN-100 on the transfection efficiency. pGL4 luc plasmid (0.15 μg) were associated to ADGN-100 solution containing 5 to 50% of ADGN-100-PEG or to ADGN-100PEG. ADGN/pGL4 plasmid DNA complexes were incubated for 3 hrs in the presence of either 25% serum or heparan sulfate prior transfection. Luciferase expression was monitored 72 hours post transfection and results were reported as RLU (luminescence):mg of protein.

FIGS. 3A-3C show luciferase expression in A375/Luc cells treated with ADGN-peptide/siRNA complexes. A375/Luc cells cultured in 48 well plates were transfected with ADGN-peptide nanoparticles. ADGN-100, ADGN-106, ADGN-100RI, ADGN-106RI, ADGN-100 Stearyl, ADGN-Hydro1, ADGN-Hydro2, ADGN-Hydro3, ADGN-Hydro4, ADGN-Hydro5, ADGN-Hydro6 and ADGN-peptide/ADGN-100PEG 10% nanoparticles containing 10 nM or 25 nM siRNA were formed in sterile water, diluted in sterile water containing 5% Sucrose and filtered with 0.45 μm PES filters. FIG. 3C impact of peGylated ADGN-100 on the transfection efficiency. siRNA Luc (10 nM and 25 nM) were associated to ADGN-100 solution containing 5 to 50% of ADGN-100-PEG or to ADGN-100PEG. ADGN/siRNA complexes were incubated for 3 hrs in the presence of 25% serum prior transfection. Luciferase expression was monitored 48 hours post transfection and results were reported as RLU (luminescence):mg of protein.

FIGS. 4A-4D show the potency of ADGN-peptide variants for in vivo delivery of Luciferase mRNA via intravenous administration in mice. ADGN-peptide/luc mRNA particles containing 5 μg mRNA were formed in sterile water, and then diluted in 5% sucrose. Mice received IV injection of 100 μl ADGN-peptide/mRNA complexes. mRNA LUC expression was monitored by bioluminescence imaging after 12 h, 24 h, 48 h and 72 h. FIG. 4B show bioluminescence imaging at 24 hr in control and treated groups. Semi-quantitative data of luciferase signal in the liver (C) and in the lung (D) were obtained using the manufacturer's software (Living Image; PerkinElmer). Results were then expressed as values relative to day 0.

FIG. 5B show bioluminescence imaging at 24 hr in control and treated groups.

FIGS. 6A-6C show the potency of ADGN-peptide variants for in vivo delivery of Luciferase expressing plasmid pGL4 via intravenous administration in mice. ADGN-peptide/pGL4 particles containing 5 µg plasmid DNA were formed in sterile water, and then diluted in 5% sucrose. Mice received IV injection of 100 µl ADGN-peptide/plasmid complexes. pGL4 Luciferase expression was monitored by bioluminescence imaging after 12 h, 24h, 48h and 72h. FIG. 6B shows bioluminescence imaging at 24 hr in control and treated groups. FIG. 6C shows semi-quantitative data of luciferase signal in the liver obtained using the manufacturer's software (Living Image; PerkinElmer). Results were then expressed as values relative to day 0.

FIG. 7B show bioluminescence imaging at 24 hr in control and treated groups.

FIG. 8 shows the particle sizes and level of aggregation of the ADGN-100 peptide variant/mRNA complexes measured on DLS NanoZS (Malvern Ltd) without filtration or with filtration.

FIG. 9 shows the particle sizes and level of aggregation of the ADGN-106 peptide variant/mRNA complexes measured on DLS NanoZS (Malvern Ltd) without filtration or with filtration.

FIG. 10 shows the particle sizes and level of aggregation of the ADGN peptide variant/DNA plasmid complexes measured on DLS NanoZS (Malvern Ltd) without filtration or with filtration.

FIGS. 11A-11C show the potency of ADGN-peptide variants for in vivo delivery of Luciferase mRNA via intravenous administration in mice.

DETAILED DESCRIPTION OF THE INVENTION

Figure 1A:
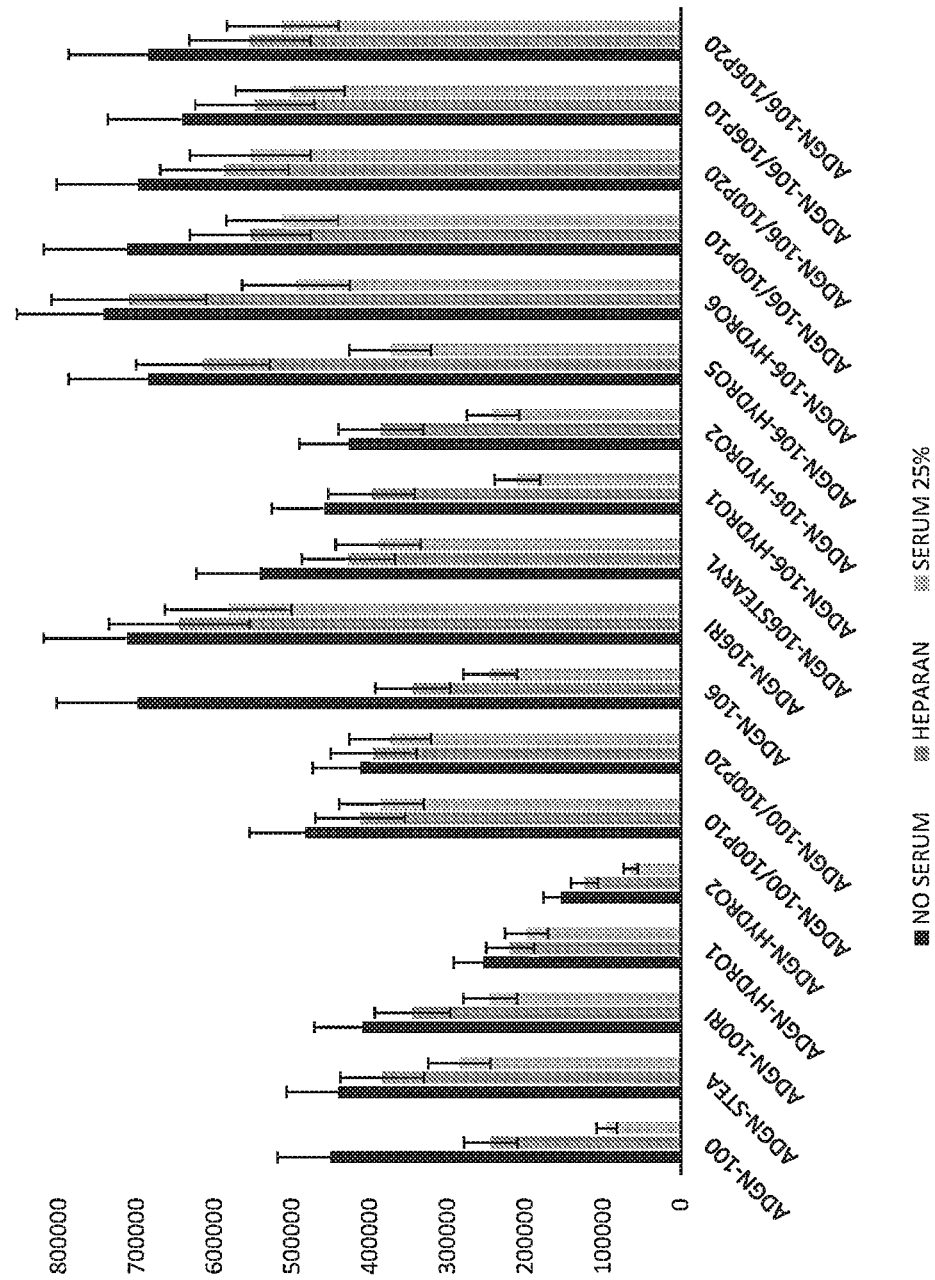

The present application provides complexes and nanoparticles comprising a cell-penetrating peptide (CPP) and one or more mRNAs, wherein the CPP is suitable for delivering into a cell the one or more mRNAs (such as mRNAs encoding a therapeutic product, e.g., a tumor suppressor). The complexes and nanoparticles may comprise a plurality of mRNAs. The mRNAs may include, for example, mRNAs encoding a therapeutic protein (e.g., tumor suppressor, immunomodulator, and the like). In some embodiments, the mRNA encodes a chimeric antigen receptor (CAR). In some embodiments, the complexes and nanoparticles preferentially localize to a target tissue, such as a disease tissue, e.g., a tumor. In some embodiments, the complexes and nanoparticles further comprise an RNAi, such as an RNAi targeting an endogenous gene. In some embodiments, the RNAi targets a disease-associated endogenous gene, e.g., an oncogene. In some embodiments, the RNAi targets an exogenous gene.

Thus, the present application in one aspect provides novel cargo delivery complexes and nanoparticles which are described further below in more detail.

In another aspect, there are provided methods of delivering an mRNA into a cell using the cell-penetrating peptides. In another aspect, there are provided methods of delivering a complex or nanoparticle comprising an mRNA and a cell-penetrating peptide into a local tissue, organ or cell. In another aspect, there are provided methods of treating a disease or disorder by administering a complex or nanoparticle described herein comprising an mRNA and a cell-penetrating peptide to a subject.

Also provided are pharmaceutical compositions comprising a cell-penetrating peptide and one or more mRNAs (for example in the forms of complexes and nanoparticles) and uses thereof for treating diseases.

Definitions

As used herein, the term "retro-inverso peptide" is a peptide made up of D-amino acids in a reversed sequence and, when extended, assumes a side chain topology similar to that of its parent molecule but with inverted amide peptide bonds.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%/, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating" refers to an approach for obtaining beneficial or desired results including but not limited to a therapeutic benefit. By therapeutic benefit is meant any therapeutically relevant improvement in or effect on one or more diseases, conditions, or symptoms under treatment.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

The compositions and methods of the present invention may comprise, consist of, or consist essentially of the essential elements and limitations of the invention described herein, as well as any additional or optional ingredients, components, or limitations described herein or otherwise useful.

Unless otherwise noted, technical terms are used according to conventional usage.

Complexes and Nanoparticles
Complexes

In some aspects, there are provided cargo delivery complexes comprising cell-penetrating peptides for delivering one or more cargo molecules into a cell.

Cargo Delivery Complexes Comprising a Peptide Mixture

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and the second cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the cargo molecule is selected from the group consisting of a nucleic acid, a virus, a polypeptide, a protein/nucleic complex, virus like particles, and a protein complex. In some embodiments, the cargo molecule is a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the cargo molecule (such as the nucleic acid) is between about 1:1 and about 100:1 (such as about between about 1:1 and about 50:1, or about 20:1). In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1). In some embodiments, the first and/or the second cell-penetrating peptide is a PTD-based peptide, an amphipathic peptide, a poly-arginine-based peptide, an MPG peptide, a CADY peptide, a PEP peptide (such as a PEP-1, PEP-2 or PEP-3 peptide), or a VEPEP peptide (such as ADGN-100, VEPEP-3, VEPEP-4, VEPEP-5, VEPEP-6, or VEPEP-9 peptide). In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the first and/or the second cell-penetrating peptides are selected from VEPEP-3 peptides, VEPEP-6 peptides, VEPEP-9 peptides, and ADGN-100 peptides. In some embodiments, the first and/or the second cell-penetrating peptide are selected from VEPEP-6 peptides, and ADGN-100 peptides. In some embodiments, the cargo molecule is selected from the group consisting of a nucleic acid, a virus, a polypeptide, a protein/nucleic complex, virus like particles, and a protein complex. In some embodiments, the cargo molecule is a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the cargo molecule (such as the nucleic acid) is between about 1:1 and about 100:1 (such as about between about 1:1 and about 50:1, or about 20:1). In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the cargo molecule is selected from the group consisting of a nucleic acid, a virus, a polypeptide, a protein/nucleic complex, virus like particles, and a protein complex. In some embodiments, the cargo molecule is/comprises a nucleic acid. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), and wherein the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), and wherein the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), and wherein the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), and wherein the first and/or the second cell-penetrating peptide is a ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), and wherein the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1 (such as about between about 1:1 and about 50:1, or about 20:1). In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises a virus. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises a polypeptide. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises a protein/nucleic complex. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises virus like particles. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, there is provided a cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, and wherein the first peptide does not have a PEG moiety, wherein the ratio of the first cell-penetrating peptide to the second cell-penetrating peptide is about 20:1 to about 1:1 (such as about 15:1 to about 2:1, about 10:1 to about 4:1), wherein the cargo molecule is or comprises a protein complex. In some embodiments, the first and/or the second cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the first and/or the second cell-penetrating peptide comprises an amino acid sequence selected from the group consisting of SEQ ID NOs: 71-74 and 81. In some embodiments, the first and the second cell-penetrating peptides are selected from the group consisting of CADY, PEP-1 peptides, PEP-2 peptides, PEP-3 peptides, VEPEP-3 peptides, VEPEP-6 peptides, VEPEP-9 peptides, and ADGN-100 peptides. In some embodiments, the first and/or the second cell-penetrating peptide is a VEPEP-3 peptide. In some embodiments, the VEPEP-3 peptide comprises an amino acid sequence selected from the group consisting of SEQ ID NOs: 1-14, 75, 76, and 113-115. In some embodiments, the first and/or the second cell-penetrating peptide is a VEPEP-6 peptide. In some embodiments, the VEPEP-6 peptide comprises an amino acid sequence selected from the group consisting of SEQ ID NOs: 15-40, 77, 85, 92-100, 105, 107-109, and 129-139. IN some embodiments, the first and/or the second cell-penetrating peptide is a VEPEP-9 peptide. In some embodiments, the VEPEP-9 peptide comprises an amino acid sequence selected from the group consisting of SEQ ID NOs: 41-52, 78, and 116-120. In some embodiments, the first and/or the second cell-penetrating peptide is an ADGN-100 peptide. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the first and the second cell-penetrating peptide are the same. In some embodiments, the first and the second cell-penetrating peptide are the different. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the PEG moiety consists of about one to ten (such as about 1-8, 2-7, 1-5, or 6-10) ethylene glycol units. In some embodiments, the molecular weight of the PEG moiety is about 0.05 kDa to about 50 kDa. In some embodiments, the molecular weight of the PEG moiety is about 0.05 kDa to about 0.5 kDa (such as about 0.05-0.1, 0.05-0.4, 0.1-0.3, 0.05-0.25, 0.25-0.5 kDa). In some embodiments, the PEG moiety is conjugated to the N- or C-terminus of the second cell-penetrating peptide. In some embodiments, the PEG moiety is conjugated to a site within the second cell-penetrating peptide.

In some embodiments, the PEG moiety is a linear PEG. In some embodiments, the PEG moiety is a branched PEG.

In some embodiments, the first and/or second peptide further comprises one or more moieties selected from the group consisting of an acetyl group, a stearyl group, a fatty acid, a cholesterol, a nuclear localization signal, a nuclear export signal, an antibody or antibody fragment thereof, a peptide, a polysaccharide, and a targeting sequence, wherein the one or more moieties are covalently linked to the N-terminus of the first or the second cell-penetrating peptide, or the PEG moiety. In some embodiments, the one or more moieties is covalently linked to the N-terminus of the first cell-penetrating peptide, the second cell-penetrating peptide or the PEG moiety via a linker. In some embodiments, the one or more moiety comprises an acetyl group and/or a stearyl group. In some embodiments, the one or more moiety comprises a targeting sequence. In some embodiments, the targeting sequence is covalently linked to the first or the second cell-penetrating peptide via a linker. In some embodiments, the targeting sequence is covalently linked to the first or the second cell-penetrating peptide without a linker.

In some embodiments, the first and/or second peptide further comprises one or more moieties selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a nuclear localization signal, nuclear export signal, an antibody, a polysaccharide and a targeting sequence, wherein the one or more moieties are covalently linked to the C-terminus of the first cell-penetrating peptide, the second cell-penetrating peptide or the PEG moiety. In some embodiments, the one or more moieties is covalently linked to the C-terminus of the first cell-penetrating peptide, the second cell-penetrating peptide or the PEG moiety via a linker. In some embodiments, the one or more moiety comprises an acetyl group and/or a stearyl group. The one or more moiety comprises a targeting sequence. In some embodiments, the targeting sequence is covalently linked to the first or the second cell-penetrating peptide via a linker. In some embodiments, the targeting sequence is covalently linked to the first or the second cell-penetrating peptide without a linker.

In some embodiments, the targeting sequence is selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), and IGSR (SEQ ID NO: 188). In some embodiments, the targeting sequence is selected from the group consisting of GYVSK (SEQ ID NO: 189), GYVS (SEQ ID NO: 158), YIGS (SEQ ID NO: 187), and YIGSR (SEQ ID NO: 157).

In some embodiments, the linker described herein comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif.

In some embodiments, the first and/or second cell-penetrating peptide is a retro-inverso peptide. In some embodiments, the retro-inverso peptide comprises a sequence of SEQ ID NO: 85 or 86.

In some embodiments, the first and/or second peptide comprises a sequence of SED ID NOs: 1-112.

Cargo Delivery Complexes Comprising a Retro-Inverso Cell-Penetrating Peptide

In some embodiments, there is provided a cargo delivery complex for intracellular delivery of a cargo molecule comprising a cell-penetrating peptide and a cargo molecule, wherein the cell-penetrating peptide is a retro-inverso peptide. In some embodiments, the cell-penetrating peptide is a PTD-based peptide, an amphipathic peptide, a poly-arginine-based peptide, an MPG peptide, a PEP peptide (such as a PEP-1, PEP-2 or PEP-3 peptide), or a VEPEP peptide (such as ADGN-100, VEPEP-3, VEPEP-4, VEPEP-5, VEPEP-6, or VEPEP-9 peptide). In some embodiments, the cargo molecule is selected from the group consisting of a nucleic acid, a polypeptide, a protein/nucleic complex, virus like particles, and a protein complex and a protein complex.

In some embodiments, there is provided a cargo delivery complex for intracellular delivery of a cargo molecule comprising a cell-penetrating peptide and a cargo molecule, wherein the cell-penetrating peptide is selected from the group consisting of PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides, and wherein the cell-penetrating peptide is a retro-inverso peptide. In some embodiments, the cell-penetrating peptide is selected from the group consisting of VEPEP-3 peptides, VEPEP-4 peptides, VEPEP-5 peptides, VEPEP-6 peptides, VEPEP-9 peptides, and ADGN-100 peptides. In some embodiments, the cargo molecule is selected from the group consisting of a nucleic acid, a polypeptide, a protein/nucleic complex, virus like particles, and a protein complex and a protein complex. In some embodiments, the cargo molecule does not comprise a virus. In some embodiments, the cargo molecule comprises a nucleic acid selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the cargo molecule (such as the nucleic acid) is between about 1:1 and about 100:1 (such as about between about 1:1 and about 50:1, or about 20:1).

In some embodiments, there is provided a cargo delivery complex for intracellular delivery of a cargo molecule comprising a cell-penetrating peptide and a cargo molecule, wherein the cell-penetrating peptide is a retro-inverso peptide, and wherein the cargo molecule does not comprise a virus. In some embodiments, the cargo molecule is selected from the group consisting of a nucleic acid, a polypeptide, a protein/nucleic complex, virus like particles, and a protein complex and a protein complex. In some embodiments, the cargo molecule comprises a nucleic acid. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the cargo molecule (such as the nucleic acid) is between about 1:1 and about 100:1 (such as about between about 1:1 and about 50:1, or about 20:1). In some embodiments, the cell-penetrating peptide is selected from the group consisting of VEPEP-3 peptides, VEPEP-4 peptides, VEPEP-5 peptides, VEPEP-6 peptides, VEPEP-9 peptides, and ADGN-100 peptides.

In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is an ADGN-100 peptide, wherein the cargo molecule does not comprise a virus. In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is an ADGN-100 peptide, wherein the cargo molecule comprises a nucleic acid. In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1 (such as about between about 1:1 and about 50:1, or about 20:1).

In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is VEPEP-3 peptide, wherein the cargo molecule does not comprise a virus. In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is a VEPEP-3 peptide, wherein the cargo molecule comprises a nucleic acid. In some embodiments, the VEPEP-3 peptide comprises an amino acid sequence selected from the group consisting of SEQ ID NOs: 1-14, 75, 76, and 113-115. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the cargo comprises a DNA plasmid. In some embodiments, the molar ratio of the cell-penetrating peptide to the nucleic acid is between about 1:1 and about 100:1 (such as about between about 1:1 and about 50:1, or about 20:1).

In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is VEPEP-6 peptide, wherein the cargo molecule does not comprise a virus. In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is a VEPEP-6 peptide, wherein the cargo molecule comprises a nucleic acid. In some embodiments, the VEPEP-6 peptide comprises an amino acid sequence selected from the group consisting of SEQ ID NOs: 15-40, 77, 85, 92-100, 105, 107-109, and 129-139. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1 (such as about between about 1:1 and about 50:1, or about 20:1).

In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is VEPEP-9 peptide, wherein the cargo molecule does not comprise a virus. In some embodiments, there is provided a cargo delivery complex for intracellular delivery of a cargo molecule comprising a cell-penetrating peptide and a cargo molecule, wherein the cell-penetrating peptide is a retro-inverso peptide, wherein the cell-penetrating peptide is a VEPEP-9 peptide, wherein the cargo molecule comprises a nucleic acid. In some embodiments, the VEPEP-9 peptide comprises an amino acid sequence selected from the group consisting of SEQ ID NOs: 41-52, 78, and 116-120. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1 (such as about between about 1:1 and about 50:1, or about 20:1).

In some embodiments, there is provided a cargo delivery complex for intracellular delivery of a cargo molecule, wherein the complex comprises a cell-penetrating peptide and a cargo molecule, wherein the cell-penetrating peptide is a retro-inverso peptide comprising a sequence of SEQ ID NO: 85 or 86, and wherein the cargo molecule does not comprise a virus. In some embodiments, the cargo molecule is selected from the group consisting of a nucleic acid, a polypeptide, a protein/nucleic complex, virus like particles, and a protein complex and a protein complex. In some embodiments, the cargo molecule comprises a nucleic acid. In some embodiments, the nucleic acid is selected from the group consisting of an RNAi (such as an siRNA, an miRNA, a shRNA), a gRNA, an mRNA, a DNA, a DNA plasmid, an oligonucleotide and an analogue thereof. In some embodiments, the cargo molecule comprises an mRNA. In some embodiments, the cargo molecule comprises or further comprises an RNAi (such as an siRNA, an miRNA, a shRNA). In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the cargo molecule (such as the nucleic acid) is between about 1:1 and about 100:1 (such as about between about 1:1 and about 50:1, or about 20:1).

In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm).

In some embodiments, the cell-penetrating peptide further comprises one or more moieties selected from the group consisting of an acetyl group, a stearyl group, a fatty acid, a cholesterol, a nuclear localization signal, a nuclear export signal, an antibody or antibody fragment thereof, a peptide, a polysaccharide, and a targeting sequence, wherein the one or more moieties are covalently linked to the N-terminus of the cell-penetrating peptide. In some embodiments, the one or more moieties is covalently linked to the N-terminus of the cell-penetrating peptide via a linker. In some embodiments, the one or more moiety comprises an acetyl group and/or a stearyl group. In some embodiments, the one or more moiety comprises a targeting sequence. In some embodiments, the targeting sequence is covalently linked to the cell-penetrating peptide via a linker. In some embodiments, the targeting sequence is covalently linked to the cell-penetrating peptide without a linker.

In some embodiments, the peptide further comprises one or more moieties selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a nuclear localization signal, nuclear export signal, an antibody, a polysaccharide and a targeting sequence, wherein the one or more moieties are covalently linked to the C-terminus of the cell-penetrating peptide. In some embodiments, the one or more moieties is covalently linked to the C-terminus of the cell-penetrating peptide via a linker. In some embodiments, the one or more moiety comprises an acetyl group and/or a stearyl group. In some embodiments, the one or more moiety comprises a targeting sequence. In some embodiments, the targeting sequence is covalently linked to the cell-penetrating peptide via a linker.

In some embodiments, the targeting sequence is covalently linked to the second cell-penetrating peptide without a linker.

In some embodiments, the targeting sequence is selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), and IGSR (SEQ ID NO: 188). In some embodiments, the targeting sequence is selected from the group consisting of GYVSK (SEQ ID NO: 189), GYVS (SEQ ID NO: 158), YIGS (SEQ ID NO: 187), and YIGSR (SEQ ID NO: 157).

In some embodiments, the linker described herein comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif.

Cargo Delivery Complexes that Comprise a Cell Penetrating Peptide with a Signaling Sequence (i.e., Targeting Moiety)

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157). In some embodiments, the cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm). In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), and wherein the cargo molecule does not comprise a virus. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cargo molecule is selected from the group consisting of a nucleic acid, a polypeptide, a protein/nucleic complex, virus like particles, and a protein complex. In some embodiments, the molar ratio of the cell-penetrating peptide to the cargo molecule is between about 1:1 and about 100:1 (such as about between about 1:1 and about 50:1, or about 20:1). In some embodiments, the cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cargo molecule is a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the nucleic acid is a DNA plasmid. In some embodiments, the molar ratio of the cell-penetrating peptide to the nucleic acid is between about 1:1 and about 100:1 (such as about between about 1:1 and about 50:1, or about 20:1). In some embodiments, the cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is an ADGN-100 peptide, wherein the cargo molecule does not comprise a virus. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is an ADGN-100 peptide, wherein the cargo molecule is selected from the group consisting of a nucleic acid, a polypeptide, a protein/nucleic complex, virus like particles, and a protein complex. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is an ADGN-100 peptide, wherein the cargo molecule is a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the nucleic acid is a DNA plasmid. In some embodiments, the molar ratio of the cell-penetrating peptide to the nucleic acid is between about 1:1 and about 100:1 (such as about between about 1:1 and about 50:1, or about 20:1). In some embodiments, the ADGN-100 peptide comprises an amino acid sequence selected from the group consisting of SEQ ID NOs: 53-70, 79, 80, 86-91, 101-104, 106, 110-112, and 121-128. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-3 peptide, wherein the cargo molecule does not comprise a virus. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-3 peptide, wherein the cargo molecule is selected from the group consisting of a nucleic acid, a polypeptide, a protein/nucleic complex, virus like particles, and a protein complex. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-3 peptide, wherein the cargo molecule is a nucleic acid. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the nucleic acid is a DNA plasmid. In some embodiments, the molar ratio of the cell-penetrating peptide to the nucleic acid is between about 1:1 and about 100:1 (such as about between about 1:1 and about 50:1, or about 20:1). In some embodiments, the VEPEP-3 peptide comprises an amino acid sequence selected from the group consisting of SEQ ID NOs: 1-14, 75, 76, and 113-115. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-6 peptide, wherein the cargo molecule does not comprise a virus. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-6 peptide, wherein the cargo molecule is selected from the group consisting of a nucleic acid, a polypeptide, a protein/nucleic complex, virus like particles, and a protein complex. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-6 peptide, wherein the cargo molecule is a nucleic acid. In some embodiments, the VEPEP-6 peptide comprises an amino acid sequence selected from the group consisting of SEQ ID NOs: 15-40, 77, 85, 92-100, 105, 107-109, and 129-139. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the nucleic acid is a DNA plasmid. In some embodiments, the molar ratio of the cell-penetrating peptide to the nucleic acid is between about 1:1 and about 100:1 (such as about between about 1:1 and about 50:1, or about 20:1). In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-9 peptide, wherein the cargo molecule does not comprise a virus. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-9 peptide, wherein the cargo molecule is selected from the group consisting of a nucleic acid, a polypeptide, a protein/nucleic complex, virus like particles, and a protein complex. In some embodiments, there is provided a cargo delivery complex for intracellular delivery of a cargo molecule comprising a) a peptide comprising a cell-penetrating peptide and b) a cargo molecule, wherein the peptide further comprises a targeting sequence selected from the group consisting of GYVSK (SEQ ID NO: 189), GYVS (SEQ ID NO: 158), YIGS (SEQ ID NO: 187), and YIGSR (SEQ ID NO: 157), wherein the cell-penetrating peptide is a VEPEP-9 peptide, wherein the cargo molecule is a nucleic acid. In some embodiments, the VEPEP-9 peptide comprises an amino acid sequence selected from the group consisting of SEQ ID NOs: 41-52, 78, and 116-120. In some embodiments, the nucleic acid is selected from the group consisting of an iRNA (such as an siRNA, an miRNA, or a shRNA), a gRNA, an mRNA, a DNA, a DNA, a DNA plasmid, an oligonucleotide and an analogue thereof. In some embodiments, the nucleic acid comprises an mRNA. In some embodiments, the nucleic acid comprises or further comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the nucleic acid is a DNA plasmid. In some embodiments, the molar ratio of the cell-penetrating peptide to the nucleic acid is between about 1:1 and about 100:1 (such as about between about 1:1 and about 50:1, or about 20:1). In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker comprises a polyglycine linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of YIGSR (SEQ ID NO: 157), wherein the targeting sequence is covalently linked to N-terminus of the cell-penetrating peptide without a linker. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of YIGSR (SEQ ID NO: 157), wherein the targeting sequence is covalently linked to N-terminus of the cell-penetrating peptide via a linker, and wherein the linker comprises at least about two, three, or four glycines. In some embodiments, the linker consists of two, three or four glycines. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of GYVS (SEQ ID NO: 158), wherein the targeting sequence is covalently linked to N-terminus of the cell-penetrating peptide via a linker, and wherein the linker comprises at least about two, three, or four glycines. In some embodiments, the linker consists of two, three or four glycines. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of YIGSR (SEQ ID NO: 157), wherein the targeting sequence is covalently linked to N-terminus of the cell-penetrating peptide via a linker, and wherein the linker comprises a Ava (5-amino pentanoic acid) moiety. In some embodiments, the Ava moiety further comprises a methylene group (i.e., CH2). In some embodiments, the Ava moiety comprises at least about two CH2. In some embodiments, the Ava moiety has two CH2. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of GYVS (SEQ ID NO: 158), wherein the targeting sequence is covalently linked to N-terminus of the cell-penetrating peptide via a linker, and wherein the linker comprises a Ava (5-amino pentanoic acid) moiety. In some embodiments, the Ava moiety further comprises a methylene group (i.e., CH2). In some embodiments, the Ava moiety comprises at least about two CH2. In some embodiments, the Ava moiety has two CH2. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of YIGSR (SEQ ID NO: 157), wherein the targeting sequence is covalently linked to N-terminus of the cell-penetrating peptide via a linker, and wherein the linker comprises a Aun (11-amino-undecanoic acid) moiety. In some embodiments, the Ava moiety further comprises a methylene group (i.e., CH2). In some embodiments, the Ava moiety comprises at least one CH2 (such as at least two, three, four, five or six). In some embodiments, the Ava moiety has about one to ten (such as about four to eight, about five to seven, or six) CH2. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of GYVS (SEQ ID NO: 158), wherein the targeting sequence is covalently linked to N-terminus of the cell-penetrating peptide via a linker, and wherein the linker comprises a Aun (11-amino-undecanoic acid) moiety. In some embodiments, the Ava moiety further comprises a methylene group (i.e., CH2). In some embodiments, the Ava moiety comprises at least one CH2 (such as at least two, three, four, five or six). In some embodiments, the Ava moiety has about one to ten (such as about four to eight, about five to seven, or six) CH2. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a Grna, an Mrna, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of GYVS (SEQ ID NO: 158) or YIGSR (SEQ ID NO: 157), wherein the targeting sequence is covalently linked to N-terminus of the cell-penetrating peptide via a linker comprising a PEG linker moiety. In some embodiments, the targeting sequence comprises or consists of YIGSR (SEQ ID NO: 157). In some embodiments, the targeting sequence comprises or consists of GYVS (SEQ ID NO: 158). In some embodiments, the PEG linker moiety consists of about one to ten (such as about 1-8, 2-7, 1-5, or 6-10) ethylene glycol units. In some embodiments, the PEG linker moiety consists of 1, 2, 3, 4, 5, 6, 7, 8, 9, or 10 ethylene glycol units. In some embodiments, the molecular weight of the PEG linker moiety is about 0.05 kDa to about 0.5 kDa (such as about 0.05-0.1, 0.05-0.4, 0.1-0.3, 0.05-0.25, 0.25-0.5 kDa). In some embodiments, the PEG linker moiety is a linear PEG. In some embodiments, the PEG linker moiety is a branched PEG. In some embodiments, the peptide further comprises an acetyl group linked to the N-terminus of the targeting sequence. In some embodiments, the cell-penetrating peptide is an ADGN-100 peptide or a VEPEP-6 peptide. In some embodiments, the cargo molecule does not comprise a virus. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of GYVS (SEQ ID NO: 158) or YIGSR (SEQ ID NO: 157), wherein the peptide comprises a sequence selected from the group consisting of SEQ ID NO: 88, 89, 94-99, 101-112.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of SYTSSTM (SEQ ID NO: 152), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises an amino acid sequence selected from the group consisting of SEQ ID NOs: 115, 128, 131, and 132. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of CKTRRVP (SEQ ID NO: 153), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 134 or 137. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of THRPPNWSPV (SEQ ID NO: 154), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 133 or 138. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of TGNYKALHPDHNG (SEQ ID NO: 155), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 122 or 123. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of CARPAR (SEQ ID NO: 156), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 121 or 139. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of ASSLNIA (SEQ ID NO: 159), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 113. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of LSSRLDA (SEQ ID NO: 160), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 114. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of KSYDTY (SEQ ID NO: 161), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 116 or 119. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, there is provided a cargo delivery complex for intracellular delivery of a cargo molecule comprising a) a peptide comprising a cell-penetrating peptide and b) a cargo molecule, wherein the peptide further comprises a targeting sequence comprising a sequence of CKRAV (SEQ ID NO: 162), wherein the targeting sequence is covalently linked to N-terminus of the cell-penetrating peptide. In some embodiments, the peptide further comprises an acetyl group linked to the N-terminus of the targeting sequence. In some embodiments, the targeting sequence is linked to N-terminus of the cell-penetrating peptide via a linker moiety. In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the cell-penetrating peptide is an ADGN-100 peptide or a VEPEP-6 peptide. In some embodiment, the ADGN-100 peptide comprises an amino acid sequence selected from the group consisting of SEQ ID NOs: 53-70, 79, 80, 86-91, 101-104, 106, 110-112, and 121-128. In some embodiment, the VEPEP-6 peptide comprises an amino acid sequence selected from the group consisting of SEQ ID NOs: 15-40, 77, 85, 92-100, 105, 107-109, and 129-139. In some embodiments, the cell-penetrating peptide comprises the amino acid sequence set forth in SEQ ID NOs: 117. In some embodiments, the cargo molecule is selected from the group consisting of a nucleic acid, a polypeptide, a protein/nucleic complex, virus like particles, and a protein complex. In some embodiments, the cargo molecule is a nucleic acid selected from the group consisting of an siRNA, an miRNA, a shRNA, a gRNA, an mRNA, a DNA, a DNA plasmid, an oligonucleotide and an analogue thereof.

In some embodiments, the average diameter of the cargo delivery complex is between about 20 nm and about 1000 nm (such as about 20 to about 500 nm, about 50 to about 400 nm, about 60 to about 300 nm, about 80 to about 200 nm, or about 100 to about 160 nm).

In some embodiments, the cell-penetrating peptide further comprises one or more moieties selected from the group consisting of an acetyl group, a stearyl group, a fatty acid, a cholesterol, a nuclear localization signal, a nuclear export signal, an antibody or antibody fragment thereof, a peptide, and a polysaccharide, wherein the one or more moieties are covalently linked to the N-terminus of the cell-penetrating peptide. In some embodiments, the one or more moieties is covalently linked to the N-terminus of the cell-penetrating peptide via a second linker. In some embodiments, the one or more moiety comprises or consists of a stearyl group.

In some embodiments, the peptide further comprises one or more moieties selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a nuclear localization signal, nuclear export signal, an antibody, and a polysaccharide, wherein the one or more moieties are covalently linked to the C-terminus of the cell-penetrating peptide. In some embodiments, the one or more moieties is covalently linked to the C-terminus of the cell-penetrating peptide via a second linker. In some embodiments, the one or more moiety comprises or consists of a stearyl group.

In some embodiments, the peptide is a retro-inverso peptide. In some embodiments, the retro-inverso peptide comprises a sequence of SEQ ID NO: 85 or 86.

In some embodiments, the peptide comprises a sequence of SED ID NOs: 1-112.

In some embodiments, cell-penetrating peptides described herein are complexed with the one or more cargo molecules. In some embodiments, the cell-penetrating peptides are non-covalently complexed with at least one of the one or more cargo molecules. In some embodiments, the cell-penetrating peptides are non-covalently complexed with each of the one or more cargo molecules. In some embodiments, the cell-penetrating peptides are covalently complexed with at least one of the one or more cargo molecule. In some embodiments, the cell-penetrating peptides are covalently complexed with each of the one or more cargo molecules.

Cell-Penetrating Peptides

Cell Penetrating Peptides (CPP) are one of the promising non-viral strategies. Although definition of CPPs is constantly evolving, they are generally described as short peptides of less than 30 amino acids either derived from proteins or from chimeric sequences. They are usually amphipathic and possess a net positive charge (Langel U (2007) *Handbook of Cell-Penetrating Peptides* (CRC Taylor & Francis, Boca Raton); Heitz et al. (2009) *Br J Pharmacol* 157, 195-206). CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models (Langel U (2007) *Handbook of Cell-Penetrating Peptides* (CRC Taylor & Francis, Boca Raton); Heitz et al. (2009) *Br J Pharmacol* 157, 195-206; Mickan et al. (2014) *Curr Pharm Biotechnol* 15, 200-209; Shukla et al. (2014) *Mol Pharm* 11, 3395-3408).

The concept of protein transduction domain (PTD) was initially proposed based on the observation that some proteins, mainly transcription factors, could shuttle within cells and from one cell to another (for review see Langel U (2007) *Handbook of Cell-Penetrating Peptides* (CRC Taylor & Francis, Boca Raton); Heitz et al. (2009) *Br J Pharmacol* 157, 195-206). The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake, and the first proofs-of-concept of the application of PTD in vivo were reported by the group of Dowdy for the delivery of small peptides and large proteins (Gump J M, and Dowdy S F (2007) *Trends Mol Med* 13, 443-448.). Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs (peptide nucleic acids) both in cultured cells and in vivo (Langel U (2007) *Handbook of Cell-Penetrating Peptides* (CRC Taylor & Francis, Boca Raton)). In 1997, the group of Heitz and Divita proposed a new strategy involving CPP in the formation of stable but non-covalent complexes with their cargo (Morris et al. (1997) *Nucleic Acids Res* 25, 2730-2736). The strategy was first based on the short peptide carrier (MPG) consisting of two domains: a hydrophilic (polar) domain and a hydrophobic (apolar) domain. MPG was designed for the delivery of nucleic acids. The primary amphipathic peptide Pep-1 was then proposed for non-covalent delivery of proteins and peptides (Morris et al. (2001) *Nat Biotechnol* 19, 1173-1176). Then the groups of Wender and of Futaki demonstrated that polyarginine sequences (Arg8) are sufficient to drive small and large molecules into cells and in vivo (Nakase et al. (2004) *Mol Ther* 10, 1011-1022; Rothbard et al. (2004) *J Am Chem Soc* 126, 9506-9507). Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides (Heitz et al. (2009) *Br J Pharmacol* 157, 195-206). More recently, a new non-covalent strategy based on secondary amphipathic CPPs has been described. These peptides such as CADY and VEPEP-families are able to self-assemble in a helical shape with hydrophilic and hydrophobic residues on different side of the molecule. WO2014/053879 discloses VEPEP-3 peptides; WO2014/053881 discloses VEPEP-4 peptides; WO2014/053882 discloses VEPEP-5 peptides; WO2012/137150 discloses VEPEP-6 peptides; WO2014/053880 discloses VEPEP-9 peptides; WO 2016/102687 discloses ADGN-100 peptides; US2010/0099626 discloses CADY peptides; and. U.S. Pat. No. 7,514,530 discloses MPG peptides; the disclosures of which are hereby incorporated herein by reference in their entirety.

The cell-penetrating peptides in the cargo delivery complexes or nanoparticles of the present invention are capable of forming stable complexes and nanoparticles with various cargos. Any of the cell-penetrating peptides in any of the cargo delivery complexes or nanoparticles described herein may comprise or consist of any of the cell-penetrating peptide sequences described in this section.

In some embodiments, a cargo delivery complex or nanoparticle described herein comprises a cell-penetrating peptide selected from the group consisting of CADY, PEP-1, PEP-2, MPG, VEPEP-3 peptides (used herein interchangeably with ADGN-103 peptides), VEPEP-4 peptides (used herein interchangeably with ADGN-104 peptides), VEPEP-5 peptides (used herein interchangeably with ADGN-105 peptides), VEPEP-6 peptides (used herein interchangeably with ADGN-106 peptides), VEPEP-9 peptides (used herein interchangeably with ADGN-109 peptides), and ADGN-100 peptides. In some embodiments, the cell-penetrating peptide is present in a cargo delivery complex. In some embodiments, the cell-penetrating peptide is present in a cargo delivery complex present in the core of a nanoparticle. In some embodiments, the cell-penetrating peptide is present in the core of a nanoparticle. In some embodiments, the cell-penetrating peptide is present in the core of a nanoparticle. In some embodiments, the cell-penetrating peptide is present in the core of a nanoparticle and is associated with a cargo molecule. In some embodiments, the cell-penetrating peptide is present in an intermediate layer of a nanoparticle. In some embodiments, the cell-penetrating peptide is present in the surface layer of a nanoparticle. In some embodiments, the cell-penetrating peptide is linked to a targeting moiety. In some embodiments, the linkage is covalent. In some embodiments, the covalent linkage is by chemical coupling. In some embodiments, the covalent linkage is by genetic methods. WO2014/053879 discloses VEPEP-3 peptides; WO2014/053881 discloses VEPEP-4 peptides; WO2014/053882 discloses VEPEP-5 peptides; WO2012/137150 discloses VEPEP-6 peptides; WO2014/053880 discloses VEPEP-9 peptides; WO 2016/102687 discloses ADGN-100 peptides; US2010/0099626 discloses CADY peptides; and. U.S. Pat. No. 7,514,530 discloses MPG peptides; the disclosures of which are hereby incorporated herein by reference in their entirety.

VEPEP-3 Peptides

In some embodiments, a cargo delivery complex or nanoparticle described herein comprises a VEPEP-3 cell-penetrating peptide comprising the amino acid sequence $X_1X_2X_3X_4X_5X_2X_3X_4X_6X_7X_3X_8X_9X_{10}X_{11}X_{12}X_{13}$ (SEQ ID NO: 1), wherein $X_1$ is beta-A or S, $X_2$ is K, R or L (independently from each other), $X_3$ is F or W (independently from each other), $X_4$ is F, W or Y (independently from each other), $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K. In some embodiments, the VEPEP-3 peptide comprises the amino acid sequence $X_1X_2WX_4EX_2WX_4X_6X_7X_3PRX_{11}RX_{13}$ (SEQ ID NO: 2), wherein $X_1$ is beta-A or S, $X_2$ is K, R or L, $X_3$ is F or W, $X_4$ is F, W or Y, $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K. In some embodiments, the VEPEP-3 peptide comprises the amino acid sequence $X_1$KWFERWFREWPRKRR (SEQ ID NO: 3), $X_1$KWWERWWREWPRKRR (SEQ ID NO: 4), $X_1$KWWERWWREWPRKRK (SEQ ID NO: 5), $X_1$RWWEKWWTRWPRKRK (SEQ ID NO: 6), or $X_1$RWYEKWYTEFPRRRR (SEQ ID NO: 7), wherein $X_1$ is beta-A or S. In some embodiments, the VEPEP-3 peptide comprises the amino acid sequence of any one of SEQ ID NOs: 1-7, wherein the cell-penetrating peptide is modified by replacement of the amino acid in position 10 by a non-natural amino acid, addition of a non-natural amino acid between the amino acids in positions 2 and 3, and addition of a hydrocarbon linkage between the two non-natural amino acids. In some embodiments, the VEPEP-3 peptide comprises the amino acid sequence $X_1KX_{14}WWERWWRX_{14}WPRKRK$ (SEQ ID NO: 8), wherein $X_1$ is beta-A or S and $X_{14}$ is a non-natural amino acid, and wherein there is a hydrocarbon linkage between the two non-natural amino acids. In some embodiments, the VEPEP-3 peptide comprises the amino acid sequence $X_1X_2X_3WX_5X_{10}X_3WX_6X_7WX_8X_9X_{10}WX_{12}R$ (SEQ ID NO: 9), wherein $X_1$ is beta-A or S, $X_2$ is K, R or L, $X_3$ is F or W, $X_5$ is R or S, $X_6$ is R or S, $X_7$ is R or S, $X_8$ is F or W, $X_9$ is R or P, $X_{10}$ is L or R, and $X_{12}$ is R or F. In some embodiments, the VEPEP-3 peptide comprises the amino acid sequence $X_1$RWWRLWWRSWFRLWRR (SEQ ID NO: 10), $X_1$LWWRRWWSRWWPRWRR (SEQ ID NO:

11), $X_1$LWWSRWWRSWFRLWFR (SEQ ID NO: 12), or $X_1$KFWSRFWRSWFRLWRR (SEQ ID NO: 13), wherein $X_1$ is beta-A or S. In some embodiments, the VEPEP-3 peptide comprises the amino acid sequence of any one of SEQ ID NOs: 1 and 9-13, wherein the cell-penetrating peptide is modified by replacement of the amino acids in position 5 and 12 by non-natural amino acids, and addition of a hydrocarbon linkage between the two non-natural amino acids. In some embodiments, the VEPEP-3 peptide comprises the amino acid sequence $X_1$RWWX$_{14}$LWWRSWX$_{14}$RLWRR (SEQ ID NO: 14), wherein $X_1$ is a beta-alanine or a serine and $X_{14}$ is a non-natural amino acid, and wherein there is a hydrocarbon linkage between the two non-natural amino acids. In some embodiments, the VEPEP-3 peptide comprises the amino acid sequence set forth in SEQ ID NO: 75 or SEQ ID NO: 76. In some embodiments, the VEPEP-3 peptide comprises the amino acid sequence of SEQ ID NO: 113. In some embodiments, the VEPEP-3 peptide comprises the amino acid sequence of SEQ ID NO: 114. In some embodiments, the VEPEP-3 peptide comprises the amino acid sequence of SEQ ID NO: 115. In some embodiments, the VEPEP-3 peptide is present in a cargo delivery complex. In some embodiments, the VEPEP-3 peptide is present in a cargo delivery complex in the core of a nanoparticle. In some embodiments, the VEPEP-3 peptide is present in the core of a nanoparticle. In some embodiments, the VEPEP-3 peptide is present in the core of a nanoparticle and is associated with a cargo. In some embodiments, the VEPEP-3 peptide is present in an intermediate layer of a nanoparticle. In some embodiments, the VEPEP-3 peptide is present in the surface layer of a nanoparticle. In some embodiments, the VEPEP-3 peptide is linked to a targeting moiety. In some embodiments, the linkage is covalent. In some embodiments, the covalent linkage is by chemical coupling. In some embodiments, the covalent linkage is by genetic methods.

VEPEP-6 Peptides

In some embodiments, a cargo delivery complex or nanoparticle described herein comprises a VEPEP-6 cell-penetrating peptide. In some embodiments, the VEPEP-6 peptide comprises an amino acid sequence selected from the group consisting of $X_1$LX$_2$RALWX$_9$LX$_3$X$_9$X$_4$LWX$_9$LX$_5$X$_6$X$_7$X$_8$ (SEQ ID NO: 15), $X_1$LX$_2$LARWX$_9$LX$_3$X$_9$X$_4$LWX$_9$LX$_5$X$_6$X$_7$X$_8$ (SEQ ID NO: 16) and $X_1$LX$_2$ARLWX$_9$LX$_3$X$_9$X$_4$LWX$_9$LX$_5$X$_6$X$_7$X$_8$ (SEQ ID NO: 17), wherein $X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S. In some embodiments, the VEPEP-6 peptide comprises the amino acid sequence $X_1$LX$_2$RALWRLX$_3$RX$_4$LWRLX$_5$X$_6$X$_7$X$_8$ (SEQ ID NO: 18), wherein $X_1$ is beta-A or S, $X_2$ is F or W, $X_3$ is L, W, C or I, $X_4$ is S, A, N or T, $X_5$ is L or W, $X_6$ is W or R, $X_7$ is K or R, and $X_8$ is A or none. In some embodiments, the VEPEP-6 peptide comprises the amino acid sequence $X_1$LX$_2$RALWRLX$_3$RX$_4$LWRLX$_5$X$_6$KX$_7$ (SEQ ID NO: 19), wherein $X_1$ is beta-A or S, $X_2$ is F or W, $X_3$ is L or W, $X_4$ is S, A or N, $X_5$ is L or W, $X_6$ is W or R, $X_7$ is A or none. In some embodiments, the VEPEP-6 peptide comprises an amino acid sequence selected from the group consisting of $X_1$LFRALWRLLRX$_2$LWRLLWX$_3$ (SEQ ID NO: 20), $X_1$LWRALWRLWRX$_2$LWRLLWX$_3$A (SEQ ID NO: 21), $X_1$LWRALWRLX$_4$RX$_2$LWRLWRX$_3$A (SEQ ID NO: 22), $X_1$LWRALWRLWRX$_2$LWRLWRX$_3$A (SEQ ID NO: 23), $X_1$LWRALWRLX$_5$RALWRLLWX$_3$A (SEQ ID NO: 24), and $X_1$LWRALWRLX$_4$RNLWRLLWX$_3$A (SEQ ID NO: 25), wherein $X_1$ is beta-A or S, $X_2$ is S or T, $X_3$ is K or R, $X_4$ is L, C or I and $X_5$ is L or I. In some embodiments, the VEPEP-6 peptide comprises an amino acid sequence selected from the group consisting of Ac-$X_1$LFRALWRLLRSLWRLLWK-cysteamide (SEQ ID NO: 26), Ac-$X_1$LWRALWRLWRSLWRLLWKA-cysteamide (SEQ ID NO: 27), Ac-$X_1$LWRALWRLLRSLWRLWRKA-cysteamide (SEQ ID NO: 28), Ac-$X_1$LWRALWRLWRSLWRLWRKA-cysteamide (SEQ ID NO: 29), Ac-$X_1$LWRALWRLLRALWRLLWKA-cysteamide (SEQ ID NO: 30), and Ac-$X_1$LWRALWRLLRNLWRLLWKA-cysteamide (SEQ ID NO: 31), wherein $X_1$ is beta-A or S. In some embodiments, the VEPEP-6 peptide comprises the amino acid sequence of any one of SEQ ID NOs: 15-31, further comprising a hydrocarbon linkage between two residues at positions 8 and 12. In some embodiments, the VEPEP-6 peptide comprises an amino acid sequence selected from the group consisting of Ac-$X_1$LFRALWR$_S$LLRS$_S$LWRLLWK-cysteamide (SEQ ID NO: 32), Ac-$X_1$LFLARWR$_S$LLRS$_S$LWRLLWK-cysteamide (SEQ ID NO: 33), Ac-$X_1$LFRALWS$_S$LLRS$_S$LWRLLWK-cysteamide (SEQ ID NO: 34), Ac-$X_1$LFLARWS$_S$LLRS$_S$LWRLLWK-cysteamide (SEQ ID NO: 35), Ac-$X_1$LFRALWRLLR$_S$SLWS$_S$LLWK-cysteamide (SEQ ID NO: 36), Ac-$X_1$LFLARWRLLR$_S$SLWS$_S$LLWK-cysteamide (SEQ ID NO: 37), Ac-$X_1$LFRALWRLLS$_S$SLWS$_S$LLWK-cysteamide (SEQ ID NO: 38), Ac-$X_1$LFLARWRLLS$_S$SLWS$_S$LLWK-cysteamide (SEQ ID NO: 39), and Ac-$X_1$LFAR$_S$LWRLLRS$_S$LWRLLWK-cysteamide (SEQ ID NO: 40), wherein $X_1$ is beta-A or S and wherein the residues followed by an inferior "S" are those which are linked by said hydrocarbon linkage. In some embodiments, the VEPEP-6 peptide comprises the amino acid sequence of SEQ ID NO: 77. In some embodiments, the VEPEP-6 peptide comprises the amino acid sequence of SEQ ID NO: 85. In some embodiments, the VEPEP-6 peptide comprises the amino acid sequence of SEQ ID NO: 92 or 93. In some embodiments, the VEPEP-6 peptide comprises an amino acid sequence selected from the group consisting of SEQ ID NOs: 94-100, 105, 107-109, and 129-139. In some embodiments, the VEPEP-6 peptide is present in a cargo delivery complex. In some embodiments, the VEPEP-6 peptide is present in a cargo delivery complex in the core of a nanoparticle. In some embodiments, the VEPEP-6 peptide is present in the core of a nanoparticle. In some embodiments, the VEPEP-6 peptide is present in the core of a nanoparticle and is associated with a cargo. In some embodiments, the VEPEP-6 peptide is present in an intermediate layer of a nanoparticle. In some embodiments, the VEPEP-6 peptide is present in the surface layer of a nanoparticle. In some embodiments, the VEPEP-6 peptide is linked to a targeting moiety. In some embodiments, the linkage is covalent. In some embodiments, the covalent linkage is by chemical coupling. In some embodiments, the covalent linkage is by genetic methods.

VEPEP-9 Peptides

In some embodiments, a cargo delivery complex or nanoparticle described herein comprises a VEPEP-9 cell-penetrating peptide comprising the amino acid sequence $X_1$X$_2$X$_3$WWX$_4$X$_5$WAX$_6$X$_3$X$_7$X$_8$X$_9$X$_{10}$X$_{11}$X$_{12}$WX$_{13}$R (SEQ ID NO: 41), wherein $X_1$ is beta-A or S, $X_2$ is L or none, $X_3$ is R or none, $X_4$ is L, R or G, $X_5$ is R, W or S, $X_6$ is S, P or T, $X_7$ is W or P, $X_8$ is F, A or R, $X_9$ is S, L, P or R, $X_{10}$ is R or S, $X_{11}$ is W or none, $X_{12}$ is A, R or none and $X_{13}$ is W or F, and wherein if $X_3$ is none, then $X_2$, $X_{11}$ and $X_{12}$ are none as well. In some embodiments, the VEPEP-9 peptide comprises the amino acid sequence $X_1X_2RWWLRWAX_6RWX_8X_9X_{10}WX_{12}WX_{13}R$ (SEQ ID NO: 42), wherein $X_1$ is beta-A or S, $X_2$ is L or none, $X_6$ is S or P, $X_8$ is F or A, $X_9$ is S, L or P, $X_{10}$ is R or S, $X_{12}$ is A or R, and $X_{13}$ is W or F. In some embodiments, the VEPEP-9 peptide comprises an amino acid sequence selected from the group consisting of $X_1$LRWWLRWASRWFSRWAWWR (SEQ ID NO: 43), $X_1$LRWWLRWASRWASRWAWFR (SEQ ID NO: 44), $X_1$RWWLRWASRWALSWRWWR (SEQ ID NO: 45), $X_1$RWWLRWASRWFLSWRWWR (SEQ ID NO: 46), $X_1$RWWLRWAPRWFPSWRWWR (SEQ ID NO: 47), and $X_1$RWWLRWASRWAPSWRWWR (SEQ ID NO: 48), wherein $X_1$ is beta-A or S. In some embodiments, the VEPEP-9 peptide comprises the amino acid sequence of $X_1WWX_4X_5WAX_6X_7X_8RX_{10}WWR$ (SEQ ID NO: 49), wherein $X_1$ is beta-A or S, $X_4$ is R or G, $X_5$ is W or S, $X_6$ is S, T or P, $X_7$ is W or P, $X_8$ is A or R, and $X_{10}$ is S or R. In some embodiments, the VEPEP-9 peptide comprises an amino acid sequence selected from the group consisting of $X_1$WWRWWASWARSWWR (SEQ ID NO: 50), $X_1$WWGSWATPRRRWWR (SEQ ID NO: 51), and $X_1$WWRWWAPWARSWWR (SEQ ID NO: 52), wherein $X_1$ is beta-A or S. In some embodiments, the VEPEP-9 peptide comprises the amino acid sequence set forth in SEQ ID NO: 78. In some embodiments, the VEPEP-9 peptide comprises an amino acid sequence selected from the group consisting of SEQ ID NOS: 116-120. In some embodiments, the VEPEP-9 peptide is present in a cargo delivery complex. In some embodiments, the VEPEP-9 peptide is present in a cargo delivery complex in the core of a nanoparticle. In some embodiments, the VEPEP-9 peptide is present in the core of a nanoparticle. In some embodiments, the VEPEP-9 peptide is present in the core of a nanoparticle and is associated with a cargo. In some embodiments, the VEPEP-9 peptide is present in an intermediate layer of a nanoparticle. In some embodiments, the VEPEP-9 peptide is present in the surface layer of a nanoparticle. In some embodiments, the VEPEP-9 peptide is linked to a targeting moiety. In some embodiments, the linkage is covalent. In some embodiments, the covalent linkage is by chemical coupling. In some embodiments, the covalent linkage is by genetic methods.

ADGN-100 Peptides

In some embodiments, a cargo delivery complex or nanoparticle described herein comprises an ADGN-100 cell-penetrating peptide comprising the amino acid sequence $X_1KWRSX_2X_3X_4RWRLWRX_5X_6X_7X_8SR$ (SEQ ID NO: 53), wherein $X_1$ is any amino acid or none, and $X_2$-$X_8$ are any amino acid. In some embodiments, the ADGN-100 peptide comprises the amino acid sequence $X_1KWRSX_2X_3X_4RWRLWRX_5X_6X_7X_8SR$ (SEQ ID NO: 54), wherein $X_1$ is βA, S, or none, $X_2$ is A or V, $X_3$ is or L, $X_4$ is W or Y, $X_5$ is V or S, $X_6$ is R, V, or A, $X_7$ is S or L, and $X_8$ is W or Y. In some embodiments, the ADGN-100 peptide comprises the amino acid sequence KWRSAGWRWRLWRVRSWSR (SEQ ID NO: 55), KWRSALYRWRLWRVRSWSR (SEQ ID NO: 56), KWRSALYRWRLWRSRSWSR (SEQ ID NO: 57), or KWRSALYRWRLWRSALYSR (SEQ ID NO: 58). In some embodiments, the ADGN-100 peptide comprises two residues separated by three or six residues that are linked by a hydrocarbon linkage. In some embodiments, the ADGN-100 peptide comprises the amino acid sequence KWRS$_S$AGWR$_S$WRLWRVRSWSR (SEQ ID NO: 59), KWR$_S$SAGWRWR$_S$LWRVRSWSR (SEQ ID NO: 60), KWR$_S$SAGWR$_S$WRLWRVR$_S$SWSR (SEQ ID NO: 61), KWRS$_S$ALYR$_S$WRLWRSRSWSR (SEQ ID NO: 62), KWR$_S$SALYRWR$_S$LWRSRSWSR (SEQ ID NO: 63), KWRSALYR$_S$WRLWRSR$_S$SWSR (SEQ ID NO: 64), KWRSALYRWR$_S$LWRS$_S$RSWSR (SEQ ID NO: 65), KWRSALYRWRLWRS$_S$RSWS$_S$R (SEQ ID NO: 66), KWR$_S$SALYRWR$_S$LWRSALYSR (SEQ ID NO: 67), KWRS$_S$ALYR$_S$WRLWRSALYSR (SEQ ID NO: 68), KWRSALYRWR$_S$LWRS$_S$ALYSR (SEQ ID NO: 69), or KWRSALYRWRLWRS$_S$ALYS$_S$R (SEQ ID NO: 70), wherein the residues marked with a subscript "S" are linked by a hydrocarbon linkage. In some embodiments, the ADGN-100 peptide comprises the amino acid sequence set forth in SEQ ID NO: 79 or 80. In some embodiments, the ADGN-100 peptide comprises the amino acid sequence set forth in SEQ ID NO: 86. In some embodiments, the ADGN-100 peptide comprises an amino acid sequence selected from the group consisting of SEQ ID NOS: 87-91, 101-104, 106, 110-112, and 121-128. In some embodiments, the ADGN-100 peptide is present in a cargo delivery complex. In some embodiments, the ADGN-100 peptide is present in a cargo delivery complex in the core of a nanoparticle. In some embodiments, the ADGN-100 peptide is present in the core of a nanoparticle. In some embodiments, the ADGN-100 peptide is present in the core of a nanoparticle and is associated with a cargo. In some embodiments, the ADGN-100 peptide is present in an intermediate layer of a nanoparticle. In some embodiments, the ADGN-100 peptide is present in the surface layer of a nanoparticle. In some embodiments, the ADGN-100 peptide is linked to a targeting moiety. In some embodiments, the linkage is covalent. In some embodiments, the covalent linkage is by chemical coupling. In some embodiments, the covalent linkage is by genetic methods.

VEPEP-4 Peptides

In some embodiments, a genome-editing complex or nanoparticle described herein comprises a VEPEP-4 cell-penetrating peptide comprising the amino acid sequence XWXRLXXXXXX (SEQ ID NO: 140), wherein X in position 1 is beta-A or S; X in positions 3, 9 and 10 are, independently from each other, W or F; X in position 6 is R if X in position 8 is S, and X in position 6 is S if X in position 8 is R; X in position 7 is L or none; X in position 11 is R or none, and X in position 7 is L if X in position 11 is none. In some embodiments, the VEPEP-4 peptide comprises an amino acid sequence of any one of SEQ ID NOs: 141-144. In some embodiments, the VEPEP-4 peptide is present in a cargo delivery complex. In some embodiments, the VEPEP-4 peptide is present in a cargo delivery complex in the core of a nanoparticle. In some embodiments, the VEPEP-4 peptide is present in the core of a nanoparticle. In some embodiments, the VEPEP-4 peptide is present in the core of a nanoparticle and is associated with a cargo. In some embodiments, the VEPEP-4 peptide is present in an intermediate layer of a nanoparticle. In some embodiments, the VEPEP-4 peptide is present in the surface layer of a nanoparticle. In some embodiments, the VEPEP-4 peptide is linked to a targeting moiety. In some embodiments, the linkage is covalent. In some embodiments, the covalent linkage is by chemical coupling. In some embodiments, the covalent linkage is by genetic methods.

VEPEP-5 Peptides

In some embodiments, a genome-editing complex or nanoparticle described herein comprises a VEPEP-5 cell-penetrating peptide comprising the amino acid sequence RXWXRLWXRLR (SEQ ID NO: 145), wherein X in position 2 is R or S; and X in positions 4 and 8 are, independently from each other, W or F. In some embodiments, the VEPEP-5 peptide comprises an amino acid sequence of any one of SEQ ID NOs: 146-151. In some embodiments, the VEPEP-5 peptide is present in a cargo delivery complex. In some embodiments, the VEPEP-5 peptide is present in a cargo delivery complex in the core of a nanoparticle. In some embodiments, the VEPEP-5 peptide is present in the core of a nanoparticle. In some embodiments, the VEPEP-5 peptide is present in the core of a nanoparticle and is associated with a cargo. In some embodiments, the VEPEP-5 peptide is present in an intermediate layer of a nanoparticle. In some embodiments, the VEPEP-5 peptide is present in the surface layer of a nanoparticle. In some embodiments, the VEPEP-5 peptide is linked to a targeting moiety. In some embodiments, the linkage is covalent. In some embodiments, the covalent linkage is by chemical coupling. In some embodiments, the covalent linkage is by genetic methods.

In some embodiments, the CPP described herein (e.g., PEP-1, PEP-2, VEPEP-3 peptide, VEPEP-6 peptide, VEPEP-9 peptide, or ADGN-100 peptide) further comprises one or more moieties linked to the N-terminus of the CPP. In some embodiments, the one or more moieties is covalently linked to the N-terminus of the CPP. In some embodiments, the one or more moieties are selected from the group consisting of an acetyl group, a stearyl group, a fatty acid, a cholesterol, a poly-ethylene glycol, a nuclear localization signal, a nuclear export signal, an antibody or antibody fragment thereof, a peptide, a polysaccharide, and a targeting molecule. In some embodiments, the one or more moieties is an acetyl group and/or a stearyl group. In some embodiments, the CPP comprises an acetyl group and/or a stearyl group linked to its N-terminus. In some embodiments, the CPP comprises an acetyl group linked to its N-terminus. In some embodiments, the CPP comprises a stearyl group linked to its N-terminus. In some embodiments, the CPP comprises an acetyl group and/or a stearyl group covalently linked to its N-terminus. In some embodiments, the CPP comprises an acetyl group covalently linked to its N-terminus. In some embodiments, the CPP comprises a stearyl group covalently linked to its N-terminus.

In some embodiments, the CPP described herein (e.g., PEP-1, PEP-2, VEPEP-3 peptide, VEPEP-6 peptide, VEPEP-9 peptide, or ADGN-100 peptide) further comprises one or more moieties linked to the C-terminus of the CPP. In some embodiments, the one or more moieties is covalently linked to the C-terminus of the CPP. In some embodiments, the one or more moieties are selected from the group consisting of a cysteamide group, a cysteine, a thiol, an amide, a nitrilotriacetic acid, a carboxyl group, a linear or ramified $C_1$-$C_6$ alkyl group, a primary or secondary amine, an osidic derivative, a lipid, a phospholipid, a fatty acid, a cholesterol, a poly-ethylene glycol, a nuclear localization signal, a nuclear export signal, an antibody or antibody fragment thereof, a peptide, a polysaccharide, and a targeting molecule. In some embodiments, the one or more moieties is a cysteamide group. In some embodiments, the CPP comprises a cysteamide group linked to its C-terminus. In some embodiments, the CPP comprises a cysteamide group covalently linked to its C-terminus.

In some embodiments, the CPP described herein (e.g., PEP-1, PEP-2, VEPEP-3 peptide, VEPEP-6 peptide, VEPEP-9 peptide, or ADGN-100 peptide) is stapled. "Stapled" as used herein refers to a chemical linkage between two residues in a peptide. In some embodiments, the CPP is stapled, comprising a chemical linkage between two amino acids of the peptide. In some embodiments, the two amino acids linked by the chemical linkage are separated by 3 or 6 amino acids. In some embodiments, two amino acids linked by the chemical linkage are separated by 3 amino acids. In some embodiments, the two amino acids linked by the chemical linkage are separated by 6 amino acids. In some embodiments, each of the two amino acids linked by the chemical linkage is R or S. In some embodiments, each of the two amino acids linked by the chemical linkage is R. In some embodiments, each of the two amino acids linked by the chemical linkage is S. In some embodiments, one of the two amino acids linked by the chemical linkage is R and the other is S. In some embodiments, the chemical linkage is a hydrocarbon linkage.

In some embodiments, the CPP is an L-peptide comprising L-amino acids. In some embodiments, the CPP is a retro-inverso peptide (e.g., a peptide made up of D-amino acids in a reversed sequence and, when extended, assumes a side chain topology similar to that of its parent molecule but with inverted amide peptide bonds).

In some embodiments, the CPP described herein (e.g., PEP-1, PEP-2, VEPEP-3 peptide, VEPEP-6 peptide, VEPEP-9 peptide, or ADGN-100 peptide) further comprises one or more moieties. In some embodiments, the one or more moieties is conjugated to the N-terminus or the C-terminus of the CPP. In some embodiments, a first moiety is conjugated to the N-terminus of the CPP and a second moiety is conjugated to the C-terminus of the CPP.

In some embodiments, the one or more moieties comprise a targeting molecule. In some embodiments, the targeting molecule is conjugated to the N-terminus or the C-terminus of the CPP. In some embodiments, a first targeting molecule is conjugated to the N-terminus of the CPP and a second targeting molecule is conjugated to the C-terminus of the CPP. In some embodiments, the targeting molecule comprises at least about 3, 4, or 5 amino acids. In some embodiments, the targeting molecule comprises no more than about 8, 7, 6, 5, or 4 amino acids. In some embodiments, the targeting molecule comprises about 3, 4, or 5 amino acids. In some embodiments, the targeting molecule comprises a sequence selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), IGSR (SEQ ID NO: 188). In some embodiments, the sequence (e.g., a targeting sequence) is selected from the group consisting of GYVSK (SEQ ID NO: 189), GYVS (SEQ ID NO: 158), YIGS (SEQ ID NO: 187), and YIGSR (SEQ ID NO: 157).

In some embodiments, the sequence (e.g., a targeting sequence) is selected from the group consisting of SEQ ID NOS: 152-162.

In some embodiments, the targeting molecule is conjugated to the CPP via a linker. In some embodiments, the linker comprises a polyglycine linker. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif.

In some embodiments, the one or more moieties comprise a polymer (e.g., PEG, polylysine, PET). In some embodiments, the polymer is conjugated to the N-terminus or the C-terminus of the CPP. In some embodiments, a first polymer is conjugated to the N-terminus of the CPP and a second polymer is conjugated to the C-terminus of the CPP. In some embodiments, the polymer is a PEG. In some embodiments, the PEG is a linear PEG. In some embodiments, the PEG is a branched PEG. In some embodiments, the molecular weight of the PEG is no more than about 5 kDa, 10 kDa, 15 kDa, 20 kDa, 30 kDa, or 40 kDa. In some embodiments, the molecular weight of the PEG is at least about 5 kDa, 10 kDa, 15 kDa, 20 kDa, 30 kDa, or 40 kDa. In some embodiments, the molecular weight of the PEG is about 5 kDa to about 10 kDa, about 10 kDa to about 15 kDa, about 15 kDa to about 20 kDa, about 20 kDa to about 30 kDa, or about 30 kDa to about 40 kDa. In some embodiments, the molecular weight of the PEG is about 5 kDa, 10 kDa, 20 kDa, or 40 kDa. In some embodiments, the molecular weight of the PEG is selected from the group consisting of 5 kDa, 10 kDa, 20 kDa or 40 kDa. In some embodiments, the molecular weight of the PEG is about 5 kDa. In some embodiments, the molecular weight of the PEG is about 10 kDa. In some embodiments, the PEG comprises at least about 1, 2, or 3 ethylene glycol units. In some embodiments, the PEG comprises no more than about 3, 2, or 1 ethylene glycol units. In some embodiments, the PEG comprises about 1, 2, or 3 ethylene glycol units.

Targeting Moiety

In some embodiments, the cell-penetrating peptide comprises a targeting moiety. In some embodiments, the targeting moiety is conjugated to the N-terminus the CPP. In some embodiments, the targeting moiety is conjugated to the C-terminus the CPP. In some embodiments, a first targeting moiety is conjugated to the N-terminus of the CPP and a second targeting moiety is conjugated to the C-terminus of the CPP.

In some embodiments, the targeting moiety comprises a targeting peptide that targets one or more organs. In some embodiments, the one or more organs are selected from the group consisting of muscle, heart, brain, spleen, lymph node, liver, lung, and kidney. In some embodiments, the targeting peptide targets brain. In some embodiments, the targeting peptide targets muscle. In some embodiments, the targeting peptide targets heart.

In some embodiments, the targeting moiety comprises at least about 3, 4, or 5 amino acids. In some embodiments, the targeting moiety comprises no more than about 8, 7, 6, 5, or 4 amino acids. In some embodiments, the targeting moiety comprises about 3, 4, or 5 amino acids. In some embodiments, the targeting moiety comprises a sequence selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), IGSR (SEQ ID NO: 188). In some embodiments, the sequence (e.g., a targeting sequence) is selected from the group consisting of GYVSK (SEQ ID NO: 189), GYVS (SEQ ID NO: 158), YIGS (SEQ ID NO: 187), and YIGSR (SEQ ID NO: 157).

In some embodiments, the targeting moiety comprises a targeting sequence selected from the group consisting of SEQ ID NOs: 152-162. In some embodiments, the targeting moiety comprises a targeting sequence SYTSSTM (SEQ ID NO: 152). In some embodiments, the targeting moiety comprises a targeting sequence CKTRRVP (SEQ ID NO: 153). In some embodiments, the targeting moiety comprises a targeting sequence THRPPNWSPV (SEQ ID NO: 154). In some embodiments, the targeting moiety comprises a targeting sequence TGNYKALHPDHNG (SEQ ID NO: 155). In some embodiments, the targeting moiety comprises a targeting sequence CARPAR (SEQ ID NO: 156). In some embodiments, the targeting moiety comprises a targeting sequence ASSLNIA (SEQ ID NO: 159). In some embodiments, the targeting moiety comprises a targeting sequence LSSRLDA (SEQ ID NO: 160). In some embodiments, the targeting moiety comprises a targeting sequence KSYDTY (SEQ ID NO: 161). In some embodiments, the targeting moiety comprises a targeting sequence CKRAV (SEQ ID NO: 162).

In some embodiments, the targeting moiety is conjugated to the CPP via a linker moiety such any one of the linker moieties described herein.

Linker Moiety

In some embodiments, the cell-penetrating peptide comprise a linker moiety.

In some embodiments, the linker moiety comprises a polyglycine linker. In some embodiments, the linker comprises a β-Alanine. In some embodiments, the linker comprises at least about two, three, or four glycines, optionally continuous glycines. In some embodiments, the linker further comprises a serine. In some embodiments, the linker comprises a GGGGS (SEQ ID NO: 190) or SGGGG (SEQ ID NO: 191) sequence. In some embodiments, the linker comprises a Glycine-β-Alanine motif.

In some embodiments, the one or more moieties comprise a polymer (e.g., PEG, polylysine, PET). In some embodiments, the polymer is conjugated to the N-terminus of the CPP. In some embodiments, the polymer is conjugated to the C-terminus of the CPP. In some embodiments, a first polymer is conjugated to the N-terminus of the CPP and a second polymer is conjugated to the C-terminus of the CPP. In some embodiments, the polymer is a PEG. In some embodiments, the PEG is a linear PEG. In some embodiments, the PEG is a branched PEG. In some embodiments, the molecular weight of the PEG is no more than about 5 kDa, 10 kDa, 15 kDa, 20 kDa, 30 kDa, or 40 kDa. In some embodiments, the molecular weight of the PEG is at least about 5 kDa, 10 kDa, 15 kDa, 20 kDa, 30 kDa, or 40 kDa. In some embodiments, the molecular weight of the PEG is about 5 kDa to about 10 kDa, about 10 kDa to about 15 kDa, about 15 kDa to about 20 kDa, about 20 kDa to about 30 kDa, or about 30 kDa to about 40 kDa. In some embodiments, the molecular weight of the PEG is about 5 kDa, 10 kDa, 20 kDa, or 40 kDa. In some embodiments, the molecular weight of the PEG is selected from the group consisting of 5 kDa, 10 kDa, 20 kDa or 40 kDa. In some embodiments, the molecular weight of the PEG is about 5 kDa. In some embodiments, the molecular weight of the PEG is about 10 kDa. In some embodiments, the PEG comprises at least about 1, 2, or 3 ethylene glycol units. In some embodiments, the PEG consists of no more than about 10, 9, 8 or 7 ethylene glycol units. In some embodiments, the PEG consists of about 1, 2, or 3 ethylene glycol units. In some embodiments, the PEG moiety consists of about one to eight, or about two to seven ethylene glycol units.

In some embodiments, the linker moiety is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker moiety comprises Aun (11-amino-undecanoic acid). In some embodiments, the linker moiety comprises Ava (5-amino pentanoic acid). In some embodiments, the linker moiety comprises Ahx (aminocaproic acid).

Carbohydrate Moiety

In some embodiments, the cell-penetrating peptide further comprises a carbohydrate moiety. In some embodiments, the carbohydrate moiety is GalNAc. In some embodiments, the cell-penetrating peptide is an ADGN-106 peptide. In some embodiments, the cell-penetrating peptide is an ADGN-100 peptide. In some embodiments, the carbohydrate moiety modifies an alanine within the cell-penetrating peptide. In some embodiments, the cell-penetrating peptide is set forth in SEQ ID NO: 124 or 129.

First Cell-Penetrating Peptide and Second Cell-Penetrating Peptide

In some embodiments, the second peptide comprises a polyethylene glycol (PEG) moiety that is covalently linked to the second cell-penetrating peptide, and the first peptide does not have a PEG moiety. In some embodiments, the ratio of the first cell-penetrating peptide to the second cell-penetrating peptide is about 50 to 1 (such as about 25 to about 2, about 20 to about 3, about 15 to about 4, about 12 to about 4, about 12 to about 5, or about 10 to about 5.)

In some embodiments, the PEG moiety is a linear PEG. In some embodiments, the PEG moiety is a branched PEG. In some embodiments, the molecular weight of the PEG moiety is about 5 kDa to about 10 kDa. In some embodiments, the PEG moiety consists of about one to ten ethylene glycol units. In some embodiments, the PEG moiety is conjugated to the N-terminus of the second cell-penetrating peptide. In some embodiments, the PEG moiety is conjugated to the C-terminus of the second cell-penetrating peptide.

Cargo Molecules

In some embodiments, the cargo molecule of the complex or nanoparticle as described above e is selected from the group consisting of a nucleic acid, a virus, a polypeptide, a protein/nucleic complex, virus like particles, and a protein complex.

In some embodiments, the cargo molecule of the complex or nanoparticle as described above is a nucleic acid. In some embodiments, the cargo molecule is selected from the group consisting of oligonucleotides, polynucleotides, single- or double-stranded oligo and polynucleotides, antisense oligonucleotides, various forms of RNAi, including for example siRNA, shRNA, etc., microRNA (miRNA), antagomirs, ribozymes, aptamers, plasmid DNA, etc. and suitable combinations of one or more thereof. In some embodiments, the nucleic acid is selected from the group consisting of an siRNA, an miRNA, a shRNA, a gRNA, an mRNA, a DNA, a DNA plasmid, an oligonucleotide and an analogue thereof. In some embodiments, the nucleic acid comprises an mRNA. In some embodiments, the nucleic acid comprises an RNAi. In some embodiments, the nucleic acid comprises an mRNA and an RNAi, and wherein the mRNA encodes a therapeutic protein for treating a disease or condition, and wherein the RNAi targets an RNA, wherein expression of the RNA is associated with the disease or condition. In some embodiments, the molar ratio of the cell-penetrating peptide to the nucleic acid is between about 1:1 and about 100:1.

In some embodiments, the cargo molecule is a protein, such as for example an enzyme or antibody, or a small molecule. In some embodiments, the cargo molecule comprises a plurality of cargo molecules that comprise a combination of nucleic acids with proteins or small molecules. In some embodiments, the combination comprises nucleic acids with proteins or small molecules that are covalently attached to each other. In some embodiments, the combination comprises nucleic acids with proteins or small molecules that are not covalently attached to each other.

"Polynucleotide," or "nucleic acid," as used interchangeably herein, refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, RNA, viral RNA (vRNA), and combinations thereof. Nucleic acids include nucleic acids containing known nucleotide analogs or modified backbone residues or linkages, including for example locked nucleic acid (LNA), unlocked nucleic acid (UNA), and zip nucleic acid (ZNA), which can be synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer e al., Nucleic Acid Res., 19:5081 (1991); Ohtsuka et a., j. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylases, and alkylhalides. "Oligonucleotide," as used herein, generally refers to short, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

In some embodiments, the nucleic acids are single stranded oligonucleotides. In some embodiments, the nucleic acids are double stranded oligonucleotides. The nucleic acids described herein may be any of a range of length of up to, but not necessarily 200 nucleotides in the case of antisense oligonucleotides, RNAi, siRNA, shRNA, iRNA, antagomirs or up to 1000 kilo bases in the case of plasmid DNA.

In some embodiments, the nucleic acids are interference RNA, such as siRNA or shRNA. The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence)

when the interfering RNA is in the same cell as the target gene or sequence, interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Interfering RNA includes "small-interfering RNA" or "siRNA," e.g., interfering RNA of about 15-60, 15-50, or 5-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 5-30, 5-25, or 19-25 base pairs in length, preferably about 8-22, 9-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. Preferably, siRNA are chemically synthesized. siRNA can also be generated by cleavage of longer dsRNA (e.g., dsRNA greater than about 25 nucleotides in length) with the E coli RNase III or Dicer. These enzymes process the dsRNA into biologically active siRNA (see, e.g., Yang et al., Proc Natl. Acad. Set. USA, 99:9942-9947 (2002); Calegari et al., Proc. Natl. Acad. Sci. USA, 99: 14236 (2002); Byrom et al., Ambion TeehNotes, 10(1):4-6 (2003); Kawasaki et al., Nucleic Acids Res., 3 1:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops). A small hairpin RNA or short hairpin RNA (shRNA) is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. Suitable length of the interference RNA are about 5 to about 200 nucleotides, or 10-50 nucleotides or base pairs or 15-30 nucleotides or base pairs. In some embodiments, the interference RNA is substantially complementary (such as at least about 60%, 70%, 80%, 90%, 95%, 98%, 99%, or more identical to) the corresponding target gene. In some embodiments, the interference RNA is modified, for example by incorporating non-naturally occurring nucleotides.

In some embodiments, the nucleic acids are double-stranded antisense RNA. Suitable length of the interference RNA are about 5 to about 200 nucleotides, or 10-50 nucleotides or base pairs or 15-30 nucleotides or base pairs n some embodiments, the interference RNA is substantially complementary (such as at least about 60%, 70%, 80%, 90%, 95%, 98%, 99%, or more identical) to the corresponding target gene. In some embodiments, the antisense RNA is modified, for example by incorporating non-naturally occurring nucleotides.

In some embodiments, the nucleic acid is an interfering RNA, such as an siRNA, that specifically targets an RNA molecule, such as an mRNA, encoding a protein involved in a disease, such as cancer. In some embodiments, the disease is cancer, such as a solid tumor or hematological malignancy, and the interfering RNA targets mRNA encoding a protein involved in the cancer, such as a protein involved in regulating the progression of the cancer.

In some embodiments, the nucleic acid is an interfering RNA, such as an siRNA, that specifically targets an RNA molecule, such as an mRNA, encoding a protein involved in negatively regulating an immune response. In some embodiments, the interfering RNA targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4.

In some embodiments, the nucleic acids are miRNA. A microRNA (abbreviated miRNA) is a short ribonucleic acid (RNA) molecule found in eukaryotic cells. A microRNA molecule has very few nucleotides (an average of 22) compared with other R As. miRNAs are post-transcriptional regulators that bind to complementary sequences on target messenger RNA transcripts (mRNAs), usually resulting in translational repression or target degradation and gene silencing. The human genome may encode over 1000 miRNAs, which may target about 60% of mammalian genes and are abundant in many human cell types. Suitable length of the miRNAs are about 5 to about 200 nucleotides, or 0-50 nucleotides or base pairs or 15-30 nucleotides or base pairs. In some embodiments, the miRNA s substantially complementary (such as at least about 60%, 70%, 80%, 90%, 95%, 98%, 99%, or more identical to) the corresponding target gene. n some embodiments, the antisense RNA is modified, for example by incorporating non-naturally occurring nucleotides.

In some embodiments, the nucleic acids are plasmid DNA or DNA (e.g., DNA fragments, for example DNA fragments of lengths of up to about 1000 bp). In addition, the plasmid DNA or DNA may be hypermethylated or hypomethylated. In some embodiments, the plasmid DNA or DNA encode one or more genes, and may contain regulatory elements necessary for the expression of said one or more genes. In some embodiments, the plasmid DNA or DNA may comprise one or more genes that encode a selectable marker, allowing for maintenance of the plasmid DNA or DNA fragment in an appropriate host cell.

In some embodiments, the plasmid DNA comprises a DNA sequence encoding a chimeric antigen receptor (CAR) comprising an extracellular antigen-binding domain that specifically binds to a target antigen, a transmembrane domain, and an intracellular signaling domain. CARs are described, for example, in U.S. Pat. No. 8,822,647, U.S.

Patent Application Publication No. 2015/0051266, WO 2014/127261, and WO2014099671, the disclosures of which are specifically incorporated herein by reference in their entirety. In some embodiments, the target antigen is an antigen specifically associated with (such as expressed by) a cancer cell. For example, in some embodiments, the plasmid DNA comprises a DNA sequence encoding a CAR comprising an extracellular antigen-binding domain that specifically binds to a cancer-associated antigen, a transmembrane domain, and an intracellular signaling domain. In some embodiments, the cancer-associated antigen is associated with a solid tumor. In some embodiments, the cancer-associated antigen is associated with a hematological malignancy, such as a B cell malignancy or leukemia.

In some embodiments, the cargo molecule comprises a virus. In some embodiments, the virus is a recombinant virus, including recombinant adeno-associated virus (AAV), adenovirus, lentivirus, retrovirus, herpes simplex virus (HSV), poxvirus, Epstein-Barr virus (EBV), vaccinia virus, and human cytomegalovirus (hCMV). In some embodiments, the recombinant virus comprises a transgene for insertion into a cell genome. In some embodiments, the transgene is a therapeutic transgene. In some embodiments, the transgene encodes a protein, such as a therapeutic protein. In some embodiments, the transgene encodes an inhibitory RNA (RNAi), such as an RNAi targeting an endogenous gene, e.g., a disease-associated endogenous gene. In some embodiments, the transgene encodes a CAR. In some embodiments, the virus comprises a first transgene encoding an RNAi. In some embodiments, the RNAi is a therapeutic RNAi targeting an endogenous gene involved in a disease or condition. In some embodiments, the therapeutic RNAi targets a disease-associated form of the endogenous gene (e.g., a gene encoding a mutant protein, or a gene resulting in abnormal expression of a protein). In some embodiments, the virus comprises a second transgene encoding a protein. In some embodiments, the protein is a therapeutic protein useful for treating a disease or condition. In some embodiments, the second transgene is a therapeutic form of an endogenous gene (e.g., the second transgene encodes a wild-type or functional form of a mutant protein encoded by the endogenous gene, or the second transgene results in normal expression of a protein encoded by the endogenous gene). In some embodiments, there is provided a virus comprising the first transgene and the second transgene.

In some embodiments, the cargo molecule comprises both an mRNA (e.g., PTEN) and an siRNA (such as an siRNA targeting an oncogene (e.g., KRAS)).

In some embodiments, the cargo molecule comprises both an mRNA (such as an mRNA encoding a DNA nuclease (e.g., Cas9)) and a guide RNA (such as a guide RNA that targets a mutated oncogene (e.g., KRAS)).

Genome-Editing System

In some embodiments, the cargo comprises a genome-editing system molecule.

In some embodiments, a genome-editing system molecule (e.g. RGEN) of a genome-editing complex or nanoparticle described herein is a protein or polypeptide. For example, in some embodiments, a genome-editing complex or nanoparticle described herein comprises an RGEN (e.g., Cas9). In some embodiments, the protein or polypeptide is between about 10 kDa and about 200 kDa (such as about any of 10, 20, 30, 40, 50, 60, 70, 80, 90, 100, 110, 120, 130, 140, 150, 160, 170, 180, 190, and 200 kDa, including any ranges between these values). In some embodiments, the genome-editing complex or nanoparticle comprises a plurality of proteins or polypeptides, wherein each of the plurality of protein or polypeptides is between about 10 kDa and about 200 kDa (such as about any of 10, 20, 30, 40, 50, 60, 70, 80, 90, 100, 110, 120, 130, 140, 150, 160, 170, 180, 190, and 200 kDa, including any ranges between these values).

In some embodiments, a genome-editing system molecule (e.g. gRNA) of a genome-editing complex or nanoparticle described herein is a nucleic acid. In some embodiments, the nucleic acid is between about 20 nt and about 20 kb (such as about any of 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, and 20 kb, including any ranges between these values). For example, in some embodiments, a genome-editing complex or nanoparticle described herein comprises a gRNA (e.g., a Cas9 gRNA). In some embodiments, the gRNA is between about 20 nt and about 200 nt (such as about any of 20, 30, 40, 50, 60, 70, 80, 90, 100, 110, 120, 130, 140, 150, 160, 170, 180, 190, and 200 nt, including any ranges between these values). In some embodiments, the nucleic acid is DNA, such as a DNA plasmid encoding a genome-editing system molecule. In some embodiments, the DNA plasmid comprises an expression cassette for expressing the genome-editing system molecule. In some embodiments, the DNA plasmid is between about 1 kb and about 20 kb (such as about any of 1, 2, 3, 4, 5, 6, 7, 8, 9, 10, 11, 12, 13, 14, 15, 16, 17, 18, 19, and 20 kb, including any ranges between these values). In some embodiments, the nucleic acid is RNA, such as mRNA encoding a genome-editing system molecule. In some embodiments, the mRNA is between about 100 nt and about 10 kb (such as about any of 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, and 10 kb, including any ranges between these values). In some embodiments, the genome-editing complex or nanoparticle comprises a plurality of nucleic acids, such as any of the nucleic acids described herein. For example, in some embodiments, the genome-editing complex or nanoparticle comprises a gRNA and a nucleic acid encoding a genome-editing system molecule (e.g., a DNA plasmid or mRNA encoding the genome-editing system molecule). In some embodiments, the genome-editing complex or nanoparticle comprises nucleic acid encoding a plurality of genome-editing system molecules (e.g., one or more DNA plasmid encoding the plurality of genome-editing system molecules, or a plurality of mRNAs encoding the plurality of genome-editing system molecules).

In some embodiments, a genome-editing system molecule (e.g. RGEN or gRNA) of a genome-editing complex or nanoparticle described herein is replaced with a nucleic acid encoding the genome-editing system molecule. For example, in some embodiments, a genome-editing complex or nanoparticle described herein comprises a nucleic acid encoding an RGEN and/or a nucleic acid encoding a gRNA. In some embodiments, the nucleic acid is DNA, such as a DNA plasmid encoding a genome-editing system molecule. In some embodiments, the DNA plasmid comprises an expression cassette for expressing the genome-editing system molecule. In some embodiments, the DNA plasmid is between about 1 kb and about 20 kb (such as about any of 1, 2, 3, 4, 5, 6, 7, 8, 9, 10, 11, 12, 13, 14, 15, 16, 17, 18, 19, and 20 kb, including any ranges between these values). In some embodiments, the nucleic acid is RNA, such as mRNA encoding a genome-editing system molecule. In some embodiments, the mRNA is between about 100 nt and about 10 kb (such as about any of 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, and 10 kb, including any ranges between these values).

In some embodiments, cargo comprises a CRISPR-associated nuclease. In some embodiments, the CRISPR-associated nuclease is a Cas nuclease. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof, such as inducible, inactivated, or split Cas proteins (see for example Dominguez et al. (2015). *Nature Reviews Molecular Cell Biology*; Polstein, L. R., & Gersbach, C. A. (2015). *Nature chemical biology*, 11(3):198-200; Dow et al. (2015). *Nature biotechnology*, 33(4):390-394; Zetsche et al. (2015). *Nature biotechnology*, 33(2):139-142; Kleinstiver et al. (2015). *Nature.* 523:481-485; Bikard et al. (2013). *Nucleic acids research*, 41(15):7429-7437; Qi et al. (2013). *Cell*, 152(5):1173-1183). These enzymes are known to those of skill in the art; for example, the amino acid sequence of *S. pyogenes* Cas9 protein may be found in the SwissProt database under accession number Q99ZW2, and the amino acid sequence of *Acidaminococcus* sp. Cpf1 protein may be found in the SwissProt database under accession number U2UMQ6. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments the CRISPR enzyme is Cpf1, and may be Cpf1 from *Acidaminococcus* or Lachnospiraceae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the CRISPR enzyme is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequences, e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, the Cas protein (such as Cas9) is a split Cas protein comprising an N-terminal Cas protein fragment, Cas(N), and a C-terminal Cas protein fragment, Cas(C), wherein Cas(N) is fused to a first dimerization domain and Cas(C) is fused to a second dimerization domain, and wherein the first and second dimerization domains facilitate dimerization of Cas(N) and Cas(C) to form a complex with a functional Cas nuclease activity. In some embodiments, dimerization of the first and second dimerization domains is sensitive to a dimerization agent. For example, in some embodiments, the first and second dimerization domains comprise the FK506 binding protein 12 (FKBP) and FKBP rapamycin binding (FRB) domains of the mammalian target of rapamycin (mTOR), and the dimerization agent is rapamycin.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a CRISPR enzyme comprises one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 163); the NLS from nucleoplasmin (e.g. the nucleoplasmin bipartite NLS with the sequence KRPAATKKAGQAKKKK (SEQ ID NO: 164)); the c-myc NLS having the amino acid sequence PAAKRVKLD (SEQ ID NO: 165) or RQRRNELKRSP (SEQ ID NO: 166); the hRNPA1 M9 NLS having the sequence NQSSNFGPMKGGNFG-GRSSGPYGGGGQYFAKPRNQGGY (SEQ ID NO: 167); the sequence RMRIZFKNKGKDTAELRRRRVEVS-VELRKAKKDEQILKRRNV (SEQ ID NO: 168) of the IBB domain from importin-alpha; the sequences VSRKRPRP (SEQ ID NO: 169) and PPKKARED (SEQ ID NO: 170) of the myoma T protein; the sequence PQPKKKPL (SEQ ID NO: 171) of human p53; the sequence SALIKKKKKMAP (SEQ ID NO: 172) of mouse c-ab1 IV; the sequences DRLRR (SEQ ID NO: 173) and PKQKKRK (SEQ ID NO: 174) of the influenza virus NS1; the sequence RKLKK-KIKKL (SEQ ID NO: 175) of the Hepatitis virus delta antigen; the sequence REKKKFLKRR (SEQ ID NO: 176) of the mouse Mx1 protein; the sequence KRKGDEVDGVDEVAKKKSKK (SEQ ID NO: 177) of the human poly(ADP-ribose) polymerase; and the sequence RKCLQAGMNLEARKTKK (SEQ ID NO: 178) of the steroid hormone receptors (human) glucocorticoid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62). Further algorithms may be found in U.S. application Ser. No. 61/836,080; incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the guide sequence, tracr sequence and tracr mate sequence are contained within a single RNA (referred to herein as a "single-guide RNA," or "sgRNA"), such that hybridization between the tracr sequence and the tracr mate sequence produces a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the sgRNA has at least two or more hairpins. In preferred embodiments, the sgRNA has two, three, four or five hairpins. In a further embodiment of the invention, the sgRNA has at most five hairpins. In some embodiments, the sgRNA further includes a transcription termination sequence; preferably this is a polyT sequence, for example six T nucleotides.

In some embodiments, a donor nucleic acid is also provided. In some embodiments, the donor nucleic acid is designed to serve as a template in homologous recombination, such as within or near a target sequence nicked or cleaved by a CRISPR enzyme as a part of a CRISPR complex. A donor nucleic acid may be of any suitable length, such as about or more than about 10, 15, 20, 25, 50, 75, 100, 150, 200, 500, 1000, or more nucleotides in length. In some embodiments, the donor nucleic acid comprises a sequence that is complementary to a portion of a polynucleotide comprising the target sequence. In some embodiments, when a donor nucleic acid and a polynucleotide comprising a target sequence are optimally aligned, the donor nucleic acid overlaps with one or more nucleotides of the target sequence (e.g. about or more than about 1, 5, 10, 15, 20, 25, 30, 35, 40, 45, 50, 60, 70, 80, 90, 100 or more nucleotides). In some embodiments, when a donor nucleic acid and a polynucleotide comprising a target sequence are optimally aligned, the nearest nucleotide of the donor nucleic acid in the region of complementarity is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, the cargo comprises a fusion protein comprising a catalytically disabled nuclease (such as a catalytically disabled Cas9 endonuclease) and a reversed transcriptase (such as a pentamutant of M-MLV reverse transcriptase). See for example, Anzalone & Liu et al., Nature. 2019 December; 576 (7785):149-157. In some embodiments, the cargo comprises a polynucleotide encoding the fusion protein.

In some embodiments, the cargo comprises a fusion protein comprising a catalytically disabled nuclease (such as a catalytically disabled Cas9 endonuclease) and a nucleobase deaminase enzyme. In some embodiments, the nucleobase deaminase enzyme is APOBEC1 cytidine deaminase. In some embodiments, the nucleobase deaminase enzyme is cytidine deaminase CDA1. In some embodiments, the fusion protein further comprises a DNA glycosylase inhibitor. In some embodiments, the DNA glycosylase inhibitor is uracil DNA glycosylase inhibitor (UGI). In some embodiments, the cargo comprises a polynucleotide encoding the fusion protein.

mRNA

In some embodiments, the cargo comprises an mRNA. Exemplary mRNA enocodes a polypeptide of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery.

In some embodiments, an mRNA contained in a cargo delivery complex according to any of the embodiments described herein comprises a region encoding a polypeptide of interest and a region of linked nucleosides according to any of the mRNAs described in U.S. Pat. Nos. 9,061,059 and 9,221,891, each of which is incorporated herein in its entirety.

In some embodiments, an mRNA contained in a cargo delivery complex according to any of the embodiments described herein encodes a polypeptide variant of a reference polypeptide. In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art.

In some embodiments, an mRNA contained in a cargo delivery complex according to any of the embodiments described herein encodes a biologic. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others. In some embodiments, the biologic is currently being marketed or in development.

In some embodiments, an mRNA contained in a cargo delivery complex according to any of the embodiments described herein encodes an antibody or fragment thereof (such as an antigen-binding fragment). In some embodiments, the antibody or fragment thereof is currently being marketed or in development.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

In some embodiments, an mRNA contained in a cargo delivery complex according to any of the embodiments described herein encodes a vaccine. As used herein, a "vaccine" is a biological preparation that improves immunity to a particular disease or infectious agent. In some embodiments, the vaccine is currently being marketed or in development.

In some embodiments, the vaccine encoded by the mRNA is utilized to treat conditions or diseases in many therapeutic areas such as, but not limited to, cardiovascular, CNS, dermatology, endocrinology, oncology, immunology, respiratory, and anti-infective.

In some embodiments, an mRNA contained in a cargo delivery complex according to any of the embodiments described herein encodes a therapeutic protein. In some embodiments, the therapeutic protein is currently being marketed or in development. In some embodiments, the therapeutic protein is useful for: (a) replacing a protein that is deficient or abnormal; (b) augmenting an existing pathway; (c) providing a novel function or activity; or (d) interfering with a molecule or organism. In some embodiments, the therapeutic protein includes, without limitation, antibody-based drugs, Fc fusion proteins, anticoagulants, blood factors, bone morphogenetic proteins, engineered protein scaffolds, enzymes, growth factors, hormones, interferons, interleukins, and thrombolytics. In some embodiments, the therapeutic protein acts by: (a) binding non-covalently to target, e.g., mAbs; (b) affecting covalent bonds, e.g., enzymes; or (c) exerting activity without specific interactions, e.g., serum albumin. In some embodiments, the therapeutic protein is a recombinant protein.

In some embodiments, the therapeutic protein encoded by the mRNA is utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective. In some embodiments, the therapeutic protein includes, without limitation, vascular endothelial growth factor (VEGF-A, VEGF-B, VEGF-C, VEGF-D), placenta growth factor (PGF), OX40 ligand (OX40L; CD134L), interleukin 12 (IL12), interleukin 23 (IL23), interleukin 36 γ (IL36γ), and CoA mutase.

In some embodiments, the therapeutic protein replaces a protein that is deficient or abnormal. In some embodiments, the therapeutic protein includes, without limitation, alpha 1 antitrypsin, frataxin, insulin, growth hormone (somatotropin), growth factors, hormones, dystrophin, insulin-like growth factor 1 (IGF1), factor VIII, factor IX, antithrombin III, protein C, β-Gluco-cerebrosidase, Alglucosidase-α, α-1-iduronidase, Iduronate-2-sulphatase, Galsulphase, human α-galactosidase A, α-1-Proteinase inhibitor, lactase, pancreatic enzymes (including lipase, amylase, and protease), Adenosine deaminase, and albumin, including recombinant forms thereof.

In some embodiments, the therapeutic protein provides a novel function or activity. In some embodiments, the therapeutic protein includes, without limitation, Botulinum toxin type A, Botulinum toxin type B, collagenase, Human deoxyribonuclease I, dornase-α, Hyaluronidase, papain, L-Asparaginase, Rasburicase, Lepirudin, Bivalirudin, Streptokinase, and anisoylated plasminogen streptokinase activator complex (APSAC).

In some embodiments, the therapeutic protein interferes with a molecule or organism. In some embodiments, the therapeutic protein includes, without limitation, anti-VEGFA antibody, anti-EGFR antibody, anti-CD52 antibody, anti-CD20 antibody, anti-HER2/Neu antibody, fusion protein between extracellular domain of human CTLA4 and the modified Fc portion of human immunoglobulin G1, interleukin 1 (IL1) receptor antagonist, anti-TNFαantibody, CD2-binding protein, anti-CD11a antibody, anti-α4-subunit of α4β1 and α4β7 integrins antibody, anti-complement protein C5 antibody, Antithymocyte globulin, Chimeric (human/mouse) IgG1, Humanized IgG1 mAb that binds the alpha chain of CD25, anti-CD3 antibody, anti-IgE antibody, Humanized IgG1 mAb that binds the A antigenic site of the F protein of respiratory syncytial virus, HIV envelope protein gp120/gp41-binding peptide, Fab fragment of chimeric (human/mouse) mAb 7E3 that binds to the glycoprotein IIb/IIIa integrin receptor, and Fab fragments of IgG that bind and neutralize venom toxins.

In some embodiments, an mRNA contained in a cargo delivery complex according to any of the embodiments described herein encodes a tumor suppressor protein, wherein the protein corresponds to a tumor suppressor gene. In some embodiments, the tumor-suppressor protein is a Retinoblastoma protein (pRb). In some embodiments, the tumor-suppressor protein is a p53 tumor-suppressor protein. In some embodiments, the corresponding tumor-suppressor gene is Phosphatase and tensin homolog (PTEN). In some embodiments, the corresponding tumor-suppressor gene is BRCA1. In some embodiments, the corresponding tumor-suppressor gene is BRCA2. In some embodiments, the corresponding tumor-suppressor gene is Retinoblastoma RB (or RB1). In some embodiments, the corresponding tumor-suppressor gene is TSC1. In some embodiments, the corresponding tumor-suppressor gene is TSC2. In some embodiments, the corresponding tumor-suppressor gene includes, without limitation, Retinoblastoma RB (or RB1), TP53, TP63, TP73, CDKN2A (INK4A), CDKN1B, CDKN1C, DLD/NP1, HEPACAM, SDHB, SDHD, SFRP1, TCF21, TIG1, MLH1, MSH2, MSH6, WT1, WT2, NF1, NF2N, VHL, KLF4, pVHL, APC, CD95, ST5, YPEL3, ST7, APC, MADR2, BRCA1, BRCA2, Patched, TSC1, TSC2, PALB2, ST14, or VHL.

In some embodiments, the mRNA encodes a tumor suppressor protein PTEN. In some embodiments, the tumor suppressor protein PTEN is encoded by a human PTEN sequence. In some embodiments, the mRNA comprises a sequence selected from the group consisting of sequences with accession number of BC005821, JF268690, U92436, CR450306, AK024986, AK313581, U96180, and U93051 and NM_000314 in NCBI GenBank.

In some embodiments, the mRNA encodes a tumor suppressor protein p53. In some embodiments, the tumor suppressor protein p53 is encoded by a human TP53 sequence. In some embodiments, the mRNA comprises a sequence selected from the group consisting of sequences with accession number of AF052180, NM_000546, AY429684, BT019622, AK223026, DQ186652, DQ186651, DQ186650, DQ186649, DQ186648, DQ263704, DQ286964, DQ191317, DQ401704, AF307851, AM076972, AM076971, AM076970, DQ485152, BC003596, DQ648887, DQ648886, DQ648885, DQ648884, AK225838, M14694, M14695, EF101869, EF101868, EF101867, X01405, AK312568, NM_001126117, NM_001126116, NM_001126115, NM_001126114, NM 001126113, NM_001126112, FJ207420, X60020, X60019, X60018, X60017, X60016, X60015, X60014, X60013, X60011, X60012, X60010, X02469, S66666, AB082923, NM_001126118, JN900492, NM 001276699, NM_001276698, NM_001276697, NM_001276761, NM 001276760, NM_001276696, and NM_001276695 in NCBI GenBank.

In some embodiments, the mRNA encodes a tumor suppressor protein BRCA1. In some embodiments, the tumor suppressor protein BRCA1 is encoded by a human BRCA1 sequence. In some embodiments, the mRNA comprises a sequence selected from the group consisting of a sequence with with accession number of NM_007294, NM_007297, NM_007298, NM_007304, NM 007299, NM_007300, BC046142, BC062429, BC072418, AY354539, AY751490, BC085615, BC106746, BC106745, BC114511, BC115037, U14680, AK293762, U68041, BC030969, BC012577, AK316200, DQ363751, DQ333387, DQ333386, Y08864, JN686490, AB621825, BC038947, U64805, and AF005068 in NCBI GenBank.

In some embodiments, the mRNA encodes a tumor suppressor protein BRCA2. In some embodiments, the tumor suppressor protein BRCA2 is encoded by a human BRCA2 sequence. In some embodiments, the mRNA comprises a sequence selected from the group consisting of a sequence with with accession number of BC047568, NM 000059, DQ897648, BC026160 in NCBI GenBank.

In some embodiments, the mRNA encodes a tumor suppressor protein TSC1. In some embodiments, the tumor suppressor protein TSC1 is encoded by a human TSC1 sequence. In some embodiments, the mRNA comprises a sequence selected from the group consisting of a sequence with with accession number of BC047772, NM_000368, BC070032, AB190910, BC108668, BC121000, NM 001162427, NM_001162426, D87683, and AF013168 in NCBI GenBank.

In some embodiments, the mRNA encodes a tumor suppressor protein TSC2. In some embodiments, the tumor suppressor protein TSC2 is encoded by a human TSC2 sequence. In some embodiments, the mRNA comprises a sequence selected from the group consisting of a sequence with with accession number of BC046929, BX647816, AK125096, NM_000548, AB210000, NM_001077183, BC150300, BC025364, NM_001114382, AK094152, AK299343, AK295728, AK295672, AK294548, and X75621 in NCBI GenBank.

In some embodiments, the mRNA encodes a tumor suppressor protein Retinoblastoma 1 (RB1). In some embodiments, the tumor suppressor protein RB1 is encoded by a human RB1 sequence. In some embodiments, the mRNA comprises a sequence selected from the group consisting of a sequence with with accession number of NM_000321, AY429568, AB208788, M19701, AK291258, L41870, AK307730, AK307125, AK300284, AK299179, M33647, M15400, M28419, BC039060, BC040540, and AF043224 in NCBI GenBank.

In some embodiments, an mRNA contained in a cargo delivery complex according to any of the embodiments described herein encodes a protein, wherein the deficiency of the protein results in a disease or disorder. In some embodiments, the protein is Frataxin. In some embodiments, the protein is alpha 1 antitrypsin. In some embodiments, the protein is factor VIII. In some embodiments, the protein is factor IX.

In some embodiments, an mRNA contained in a cargo delivery complex according to any of the embodiments described herein encodes a protein, wherein expression of the protein in an individual modulates an immune response to the protein in the individual. In some embodiments, the protein is an antigen. In some embodiments, the antigen is a disease-associated antigen (e.g., a tumor-associated antigen), and expression of the antigen in the individual results in an increased immune response to the antigen in the individual. In some embodiments, the antigen is a self-antigen, and expression of the antigen in the individual results in a decreased immune response to the antigen in the individual.

In some embodiments, an mRNA contained in a cargo delivery complex according to any of the embodiments described herein encodes an antibody or antigen-binding fragment thereof. In some embodiments, the antibody is a therapeutic antibody. In some embodiments, the antibody is a bispecific antibody, such as a bispecific T cell engager (BiTE). In some embodiments, the antibody specifically binds to a disease-associated antigen, such as a tumor-associated antigen.

In some embodiments, an mRNA contained in a cargo delivery complex according to any of the embodiments described herein comprises a reporter mRNA. In some embodiments, the mRNA comprises an EGFP mRNA, for example, CleanCap EGFP mRNA, CleanCap EGFP mRNA (5moU), or CleanCap Cyanine 5 EGFP mRNA (5moU). In some embodiments, the mRNA comprises a Luc mRNA, for example, CleanCap Fluc mRNA, CleanCap Fluc mRNA (5moU), CleanCap Cyanine 5 Fluc mRNA (5moU), CleanCap *Gaussia* Luc mRNA (5moU), or CleanCap *Renilla* Luc mRNA (5moU). In some embodiments, the mRNA comprises an mRNA selected from CleanCap β-gal mRNA, CleanCap β-gal mRNA (5moU) and CleanCap mCherry mRNA (5moU).

RNAi

In some embodiments, the cargo molecule comprises an interfering RNA (RNAi). In some embodiments, the RNAi includes, without limitation, an siRNA, shRNA, or miRNA. In some embodiments, the RNAi is an siRNA. In some embodiments, the RNAi is a microRNA. In some embodiments, the RNAi targets an endogenous gene. In some embodiments, the RNAi targets an exogenous gene. In some embodiments, the RNAi targets a disease-associated gene, e.g., a cancer-associated genes, such as an oncogene. In some embodiments, the RNAi targets an oncogene. In some embodiments, the oncogene is Smoothened. In some embodiments, the oncogene is rasK. In some embodiments, the oncogene is KRAS.

In some embodiments, the cargo molecule comprises both an mRNA (such as any one of the mRNAs described herein) and an RNAi (such as a siRNA).

In some embodiments, the RNAi (e.g., siRNA) targets an oncogene, wherein the oncogene is KRAS. In some embodiments, the individual comprises an aberration of KRAS. In some embodiments, the aberration of KRAS comprises a mutation on codon 12, 13, 17, 34 or 61 of KRAS. In some embodiments, an aberration of KRAS is selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the aberration of KRAS is selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the aberration of KRAS is selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the aberration of KRAS is selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the aberration of KRAS comprises G12C. In some embodiments, the aberration of KRAS comprises G12D. In some embodiments, the aberration of KRAS comprises Q61K. In some embodiments, the aberration of KRAS comprises G12C and G12D. In some embodiments, the aberration of KRAS comprises G12C and Q61K. In some embodiments, the aberration of KRAS comprises G12D and Q61K. In some embodiments, the aberration of KRAS comprises G12C, G12D and Q61K.

In some embodiments, the RNAi (e.g., siRNA) targets a mutant form of KRAS. In some embodiments, the RNAi (e.g., siRNA) specifically targets a mutant form of KRAS but not the wildtype form of KRAS. In some embodiments, the mutant form comprises an aberration of KRAS, wherein the aberration of KRAS comprises a mutation on codon 12, 13, 17, 34 or 61 of KRAS. In some embodiments, the mutant form comprises an aberration of KRAS, wherein the aberration of KRAS is selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the mutant form comprises an aberration of KRAS, wherein the aberration of KRAS is selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the mutant form comprises an aberration of KRAS, wherein the aberration of KRAS is selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the mutant form comprises an aberration of KRAS, wherein the aberration of KRAS is selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the aberration of KRAS is selected from the group consisting of KRAS G12C, G12D, G12R, G12S, G12V and G13D. In some embodiments, the aberration of KRAS comprises G12C. In some embodiments, the aberration of KRAS comprises G12D. In some embodiments, the aberration of KRAS comprises Q61K. In some embodiments, the aberration of KRAS comprises G12C and G12D. In some embodiments, the aberration of KRAS comprises G12C and Q61K. In some embodiments, the aberration of KRAS comprises G12D and Q61K. In some embodiments, the aberration of KRAS comprises G12C, G12D and Q61K.

In some embodiments, the RNAi (e.g., siRNA) targets a plurality of mutant forms of KRAS. In some embodiments, the plurality of mutant forms comprises a plurality of aberrations of KRAS, wherein the plurality of aberrations of KRAS comprise at least two or more mutations on codon 12, 13, 17, 34 and/or 61 of KRAS. In some embodiments, the plurality of aberrations of KRAS comprises at least two or more mutations on codon 12 and 61 of KRAS. In some embodiments, the aberration of KRAS is selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the aberrations of KRAS are selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the aberrations of KRAS are selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the aberrations of KRAS is selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the aberrations of KRAS are selected from the group consisting of KRAS G12C, G12D, G12R, G12S, G12V and G13D. In some embodiments, the aberrations of KRAS are selected from the group consisting of KRAS G12C, G12D, and Q61K. In some embodiments, the aberrations of KRAS comprise G12C and G12D. In some embodiments, the aberrations of KRAS comprise G12C and Q61K. In some embodiments, the aberrations of KRAS comprise G12D and Q61K. In some embodiments, the aberration of KRAS comprises G12C, G12D and Q61K.

In some embodiments, the RNAi (e.g., siRNA) comprises a plurality of RNAi (e.g., siRNA) comprising a first RNAi (e.g., a first siRNA) and a second RNAi (e.g., a second siRNA), wherein the first RNAi targets a first mutant form of KRAS, and wherein the second RNAi targets a second mutant form of KRAS. In some embodiments, the first RNAi and/or the second RNAi do not target the wildtype form of KRAS. In some embodiments, the first mutant form and/or the second mutant form comprises an aberration of KRAS, wherein the aberration of KRAS comprises a mutation on codon 12, 13, 17, 34 and/or 61 of KRAS. In some embodiments, the first mutant form and/or the second mutant form comprises an aberration of KRAS, wherein the aberration of KRAS comprises a mutation on codon 12 or 61 of KRAS. In some embodiments, the first mutant form comprises an aberration of KRAS comprising a mutation on codon 12, and the second mutant form comprises an aberration of KRAS comprising a mutation on codon 61. In some embodiments, the first mutant form and/or the second mutant form comprises an aberration of KRAS, wherein the aberration of KRAS is selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the first mutant form and/or the second mutant form comprises an aberration of KRAS, wherein the aberration of KRAS is selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the first mutant form and/or the second mutant form comprises an aberration of KRAS, wherein the aberration of KRAS is selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the first mutant form and/or the second mutant form comprises an aberration of KRAS, wherein the aberration of KRAS is selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the first mutant form and/or the second mutant form comprises an aberration of KRAS, wherein the aberration of KRAS is selected from the group consisting of KRAS G12C, G12D, G12R, G12S, G12V and G13D. In some embodiments, the first mutant form and/or the second mutant form comprises an aberration of KRAS, wherein the aberration of KRAS is selected from G12C, G12D and Q61K. In some embodiments, the first mutant form comprises an aberration of KRAS comprising KRAS G12C, and the second mutant form comprises an aberration of KRAS comprising KRAS G12D. In some embodiments, the first mutant form comprises an aberration of KRAS comprising KRAS G12C, and the second mutant form comprises an aberration of KRAS comprising KRAS Q61K. In some embodiments, the first mutant form comprises an aberration of KRAS comprising KRAS G12D, and the second mutant form comprises an aberration of KRAS comprising KRAS Q61K.

In some embodiments, the RNAi (e.g., siRNA) comprises a plurality of RNAi (e.g., siRNA) comprising a first RNAi (e.g., a first siRNA), a second RNAi (e.g., a second siRNA), and a third RNAi (e.g., siRNA). In some embodiments, the first RNAi targets a first mutant form of KRAS, the second RNAi targets a second mutant form of KRAS, and the third RNAi targets a third mutant form of KRAS. In some embodiments, the first, second and third KRAS mutant form each comprises an aberration of KRAS comprising a mutation on codon 12, 13, 17, 34 and/or 61 of KRAS. In some embodiments, the first, second and third KRAS mutant form each comprises an aberration of KRAS selected from the group consisting of G12C, G12S, G12R, G12F, G12L, G12N, G12A, G12D, G12S, G12V, G13C, G13S, G13R, G13A, G13D, G13V, G13P, S17G, P34S, Q61E, Q61K, Q61L, Q61R, Q61P, Q61H, K117N, A146P, A146T and A146V. In some embodiments, the first, second and third KRAS mutant form each comprises an aberration of KRAS selected from the group consisting of G12C, G12S, G12R, G12F, G12L, G12N, G12A, G12D, G12V, G13C, G13S, G13D, G13V, G13P, S17G, P34S, Q61K, Q61L, Q61R, and Q61H. In some embodiments, the first, second and third KRAS mutant form each comprises an aberration of KRAS selected from the group consisting of G12C, G12R, G12S, G12A, G12D, G12V, G13C, G13R, G13S, G13A, G13D, G13V, Q61K, Q61L, Q61R, Q61H, K117N, A146P, A146T and A146V. In some embodiments, the first, second and third KRAS mutant form each comprises an aberration of KRAS selected from the group consisting of KRAS G12A, G12C, G12D, G12R, G12S, G12V, G13A, G13C, G13D, G13R, G13S, G13V, Q61E, Q61H, Q61K, Q61L, Q61P, and Q61R. In some embodiments, the first, second and third KRAS mutant form each comprises an aberration of KRAS selected from the group consisting of KRAS G12C, G12D, G12R, G12S, G12V, G13D and Q61K. In some embodiments, the first, second and third KRAS mutant form each comprises an aberration of KRAS selected from the group consisting of G12C, G12D and Q61K. In some embodiments, the first mutant form comprises an aberration of KRAS comprising KRAS G12C, the second mutant form comprises an aberration of KRAS comprising KRAS G12D, and the third mutant form comprises an aberration of KRAS comprising KRAS Q61K.

In some embodiments, the RNAi (e.g., siRNA) comprises an RNAi (e.g., siRNA) targeting KRAS comprising a sequence of 5'-GUUGGAGCUUGUGGCGUAGTT-3' (sense) (SEQ ID NO: 179), 5'-CUACGCCACCAGCUC-CAACTT-3 (anti-sense) (SEQ ID NO: 185), 5'-GAAGUG-CAUACACCGAGACTT-3' (sense) (SEQ ID NO: 182), 5'-GUCUCGGUGUAGCACUUCTT-3' (anti-sense) (SEQ ID NO: 183), 5'-GUUGGAGCUGUUGGCGUAGTT-3' (sense) (SEQ ID NO: 184) and/or 5'-CUACGCCAACAG-CUCCAACTT-3' (anti-sense) (SEQ ID NO: 185). In some embodiments, the RNAi (e.g., siRNA) comprises an RNAi (e.g., siRNA) targeting KRAS comprising a nucleic acid sequence selected from sequences with SEQ ID NOS: 179, 180, 182-185. In some embodiments, the RNAi (e.g., siRNA) comprises an RNAi (e.g., siRNA) targeting KRAS comprising a sequence targeting KRAS G12S, such as the siRNA sequences disclosed in Acunzo, M. et al., Proc Natl Acad Sci USA. 2017 May 23; 114(21):E4203-E4212. In some embodiments, the RNAi (e.g., siRNA) comprises an RNAi (e.g., siRNA) targeting KRAS as disclosed in WO2014013995, JP2013212052, WO2014118817, WO2012129352, WO2017179660, JP2013544505, U.S. Pat. Nos. 8,008,474, 7,745,611, 7,576,197, 7,507,811, each of which is incorporated fully in this application.

In some embodiments, the RNAi includes, without limitation, siRNA, shRNA, and miRNA. The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence, interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Interfering RNA includes "small-interfering RNA" or "siRNA," e.g., interfering RNA of about 15-60, 15-50, or 5-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 5-30, 5-25, or 19-25 base pairs in length, preferably about 8-22, 9-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. Preferably, siRNA are chemically synthesized. siRNA can also be generated by cleavage of longer dsRNA (e.g., dsRNA greater than about 25 nucleotides in length) with the E coli RNase III or Dicer. These enzymes process the dsRNA into biologically active siRNA (see, e.g., Yang et al., Proc Natl. Acad. Set. USA, 99:9942-9947 (2002); Calegari et al., Proc. Natl. Acad. Sci. USA, 99: 14236 (2002); Byrom et al., Ambion TeehNotes, 10(1):4-6 (2003); Kawasaki et al., Nucleic Acids Res., 3 1:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops). A small hairpin RNA or short hairpin RNA (shRNA) is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. Suitable lengths of the RNAi include, without limitation, about 5 to about 200 nucleotides, or 10-50 nucleotides or base pairs or 15-30 nucleotides or base pairs. In some embodiments, the RNAi is substantially complementary (such as at least about 60%, 70%, 80%, 90%, 95%, 98%, 99%, or more identical to) the corresponding target gene. In some embodiments, the RNAi is modified, for example by incorporating non-naturally occurring nucleotides.

In some embodiments, the RNAi is a double-stranded RNAi. Suitable lengths of the RNAi include, without limitation, about 5 to about 200 nucleotides, or 10-50 nucleotides or base pairs or 15-30 nucleotides or base pairs. In some embodiments, the RNAi is substantially complementary (such as at least about 60%, 70%, 80%, 90%, 95%, 98%, 99%, or more identical) to the corresponding target gene. In some embodiments, the RNAi is modified, for example by incorporating non-naturally occurring nucleotides.

In some embodiments, the RNAi specifically targets an RNA molecule, such as an mRNA, encoding a protein involved in a disease, such as cancer. In some embodiments, the disease is cancer, such as a solid tumor or hematological malignancy, and the interfering RNA targets mRNA encoding a protein involved in the cancer, such as a protein involved in regulating the progression of the cancer. In some embodiments, the RNAi targets an oncogene involved in the cancer.

In some embodiments, the RNAi specifically targets an RNA molecule, such as an mRNA, encoding a protein involved in negatively regulating an immune response. In some embodiments, the interfering RNA targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4.

In some embodiments, the RNAi is an miRNA. A microRNA (abbreviated miRNA) is a short ribonucleic acid (RNA) molecule found in eukaryotic cells. A microRNA molecule has very few nucleotides (an average of 22) compared with other RNAs. miRNAs are post-transcriptional regulators that bind to complementary sequences on target messenger RNA transcripts (mRNAs), usually resulting in translational repression or target degradation and gene silencing. The human genome may encode over 1000 miRNAs, which may target about 60% of mammalia genes and are abundant in many human cell types. Suitable lengths of the miRNAs include, without limitation, about 5 to about 200 nucleotides, or about 0-50 nucleotides or base pairs or 15-30 nucleotides or base pairs. In some embodiments, the miRNA is substantially complementary (such as at least about 60%, 70%, 80%, 90%, 95%, 98%, 99%, or more identical to) the corresponding target gene. In some embodiments, the miRNA is modified, for example by incorporating non-naturally occurring nucleotides.

Virus

In some embodiments, according to any of the complexes and/or nanoparticles described herein, the virus is a recombinant virus, including recombinant adeno-associated virus (AAV), adenovirus, lentivirus, retrovirus, herpes simplex virus (HSV), poxvirus, Epstein-Barr virus (EBV), vaccinia virus, and human cytomegalovirus (hCMV). In some embodiments, the recombinant virus comprises a transgene for insertion into a cell genome. In some embodiments, the transgene is a therapeutic transgene. In some embodiments, the transgene encodes a protein, such as a therapeutic protein. In some embodiments, the transgene encodes an inhibitory RNA (RNAi), such as an RNAi targeting an endogenous gene, e.g., a disease-associated endogenous gene. In some embodiments, the transgene encodes a CAR. In some embodiments, the virus comprises a first transgene encoding an RNAi. In some embodiments, the RNAi is a therapeutic RNAi targeting an endogenous gene involved in a disease or condition. In some embodiments, the therapeutic RNAi targets a disease-associated form of the endogenous gene (e.g., a gene encoding a mutant protein, or a gene resulting in abnormal expression of a protein). In some embodiments, the virus comprises a second transgene encoding a protein. In some embodiments, the protein is a therapeutic protein useful for treating a disease or condition. In some embodiments, the second transgene is a therapeutic form of an endogenous gene (e.g., the second transgene encodes a wild-type or functional form of a mutant protein encoded by the endogenous gene, or the second transgene results in normal expression of a protein encoded by the endogenous gene). In some embodiments, there is provided a virus comprising the first transgene and the second transgene.

In some embodiments, according to any of the complexes and/or nanoparticles described herein, the virus is a modified virus, including modified adeno-associated virus (AAV), adenovirus, lentivirus, retrovirus, herpes simplex virus (HSV), poxvirus, Epstein-Barr virus (EBV), vaccinia virus, and human cytomegalovirus (hCMV). In some embodiments, according to any of the complexes and/or nanoparticles described herein, the virus is an inactivated virus, including inactivated adeno-associated virus (AAV), adenovirus, lentivirus, retrovirus, herpes simplex virus (HSV), poxvirus, Epstein-Barr virus (EBV), vaccinia virus, and human cytomegalovirus (hCMV). In some embodiments, according to any of the complexes and/or nanoparticles described herein, the virus is a replication-deficient virus, including replication-deficient adeno-associated virus (AAV), adenovirus, lentivirus, retrovirus, herpes simplex virus (HSV), poxvirus, Epstein-Barr virus (EBV), vaccinia virus, and human cytomegalovirus (hCMV). In some embodiments, according to any of the complexes and/or nanoparticles described herein, the virus is only able to replicate in target cells.

Nanoparticles

In some embodiments, there is provided a nanoparticle for intracellular delivery of a cargo molecule that comprises a core comprising any one or more cargo delivery complex as described herein.

In some embodiments, there is provided a nanoparticle for intracellular delivery of a cargo molecule comprising a core comprising one or more cargo delivery complexes described herein. In some embodiments, the nanoparticle core comprises a plurality of cargo delivery complexes. In some embodiments, the nanoparticle core comprises a plurality of cargo delivery complexes present in a predetermined ratio. In some embodiments, the predetermined ratio is selected to allow the most effective use of the nanoparticle in any of the methods described below in more detail. In some embodiments, the nanoparticle core further comprises one or more additional cell-penetrating peptides and/or one or more additional cargo.

In some embodiments, there is provided a nanoparticle for intracellular delivery of a cargo molecule comprising a core comprising a cargo delivery complex described herein, wherein at least one cell-penetrating peptide in the cargo delivery complex is associated with the cargo. In some embodiments, the association is non-covalent. In some embodiments, the association is covalent.

In some embodiments, the nanoparticle further comprises a surface layer (e.g., a shell) comprising a peripheral cell-penetrating peptide (i.e., CPP), wherein the core is coated by the shell. In some embodiments, the peripheral CPP is the same as a CPP in the core. In some embodiments, the peripheral CPP is different than any of the CPPs in the core. In some embodiments, the peripheral CPP includes, but is not limited to, a PTD-based peptide, an amphipathic peptide, a poly-arginine-based peptide, an MPG peptide, a CADY peptide, a VEPEP peptide (such as a VEPEP-3, VEPEP-4, VEPEP-5, VEPEP-6, or VEPEP-9 peptide), an ADGN-100 peptide, a Pep-1 peptide, and a Pep-2 peptide. In some embodiments, the peripheral CPP is a VEPEP-3 peptide, a VEPEP-6 peptide, a VEPEP-9 peptide, or an ADGN-100 peptide. IN some embodiments, the peripheral cell-penetrating peptide is selected from the group consisting of PEP-1 peptides, PEP-2 peptides, PEP-3 peptides, VEPEP-3 peptides, VEPEP-6 peptides, VEPEP-9 peptides, and ADGN-100 peptides. In some embodiments, at least some of the peripheral cell-penetrating peptides in the surface layer are linked to a targeting moiety. In some embodiments, the linkage is covalent. In some embodiments, the covalent linkage is by chemical coupling. In some embodiments, the covalent linkage is by genetic methods. In some embodiments, the nanoparticle further comprises an intermediate layer between the core of the nanoparticle and the surface layer. In some embodiments, the intermediate layer comprises an intermediate CPP. In some embodiments, the intermediate CPP is the same as a CPP in the core. In some embodiments, the intermediate CPP is different than any of the CPPs in the core. In some embodiments, the intermediate CPP includes, but is not limited to, a PTD-based peptide, an amphipathic peptide, a poly-arginine-based peptide, an MPG peptide, a CADY peptide, a VEPEP peptide (such as a VEPEP-3, VEPEP-6, or VEPEP-9 peptide), an ADGN-100 peptide, a Pep-1 peptide, and a Pep-2 peptide. In some embodiments, the intermediate CPP is a VEPEP-3 peptide, a VEPEP-6 peptide, a VEPEP-9 peptide, or an ADGN-100 peptide.

In some embodiments, according to any of the nanoparticles described herein, the mean size (diameter) of the nanoparticle is from about 20 nm to about 1000 nm, including for example from about 50 nm to about 800 nm, from about 75 nm to about 600 nm, from about 100 nm to about 600 nm, and from about 200 nm to about 400 nm. In some embodiments, the mean size (diameter) of the nanoparticle is no greater than about 1000 nanometers (nm), such as no greater than about any of 900, 800, 700, 600, 500, 400, 300, 200, or 100 nm. In some embodiments, the average or mean diameter of the nanoparticle is no greater than about 200 nm. In some embodiments, the average or mean diameters of the nanoparticles is no greater than about 150 nm. In some embodiments, the average or mean diameter of the nanoparticle is no greater than about 100 nm. In some embodiments, the average or mean diameter of the nanoparticle is about 20 nm to about 400 nm. In some embodiments, the average or mean diameter of the nanoparticle is about 30 nm to about 400 nm. In some embodiments, the average or mean diameter of the nanoparticle is about 40 nm to about 300 nm. In some embodiments, the average or mean diameter of the nanoparticle is about 50 nm to about 200 nm. In some embodiments, the average or mean diameter of the nanoparticle is about 60 nm to about 150 nm. In some embodiments, the average or mean diameter of the nanoparticle is about 70 nm to about 100 nm. In some embodiments, the nanoparticles are sterile-filterable.

In some embodiments, the zeta potential of the nanoparticle is from about −30 mV to about 60 mV (such as about any of −30, −25, −20, −15, −10, −5, 0, 5, 10, 15, 20, 25, 30, 35, 40, 45, 50, 55, and 60 mV, including any ranges between these values). In some embodiments, the zeta potential of the nanoparticle is from about −30 mV to about 30 mV, including for example from about −25 mV to about 25 mV, from about −20 mV to about 20 mV, from about −15 mV to about 15 mV, from about −10 mV to about 10 mV, and from about −5 mV to about 10 mV. In some embodiments, the polydispersity index (PI) of the nanoparticle is from about 0.05 to about 0.6 (such as about any of 0.05, 0.1, 0.15, 0.2, 0.25, 0.3, 0.35, 0.4, 0.45, 0.5, 0.55, and 0.6, including any ranges between these values). In some embodiments, the nanoparticle is substantially non-toxic.

Compositions

In some embodiments, there is provided a composition (e.g., a pharmaceutical composition) comprising a cargo delivery complex or nanoparticle as described herein. In some embodiments, the composition is a pharmaceutical composition comprising a cargo delivery complex or nanoparticle as described herein and a pharmaceutically acceptable diluent, excipient, and/or carrier. In some embodiments, the concentration of the complex or nanoparticle in the composition is from about 1 nM to about 100 mM, including for example from about 10 nM to about 50 mM, from about 25 nM to about 25 mM, from about 50 nM to about 10 mM, from about 100 nM to about 1 mM, from about 500 nM to about 750 µM, from about 750 nM to about 500 µM, from about 1 µM to about 250 µM, from about 10 µM to about 200 µM, and from about 50 µM to about 150 µM. In some embodiments, the pharmaceutical composition is lyophilized.

The term "pharmaceutically acceptable diluent, excipient, and/or carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" refers to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like, including lyophilization aids. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical diluent, excipient, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

In some embodiments, a composition comprising a cargo delivery complex or nanoparticle as described herein further comprises a pharmaceutically acceptable diluent, excipient, and/or carrier. In some embodiments, the pharmaceutically acceptable diluent, excipient, and/or carrier affects the level of aggregation of a cargo delivery complex or nanoparticle in the composition and/or the efficiency of intracellular delivery mediated by a cargo delivery complex or nanoparticle in the composition. In some embodiments, the extent and/or direction of the effect on aggregation and/or delivery efficiency mediated by the pharmaceutically acceptable diluent, excipient, and/or carrier is dependent on the relative amount of the pharmaceutically acceptable diluent, excipient, and/or carrier in the composition.

For example, in some embodiments, the presence of a pharmaceutically acceptable diluent, excipient, and/or carrier (such as a salt, sugar, chemical buffering agent, buffer solution, cell culture medium, or carrier protein) at one or more concentrations in the composition does not promote and/or contribute to aggregation of the cargo delivery complex or nanoparticle, or promotes and/or contributes to the formation of aggregates of the cargo delivery complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the cargo delivery complex or nanoparticle. In some embodiments, the composition comprises the pharmaceutically acceptable diluent, excipient, and/or carrier at a concentration that does not promote and/or contribute to aggregation of the cargo delivery complex or nanoparticle, or promotes and/or contributes to the formation of aggregates of the cargo delivery complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 150% larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 100% larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 50% larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 20% larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 15% larger than the size of the cargo delivery complex or nanoparticle. In some embodiments, the composition comprises the pharmaceutically acceptable diluent, excipient, and/or carrier at a concentration that promotes and/or contributes to the formation of aggregates of the cargo delivery complex or nanoparticles having a size no more than about 10% larger than the size of the cargo delivery complex or nanoparticle. In some embodiments, the pharmaceutically acceptable diluent, excipient, and/or carrier is a salt, including, without limitation, NaCl. In some embodiments, the pharmaceutically acceptable diluent, excipient, and/or carrier is a sugar, including, without limitation, sucrose, glucose, and mannitol. In some embodiments, the pharmaceutically acceptable diluent, excipient, and/or carrier is a chemical buffering agent, including, without limitation, HEPES. In some embodiments, the pharmaceutically acceptable diluent, excipient, and/or carrier is a buffer solution, including, without limitation, PBS. In some embodiments, the pharmaceutically acceptable diluent, excipient, and/or carrier is a cell culture medium, including, without limitation, DMEM. Particle size can be determined using any means known in the art for measuring particle size, such as by dynamic light scattering (DLS). For example, in some embodiments, an aggregate having a Z-average as measured by DLS that is 10% greater than the Z-average as measured by DLS of a cargo delivery complex or nanoparticle is 10% larger than the cargo delivery complex or nanoparticle.

In some embodiments, the composition comprises a salt (e.g., NaCl) at a concentration that does not promote and/or contribute to aggregation of the cargo delivery complex or nanoparticle, or promotes and/or contributes to the formation of aggregates of the cargo delivery complex or nanoparticles having a size no more than about 100% (such as no more than about any of 90, 80, 70, 60, 50, 40, 30, 20, 10, 9, 8, 7, 6, 5, 4, 3, 2, or 1%, including any ranges between any of these values) larger than the size of the cargo delivery complex or nanoparticle. In some embodiments, the composition comprises a salt (e.g., NaCl) at a concentration that promotes and/or contributes to the formation of aggregates of the cargo delivery complex or nanoparticles having a size no more than about 75% larger than the size of the cargo delivery complex or nanoparticle. In some embodiments, the composition comprises a salt (e.g., NaCl) at a concentration that promotes and/or contributes to the formation of aggregates of the cargo delivery complex or nanoparticles having a size no more than about 50% larger than the size of the cargo delivery complex or nanoparticle. In some embodiments, the composition comprises a salt (e.g., NaCl) at a concentration that promotes and/or contributes to the formation of aggregates of the cargo delivery complex or nanoparticles having a size no more than about 20% larger than the size of the cargo delivery complex or nanoparticle. In some embodiments, the composition comprises a salt (e.g., NaCl) at a concentration that promotes and/or contributes to the formation of aggregates of the cargo delivery complex or nanoparticles having a size no more than about 15% larger than the size of the cargo delivery complex or nanoparticle. In some embodiments, the composition comprises a salt (e.g., NaCl) at a concentration that promotes and/or contributes to the formation of aggregates of the cargo delivery complex or nanoparticles having a size no more than about 10% larger than the size of the cargo delivery complex or nanoparticle. In some embodiments, the concentration of the salt in the composition is no more than about 100 mM (such as no more than about any of 90, 80, 70, 60, 50, 40, 30, 20, 10, 9, 8, 7, 6, 5, 4, 3, 2, or 1 mM, including any ranges between any of these values). In some embodiments, the salt is NaCl.

In some embodiments, the composition comprises a sugar (e.g., sucrose, glucose, or mannitol) at a concentration that does not promote and/or contribute to aggregation of the cargo delivery complex or nanoparticle, or promotes and/or contributes to the formation of aggregates of the cargo delivery complex or nanoparticles having a size no more than about 25% (such as no more than about any of 24, 23, 22, 21, 20, 19, 18, 17, 16, 15, 14, 13, 12, 11, 10, 9, 8, 7, 6, 5, 4, 3, 2, or 1%, including any ranges between any of these values) larger than the size of the cargo delivery complex or nanoparticle. In some embodiments, the composition comprises a sugar (e.g., sucrose, glucose, or mannitol) at a concentration that promotes and/or contributes to the formation of aggregates of the cargo delivery complex or nanoparticles having a size no more than about 75% larger than the size of the cargo delivery complex or nanoparticle. In some embodiments, the composition comprises a sugar (e.g., sucrose, glucose, or mannitol) at a concentration that promotes and/or contributes to the formation of aggregates of the cargo delivery complex or nanoparticles having a size no more than about 50% larger than the size of the cargo delivery complex or nanoparticle. In some embodiments, the composition comprises a sugar (e.g., sucrose, glucose, or mannitol) at a concentration that promotes and/or contributes to the formation of aggregates of the cargo delivery complex or nanoparticles having a size no more than about 20% larger than the size of the cargo delivery complex or nanoparticle. In some embodiments, the composition comprises a sugar (e.g., sucrose, glucose, or mannitol) at a concentration that promotes and/or contributes to the formation of aggregates of the cargo delivery complex or nanoparticles having a size no more than about 15% larger than the size of the cargo delivery complex or nanoparticle.

In some embodiments, the composition comprises a sugar (e.g., sucrose, glucose, or mannitol) at a concentration that promotes and/or contributes to the formation of aggregates of the cargo delivery complex or nanoparticles having a size no more than about 10% larger than the size of the cargo delivery complex or nanoparticle. In some embodiments, the concentration of the sugar in the composition is no more than about 20% (such as no more than about any of 18, 16, 14, 12, 10, 9, 8, 7, 6, 5, 4, 3, 2, or 1%, including any ranges between any of these values). In some embodiments, the sugar is sucrose. In some embodiments, the sugar is glucose. In some embodiments, the sugar is mannitol.

In some embodiments, the composition comprises a chemical buffering agent (e.g., HEPES or phosphate) at a concentration that does not promote and/or contribute to aggregation of the cargo delivery complex or nanoparticle, or promotes and/or contributes to the formation of aggregates of the cargo delivery complex or nanoparticles having a size no more than about 10% (such as no more than about any of 9, 8, 7, 6, 5, 4, 3, 2, or 1%, including any ranges between any of these values) larger than the size of the cargo delivery complex or nanoparticle. In some embodiments, the composition comprises a chemical buffering agent (e.g., HEPES or phosphate) at a concentration that promotes and/or contributes to the formation of aggregates of the cargo delivery complex or nanoparticles having a size no more than about 7.5% larger than the size of the cargo delivery complex or nanoparticle. In some embodiments, the composition comprises a chemical buffering agent (e.g., HEPES or phosphate) at a concentration that promotes and/or contributes to the formation of aggregates of the cargo delivery complex or nanoparticles having a size no more than about 5% larger than the size of the cargo delivery complex or nanoparticle. In some embodiments, the composition comprises a chemical buffering agent (e.g., HEPES or phosphate) at a concentration that promotes and/or contributes to the formation of aggregates of the cargo delivery complex or nanoparticles having a size no more than about 3% larger than the size of the cargo delivery complex or nanoparticle. In some embodiments, the composition comprises a chemical buffering agent (e.g., HEPES or phosphate) at a concentration that promotes and/or contributes to the formation of aggregates of the cargo delivery complex or nanoparticles having a size no more than about 1% larger than the size of the cargo delivery complex or nanoparticle. In some embodiments, the composition comprises a chemical buffering agent (e.g., HEPES or phosphate) at a concentration that does not promote and/or contribute to the formation of aggregates of the cargo delivery complex or nanoparticles. In some embodiments, the chemical buffering agent is HEPES. In some embodiments, the HEPES is added to the composition in the form of a buffer solution comprising HEPES. In some embodiments, the solution comprising HEPES has a pH between about 5 and about 9 (such as about any of 5, 5.5, 6, 6.5, 7, 7.5, 8, 8.5, and 9, including any ranges between these values). In some embodiments, the composition comprises HEPES at a concentration of no more than about 75 mM (such as no more than about any of 70, 65, 60, 55, 50, 45, 40, 35, 30, 25, 20, 15, 10 mM or less, including any ranges between any of these values). In some embodiments, the chemical buffering agent is phosphate. In some embodiments, the phosphate is added to the composition in the form of a buffer solution comprising phosphate. In some embodiments, the composition does not comprise PBS.

In some embodiments, the composition comprises a cell culture medium (e.g., DMEM or Opti-MEM) at a concentration that does not promote and/or contribute to aggregation of the cargo delivery complex or nanoparticle, or promotes and/or contributes to the formation of aggregates of the cargo delivery complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the cargo delivery complex or nanoparticle. In some embodiments, the composition comprises a cell culture medium (e.g., DMEM or Opti-MEM) at a concentration that promotes and/or contributes to the formation of aggregates of the cargo delivery complex or nanoparticles having a size no more than about 150% larger than the size of the cargo delivery complex or nanoparticle. In some embodiments, the composition comprises a cell culture medium (e.g., DMEM or Opti-MEM) at a concentration that promotes and/or contributes to the formation of aggregates of the cargo delivery complex or nanoparticles having a size no more than about 100% larger than the size of the cargo delivery complex or nanoparticle. In some embodiments, the composition comprises a cell culture medium (e.g., DMEM or Opti-MEM) at a concentration that promotes and/or contributes to the formation of aggregates of the cargo delivery complex or nanoparticles having a size no more than about 50% larger than the size of the cargo delivery complex or nanoparticle. In some embodiments, the composition comprises a cell culture medium (e.g., DMEM or Opti-MEM) at a concentration that promotes and/or contributes to the formation of aggregates of the cargo delivery complex or nanoparticles having a size no more than about 25% larger than the size of the cargo delivery complex or nanoparticle. In some embodiments, the composition comprises a cell culture medium (e.g., DMEM or Opti-MEM) at a concentration that promotes and/or contributes to the formation of aggregates of the cargo delivery complex or nanoparticles having a size no more than about 10% larger than the size of the cargo delivery complex or nanoparticle. In some embodiments, the cell culture medium is DMEM. In some embodiments, the composition comprises DMEM at a concentration of no more than about 70% (such as no more than about any of 65, 60, 55, 50, 45, 40, 35, 30, 25, 20, 15, 10%, or less, including any ranges between any of these values).

In some embodiments, the composition comprises a carrier protein (e.g., albumin) at a concentration that does not promote and/or contribute to aggregation of the cargo delivery complex or nanoparticle, or promotes and/or contributes to the formation of aggregates of the cargo delivery complex or nanoparticles having a size no more than about 200% (such as no more than about any of 190, 180, 170, 160, 150, 140, 130, 120, 110, 100, 90, 80, 70, 60, 50, 40, 30, 20, 10, 9, 8, 7, 6, 5, 4, 3, 2, or 1%, including any ranges between any of these values) larger than the size of the cargo delivery complex or nanoparticle. In some embodiments, the composition comprises a carrier protein (e.g., albumin) at a concentration that promotes and/or contributes to the formation of aggregates of the cargo delivery complex or nanoparticles having a size no more than about 150% larger than the size of the cargo delivery complex or nanoparticle. In some embodiments, the composition comprises a carrier protein (e.g., albumin) at a concentration that promotes and/or contributes to the formation of aggregates of the cargo delivery complex or nanoparticles having a size no more than about 100% larger than the size of the cargo delivery complex or nanoparticle. In some embodiments, the composition comprises a carrier protein (e.g., albumin) at a concentration that promotes and/or contributes to the formation of aggregates of the cargo delivery complex or nanoparticles having a size no more than about 50% larger than the size of the cargo delivery complex or nanoparticle. In some embodiments, the composition comprises a carrier protein (e.g., albumin) at a concentration that promotes and/or contributes to the formation of aggregates of the cargo delivery complex or nanoparticles having a size no more than about 25% larger than the size of the cargo delivery complex or nanoparticle. In some embodiments, the composition comprises a carrier protein (e.g., albumin) at a concentration that promotes and/or contributes to the formation of aggregates of the cargo delivery complex or nanoparticles having a size no more than about 10% larger than the size of the cargo delivery complex or nanoparticle. In some embodiments, the carrier protein is albumin. In some embodiments, the albumin is human serum albumin.

In some embodiments, a pharmaceutical composition as described herein is formulated for intravenous, intratumoral, intraarterial, topical, intraocular, ophthalmic, intraportal, intracranial, intracerebral, intracerebroventricular, intrathecal, intravesicular, intradermal, subcutaneous, intramuscular, intranasal, intratracheal, pulmonary, intracavity, or oral administration.

Exemplary dosing frequencies include, but are not limited to, no more than once every three days.

Methods of Preparation

In some embodiments, there is provided a method of preparing a cargo delivery complex or nanoparticle as described herein.

In some embodiments, there is provided a method of preparing the cargo delivery complex comprising a first peptide and a second peptide as described above, comprising a) combining the first peptide and the second peptide, thereby forming a peptide mixture; b) combining the peptide mixture with the cargo, thereby forming the cargo delivery complex.

In some embodiments, there is provided a method of preparing the cargo delivery complex comprising a peptide and a cargo molecule as described above, comprising combining the peptide with the cargo molecule, thereby forming the cargo delivery complex.

In some embodiments, the peptide or the peptide mixture and the cargo molecule are combined at a molar ratio from about 1:1 to about 100:1 (such as about between about 1:1 and about 50:1, or about 20:1), respectively.

In some embodiments, the method comprises mixing a first solution comprising the cargo molecule with a second solution comprising the peptide or peptide mixture to form a third solution, wherein the third solution comprises or is adjusted to comprise i) about 0-5% sucrose, ii) about 0-5% glucose, iii) about 0-50% DMEM, iv) about 0-80 mM NaCl, or v) about 0-20% PBS, and wherein the third solution is incubated to allow formation of the cargo delivery complex. In some embodiments, the first solution comprises the cargo in sterile water and/or wherein the second solution comprises the peptide or peptide mixture in sterile water. In some embodiments, the third solution is adjusted to comprise i) about 0-5% sucrose, ii) about 0-5% glucose, iii) about 0-50% DMEM, iv) about 0-80 mM NaCl, or v) about 0-20% PBS after incubating to form the cargo delivery complex.

In some embodiments, the method further comprises a filtration process, wherein the cargo delivery complex is filtered through a pore-sized membrane. In some embodiments, the pore has a diameter of at least about 0.1 μm (such as at least about 0.1 μm, 0.15 μm, 0.2 μm, 0.25 μm, 0.3 μm, 0.35 μm, 0.4 μm, 0.45 μm, 0.5 μm, 0.6 μm, 0.7 μm, 0.8 μm, 0.9 μm, 1.0 μm, 1.1 μm or 1.2 μm). In some embodiments, the pore has a diameter of no more about 1.2 μm, 1.0 μm, 0.8 μm, 0.6 μm, 0.5 μm, 0.45 μm, 0.4 μm, 0.35 μm, 0.3 μm, or 0.25 m. In some embodiments, the port has a diameter of about 0.1 μm to about 1.2 μm (such as about 0.1 to about 0.8 μm, about 0.2 to about 0.5 μm).

In some embodiments, for a stable composition comprising a cargo molecule delivery complex or nanoparticle of the application, the average diameter of the complex or nanoparticle does not change by more than about 10%, and the polydispersity index does not change by more than about 10%.

Also provided are methods of preparing any of the peptides comprising cell-penetrating peptides described herein.

Methods of Use

The present application also provides methods of delivering one or more cargo into a cell. In some embodiments, the methods comprise contacting the cell with the cargo delivery complex or the nanoparticle, wherein the cargo delivery complex comprises one or more cargo.

In some embodiments, there is provided a method of delivering one or more cargo into a cell, comprising contacting a cell with a cargo delivery complex described herein, wherein the cargo delivery complex comprises one or more cargo. In some embodiments, the cell is a cancer cell. In some embodiments, the cell is a human cell. In some embodiments, the cell expresses an antigen (such as a tumor antigen), wherein the cargo molecule in the cargo delivery complex specifically binds to or targets the antigen.

The present application also provides methods of delivering one or more cargo into a tissue or organ of an individual, comprising administering into the individual an effective amount of the cargo delivery complexes, nanoparticles, or pharmaceutical compositions as described herein, wherein the tissue or organ is selected from the group consisting of liver, lung, kidney, brain, intestine, spleen, heart, muscle, and lymph node.

In some embodiments, there is provided a method of delivering one or more cargo molecule into a tissue or organ of an individual, comprising administering into the individual an effective amount of a cargo delivery complex described herein, wherein the tissue or organ is selected from the group consisting of liver, lung, kidney, brain, intestine, spleen, heart, muscle, and lymph node. In some embodiments, the tissue or organ is selected from the group consisting of liver, lung, kidney, brain, spleen and lymph node.

In some embodiments, there is provided a method of promoting retention of one or more cargo molecule in a tissue or organ of an individual, comprising administering into the individual an effective amount of a cargo delivery complex described herein, wherein the tissue or organ is selected from the group consisting of liver, lung, kidney, brain, intestine, spleen, heart, muscle, and lymph node. In some embodiments, the tissue or organ is selected from the group consisting of liver, lung, kidney, brain, spleen and lymph node.

In some embodiments, there is provided a method of promoting stability of one or more cargo molecule in an individual, comprising administering into the individual an effective amount of a cargo delivery complex described herein.

In some embodiments, there is provided a method of promoting retention of one or more cargo molecule in a tissue or organ of an individual, comprising a) combining a first peptide comprising a first cell-penetrating peptide and a secom peptide comprising a second cell-penetrating peptide thereby forming a peptide mixture, wherein the second peptide comprises a polyethylene glycol (PEG) moiety that is covalently linked to the second cell-penetrating peptide, and wherein the first peptide does not have a PEG moiety; b) combining the peptide mixture with the cargo molecule, thereby forming the cargo delivery complex; and c) administering the cargo delivery complex into an individual. In some embodiments, the tissue or organ is selected from the group consisting of liver, lung, kidney, brain, intestine, spleen, heart, muscle, and lymph node. In some embodiments, the tissue or organ is selected from the group consisting of liver, lung, kidney, brain, spleen and lymph node. In some embodiments, there is provided a method of promoting stability of one or more cargo molecule in an individual, comprising a) combining a first peptide comprising a first cell-penetrating peptide and a secom peptide comprising a second cell-penetrating peptide thereby forming a peptide mixture, wherein the second peptide comprises a polyethylene glycol (PEG) moiety that is covalently linked to the second cell-penetrating peptide, and wherein the first peptide does not have a PEG moiety; b) combining the peptide mixture with the cargo molecule, thereby forming the cargo delivery complex; and c) administering the cargo delivery complex into an individual. In some embodiments, the ratio of the first cell-penetrating peptide to the second cell-penetrating peptide is about 20:1 to about 1:1 (such as about 15:1 to about 2:1, about 10:1 to about 4:1). Examples of peptides (e.g., cell-penetrating peptides or peptides comprising cell-penetrating peptides), cargos, and PEG moiety include those described herein. In some embodiments, the PEG moiety is conjugated to the N- or C-terminus of the second cell-penetrating peptide. In some embodiments, the PEG moiety is conjugated to a site within the second cell-penetrating peptide.

The present application also provides methods of delivering a cargo molecule into an organ/tissue in an individual, comprising administering into the individual a cargo delivery complex as described above.

In some embodiments, there is provided a method of delivering a cargo molecule into an organ/tissue in an individual, comprising administering into the individual a cargo delivery complex, wherein the cargo delivery complex comprises a) a peptide comprising a cell-penetrating peptide and b) a cargo molecule, wherein the peptide further comprises a targeting sequence selected from the group consisting of SEQ ID NOs: 152-162. In some embodiments, the organ or tissue is a tumor tissue, kidney, pancreas, muscle, heart, brain, liver, kidney, lymph node, lung or spleen. In some embodiments, the cell-penetrating peptide is a PTD-based peptide, an amphipathic peptide, a poly-arginine-based peptide, an MPG peptide, a CADY peptide, a PEP-1 peptide, a PEP-2 peptide, or a PEP-3 peptide. In some embodiments, the cell-penetrating peptides are selected from the group consisting of CADY, PEP-1 peptides, PEP-2 peptides, PEP-3 peptides, VEPEP-3 peptides, VEPEP-4 peptides, VEPEP-5 peptides, VEPEP-6 peptides, VEPEP-9 peptides, and ADGN-100 peptides. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., heart or muscle) in an individual, comprising administering (e.g., intravenously) into the individual a cargo delivery complex, wherein the cargo delivery complex comprises a) a peptide comprising a cell-penetrating peptide and b) a cargo molecule (e.g., PNA, oligonucleotide, mRNA), wherein the peptide further comprises a targeting sequence LSSRLDA (SEQ ID NO: 160). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 114. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., brain or liver) in an individual, comprising administering (e.g., intravenously) into the individual a cargo delivery complex, wherein the cargo delivery complex comprises a) a peptide comprising a cell-penetrating peptide and b) a cargo molecule (e.g., siRNA/mRNA), wherein the peptide further comprises a targeting sequence SYTSSTM (SEQ ID NO: 152). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 115, 128, 131, or 132. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., brain or lymph node) in an individual, comprising administering (e.g., intravenously) into the individual a cargo delivery complex, wherein the cargo delivery complex comprises a) a peptide comprising a cell-penetrating peptide and b) a cargo molecule (e.g., siRNA/mRNA/peptide), wherein the peptide further comprises a targeting sequence KSYDTY (SEQ ID NO: 161). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 116 or 119. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., heart or lung) in an individual, comprising administering (e.g., intravenously) into the individual a cargo delivery complex, wherein the cargo delivery complex comprises a) a peptide comprising a cell-penetrating peptide and b) a cargo molecule (e.g., siRNA/mRNA), wherein the peptide further comprises a targeting sequence CARPAR (SEQ ID NO: 156). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 121 or 139. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., brain or lung) in an individual, comprising administering (e.g., intravenously) into the individual a cargo delivery complex, wherein the cargo delivery complex comprises a) a peptide comprising a cell-penetrating peptide and b) a cargo molecule (e.g., siRNA/mRNA), wherein the peptide further comprises a targeting sequence TGNYKA-LHPDHNG (SEQ ID NO: 155). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 122 or 123. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., lung, kidney, liver, tumor, pancreas) in an individual, comprising administering (e.g., intravenously or intramuscularly) into the individual a cargo delivery complex, wherein the cargo delivery complex comprises a) a peptide comprising a cell-penetrating peptide and b) a cargo molecule (e.g., siRNA/mRNA/CRISPR molecule), wherein the peptide further comprises a targeting sequence YIGSR (SEQ ID NO: 157). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence selected from the group consisting of SEQ ID NOs: 88, 94, 96, 98, 101, 103, 105-112, 125, 126, 130, and 135. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., lung, kidney, liver, spleen, brain, tumor, pancreas) in an individual, comprising administering (e.g., intravenously or intramuscularly) into the individual a cargo delivery complex, wherein the cargo delivery complex comprises a) a peptide comprising a cell-penetrating peptide and b) a cargo molecule (e.g., siRNA/mRNA/CRISPR molecule), wherein the peptide further comprises a targeting sequence GYVS (SEQ ID NO: 158). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence selected from the group consisting of SEQ ID NOs: 89, 95, 97, 99, 102, 104, 127, and 136. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., heart) in an individual, comprising administering (e.g., intravenously) into the individual a cargo delivery complex, wherein the cargo delivery complex comprises a) a peptide comprising a cell-penetrating peptide and b) a cargo molecule (e.g., oligonucleotide), wherein the peptide further comprises a targeting sequence CKRAV (SEQ ID NO: 162). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 117. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., brain) in an individual, comprising administering (e.g., intravenously or intramuscularly) into the individual a cargo delivery complex, wherein the cargo delivery complex comprises a) a peptide comprising a cell-penetrating peptide and b) a cargo molecule (e.g., mRNA, siRNA, CRISPR molecule), wherein the peptide further comprises a targeting sequence THRPPNWSPV (SEQ ID NO: 154). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 133 or 138. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., muscle, heart) in an individual, comprising administering (e.g., intravenously or intramuscularly) into the individual a cargo delivery complex, wherein the cargo delivery complex comprises a) a peptide comprising a cell-penetrating peptide and b) a cargo molecule (e.g., mRNA, siRNA, CRISPR molecule), wherein the peptide further comprises a targeting sequence CKTRRVP (SEQ ID NO: 153). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 134 or 137. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., muscle) in an individual, comprising administering (e.g., intravenously or intramuscularly) into the individual a cargo delivery complex, wherein the cargo delivery complex comprises a) a peptide comprising a cell-penetrating peptide and b) a cargo molecule (e.g., peptide, protein, PNA), wherein the peptide further comprises a targeting sequence ASSL-NIA (SEQ ID NO: 159). In some embodiments, the peptide comprises a VEPEP-3 peptide, a VEPEP-6 peptide, a VEPEP-9 peptide, or an ADGN-100 peptide. In some embodiments, the peptide comprises an amino acid sequence selected from the group consisting of SEQ ID NOs: 1-14, 75, 76, and 113-115. In some embodiments, the peptide comprises an amino acid sequence selected from the group consisting of SEQ ID NOs: 15-40, 77, 85, 92-100, 105, 107-109, and 129-139. In some embodiments, the peptide comprises an amino acid sequence selected from the group consisting of SEQ ID NOs: 41-52, 78, and 116-120. In some embodiments, the peptide comprises an amino acid sequence selected from the group consisting of SEQ ID NOs: 53-70, 79, 80, 86-91, 101-104, 106, 110-112, and 121-128. In some embodiments, the peptide comprises an amino acid sequence set forth in SEQ ID NO: 113. In some embodiments, the targeting sequence is covalently linked to N-terminus of the cell-penetrating peptide. In some embodiments, the targeting sequence is covalently linked to N-terminus of the cell-penetrating peptide via a linker. In some embodiments, the linker is selected from the group consisting of beta alanine, cysteine, cysteamide bridge, poly glycine (such as G2 or G4), a PEG linker moiety, Aun (11-amino-undecanoic acid), Ava (5-amino pentanoic acid), and Ahx (aminocaproic acid). In some embodiments, the linker comprises a PEG linker moiety. In some embodiments, the PEG linker moiety consists of about one to ten (such as about 1-8, 2-7, 1-5, or 6-10) ethylene glycol units. In some embodiments, the targeting sequence is covalently linked to N-terminus of the cell-penetrating peptide without a linker. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., pancreas, kidney) in an individual, comprising administering (e.g., intravenously) into the individual a cargo delivery complex, wherein the cargo delivery complex comprises a) a peptide comprising a cell-penetrating peptide comprising an amino acid sequence set forth in SEQ ID NO: 75, and b) a cargo molecule (e.g., mRNA, protein, peptide, virus or virus like particle). In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., brain, liver, lung, kidney) in an individual, comprising administering (e.g., intravenously, intramuscularly) into the individual a cargo delivery complex, wherein the cargo delivery complex comprises a) a peptide comprising a cell-penetrating peptide comprising an amino acid sequence set forth in SEQ ID NO: 78, and b) a cargo molecule (e.g., peptide, oliogonucleotide, plasmid DNA, virus or virus like particle). In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., liver, lung, kidney, brain) in an individual, comprising administering (e.g., intravenously) into the individual a cargo delivery complex, wherein the cargo delivery complex comprises a) a peptide comprising a cell-penetrating peptide comprising an amino acid sequence set forth in SEQ ID NO: 118, and b) a cargo molecule (e.g., peptide, oliogonucleotide, plasmid DNA, virus or virus like particle). In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., liver, lung, kidney, pancreas) in an individual, comprising administering (e.g., intravenously, intramuscularly, subcutaneously) into the individual a cargo delivery complex, wherein the cargo delivery complex comprises a) a peptide comprising a cell-penetrating peptide comprising an amino acid sequence set forth in SEQ ID NO: 79 or 80, and b) a cargo molecule (e.g., plasmid DNA, peptide, siRNA, CRISPR molecule, mRNA). In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., liver, lung, kidney, spleen) in an individual, comprising administering (e.g., intravenously, intramuscularly) into the individual a cargo delivery complex, wherein the cargo delivery complex comprises a) a peptide comprising a cell-penetrating peptide, and b) a cargo molecule (e.g., plasmid DNA, siRNA, mRNA), wherein the cell-penetrating peptide is a retro-inverso peptide. In some embodiments, the cell-penetrating peptide is an ADGN-100 peptide or VEPEP-6 peptide. In some embodiments, the peptide comprises the amino acid sequence set forth in SEQ ID NO: 85 or 86. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

In some embodiments, there is provided a method of delivering a cargo molecule into an organ or tissue (e.g., liver) in an individual, comprising administering (e.g., intravenously, subcutaneously) into the individual a cargo delivery complex, wherein the cargo delivery complex comprises a) a peptide comprising a cell-penetrating peptide, and b) a cargo molecule (e.g., plasmid DNA, CRISPR molecule, mRNA), wherein the cell-penetrating peptide comprises a carbohydrate moiety (such as GalNAc). In some embodiments, the cell-penetrating peptide is an ADGN-100 peptide or VEPEP-6 peptide. In some embodiments, the peptide comprises the amino acid sequence set forth in SEQ ID NO: 124 or 129. In some embodiments, the peptide further comprises one or more moieties linked to the N-terminus of the targeting sequence, wherein the one or more moieties are selected from the group consisting of an acetyl group and a stearyl group. In some embodiments, the cargo molecule is selected from the group consisting of a nucleic acid, a virus, a polypeptide, a protein/nucleic complex, virus like particles, and a protein complex.

Disease and Conditions

The present application also provides methods of treating a disease or condition in an individual, comprising administering into the individual an effective amount of the cargo delivery complex, nanoparticals, or pharmaceutical compositions as described herein. In some embodiments, the disease or condition is associated with a pathological cell in an organ or tissue selected from the group consisting of liver, lung, kidney, brain, intestine, spleen, heart, muscle, and lymph node. In some embodiments, the disease or condition is selected from the group consisting of cancer, diabetes, autoimmune diseases, hematological diseases, cardiac diseases, vascular diseases, inflammatory diseases, fibrotic diseases, viral infectious diseases, hereditary diseases, ocular diseases, liver diseases, lung diseases, muscle diseases, protein deficiency diseases, lysosomal storage diseases, neurological diseases, kidney diseases, aging and degenerative diseases, and diseases characterized by cholesterol level abnormality.

In some embodiments of the methods described herein, the disease to be treated is cancer. In some embodiments, the cancer is a solid tumor, and the pharmaceutical composition comprises a cargo delivery complex or nanoparticle comprising one or more mRNA that encode proteins including, but not limited to, growth factors and cytokines, cell surface receptors, signaling molecules and kinases, transcription factors and other modulators of transcription, regulators of protein expression and modification, tumor suppressors, and regulators of apoptosis and metastasis.

In some embodiments, the solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, the cargo delivery complexes or nanoparticles in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV, Chikungunya virus, Zika virus, influenza virus), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

In some embodiments, the cargo delivery complexes or nanoparticles described herein can be used for treating diseases characterized by dysfunctional or aberrant protein activity include cystic fibrosis, sickle cell anemia, epidermolysis bullosa, amyotrophic lateral sclerosis, and glucose-6-phosphate dehydrogenase deficiency. For example, the present invention provides a method for treating such conditions or diseases in a subject by administering a cargo delivery complex comprising a nucleic acid or cell-based therapeutic containing an mRNA, wherein the mRNA encode for a protein that antagonizes or otherwise overcomes the aberrant protein activity present in the cell of the subject. Specific examples of a dysfunctional protein are the missense mutation variants of the cystic fibrosis transmembrane conductance regulator (CFTR) gene, which produce a dysfunctional protein variant of CFTR protein, which causes cystic fibrosis.

Diseases characterized by missing (or substantially diminished such that proper (normal or physiological protein function does not occur) protein activity include cystic fibrosis, Niemann-Pick type C, .beta. thalassemia major, Duchenne muscular dystrophy, Hurler Syndrome, Hunter Syndrome, and Hemophilia A. Such proteins may not be present, or are essentially non-functional. The present invention provides a method for treating such conditions or diseases in a subject by administering a cargo delivery complex comprising a nucleic acid or cell-based therapeutic containing an mRNA, wherein the mRNA encode for a protein that replaces the protein activity missing from the target cells of the subject. Specific examples of a dysfunctional protein are the nonsense mutation variants of the cystic fibrosis transmembrane conductance regulator (CFTR) gene, which produce a nonfunctional protein variant of CFTR protein, which causes cystic fibrosis.

In some embodiments of the methods described herein, the disease to be treated is cancer, wherein the cancer is a solid tumor, and the pharmaceutical composition comprises an cargo delivery complex or nanoparticle comprising one or more mRNA encoding proteins involved in tumor development and/or progression. In some embodiments, the mRNA encodes proteins involved in tumor development and/or progression include, but are not limited to, IL-2, IL-12, interferon-gamma, GM-CSF, B7-1, caspase-9, p53, MUC-1, MDR-1, HLA-B7/Beta 2-Microglobulin, Her2, Hsp27, thymidine kinase, and MDA-7, including mutants thereof. In some embodiments, the mRNA encodes a protein, such as a therapeutic protein. In some embodiments, mRNA encodes a CAR. In some embodiments, the complex or nanoparticle comprises a plurality of mRNA encoding a plurality of protein. In some embodiments, the complex or nanoparticle comprises a plurality of mRNA encoding a single protein. In some embodiments, the complex or nanoparticle comprises a single mRNA encoding a first protein and a second protein. In some embodiments, the complex or nanoparticle further comprises a RNAi such as siRNA, such as an RNAi targeting an endogenous gene, e.g., a disease-associated endogenous gene. In some embodiments, the RNAi targets an exogenous gene. In some embodiments, the RNAi is a therapeutic RNAi targeting an endogenous gene involved in a disease or condition, and the protein is a therapeutic protein useful for treating the disease or condition. In some embodiments, the complex or nanoparticle comprises a therapeutic mRNA and a therapeutic RNAi, wherein the therapeutic RNAi targets a disease-associated form of the endogenous gene (e.g., a gene encoding a mutant protein, or a gene resulting in abnormal expression of a protein), and the therapeutic mRNA corresponds to a therapeutic form of the endogenous gene (e.g., the second transgene encodes a wild-type or functional form of the mutant protein, or the second transgene results in normal expression of the protein).

In some embodiments of the methods described herein, the pharmaceutical composition is administered to the individual by any of intravenous, intratumoral, intraarterial, topical, intraocular, ophthalmic, intraportal, intracranial, intracerebral, intracerebroventricular, intrathecal, intravesicular, intradermal, subcutaneous, intramuscular, intranasal, intratracheal, pulmonary, intracavity, intratraccheal instillation, nebulization, or oral administration.

In some embodiments of the methods described herein, the individual is a mammal. In some embodiments, the individual is human.

Kits

Also provided herein are kits, reagents, and articles of manufacture useful for the methods described herein. Such kits may contain the cargo delivery complexes, nanoparticals, or pharmaceutical compositions as described herein.

The kits described herein may further comprise instructions for using the components of the kit to practice the subject methods (for example instructions for making the pharmaceutical compositions described herein and/or for use of the pharmaceutical compositions). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kits or components thereof (i.e., associated with the packaging or sub packaging) etc. In some embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate The various components of the kit may be in separate containers, where the containers may be contained within a single housing, e.g., a box.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1: Optimization of ADGN-Peptides/mRNA/Plasmid-DNA/siRNA Nanoparticles for In Vivo Applications Materials mRNA: CleanCap™ Luc mRNA (5moU) was obtained for Trilink Biotechnology (USA).

Plasmid: pGL4 reporter vector expressing luciferase under CMV promoter was obtained by Promega.

siRNA luc: siRNA targeting Luciferase Luc2 5' CUU-ACG-CUG-AGU-ACU-UCG-ATT-3' (sense strand) (SEQ ID NO: 192) and 5'-UCG-AAG-UAC-UCA-GCG-UAA-GTT-3'(antisense strand) (SEQ ID NO: 193) were obtained from Eurogentec.

ADGN Peptides: the following peptides were used:

```
ADGN-106:
                                 (SEQ ID NO: 77)
βALWRALWRLWRSLWRLLWKA

ADGN-106-RI:
                                 (SEQ ID NO: 85)
akwllrwlsrwlrwlarwlr ADGN-106-PEG7:
                                 (SEQ ID NO: 92)
Ac-(PEG)7-βALWRALWRLWRSLWRLLWKA-NH2

ADGN-106-PEG2:
                                 (SEQ ID NO: 93)
Ac-(PEG)2-βALWRALWRLWRSLWRLLWKA-NH2

ADGN-106-Hydro-1:
                                 (SEQ ID NO: 94)
Ac-YIGSR-(G)4-ALWRALWRLWRSLWRLLWKA-NH2

ADGN-106 hydro-2:
                                 (SEQ ID NO: 95)
Ac-GYVS-(G)4-ALWRALWRLWRSLWRLLWKA-NH2

ADGN-106-Hydro-3:
                                 (SEQ ID NO: 198)
Ac-YIGSR-Ava(CH2)2-ALWRALWRLWRSLWRLLWKA-NH2

ADGN-106 hydro-4:
                                 (SEQ ID NO: 199)
Ac-GYVS-Ava(CH2)2-ALWRALWRLWRSLWRLLWKA-NH2
```

```
-continued
ADGN-106-Hydro-5:
                                 (SEQ ID NO: 200)
Ac-YIGSR-Aun(CH2)6-ALWRALWRLWRSLWRLLWKA-NH2

ADGN-106 hydro-6:
                                 (SEQ ID NO: 201)
Ac-GYVS-Aun(CH2)6-ALWRALWRLWRSLWRLLWKA-NH2

ADGN-106-Hydro-8:
                                 (SEQ ID NO: 130)
Ac-YIGSR-Ahx-ALWRALWRLWRSLWRLLWKA-NH2

ADGN-106 Stearyl:
                                 (SEQ ID NO: 100)
Stearyl-βA-ALWRALWRLWRSLWRLLWKA-NH2

ADGN-100:
                                 (SEQ ID NO: 79)
βAKWRSAGWRWRLW RVRSWSR

ADGN-100-RI:
                                 (SEQ ID NO: 86)
rswsrvrwlrwrwgasrwk ADGN-100-PEG7:
                                 (SEQ ID NO: 87)
Ac-(PEG)7-βA-KWRSALWRWRLWRVRSWSR-NH2

ADGN-100-PEG2:
                                 (SEQ ID NO: 91)
Ac-(PEG)2-βA-KWRSALWRWRLWRVRSWSR-NH2

ADGN-100-Hydro-1:
                                 (SEQ ID NO: 88)
Ac-YIGSR-(G)4-KWRSALWRWRLWRVRSWSR-NH2

ADGN-100 hydro-2:
                                 (SEQ ID NO: 89)
Ac-GYVS-(G)4-KWRSALWRWRLWRVRSWSR-NH2

ADGN-100-Hydro-3:
                                 (SEQ ID NO: 101)
Ac-YIGSR-Ava-KWRSALWRWRLWRVRSWSR-NH2

ADGN-100 hydro-4:
                                 (SEQ ID NO: 102)
Ac-GYVS-Ava-KWRSALWRWRLWRVRSWSR-NH2

ADGN-100-Hydro-5:
                                 (SEQ ID NO: 103)
Ac-YIGSR-Aun-KWRSALWRWRLWRVRSWSR-NH2

ADGN-100 hydro-6:
                                 (SEQ ID NO: 104)
Ac-GYVS-Aun-KWRSALWRWRLWRVRSWSR-NH2

ADGN-100-Hydro-8:
                                 (SEQ ID NO: 125)
Ac-YIGSR-Ahx-KWRSALWRWRLWRVRSWSR-NH2

ADGN-100 Stearyl:
                                 (SEQ ID NO: 90)
Stearyl-βA-KWRSALWRWRLWRVRSWSR-NH2

ADGN-103C:
                                 (SEQ ID NO: 203)
Ac-ASSLNIA-Ava-KWWERWWREWPRKRR-NH2

ADGN-104
                                 (SEQ ID NO: 204)
Ac-LSSRLDA-Ava-KWWERWWREWPRKRR

ADGN-105
                                 (SEQ ID NO: 205)
Ac-SYTSSTM-Ava-KWWERWWREWPRKRR

ADGN-106TB:
                                 (SEQ ID NO: 131)
Ac-SYTSSTM-Ava-βALWRALWRLWRSLWRLLWKA-NH2
```

-continued

ADGN-109:
(SEQ ID NO: 206)
Ac-KSYDTY-Ava-ALRWLRWASRWFSRWAWR-NH2

ADGN-109D:
(SEQ ID NO: 208)
Ac-KSYDTYAAETR-RWASRWFSRWAWWR-NH2

ADGN-109b:
(SEQ ID NO: 207)
Ac-CKRAV-RWWLRWASRWFSRWAWWR-NH2

ADGN-101:
(SEQ ID NO: 121)
Ac-CARPAR-WRSAGWRWRLWRVRSWSR-NH2

ADGN-102:
(SEQ ID NO: 209)
Ac-TGNYKALHPDHNG-WRSALRWRLWRWSR-NH2

ADGN-100GALNAC:
(SEQ ID NO: 124)
Ac-KWRSA(GalNac)LWRWRLWRVRSWSR-NH2

ADGN-106GALNAC:
(SEQ ID NO: 210)
AC-ALWRA(GalNac)LWRLWRSLWRLLWKA-NH2

ADGN-106TC:
(SEQ ID NO: 133)
Ac-THRPPNWSPVWP-RALWRLWRSLWRLRWKA-NH2

ADGN-106TD:
(SEQ ID NO: 134)
Ac-CKTRRVP-WRALWRLWRSLWRLLWKA-NH2

It was noted that the yield of peptide preparation is about 20 fold higher with the ones obtained with a Ahx linker.

Cell lines: 293T cells (ATCC® CRL-3216TM) and HepG2 (ATCC® HB-8065™) cells were obtained from ATCC. SKOV-3/Luc Cells and A375/Luc cells were obtained from clinisciences.

Methods

Complex formation with mRNA. The following protocols were used for the transfection of 2-5 106 Cells or Cells at confluency of about 70-80% cultured in 24 well plates. ADGN peptide/mRNA particles were prepared at a 20:1 molar ratio of ADGN-Peptide/mRNA. using (0.25 µg) mRNA. Luc mRNA (0.25 µg) was diluted in 20 µl of sterile water (GIBCO) at room temperature. 5 µl Final Peptide Solution was added to obtain a total volume of 20 µl. The volume was adjusted to 50 µl with sterile water and was mixed gently with vortex 1 min low speed and incubated 30 min at room temperature. Then the volume was made up to 100 µl by adding sterile water containing 5% sucrose, and the solution was mixed gently with vortex 1 min low speed and incubate 5 min at 37° C. and then was proceeded to cell transfection.

Optimized Complex formation with mRNA. ADGN peptide/mRNA/gRNA particles were prepared at a 2:1 molar ratio (2×) of ADGN-Peptide/nucleic acid. ADGN/CAS9mRNA/sgRNA complexes were prepared at a 1:2 molar ratio (2×) with 0.2 µg mRNA: 0.15 µg sgRNA and 5% Glucose or DMEM (example for 96 well plates). Premixed CAS9 mRNA/gRNA (5 µg/15 µg) were prepared in sterile water at room temperature in a glass vial (1-4 ml). ADGN-peptide solution was added dropwise (1 drop/sec) under magnetic agitation at 400 rpm to obtain a 1:2 ratio. The solution was then incubated for 30 minutes at room temperature or 37° C. Just before transfection, 150 µl Glucose or DMEM was added. The solution was then mixed under magnetic agitation at 400 rpm for 1 minute then incubated for 5 min at 37° C. Then, the solution was ready for cell transfection or IV administration. Prior to IV administration, complexes were diluted in sucrose 5% solution.

Complex formation with plasmid DNA. The following protocols were used for the transfection of 2-5 106 Cells or Cells at confluency of about 70-80% cultured in 24 well plates. ADGN peptide/plasmid DNA pGL4 particles were prepared at a 20:1 molar ratio of ADGN-Peptide/pGL4. using (0.2 µg). PGL4 plasmid (0.15 µg) was diluted in 20 µl of sterile water (GIBCO) at room temperature. 10 µl Final Peptide Solution was added to obtain a total volume of 20 µl. The volume was adjusted to 50 µl with sterile water and was mixed gently with vortex 1 min low speed and incubated 30 min at room temperature. Then the volume was made up to 100 µl by adding sterile water containing 5% sucrose, and the solution was mixed gently with vortex 1 min low speed and incubate 5 min at 37° C. and then was proceeded to cell transfection.

Complex formation with siRNA. The following protocols were used for the transfection of 2-5 106 Cells or Cells at confluency of about 70-80% cultured in 24 well plates. ADGN peptide/siRNA Luc particles were prepared at a 20:1 molar ratio of ADGN-Peptide/pGL4. using 20 nM siRNA. The siRNA duplex (10 and 25 nM) was diluted in 20 µl of sterile water (GIBCO) at room temperature. 1.5 or 3 µl of a Final Peptide Solution (55 µM) was added to obtain a total volume of 20 µl. The volume was adjusted to 50 µl with sterile water and was mixed gently with vortex 1 min low speed and incubated 30 min at room temperature. Then the volume was made up to 100 µl by adding sterile water containing 5% sucrose, and the solution was mixed gently with vortex 1 min low speed and incubate 5 min at 37° C. and then was proceeded to cell transfection.

Transfection protocol. Protocol is reported for 24 well plate format. Cells were cultured in Dulbecco's Modified Eagle's Medium (DMEM), supplemented with 2 mM glutamine, 1% antibiotics (streptomycin 10,000 µg/mL, penicillin, 10,000 IU/mL) and 10% (w/v) foetal calf serum (FCS), at 37° C. in a humidified atmosphere containing 5% CO2. 24 well plates seeded with 150,000 cells the day prior to transfection were grown to 50-60% confluence and set up to be at about 70% confluences at the time of transfection. Before transfection, cells were washed twice with DMEM. Cells were then overlaid with 0.1 ml of ADGN-peptide/cargo complex solution containing 0.25 µg mRNA, 0.15 µg plasmid DNA or 10-25 nM siRNA, mixed gently, and incubated for 10 min at 37° C. 0.2 mL of fresh DMEM, were added and cells were incubated for 20 min at 37° C. 1 mL of complete DMEM containing 15% FCS were then added in order to reach a final FCS concentration of 10%, without removing the overlay of ADGN-peptide/cargo complexes. Cells were returned to the incubator (37° C., 5% CO2) and 72 hrs post transfection.

Results

The purpose of the study was to evaluate which ADGN formulations may result in superior ADGN-nanoparticles with mRNA or plasmid DNA or siRNA for in vivo systemic IV and topical or IM delivery. Several different modifications of ADGN peptides have been evaluated, including stearyl, PEGylation with different PEG length, signaling sequences and retro-inverso transformation. Retro-inverso peptides-peptides consists of D-amino acids in the reverse sequence of the naturally occurring L-isoforms to investigate if they result in proteolytically stable peptide analogues while maintaining the structural features. The ADGN-peptide/cargo formulations have been characterized in vitro and their potency to deliver mRNA, plasmid DNA and siRNA was evaluated on cultured cells and in vivo.

Example 2: Characterization and Stability of ADGN-Peptide Variant/mRNA Complexes The ability of the different ADGN-peptides to form stable nanoparticles with mRNA was analyzed. The particle sizes and level of aggregation were measured on DLS NanoZS (Malvern Ltd). The mean size and the polydispersity of the ADGN/mRNA complexes were determined at 25° C. for 3 minute per measurement. In order to remove large particles, ADGN/mRNA complexed were filtered using either PES or PVDF 0.45 µm filters. Data are shown in FIG. 8 and FIG. 9 for a mean of 3 separate experiments.

As reported in FIG. 8, all ADGN-100 peptides formed stable nanoparticles with mRNA with a mean size ranging between 100 to 160 nm. ADGN/mRNA complex solution contained a small fraction, between 5% to 13%, of nanoparticles with mean size higher than 400 nm. Retro inverso modifications of ADGN-100 did not modify the ability of the peptide to form stable complex with mRNA. Highly homogenous nanoparticles, with less than 4% aggregates are obtained with ADGN-100Retro inverso, ADGN-100 Hydro5 and ADGN-100 Hydro6 peptides.

As reported in FIG. 9, all ADGN-106 peptides formed stable nanoparticles with mRNA with a mean size ranging between 110 to 160 nm. ADGN/mRNA complex solution contained a small fraction, between 5% to 13%, of nanoparticles with mean size higher than 400 nm. Retro inverso modifications of ADGN-106 did not modify the ability of the peptide to form stable complex with mRNA. Highly homogenous nanoparticles, with less than 3% aggregates are obtained with ADGN-106 Retro inverso and ADGN-100 Hydro6 peptides.

For both ADGN-100 and ADGN-106 peptide variants, the large particles and aggregates are efficiently removed by filtration on 0.45 µm filters and results in about 15-20% loss of material in PES filter and about 30% in PVDF filter. Therefore a filtration step with 0.45 µm PES filters will be added for further investigation.

Example 3: Characterization and Stability of ADGN-Peptide Variant/DNA Plasmid Complexes The ability of the different ADGN-peptides to form stable nanoparticles with DNA pGL4 a 5.6KpB plasmid expression Luciferase was analyzed. The particle sizes and level of aggregation were measured on DLS NanoZS (Malvern Ltd). The mean size and the polydispersity of the ADGN/plasmid DNA complexes were determined at 25° C. for 3 minute per measurement. In order to remove large particles, ADGN/plasmid DNA complexed were filtered using either PES or PVDF 0.45 µm filters. Data are shown in FIG. 10 for a mean of 3 separate experiments.

As reported in FIG. 10, All ADGN peptides, except ADGN-106, ADGN-106RI, ADGN-100HYDRO2A and ADGN-100HYDRO3, formed stable nanoparticles with PGL4 in the range of 100-150 nm. Stable ADGN/plasmid DNA complex solution contained a small fraction, between 5% to 20%, of nanoparticles with mean size higher than 400 nm. The large particles and aggregates are efficiently removed by filtration on 0.45 µm filters and results in about 15-30% loss of material in PES filter and about 40% in PVDF filter. Therefore a filtration step with 0.45 µm PES filters will be added for further investigation. Retro inverso modification of ADGN-100 did not modifie the ability of the peptide to form stable complex with plasmid DNA. Retro inverso modification of ADGN-106 did not improve the potency of ADGN-106 to form stable particle with plasmid. Highly homogenous nanoparticles, with less than 4% aggregates are obtained with ADGN-100 Retro inverso, ADGN-100 Hydro5 and ADGN-100 Hydro6 peptides.

Example 4: ADGN-Peptide Variants Improve Cargo Delivery in 293T Cells

ADGN-peptides were evaluated for cellular delivery of Luciferase mRNA in 293T cells. A single dose of mRNA of 0.25 µg was evaluated. Luc mRNA (0.25 µg) in sterile water (GIBCO) were mixed with ADGN-100, ADGN-100RI, ADGN-106, ADGN-106RI, ADGN-100 Stearyl, ADGN-Hydro1, ADGN-Hydro2, ADGN-Hydro5 and ADGN-Hydro6. ADGN-peptide/mRNA complexes were filtered with 0.45 µm PES filter. In order to evaluate the stability of the ADGN/mRNA complexes in high serum and cell culture conditions, the complexes were incubated for 3 hrs in the presence of either 25% serum or heparan sulfate prior transfection, then 293T cells were transfected and Luciferase expression was monitored at 72 hrs.

As reported in FIGS. 1A and 1B, filtration did not affect ADGN particle efficiency. In the absence of serum or of heparan sulfate treatments, high level of luciferase expression was obtained for both ADGN-100 and ADGN-106 peptides, ADGN-106 being 2 fold more potent than ADGN-100. Luciferase expression is not significantly affected by the presence of stearyl, Hydro5 and Hydro 6 motif linked to ADGN peptide. In contrast, the presence of Hydro1 and Hydro2 motif reduced by 20 to 50% efficiency of ADGN peptide. Retro-inverso modification did not modify ADGN-100 and ADGN-106 efficiency.

The presence of serum or of heparan sulfate reduced the stability of the ADGN/mRNA complexes, which is correlated with a significant decrease in luciferase expression. ADGN-106 efficiency is reduced by 71% in the presence of serum and 50% in heparan sulfate and ADGN-100 efficiency is reduced by 90% in serum and 50% in heparan. The presence of Stearyl or Hydro-1, Hydro-5 and Hydro-6 motifs stabilized ADGN/mRNA particles and luciferase expression is reduced by only 30-40% in serum and 10-20% in heparan sulfate. Introducing Retro-inverso modification strongly stabilized the ADGN-mRNA complexes particularly in the presence of serum and heparan sulfate. ADGN-100 RI mediated luciferase expression is reduced by 40% in the presence of serum and by 16% with heparan sulfate. ADGN-106RI mediated luciferase expression is reduced by 26% in the presence of serum and by 13% with heparan sulfate.

Luc mRNA (0.25 µg) were associated to ADGN-100 or ADGN-106 solution containing 10% or 20% of ADGN-100-PEG and to ADGN-106 containing 10% or 20% of ADGN-106-PEG. Combining ADGN-100 or ADGN-106 with 10% or 20% of pegylated ADGN-100 or pegylated ADGN-106 significantly stabilized complexes. Transfection efficiency after serum treatment is reduced by only 20% or 17% using ADGN-100 PEG 10% and 20% respectively.

In order to evaluate the impact of the linker sequence, the YIGSR targeting sequence was linked to ADGN-106 using various linker motifs.

ADGN-106:

(SEQ ID NO: 195)

Ac-βALWRALWRLWRSLWRLLWKA-NH2

-continued

ADGN-106-Hydro:
(SEQ ID NO: 105)
Ac-YIGSR-Balwralwrlwrslwrllwka-NH2

ADGN-106-HYPEG2:
(SEQ ID NO: 107)
Ac-YIGSR-(PEG)2-βALWRALWRLWRSLWRLLWKA-NH2

ADGN-106-HYPEG4:
(SEQ ID NO: 108)
Ac-YIGSR-(PEG)4-βALWRALWRLWRSLWRLLWKA-NH2

ADGN-106-HYPEG7:
(SEQ ID NO: 109)
Ac-YIGSR-(PEG)7-βALWRALWRLWRSLWRLLWKA-NH2

ADGN-106-Hydro-1:
(SEQ ID NO: 94)
Ac-YIGSR-(G)4-ALWRALWRLWRSLWRLLWKA-NH2

ADGN-106-Hydro-7:
(SEQ ID NO: 194)
Ac-YIGSR-(G)2-ALWRALWRLWRSLWRLLWKA-NH2

ADGN-106-Hydro-3:
(SEQ ID NO: 198)
Ac-YIGSR-Ava(CH2)$_2$-ALWRALWRLWRSLWRLLWKA-NH2

ADGN-106-Hydro-5:
(SEQ ID NO: 200)
Ac-YIGSR-Aun(CH2)$_6$-ALWRALWRLWRSLWRLLWKA-NH2

ADGN-106-Hydro-8:
(SEQ ID NO: 130)
Ac-YIGSR-Ahx-ALWRALWRLWRSLWRLLWKA-NH2

ADGN-106 peptides containing YIGSR targeting sequence were evaluated for cellular delivery of Luciferase mRNA in 293T cells. A single dose of mRNA of 0.25 µg was evaluated. Luc mRNA (0.25 µg) in sterile water (GIBCO) were mixed with ADGN-106 and ADGN-106Hydro variant. ADGN-peptide/mRNA complexes were filtered with 0.45 µm PES filter. The ADGN-106/mRNA complexes were incubated for 3 hrs in the presence of 25% serum prior transfection, then 293T cells were transfected and Luciferase expression was monitored at 72 hrs.

Figure 1C:
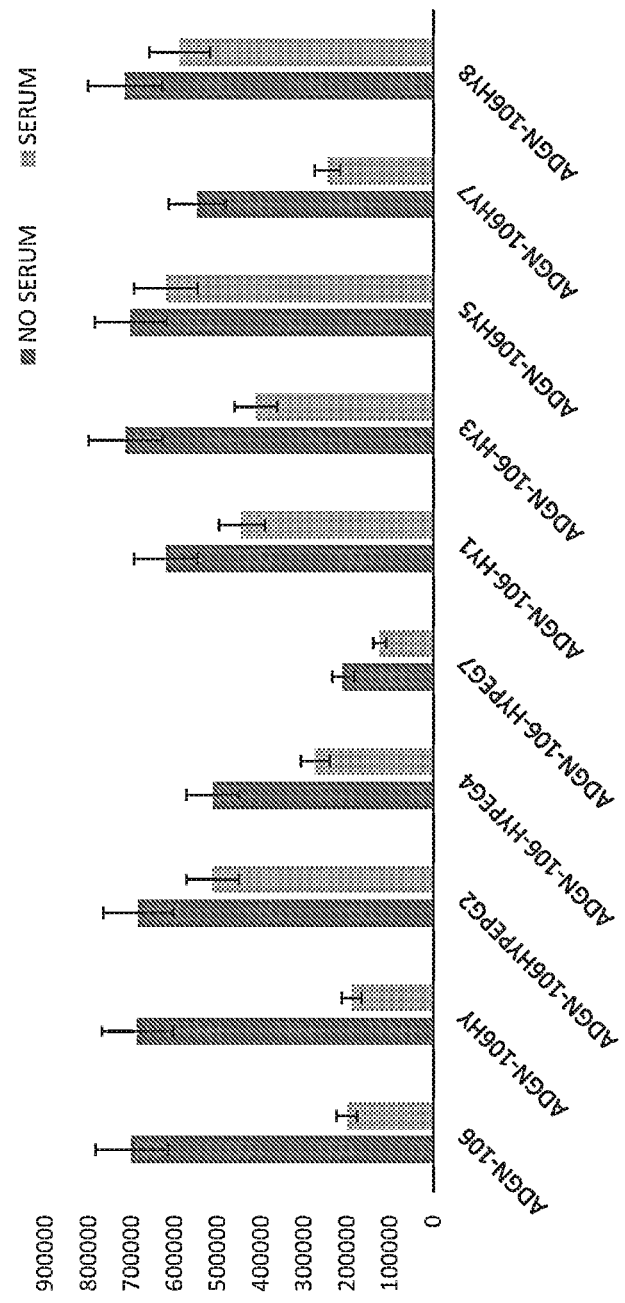

As reported in FIG. 1C, in the absence of serum treatment, high level of luciferase expression was obtained for ADGN-106, ADGN-106 Hydro, ADGN-106HYPEG2, ADGN-106-Hydro1, hydro3, hydro5 and hydro8 suggesting that using linkers such as beta Ala, PEG2, Ava, Aun, Ahx, and (Gly)4, do not affected transfection efficiency. In contrast, using PEG4, PEG7 and Gly-Gly as linker, reduced luciferase expression by 35%, 72% and 28%, respectively.

In the presence of serum the stability of the ADGN-106/mRNA complexes, is significantly reduced which is correlated with a significant decrease in luciferase expression. ADGN-106 and ADGN-106Hydro efficiency are reduced by 80%. Using PEG2, Ava, Ahx, (Gly)4 and Aun as a linker reduced the impact of the serum on the stability of the particles. Best results were obtained with Aun>Ahx>PEG2>Ava>Gly$_4$ linkers with a decrease in luciferase expression of 15%, 17%, 21%, 32% and 40%, respectively. The results demonstrated that both the length and the nature of the linker are important and the best results are obtained for (CH2)$_4$ motifs.

The results demonstrated that ADGN-100 and ADGN-106 promote efficient delivery of mRNA in 293T cells. Filtration can be used to clarify nanoparticle preparation without affecting efficiency. The results showed than using retro-inverso or hydro-6 modification of ADGN peptides, or combining 10% to 20% of pegylated-ADGN peptide within the ADGN/mRNA particles strongly stabilize the complexes in the presence of high serum conditions.

Example 5: ADGN-Peptide Variants Improve pGL4 DNA Plasmid Delivery in 293T Cells ADGN-peptides were evaluated for cellular delivery of pGL4 plasmid DNA expressing Luciferase in 293T cells. Luc pGL4 plasmid (0.15 µg) in sterile water (GIBCO) were mixed with ADGN-100, ADGN-100RI, ADGN-106, ADGN-106RI, ADGN-100 Stearyl, ADGN-100Hydro1, ADGN-100Hydro2, ADGN-100Hydro4, ADGN-100Hydro3, ADGN-100Hydro5 and ADGN-100Hydro6. ADGN-peptide/mRNA complexes were filtered with 0.45 µm PES filter. In order to evaluate the stability of the ADGN/pGL4 plasmid complexes in high serum and cell culture conditions, the complexes were incubated for 3 hrs in the presence of either 25% serum or heparan sulfate prior transfection, then 293T cells were transfected and Luciferase expression was monitored at 72 hrs.

Figure 2A:
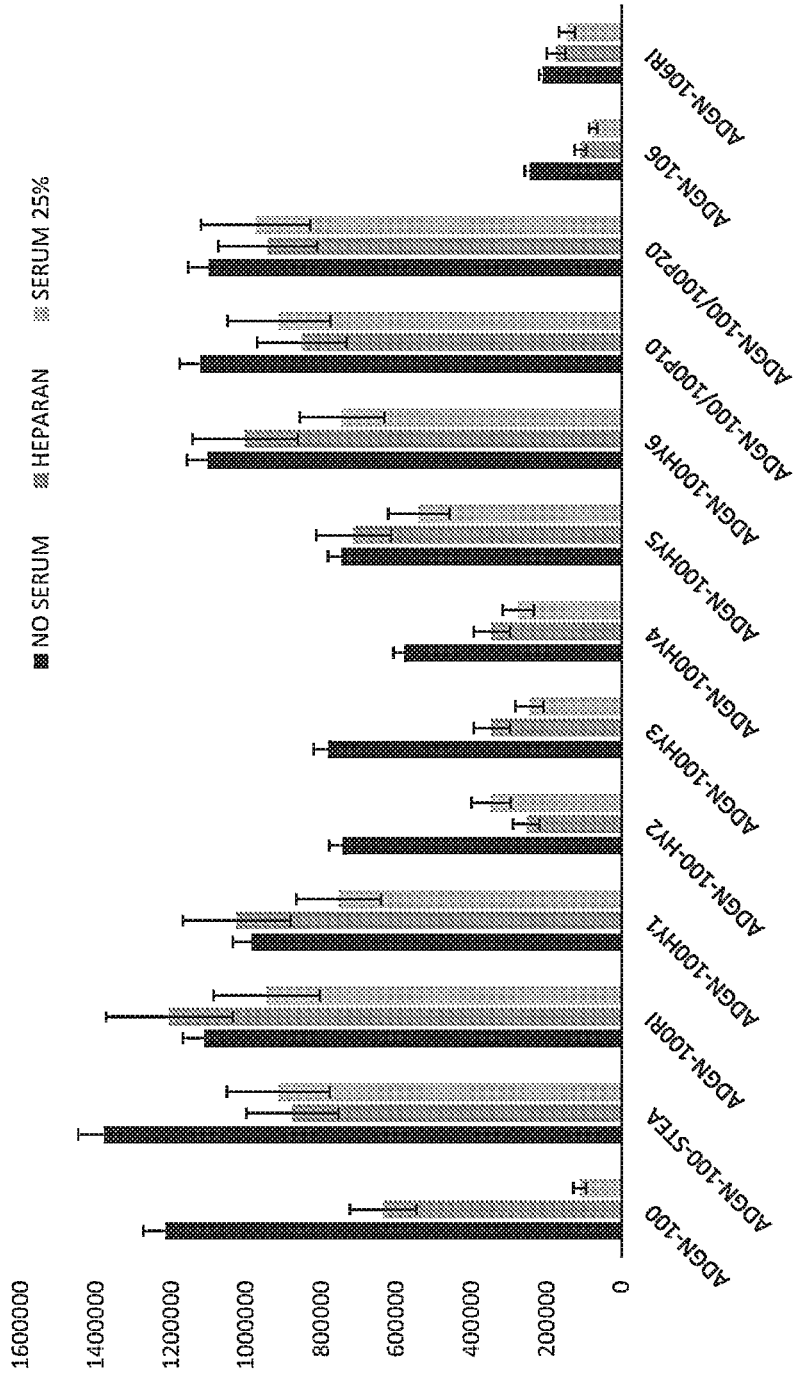

As reported in FIGS. 2A and 2B, filtration does not affect ADGN particle efficiency. In the absence of serum or of heparan sulfate treatments, high level of luciferase expression was obtained with ADGN-100 and ADGN-100 variant peptides. The presence of Hydro1, 2, 3, 4, 5 motifs reduced by 20 to 40% ADGN-100 efficiency. In contrast, Stearyl, retro inverso and Hydro 6 modifications do not affected ADGN-100 efficiency. As shown in FIGS. 2A and B, poor luciferase expression was monitored using ADGN-106 and ADGN-106RI in the absence or presence of serum, which correlated well with the large size and a the poor stability of ADGN-106/plasmid DNA particles. The presence of serum or of heparan sulfate reduced the stability of the ADGN/pGL4 plasmid complexes, which is correlated with a significant decrease in luciferase expression. ADGN-100 efficiency is reduced by 90% in the presence of serum and 50% in heparan sulfate. The presence of Stearyl or Hydro-1, Hydro-5 and Hydro-6 motifs stabilized ADGN/pGL4 particles and luciferase expression is reduced by only 30-40% in serum and 10-20% in heparan sulfate. In contrast, Hydro-2, Hydro-3 and hydro-4 modification do not significantly improved transfection in the presence of serum and upon heparan treatment. Introducing Retro-inverso modification strongly stabilized the ADGN-Plasmid DNA complexes in particularly in the presence of serum and heparan sulfate. ADGN-100RI mediated luciferase expression is reduced by 25% in the presence of serum and by less than 10% with heparan sulfate.

Figure 2C:
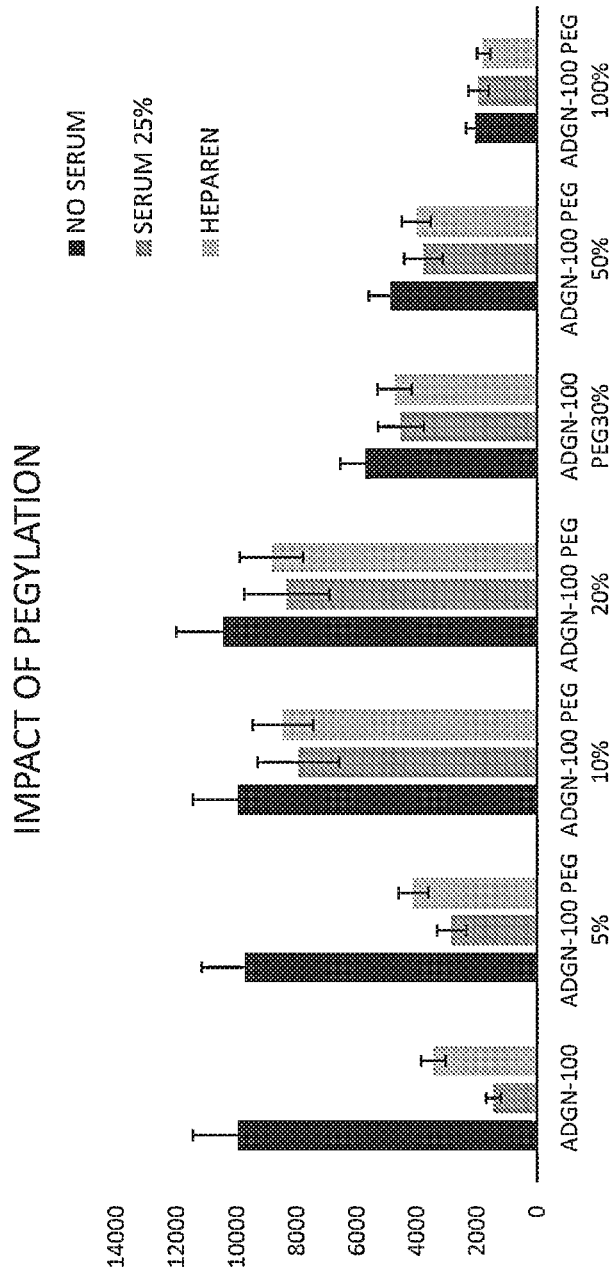

We have evaluated the impact of combining ADGN-100 with PeGylated ADGN-100 on the transfection efficiency. pGL4 luc plasmid (0.15 µg) were associated to ADGN-100 solution containing 5 to 50% of ADGN-100-PEG or to ADGN-100PEG. As reported in FIG. 2C, combining ADGN-100 with 10% or 20% of pegylated ADGN-100 significantly stabilized complexes. Transfection efficiency is increased in the presence of 25% serum, by 2.3 and 2.4 folds. In contrast, using 50% and 100% ADGN-100 PEG reduced by 50% and 80% level of Luciferase expression.

The results demonstrated that ADGN-100 promote efficient delivery of plasmid DNA in 293T cells. Filtration can be used to clarify nanoparticle preparation without affecting efficiency. The results showed than using stearylation, retro-inverso or Hydro-6 modification of ADGN peptides, or combining 10% to 20% of pegylated-ADGN peptide within the ADGN/Plasmid particles strongly stabilize the complexes in the presence of high serum conditions.

Example 6: ADGN-Peptide Variants Improve siRNA Delivery in A375/Luc Cells

ADGN-peptides were evaluated for cellular delivery of siRNA duplex targeting Luciferase in A375/Luc cells. siRNA targeting luciferase (10 and 25 nM) in sterile water (GIBCO) were mixed with ADGN-100, ADGN-100RI, ADGN-106, ADGN-106RI, ADGN-100 Stearyl, ADGN-100Hydro1, ADGN-100Hydro2, ADGN-100Hydro4, ADGN-100Hydro3, ADGN-100Hydro5 and ADGN-100Hydro6. ADGN-peptide/siRNA complexes were filtered with 0.45 µm PES filter. In order to evaluate the stability of the ADGN/siRNA complexes in high serum conditions, the complexes were incubated for 3 hrs in the presence of 25% serum, then A375/Luc cells were transfected and Luciferase expression was monitored at 48 hrs.

Figure 3B:
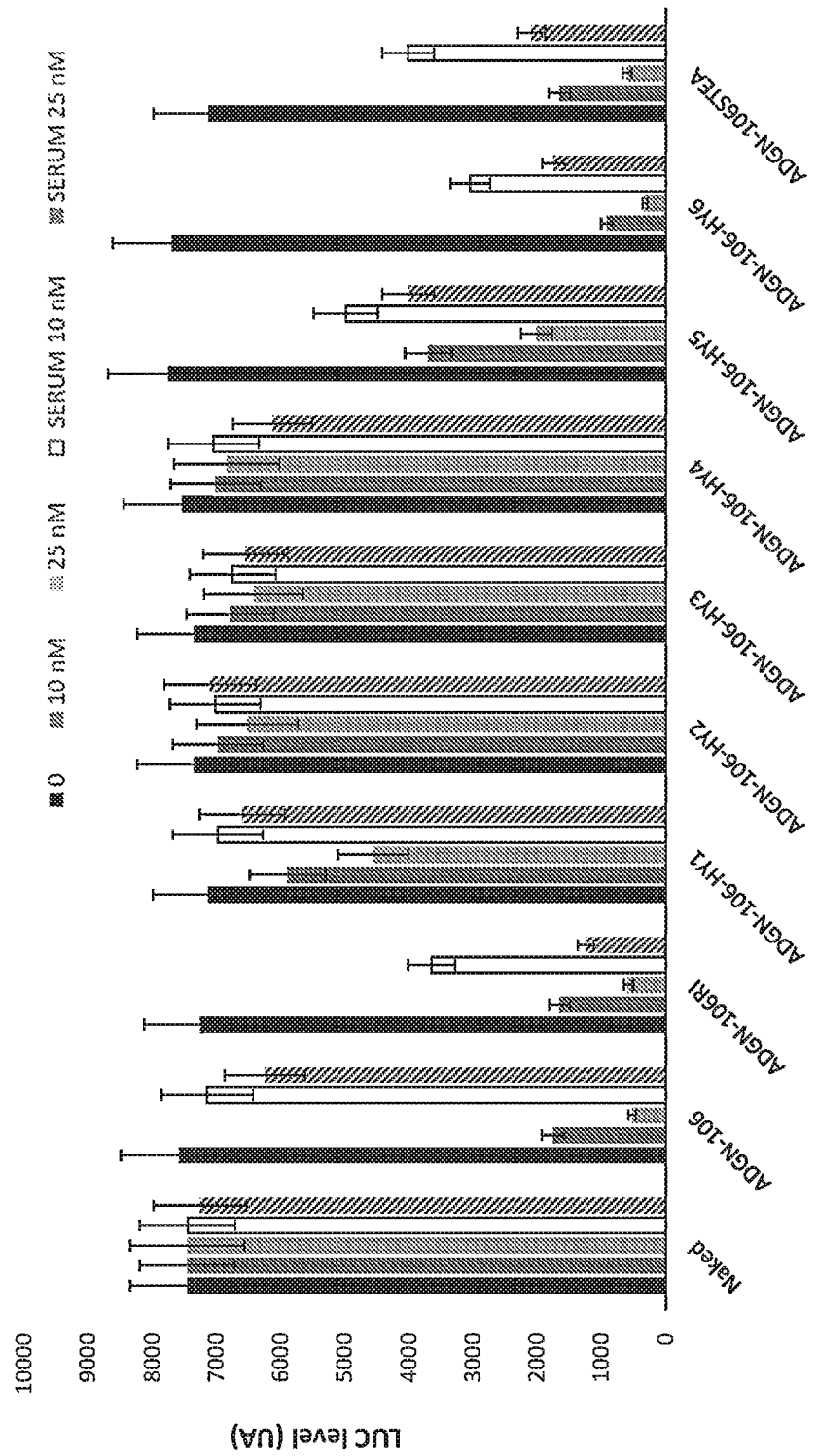

As reported in FIGS. 3A and 3B, In the absence of serum treatment, high level of siRNA mediated luciferase silencing was obtained with both ADGN-100 and ADGN-106 peptides. Level of luciferase ix reduced by 78% using 10 nM siRNA and 93% using 25 nM siRNA. The presence of Hydro1, 2, 3, 4, 5 motifs reduced by 50 to 90% ADGN-100 or ADGN-106 efficiency. In contrast, Stearyl, retro inverso and Hydro 6 modifications do not affected ADGN-100 and ADGN-106 efficiency. The presence of serum reduced the stability of the ADGN/siRNA complexes, which is correlated with a significant decrease in siRNA mediated luciferase silencing. ADGN-100 and ADGN-106 efficiency are reduced by 90% in the presence of serum. The presence of Stearyl and Hydro-6 motifs stabilized ADGN/siRNA particles and siRNA mediated luciferase silencing is reduced by only 20% in serum. Introducing Retro-inverso modification strongly stabilized the ADGN/siRNA complexes. As reported in FIGS. 3A and 3B, when using ADGN-100RI or ADGN-106RI, siRNA mediated luciferase silencing is not affected by the presence of serum and luciferase expression level is reduced of 77% with 10 nM siRNA and 95% with 25 nM siRNA.

Figure 3C:
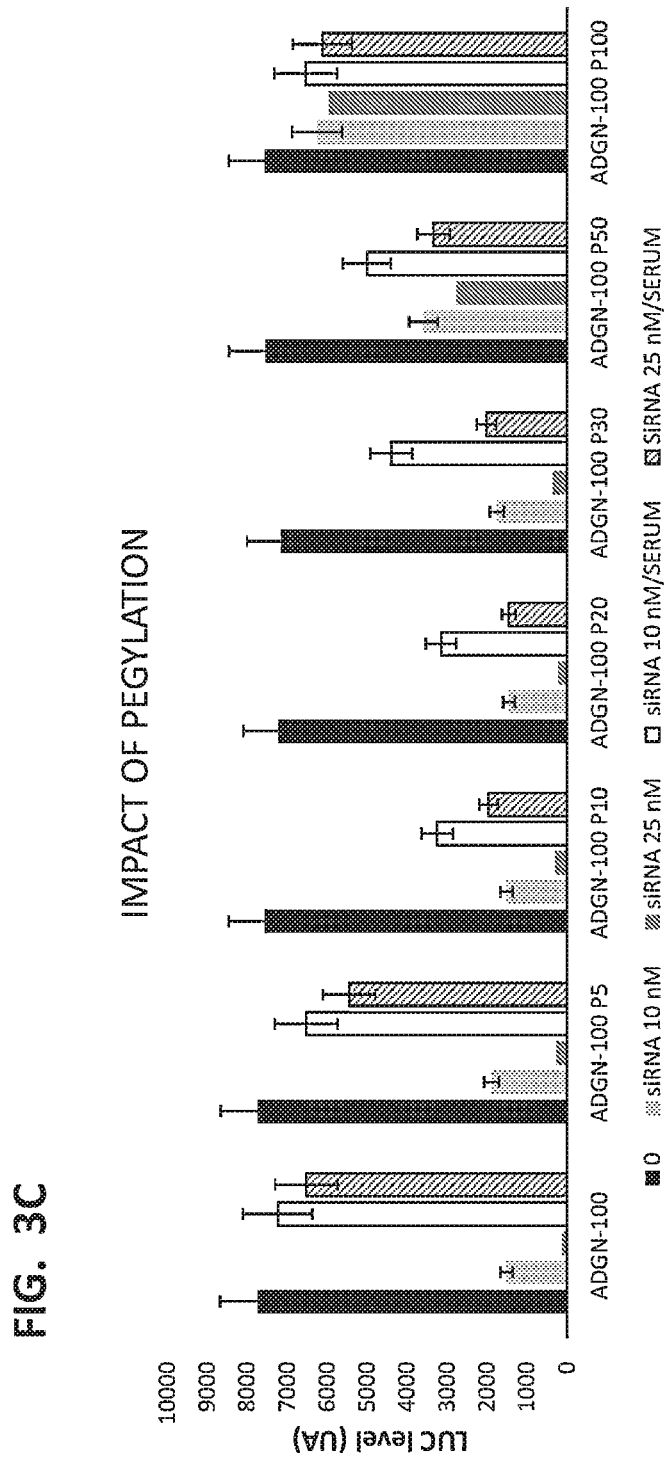

We have evaluated the impact of combining ADGN-100 with PeGylated ADGN-100 on the siRNA transfection efficiency. siRNA targeting luciferase (10 nM and 25 nM) were associated to ADGN-100 solution containing 5 to 50% of ADGN-100-PEG or to ADGN-100PEG. As reported in FIG. 3C, combining ADGN-100 with 10% or 20% of pegylated ADGN-100 significantly stabilized complexes. Luciferase expression is reduced by 75% and 81% using 10% and 20% of pegylated-ADGN-100, respectively. In contrast, using 50% and 100% ADGN-100 PEG reduced by 50% and 80% transfection efficiency.

The results demonstrated that ADGN-100 and ADGN-106 promote efficient delivery of siRNA in A375/Luc cells. The results showed than using stearylation, retro-inverso or Hydro-6 modification of ADGN peptides, or combining 10% to 20% of pegylated-ADGN peptide within the ADGN/siRNA particles strongly stabilize the complexes in the presence of high serum conditions.

Example 7: ADGN-Peptide Variant Improve Cargo Delivery In Vivo

Stable ADGN-peptides/mRNA were evaluated for in vivo delivery of Luciferase mRNA via intravenous and intramuscular administrations. Animals were treated with single dose of 5 moU modified Luc mRNA of 5 µg. 5 moU modified Luc mRNA (5 µg) in sterile water (GIBCO) were mixed with ADGN peptide (sterile water), volume for each sample was adjusted to 100 µl, with sterile water containing 5% Sucrose. Samples were mixed gently with vortex for 1 minute at low speed and incubated for 30 min at room temperature. Samples were filtered on 0.45 µm PES filters prior administration. For IV administration Mice received 100 µl intravenous (IV) injection of either ADGN-106/mRNA, ADGN-100/mRNA, ADGN-106RI/mRNA, ADGN-100-stearyl/mRNA, ADGN-100Hydro1/mRNA, ADGN-100Hydro2 or ADGN/mRNA complexes containing 10% of ADGN-100PEG (3 animals per group). As control, mice from group 3 (2 animals per group) received IV injection of 100 µl of naked 5 moU modified Luc mRNA (5 µg). For IM administration, mice received 25 µl (5 µg mRNA) IV injection of either ADGN-100/mRNA, ADGN-106/mRNA, ADGN-106RI/mRNA or ADGN/mRNA complexes containing 10% or 20% of ADGN-100PEG (2 animals per group). As control, mice from group 3 (2 animals per group) received IV injection of 25 µl of naked 5 moU modified Luc mRNA (5 µg).

mRNA Luc expression was monitored by bioluminescence. Bioluminescence imaging was performed after 12, 24, 48 and 72 hrs. Mice received an i.p. injection of 150 µg/g luciferin for noninvasive bioluminescence imaging (IVIS Kinetic; PerkinElmer, Waltham, MA, USA). Results were then expressed as values relative to day 0 and shown in FIGS. 4A-4D and FIG. 5.

As shown in FIG. 4A; ADGN-106, ADGN-106RI, ADGN-100 and ADGN-100 Stearyl mediated in vivo cargo delivery and mRNA expression was mainly observed in the liver and at lower level in the lung and the kidney. ADGN-106 is 2 and 4 folds more efficient than ADGN-100 stearyl and ADGN-100, respectively. ADGN-106RI modification increased by 2 fold ADGN-106 efficiency in all the tissues. In contrast, negligible luciferase expression was obtained using ADGN-100 hydro1 or ADGN-100Hydro2.

Figure 4B:
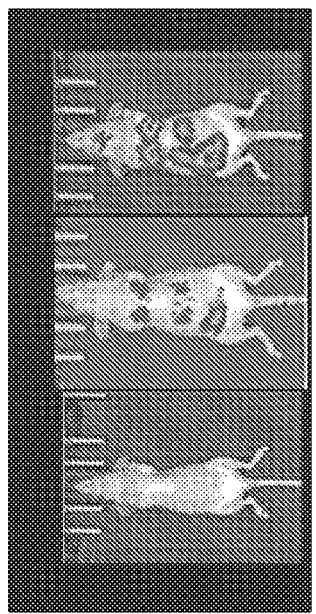

As shown in FIGS. 4A and 4B, combining ADGN-106 with 10% ADGN-100PEG improved by 3-6 fold luciferase expression in the different tissues. Moreover, the presence of 10% ADGN-100PEG in the ADGN106/mRNA complex promotes mRNA targeting in the brain, lymph node and in the spleen.

Figure 4C:
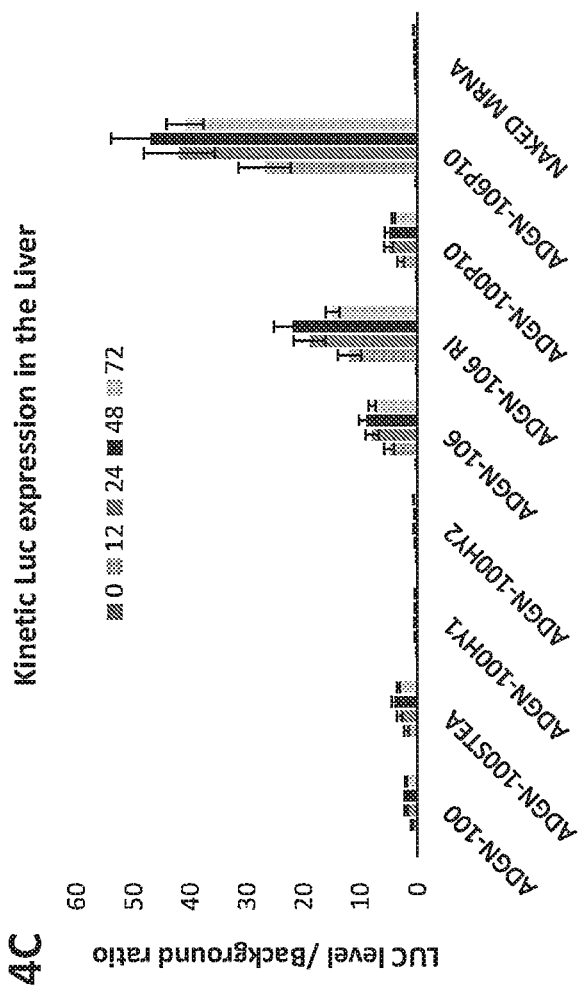
Figure 4D:
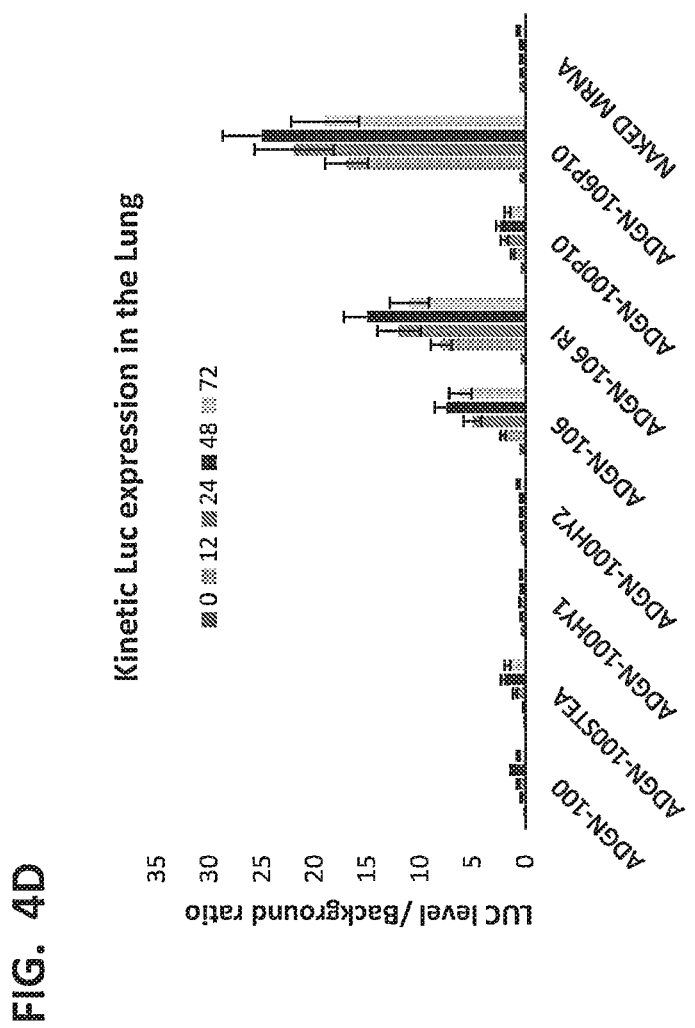

As shown in FIGS. 4C and 4D kinetic of luciferase expression in the liver and the lung, started after 12 h with optimal expression at 48h and remains stable at least 72 hr.

As shown in FIGS. 4C and 4D kinetic of luciferase expression in the liver and the lung, started after 12 h with optimal expression at 48h and remains stable at least 72 hr.

Figure 5A:
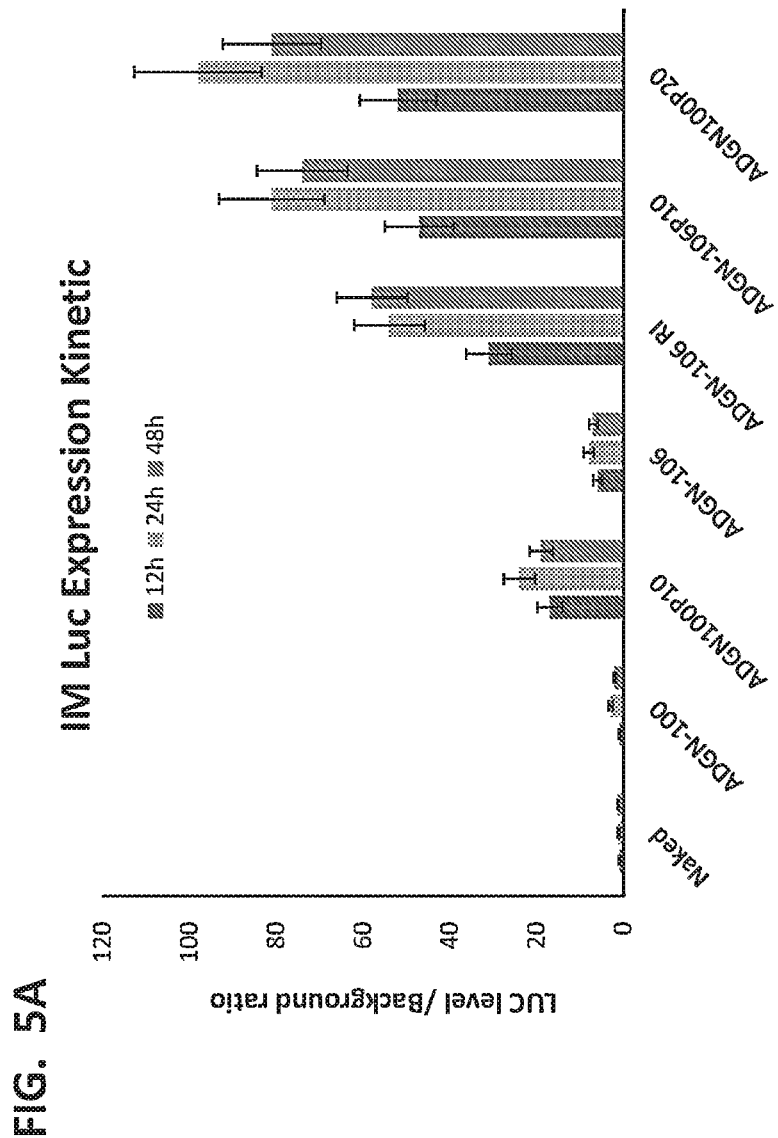
FIGS. 5A-5B show the potency of ADGN-peptide variants for in vivo delivery of Luciferase mRNA via intramuscular administration in mice. ADGN-peptide/luc mRNA particles containing 2.5 μg mRNA were formed in sterile water, and then diluted in 5% sucrose. Mice received IV injection o 25 µl ADGN-peptide/mRNA complexes. mRNA LUC expression was monitored by bioluminescence imaging after 12 h, 24 h and 48h (A).
Figure 5B:
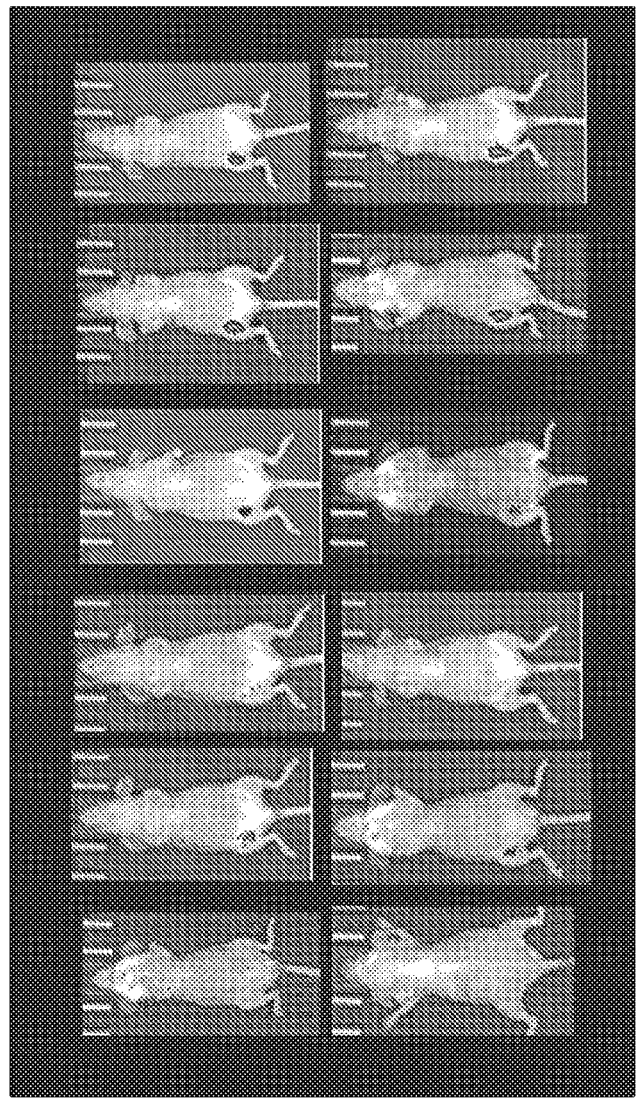

As shown in FIGS. 5A and 5B, ADGN-106, ADGN106-Hydro-6, ADGN-106RI and ADGN-106/ADGN-100P mediated Luciferase expression following intramuscular (IM) administration. ADGN-106RI and hydro-6 modifications increased by 6 and 4 fold ADGN-106 efficiency. Combining ADGN-106 with 10% or 20% of ADGN-100 PEG improves by 8 to 12 folds luciferase expression in the muscle. In contrast, no significant expression was observed using ADGN-100 and combining ADGN-100 with 10% of ADGN-100PEG improves by 3-fold luciferase expression in comparison to ADGN-106. As reported in FIG. 5A, of luciferase expression started after 12 h with optimal expression at 24 h and remains stable at least 48 hr.

The results demonstrated that ADGN-106 promotes significantly higher delivery of mRNA in vivo following IV administration as compared to ADGN-100. Introducing retro-inverso modification on ADGN-106 increased complex stability and cargo delivery in vivo. The results demonstrated than combining pegylated-ADGN peptide within the ADGN-106/mRNA particles strongly stabilize the complexes for both IM and IV administrations. Pegylated ADGN significantly improves luciferase expression in vivo and tissues distribution.

Example 8: ADGN-Peptide Variant Improve Plasmid DNA Delivery In Vivo

Stable ADGN-peptides/pGL4.11 DNA were evaluated for in vivo delivery of Luciferase mRNA via intravenous and intramuscular administrations. Animals were treated with single dose of pGL4.11 plasmid DNA of 5 μg. via IV and 2.5 μg via intramuscular administration.

pGL4.11 DNA plasmid (5 μg) in sterile water (GIBCO) were mixed with ADGN peptide (sterile water), volume for each sample was adjusted to 100 μl, with sterile water containing 5% Sucrose. Samples were mixed gently with vortex for 1 minute at low speed and incubated for 30 min at room temperature. Samples were filtered on 0.45 μm PES filters prior administration. For IV administration Mice received 100 μl IV injection of either ADGN-106/pGL4, ADGN-100/pGL4, ADGN-100RI/pGL4, ADGN-100-stearyl/PGL4, ADGN-100Hydro1/PGL4, ADGN-100Hydro2/PGL4, ADGN100 Hydro6/PGL4 or ADGN/PGL4 complexes containing 10% or 20% of ADGN-100PEG (3 animals per group). As control, mice from group 3 (2 animals per group) received IV injection of 100 μl of naked pGL4 plasmids (5 μg).

For IM administration, mice received 25 μl (2.5 μg of pGL4 plasmid) IV injection of either ADGN-100/PGL4, ADGN-106/PGL4, ADGN-100RI/PGL4, ADGN-100hydro1/PGL4, ADGN-100hydro6/PGL4, ADGN-100 stearyl/PGL4 or ADGN-100/PGL4 complexes containing 10% or 20% of ADGN-100PEG (2 animals per group). As control, mice from group 3 (2 animals per group) received IV injection of 25 μl of naked PGL4 plasmid (2.5 μg).

Luciferase expression was monitored by bioluminescence. Bioluminescence imaging was performed after 12, 24, 48 and 72 hrs. Mice received an i.p. injection of 150 μg/g luciferin for noninvasive bioluminescence imaging (IVIS Kinetic; PerkinElmer, Waltham, MA, USA). Results were then expressed as values relative to day 0 and shown in FIG. 6 and FIG. 7.

Figure 6A:
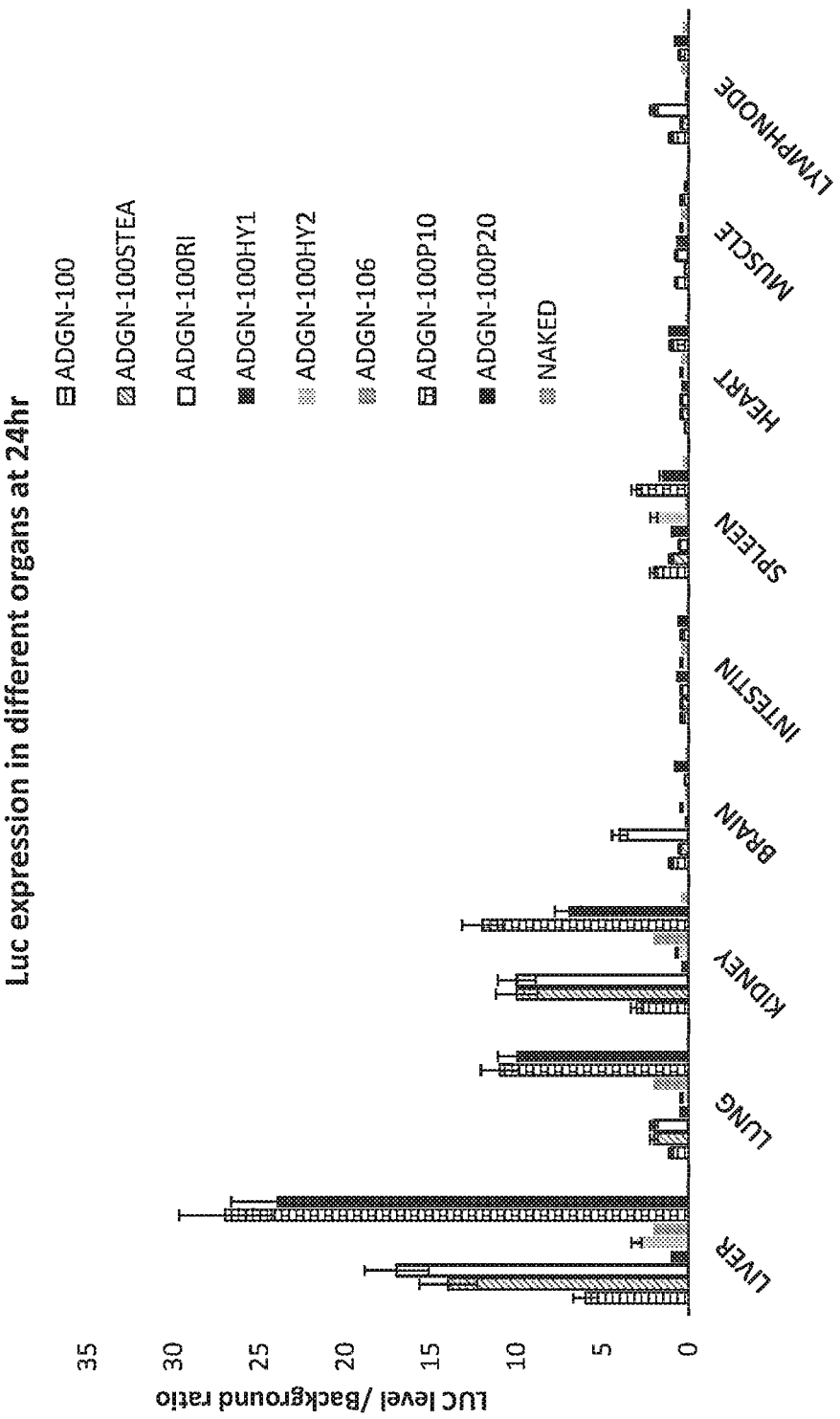
Figure 6C:
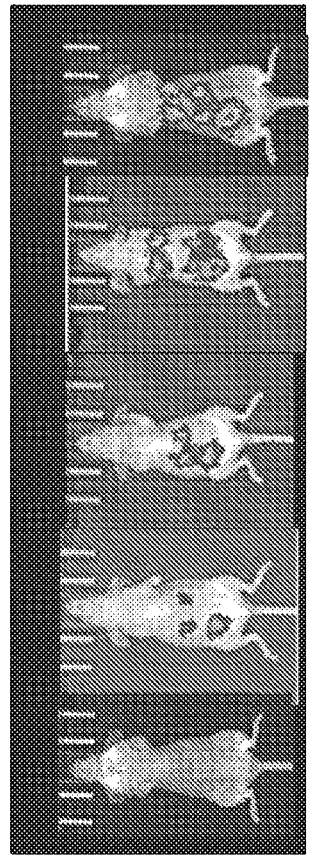

As shown in FIG. 6A; after IV injection, ADGN-100, ADGN-100RI, ADGN-100-Hydro6 and ADGN-100 Stearyl mediated in vivo plasmid delivery and luciferase expression was mainly observed in the liver and at lower level in the lung and the kidney. In contrast, no or minimal expression was observed with ADGN-106. Retro inverso, stearylation and Hydro-6 modifications increased by 4, 2.7 and 3.4 fold, ADGN-100 efficiency in all the tissues, respectively. In contrast, negligible luciferase expression was obtained using ADGN-100 hydro1 or ADGN-100Hydro2.

As shown in FIGS. 6A and 6B, combining ADGN-100 with 10% ADGN-100PEG improved by 5-6 fold luciferase expression in the different tissues. As shown in FIG. 6B kinetic of luciferase expression in the liver, started after 12 h with optimal expression at 48h and remains stable at least 72 hr.

Figure 7A:
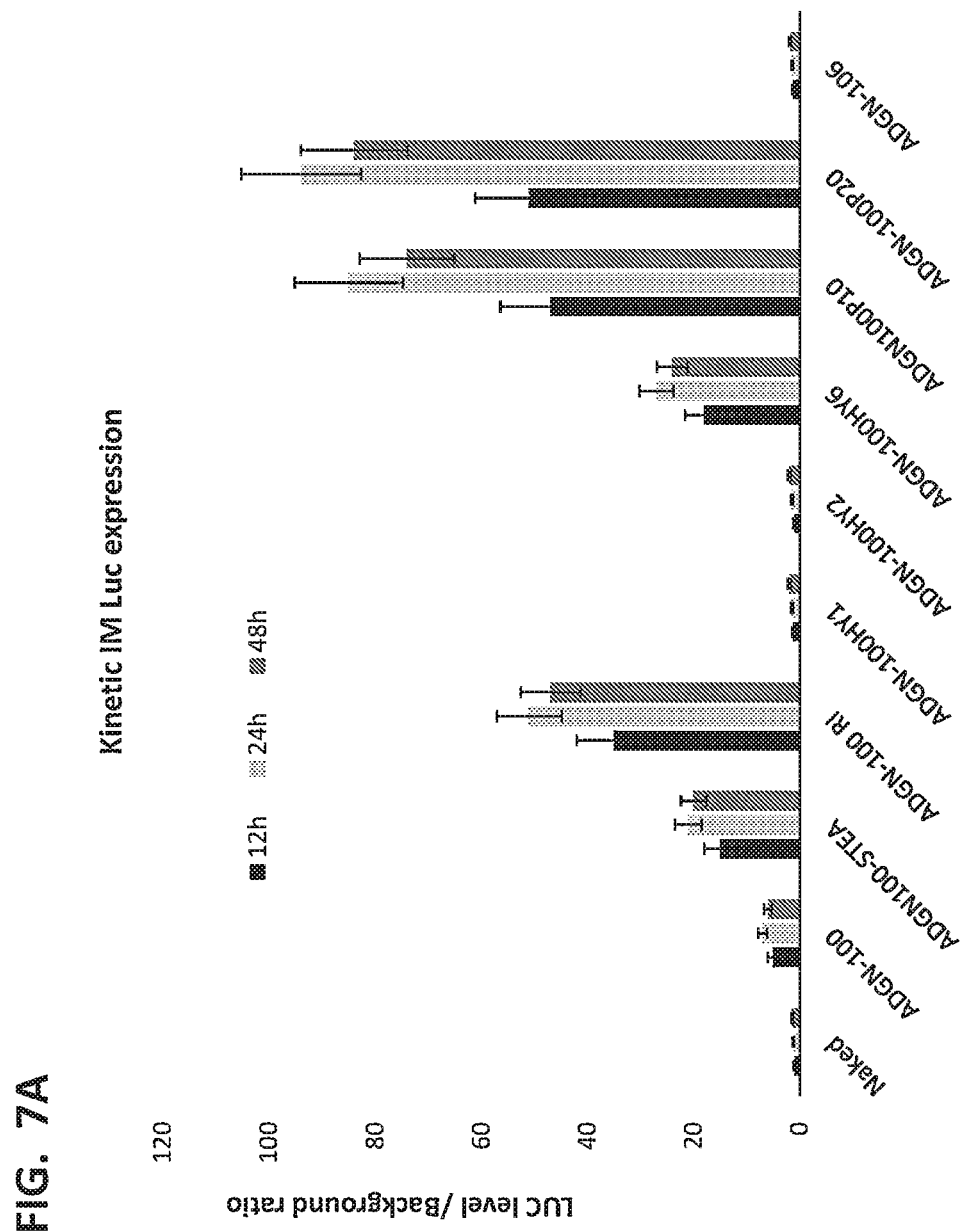
FIGS. 7A-7B show the potency of ADGN-peptide variants for in vivo delivery of Luciferase expressing plasmid pGL4 via intramuscular administration in mice. ADGN-peptide/pGL4 luc particles containing 2.5 µg plasmid DNA were formed in sterile water, and then diluted in 5% sucrose. Mice received IV injection of 25 µl ADGN-peptide/pGL4 complexes. Luciferase expression was monitored by bioluminescence imaging after 12 h, 24 h and 48h (A).
Figure 7B:
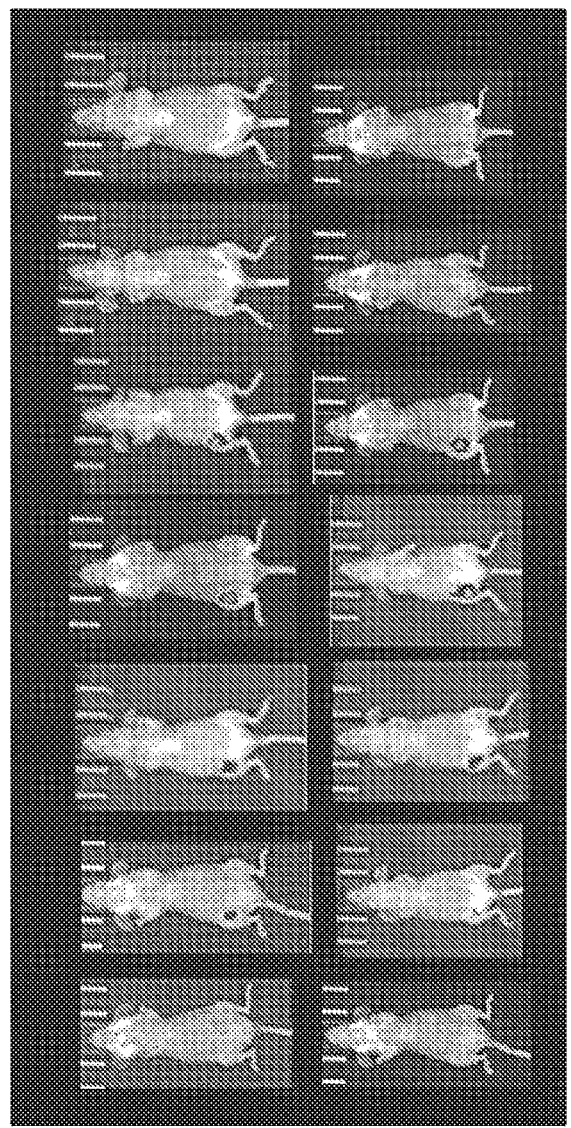

As shown in FIGS. 7A and 7B, ADGN-100, ADGN-100RI, ADGN-100 HYDRO6 and ADGN-100/ADGN-100P mediated Luciferase expression following IM administration. ADGN-100RI modification increased by 6 fold ADGN-100 efficiency. Stearyl and Hydro-6 modification increased by 3-4 fold ADGN-100 efficiency. Combining ADGN-100 with 10% or 20% of ADGN-100 PEG improves by 10 to 12 folds luciferase expression in the muscle. In contrast, no significant expression was observed using ADGN-106 and Hydro-1 or hydro-2 modification. As reported in FIG. 7A, of luciferase expression started after 12 h with optimal expression at 24 h and remains stable at least 48 hr.

The results demonstrated that ADGN-100 promotes significantly higher delivery of plasmid DNA in vivo following IV administration as compared to ADGN-106. Introducing retro-inverso, stearyl or hydro-6 modifications on ADGN-100, increased complex stability as previously observed on cultured cells and plasmid DNA delivery in vivo. The results demonstrated than combining pegylated-ADGN peptide within the ADGN-100/pGL4 plasmid particles strongly stabilize the complexes for both IM and IV administrations. Pegylated ADGN significantly improves luciferase expression in vivo and tissues distribution.

Example 9. ADGN-Peptide Variant Improve Cargo Delivery In Vivo

Stable ADGN-peptides/mRNA were evaluated for in vivo delivery of Luciferase mRNA via intravenous administrations. Animals were treated with single dose of 5 moU modified Luc mRNA of 5 μg. 5 moU modified Luc mRNA (5 μg) in sterile water (GIBCO) were mixed with ADGN peptide (sterile water), volume for each sample was adjusted to 100 μl, with sterile water containing 5% Sucrose. 5 moU modified Luc mRNA (5 μg) was prepared in sterile water at room temperature in a glass vial (1-4 ml). ADGN-peptide solution was added dropwise (1 drop/sec) under magnetic agitation at 400 rpm and incubated for 30 min at room temperature. Prior to IV administration ADGN-peptides/mRNA complexes were diluted in sucrose 5% solution and mixed under magnetic agitation at 400 rpm for 1 minute. Samples were filtered on 0.45 μm PES filters prior administration.

For IV administration Mice received 100 μl intravenous (IV) injection of either ADGN-103C/mRNA, ADGN-104/mRNA, ADGN-105/mRNA ADGN-106 TB/mRNA, ADGN-109/mRNA, ADGN-109D/mRNA, ADGN-109b/mRNA, ADGN-101/mRNA, ADGN-102/mRNA: ADGN-100GALNAC/mRNA, ADGN-106GALNAC/mRNA, ADGN-106TC/mRNA, ADGN-106TD/mRNA, ADGN-106/mRNA, ADGN-100/mRNA, ADGN-106hydro8/mRNA and ADGN-100-Hydro8. (3 animals per group). As control, mice from group 3 (2 animals per group) received IV injection of 100 μl of naked 5 moU modified Luc mRNA (5 μg).

mRNA Luc expression was monitored by bioluminescence. Bioluminescence imaging was performed after 12, 24, 48 and 72 hours. Mice received an i.p. injection of 150 μg/g luciferin for noninvasive bioluminescence imaging (IVIS Kinetic; PerkinElmer, Waltham, MA, USA). Results were then expressed as values relative to day 0 and shown in FIGS. 11A-11C.

Figure 11A:
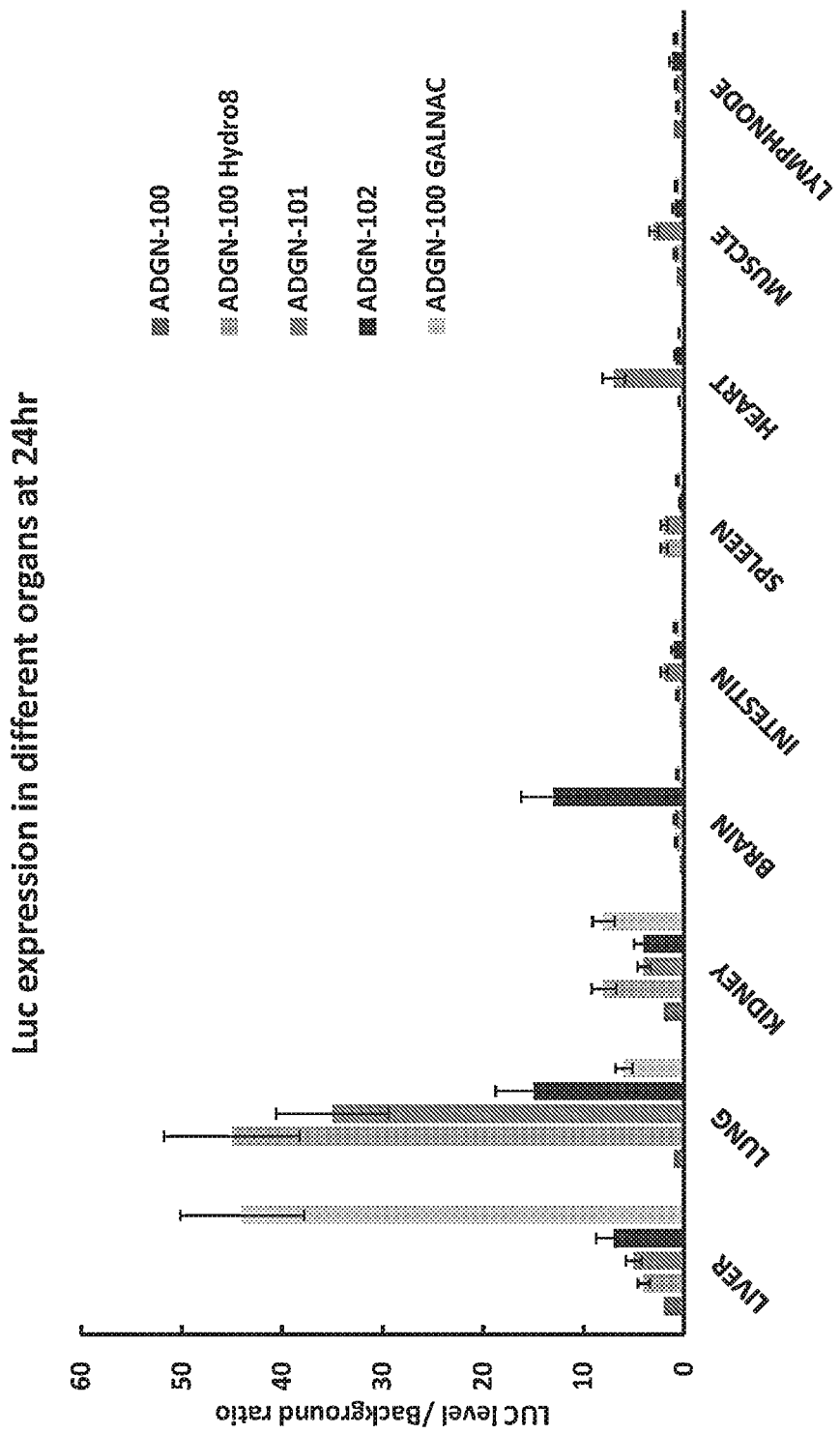

As shown in FIGS. 11A and 11B; ADGN-100GALNAC and ADGN-106GALNAC mediated mRNA accumulation in the liver with an increase of mRNA expression by 10-to 20-folds in comparison to ADGN-106 or ADGN-100.

As shown in FIGS. 11A and 11B, ADGN-100 hydro 8 modification increased by 22 and 4 folds ADGN-100 efficiency in the lung and kidney, respectively. ADGN-106 Hydro8 modification increased by 5folds ADGN-106 peptides efficiency in the lung and muscle and by 2 folds in the liver.

As shown in FIGS. 11A, ADGN-101 modification improved by 6 fold luciferase expression in the lung and promoted target delivery and expression of mRNA in heart and muscles. ADGN-102 modification improved by 3 fold luciferase expression in the lung and promoted target delivery and expression of mRNA in the brain.

As shown in FIGS. 11B, ADGN-106 modification improved by 2-3 fold luciferase expression in the lung. ADGN-106 TB and ADGN-106 TC modifications promoted target delivery and expression of mRNA in the brain. ADGN-106 TD modification promoted target delivery and expression of mRNA in heart and muscles.

Figure 11C:
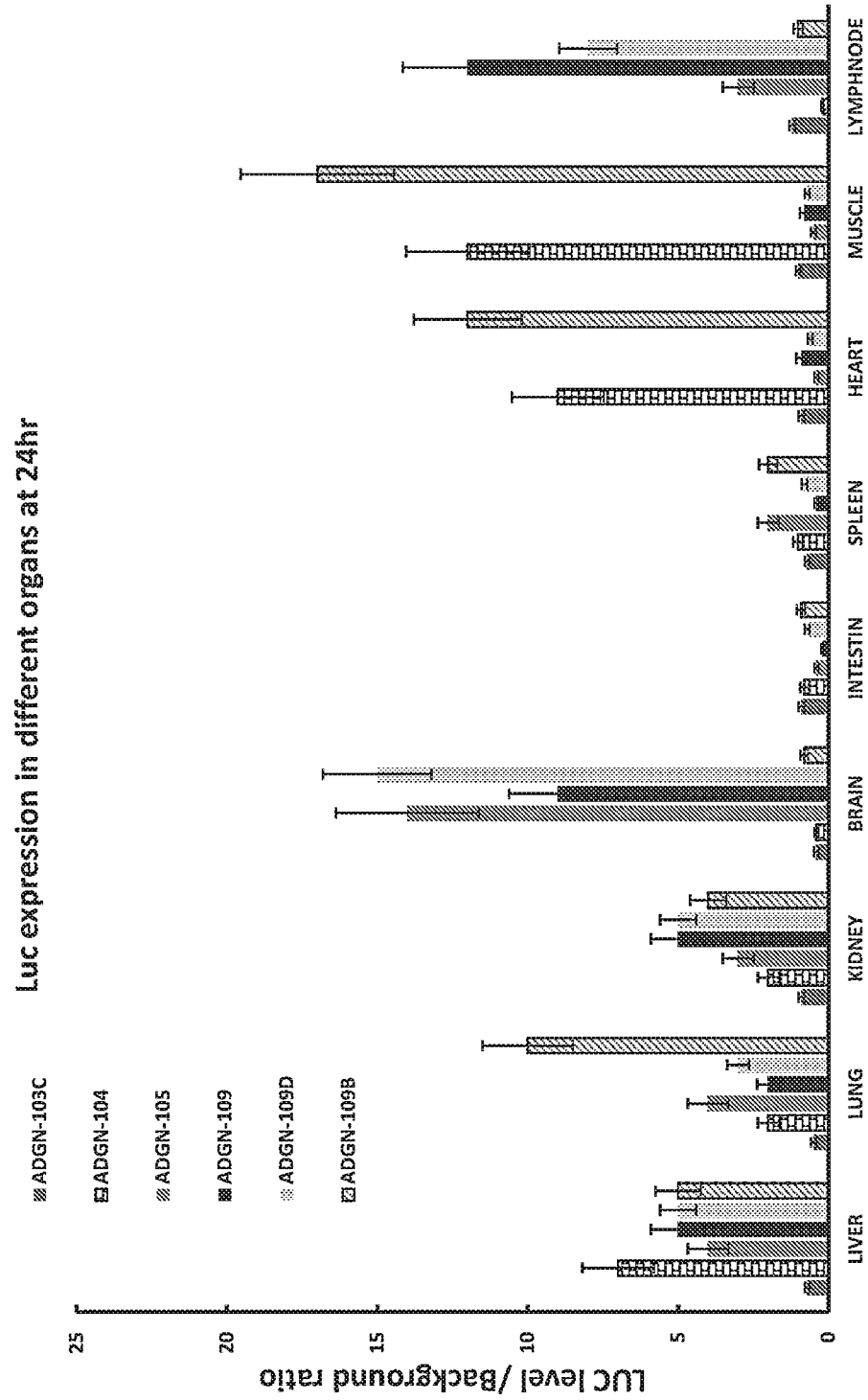

As shown in FIGS. 11C, ADGN-104, ADGN105, ADGN-109, ADGN-109D, ADGN-109B mediated Luciferase expression following intravenous administration. ADGN-104 promoted target delivery and expression of mRNA in heart and muscles and at lower level in the liver. ADGN-105 promoted target delivery and expression of mRNA in the brain and at lower level in liver, lung and lymphnode. ADGN-109 and ADGN-109D promoted target delivery and expression of mRNA in the brain and lymphnode and at lower level in liver and kidney. ADGN-109B promoted target delivery and expression of mRNA in the lung, heart and muscles. In contrast, negligible luciferase expression was obtained using ADGN-103C.

Example 10

Table 1 lists a summary of cell-penetrating peptides that have been proven successful in delivering various cargo molecules to on or more targeted organ (e.g., by intravenous (IV), intramuscular (IM), or subcutaneous (SQ) administration, or intratracheal instillation or nebulization (NB)) in mice or rat models.

TABLE 1

| Code Peptide | Sequences | Cargoes | Route | Targeted Organ |
|---|---|---|---|---|
| VEPEP-3a | beta-AKWFERWFREWPRKRR (SEQ ID NO: 75) | AAV/Mrna/ protien:peptide | IV | Kidney/Pancreas |
| VEPEP-3C | ASSLNIA-Ava-KWWERWWREWPRKRR (SEQ ID NO: 113) | peptide/ protein/PNA | IV/IM | Muscle |
| VEPEP-3D | LSSRLDA Ava-KWWERWWREWPRKRR (SEQ ID NO: 114) | PNA/oligo/mRNA | IV | Heart/Muscle |
| VEPEP-3E | Ac-SYTSSTM-ava-KWWERWWREWPRKRR (SEQ ID NO: 115) | siRNA/Mrna | IV | Brain |
| VEPEP-9 | Beta-ALRWWLRWASRWFSRWAWWR (SEQ ID NO: 78) | AAV/Peptide/ Oligo/plasmid | IV/IM | Brain/Liver/ Lung/Kidney/ |
| VEPEP-9A | KSYDTY-ava-ALRWLRWASRWFSRWAWR (SEQ ID NO: 116) | siRNA/mRNA | IV | Brain/Lymphnode |
| VEPEP-9B | ac-CKRAVRWWLRWASRWFSRWAWWR (SEQ ID NO: 117) | Oligo | IV | Heart |
| VEPEP-9C | Beta-RWWLRWASRWFSRWAWR (SEQ ID NO: 118) | AAV/Peptide/ Oligo/plasmid | IV | Liver/Lung/ Kidney/Brain |
| VEPEP-9D | KSYDTYAAETRRWASRWFSRWAWWR (SEQ ID NO: 119) | siRNA/Peptide | IV | Brain/Lymphnode |
| ADGN-100a | Beta-AKWRSAGWRWRLWRVRSWSR (SEQ ID NO: 79) | Plasmid/ peptide:siRNA/ CRISPR/mRNA | IV/IM/ SQ/NB | Lung/Liver/ Kidney/Pancreas |
| ADGN-100b | beta-AKWRSALYRWRLWRVRSWSR (SEQ ID NO: 80) | Plasmid/ peptide:siRNA/ CRISPR/mRNA | IV/IM/SQ | Lung/Liver/ Kidney/Pancreas |
| ADGN-101 | Ac-CARPARWRSAGWRWRLWRVRSWSR-NH2 (SEQ ID NO: 121) | siRNA/mRNA | IV | Heart/Lung |
| ADGN-102 | TGNYKALHPDHNGWRSALRWRLWRWSR-NH2 (SEQ ID NO: 122) | siRNA/Mrna | IV | Brain/Lung |
| ADGN-100 Stearyl | Stearyl-A-KWRSALWRWRLWRVRSWSR-NH2 (SEQ ID NO: 196) | plasmid/mRNA/ siRNA | IV/IM/SQ | Lung/Liver/ Kidney/Pancreas |

TABLE 1-continued

| Code Peptide | Sequences | Cargoes | Route | Targeted Organ |
|---|---|---|---|---|
| ADGN-100 GALNAC | Ac-KWRSA(GALNAC)LWRWRLWRVRSWSR-NH2 (SEQ ID NO: 124) | Plasmid/Mrna/CRISPR | IV/SQ | Liver |
| ADGN-100-RI | RSWSRVRWLRWRWGASRWK (SEQ ID NO: 86) | Plasmid/Mrna | IV/IM | Liver/Lung/Kidney/Spleen |
| ADGN-100-Hydro | Ac-YIGSR-A-KWRSALWRWRLWRVRSWSR-NH2 (SEQ ID NO: 202) | Plasmid/Mrna | IV/IM | Lung/Kidney |
| ADGN-100-Hydro-1 | Ac-YIGSR-(G)4-KWRSALWRWRLWRVRSWSR-NH2 (SEQ ID NO: 88) | Plasmid/mRNA | IV/IM | Lung/Kidney/Liver |
| ADGN-100-Hydro-3 | Ac-YIGSR-Ava-KWRSALWRWRLWRVRSWSR-NH2 (SEQ ID NO: 101) | Plasmid/mRNA/CRISPR | IV/IM | Tumor/Lung |
| ADGN-100 hydro-4 | Ac-GYVS-Ava-KWRSALWRWRLWRVRSWSR-NH2 (SEQ ID NO: 102) | mRNA | IV/IM | Liver/Lung/Kidney/Spleen |
| ADGN-100 Hydro-7 | Ac-YIGSR-Ahx-KWRSALWRWRLWRVRSWSR-NH2 (SEQ ID NO: 125) | mRNA/CRISPR | IV/IM | Tumor/Lung |
| ADGN-100-PEG2 | Ac-(PEG)2-A-KWRSALWRWRLWRVRSWSR-NH2 (SEQ ID NO: 197) | mRNA/CRISPR | IV/IM | Lung:Liver/Spleen |
| ADGN-100-HYPEG2 | Ac-YIGSR-(PEG)2-βA-KWRSALWRWRLWRVRSWSR-NH2 (SEQ ID NO: 110) | mRNA/CRISPR | IV/IM | Lung |
| ADGN-100-HYPEG4 | Ac-YIGSR-(PEG)4-βA-KWRSALWRWRLWRVRSWSR-NH2 (SEQ ID NO: 111) | mRNA | IV/IM | Lung |
| VEPEP-6 (ADGN-106) | beta-ALWRALWRLWRSLWRLLWKA (SEQ ID NO: 77) | mRNA/siRNA/CRISPR | IV/IM/NB/SQ | Liver/Lung |
| ADGN-106 Stearyl | Stearyl-βA-ALWRALWRLWRSLWRLLWKA-NH2 (SEQ ID NO: 100) | mRNA/siRNA | IV/IM | Liver/Spleen |
| ADGN-106 gaLnaC | ALWRA(GalNac)LWRLWRSLWRLLWKA-NH2 (SEQ ID NO: 129) | Mrna/siRNA | IV/IM/SQ | Liver |
| ADGN-106-RI | AKWLLRWLSRWLRWLARWLR (SEQ ID NO: 85) | mRNA/siRNA | IV/IM | Liver/Lung |
| ADGN-106-Hydro-3: | Ac-YIGSR-Ava-ALWRALWRLWRSLWRLLWKA-NH2 (SEQ ID NO: 96) | mRNA/siRNA/CRISPR | IV/IM | Tumor/Muscle |
| ADGN-106 hydro-4 | Ac-GYVS-Ava-ALWRALWRLWRSLWRLLWKA-NH2 (SEQ ID NO: 97) | mRNA/siRNA/CRISPR | IV/IM | Brain/Kidney |
| ADGN-106-Hydro-5 | Ac-YIGSR-Aun-ALWRALWRLWRSLWRLLWKA-NH2 (SEQ ID NO: 98) | mRNA/siRNA/CRISPR | IV/IM | Tumor/Lung/Pancreas/Liver |
| ADGN-106 hydro-6 | Ac-GYVS-Aun-ALWRALWRLWRSLWRLLWKA-NH2 (SEQ ID NO: 99) | mRNA/siRNA/CRISPR | IV/IM | Tumor/Pancreas/Lung |
| ADGN-106 hydro-7 | Ac-YIGSR-Ahx-ALWRALWRLWRSLWRLLWKA-NH2 (SEQ ID NO: 130) | mRNA/siRNA/CRISPR | IV/IM | Lung/Tumor |

TABLE 1-continued

| Code Peptide | Sequences | Cargoes | Route | Targeted Organ |
|---|---|---|---|---|
| ADGN-106-PEG2 | Ac-(PEG)2-βALWRALWRLWRSLWRLLWKA-NH2 (SEQ ID NO: 93) | mRNA/siRNA/CRISPR | IV/IM | Lung/Kidney/Spleen |
| ADGN-106-HYPEG2 | Ac-YIGSR-(PEG)2-βALWRALWRLWRSLWRLLWKA-NH2 (SEQ ID NO: 107) | mRNA/siRNA/CRISPR | IV/IM | Tumor/Lung |
| ADGN-106-HYPEG4 | Ac-YIGSR-(PEG)4-βALWRALWRLWRSLWRLLWKA-NH2 (SEQ ID NO: 108) | mRNA/siRNA/CRISPR | IV/IM | Tumor/Lung |
| ADGN-106-TB | Ac-SYTSSTM-ava-βALWRALWRLWRSLWRLLWKA-NH2 (SEQ ID NO: 131) | mRNA/siRNA/CRISPR | IV/IM | Brain/Liver |
| ADGN-106-TC | Ac-THRPPNWSPVWPRALWRLWRSLWRLRWKA-NH2 (SEQ ID NO: 133) | mRNA/siRNA/CRISPR | IV/IM | Brain |
| ADGN-106-TD | Ac-CKTRRVPWRALWRLWRSLWRLLWKA-NH2 (SEQ ID NO: 134) | mRNA/siRNA/CRISPR | IV/IM | Muscle/Heart |

SEQUENCE LISTING

| SEQ ID | Sequence | Annotations |
|---|---|---|
| 1. | $X_1X_2X_3X_4X_5X_2X_3X_4X_6X_7X_3X_8X_9X_{10}X_{11}X_{12}X_{13}$<br>$X_1$ is beta-A or S, $X_2$ is K, R or L, $X_3$ is F or W, $X_4$ is F, W or Y, $X_5$ is E, R or S, $X_6$ is R, T or S, $X_7$ is E, R, or S, $X_8$ is none, F or W, $X_9$ is P or R, $X_{10}$ is R or L, $X_{11}$ is K, W or R, $X_{12}$ is R or F, and $X_{13}$ is R or K | VEPEP-3 |
| 2. | $X_1X_2WX_4EX_2WX_4X_6X_7X_3PRX_{11}RX_{13}$<br>$X_1$ is beta-A or S, $X_2$ is R or K, $X_3$ is W or F, $X_4$ is F, W, or Y, $X_6$ is T or R, $X_7$ is E or R, $X_{11}$ is R or K, and $X_{13}$ is R or K | VEPEP-3 1 |
| 3. | $X_1$KWFERWFREWPRKRR<br>$X_1$ is beta-A or S | VEPEP-3 1a |
| 4. | $X_1$KWWERWWREWPRKRR<br>$X_1$ is beta-A or S | VEPEP-3 1b |
| 5. | $X_1$KWWERWWREWPRKRK<br>$X_1$ is beta-A or S | VEPEP-3 1c |
| 6. | $X_1$RWWEKWWTRWPRKRK<br>$X_1$ is beta-A or S | VEPEP-3 1d |
| 7. | $X_1$RWYEKWYTEFPFRRR<br>$X_1$ is beta-A or S | VEPEP-3 1e |
| 8. | $X_1KX_{14}WWERWWRX_{14}WPRKRK$<br>$X_1$ is beta-A or S and $X_{14}$ is a non-natural amino acid, and wherein there is a hydrocarbon linkage between the two non-natural amino acids | VEPEP-3 1S |
| 9. | $X_1X_2X_3WX_5X_{10}X_3WX_6X_7WX_8X_9X_{10}WX_{12}R$<br>$X_1$ is beta-A or S, $X_2$ is K, R or L, $X_3$ is F or W, $X_5$ is R or S, $X_6$ is R or S, $X_7$ is R or S, $X_8$ is F or W, $X_9$ is R or P, $X_{10}$ is L or R, and $X_{12}$ is R or F | VEPEP-3 2 |
| 10. | $X_1$RWWRLWWRSWFRLWRR<br>$X_1$ is beta-A or S | VEPEP-3 2a |
| 11. | $X_1$LWWRRWWSRWWPRWRR<br>$X_1$ is beta-A or S | VEPEP-3 2b |
| 12. | $X_1$LWWSRWWRSWFRLWFR<br>$X_1$ is beta-A or S | VEPEP-3 2c |

SEQUENCE LISTING

| SEQ ID | Sequence | Annotations |
|---|---|---|
| 13. | $X_1$KFWSRFWRSWFRLWRR<br>$X_1$ is beta-A or S | VEPEP-3 2d |
| 14. | $X_1$RWW$X_{14}$LWWRSW$X_{14}$RLWRR<br>$X_1$ is a beta-alanine or a serine and $X_{14}$ is a non-natural amino acid, and wherein there is a hydrocarbon linkage between the two non-natural amino acids | VEPEP-3 2S |
| 15. | $X_1$L$X_2$RALW$X_9$L$X_3X_9X_4$LW$X_9$L$X_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S | VEPEP-6 1 |
| 16. | $X_1$L$X_2$LARW$X_9$L$X_3X_9X_4$LW$X_9$L$X_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S | VEPEP-6 2 |
| 17. | $X_1$L$X_2$ARLW$X_9$L$X_3X_9X_4$LW$X_9$L$X_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, $X_8$ is A or none, and $X_9$ is R or S | VEPEP-6 3 |
| 18. | $X_1$L$X_2$RALWR$X_3$R$X_4$LWR$X_5X_6X_7X_8$<br>$X_1$ is beta-A or S, $X_2$ is F or W, $X_3$ is L, W, C or I, $X_4$ is S, A, N or T, $X_5$ is L or W, $X_6$ is W or R, $X_7$ is K or R, and $X_8$ is A or none | VEPEP-6 4 |
| 19. | $X_1$L$X_2$RALWR$X_3$R$X_4$LWRL$X_5X_6$K$X_7$<br>$X_1$ is beta-A or S, $X_2$ is F or NV, $X_3$ is L or W, $X_4$ is S, A or N, $X_5$ is L or W, $X_6$ is W or R, $X_7$ is A or none | VEPEP-6 5 |
| 20. | $X_1$LFRALWRLLR$X_2$LWRLLW$X_3$<br>$X_1$ is beta-A or S, $X_2$ is S or T, and $X_3$ is K or R | VEPEP-6 6 |
| 21. | $X_1$LWRALWRLWR$X_2$LWRLLW$X_3$A<br>$X_1$ is beta-A or S, $X_2$ is S or T, and $X_3$ is K or R | VEPEP-6 7 |
| 22. | $X_1$LWRALWRL$X_4$R$X_2$LWRLWR$X_3$A<br>$X_1$ is beta-A or S, $X_2$ is S or T, $X_3$ is K or R, and $X_4$ is L, C or I | VEPEP-6 8 |
| 23. | $X_1$LWRALWRLWR$X_2$LWRLWR$X_3$A<br>$X_1$ is beta-A or S, $X_2$ is S or T, and $X_3$ is K or R | VEPEP-6 9 |
| 24. | $X_1$LWRALWRL$X_5$RALWRLLW$X_3$A<br>$X_1$ is beta-A or 5, $X_3$ is K or R, and $X_5$ is L or I | VEPEP-6 10 |
| 25. | $X_1$LWRALWRL$X_4$RNLWRLLW$X_3$A<br>$X_1$ is beta-A or S, $X_3$ is K or R, and $X_4$ is L, C or I | VEPEP-6 11 |
| 26. | Ac-$X_1$LFRALWRLLRSLWRLLWK-cysteamide<br>$X_1$ is beta-A or S | VEPEP-6a |
| 27. | Ac-$X_1$LWRALWRLWRSLWRLLWKA-cysteamide<br>$X_1$ is beta-A or S | VEPEP-6b |
| 28. | Ac-$X_1$LWRALWRLLRSLWRLWRKA-cysteamide<br>$X_1$ is beta-A or S | VEPEP-6c |
| 29. | Ac-$X_1$LWRALWRLWRSLWRLWRKA-cysteamide<br>$X_1$ is beta-A or S | VEPEP-6d |
| 30. | Ac-$X_1$LWRALWRLLRALWRLLLWKA-cysteamide<br>$X_1$ is beta-A or S | VEPEP-6e |
| 31. | Ac-$X_1$LWRALWRLLRNLWRLLWKA-cysteamide<br>$X_1$ is beta-A or S | VEPEP-6f |
| 32. | Ac-$X_1$LFRALWR$_s$LLR$_s$LWRLLWK-cysteamide<br>$X_1$ is beta-A or S and the residues followed by an inferior "s" are linked by a hydrocarbon linkage | ST-VEPEP-6a |

| SEQ ID | Sequence | Annotations |
|---|---|---|
| 33. | Ac-X$_1$LFLARWR$_s$LLRS$_s$LWRLLWK-cysteatmide<br>X$_1$ is beta-A or S and the residues followed by an inferior "s" are linked by a hydrocarbon linkage | ST-VEPEP-6aa |
| 34. | Ac-X$_1$LFRALWS$_s$LLRS$_s$LWRLLWK-cysteamide<br>X$_1$ is beta-A or S and the residues followed by an inferior "s" are linked by a hydrocarbon linage | ST-VEPEP-6ab |
| 35. | Ac-X$_1$LFLARWS$_s$LLRS$_s$LWRLLWK-cysteamide<br>X$_1$ is beta-A or S and the residues followed by an inferior "s" are linked by a hydrocarbon linkage | ST-VEPEP-6ad |
| 36. | Ac-X$_1$LFRALWRLLR$_s$SLWS$_s$LLWK-cysteamide<br>X$_1$ is beta-A or S and the residues followed by an inferior "s" are linked by a hydrocarbon linkage | ST-VEPEP-6b |
| 37. | Ac-X$_1$LFLARWRLLR$_s$SLWS$_s$LLWK-cysteamide<br>X$_1$ is beta-A or S and the residues followed by an inferior "s" are linked by a hydrocarbon linkage | ST-VEPEP-6ba |
| 38. | Ac-X$_1$LFRALWRLLS$_s$SLWS$_s$LLWK-cysteamide<br>X$_1$ is beta-A or S and the residues followed by an inferior "s" are linked by a hydrocarbon linkage | ST-VEPEP-6bb |
| 39. | Ac-X$_1$LFLARWRLLS$_s$SLWS$_s$LLWK-cysteamide<br>X$_1$ is beta-A or S and the residues followed by an inferior "s" are linked by a hydrocarbon linkage | ST-VEREP-6bd |
| 40. | Ac-X$_1$LFAR$_s$LWRLLRS$_s$LWRLLWK-cysteamide<br>X$_1$ is beta-A or S and the residues followed by an inferior "s" are linked by a hydrocarbon linkage | ST-VEPEP-6c |
| 41. | X$_1$X$_2$X$_3$WWX$_4$X$_5$WAX$_6$X$_3$X$_7$X$_8$X$_9$X$_{10}$X$_{11}$X$_{12}$WX$_{13}$R<br>X$_1$ is beta-A or S, X$_2$ is L or none, X$_3$ is R or none, X$_4$ is L, R or G, X$_5$ is R, W or S, X$_6$ is S, P or T, X$_7$ is W or P, X$_8$ is F, A or R, X$_9$ is S, L, P or R, X$_{10}$ is R or S, X$_{11}$ is W or none, X$_{12}$ is A, R or none and X$_{13}$ is W or F, and wherein if X$_3$ is none, then X$_2$, X$_{11}$ and X$_{12}$ are none as well | VEPEP-9 1 |
| 42. | X$_1$X$_2$RWWLRWAX$_6$RWX$_8$X$_9$X$_{10}$WX$_{12}$WX$_{13}$R<br>X$_1$ is beta-A or S, X$_2$ is L or none, X$_6$ is S or P, X$_8$ is F or A, X$_9$ is S, L or P, X$_{10}$ is R or S, X$_{12}$ is A or R, and X$_{13}$ is W Or F | VEPEP-9 2 |
| 43. | X$_1$LRWWLRWASRWFSRWAWWR<br>X$_1$ is beta-A or S | VEPEP9a1 |
| 44. | X$_1$LRWWLRWASRWASRWAWFR<br>X$_1$ is beta-A or S | VEPEP9a2 |
| 45. | X$_1$RWWLRWASRWALSWRWWR<br>X$_1$ is beta-A or S | VEPEP9b1 |
| 46. | X$_1$RWWLRWASRWFLSWRWWR<br>X$_1$ is beta-A or S | VEPEP9b2 |
| 47. | X$_1$RWWLRWAPRWFPSWRWWR<br>X$_1$ is beta-A or S | VEPEP9c1 |
| 48. | X$_1$RWWLRWASRWAPSWRWWR<br>X$_1$ is beta-A or S | VEPEP9c2 |
| 49. | X$_1$WWX$_4$X$_5$WAX$_6$X$_7$X$_8$RX$_{10}$WWR<br>X$_1$ is beta-A or S | VEPEP-9 3 |
| 50. | X$_1$WWRWWASWARSWWR<br>X$_1$ is beta-A or S | VEPEP9d |
| 51. | X$_1$WWGSWATPRRRWWR<br>X$_1$ is beta-A or S | VEPEP9e |
| 52. | X$_1$WWRWWAPWARSWWR<br>X$_1$ is beta-A or S | VEPEP9f |
| 53. | X$_1$KWRSX$_2$X$_3$X$_4$RWRLWRX$_5$X$_6$X$_7$X$_8$SR<br>X$_1$ is any amino acid or none, and X$_2$-X$_8$ are any amino acid | ADGN-100 |

| SEQ ID | Sequence | Annotations |
|---|---|---|
| 54. | $X_1$KWRS$X_2X_3X_4$RWRLWR$X_5X_6X_7X_8$SR<br>$X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y | ADGN-100 1 |
| 55. | KWRSAGWRWRLWRVRSWSR | ADGN-100a |
| 56. | KWRSALYRWRLWRVRSWSR | ADGN-100b |
| 57. | KWRSALYRWRLWRSRSWSR | ADGN-100c |
| 58. | KWRSALYRWRLWRSALYSR | ADGN-100d |
| 59. | KWRS$_S$AGWR$_S$WRLWRVRSWSR<br>the residues marked with a subscript "S" are linked by a hydrocarbon linkage | ADGN-100 aa |
| 60. | KWR$_S$SAGWRWR$_S$LWRVRSWSR<br>the residues marked with a subscript "S" are linked by a hydrocarbon linkage | ADGN-100 ab |
| 61. | KWRSAGWR$_S$WRIAVRVR$_S$SWSR<br>the residues marked with a subscript "S" are linked by a hydrocarbon linkage | ADGN-100 ac |
| 62. | KWRS$_S$ALYR$_S$WRLWRSRSWSR<br>the residues marked with a subscript "S" are linked by a hydrocarbon linkage | ADGN-100 ba |
| 63. | KWR$_S$SALYRWR$_S$LWRSRSWSR<br>the residues marked with a subscript "S" are linked by a hydrocarbon linkage | ADGN-100 bb |
| 64. | KWRSALYR$_S$WRLWRSR$_S$SWSR<br>the residues marked with a subscript "S" are linked by a hydrocarbon linkage | ADGN-100 bc |
| 65. | KWRSALYRWR$_S$LWRS$_S$RSWSR<br>the residues marked with a subscript "5" are linked by a hydrocarbon linkage | ADGN-100 bd |
| 66. | KWRSALYRWRLWRS$_S$RSWS$_S$R<br>the residues marked with a subscript "S" are linked by a hydrocarbon linkage | ADGN-100 be |
| 67. | KWR$_S$SALYRWR$_S$LWRSALYSR<br>the residues marked with a subscript "S" are linked by a hydrocarbon linkage | ADGN-100 ca |
| 68. | KWRS$_S$ALYR$_S$WRLWRSALYSR<br>the residues marked with a subscript "S" are linked by a hydrocarbon linkage | ADGN-100 cb |
| 69. | KWRSALYRWR$_S$LWRS$_S$ALYSR<br>the residues marked with a subscript "S" are linked by a hydrocarbon linkage | ADGN-100 cc |
| 70. | KWRSALYRWRLWRS$_S$ALYS$_S$R<br>the residues marked with a subscript "S" are linked by a hydrocarbon linkage | ADGN-100 cd |
| 71. | KETWWETWWTEWSQPKKKRKV | PEP-1 |
| 72. | KETWFETWFFEWSQPKKKRKV | PEP-2 |
| 73. | KWFETWFTEWPKKRK | PEP-3 |
| 74. | GALFLGFLGAAGSTMGAWSQPKKKRKV | MPG |
| 75. | beta-AKWFERWFREWPRKRR | VEPEP-3a |
| 76. | beta-AKWWERWWREWPRKRR | VEPEP-3b |
| 77. | beta-ALWRALWRLWRSLWRLLWKA | VEPEP-6 (ADGN-106) |

-continued

| SEQ ID | Sequence | Annotations |
|---|---|---|
| 78. | beta-ALRWWLRWASRWFSRWAWWR | VEPEP-9 |
| 79. | beta-AKWRSAGWRWRLWRVRSWSR | ADGN-100a (ADGN-100) |
| 80. | beta-AKWRSALYRWRLWRVRSWSR | ADGN-100b |
| 81. | GLWRALWRLLRSLWRLLWKV | CADY |
| 82. | RQIKIWFQNRRMKWKKC | pANT |
| 83. | CRRRQRRKKRGGDIMGEWGNEIFGAIAGFLG | TAT-HA2 |
| 84. | KKALLALALHHLAHLALHLALALKKAC | LAH4 |
| 85. | AKWLLRWLSRWLRWLARWLR | ADGN-106-RI |
| 86. | RSWSRVRWLRWRWGASRWK | ADGN-100-RI |
| 87. | Ac-(PEG)7-bA-KWRSALWRWRLWRVRSWSR-NH2 | ADGN-100-PEG |
| 88. | Ac-YIGSR-(G)4-KWRSALWRWRLWRVRSWSR-NH2 | ADGN-100-Hydro-1 |
| 89. | Ac-GYVS-(G)4-KWRSALWRWRLWRVRSWSR-NH2 | ADGN-100 hydro-2 |
| 90. | Stearyl-βA-KWRSALWRWRLWRVRSWSR-NH2 | ADGN-100 Stearyl |
| 91. | Ac-(PEG)2-βA-KWRSALWRWRLWRVRSWSR-NH2 | ADGN-100-PEG-2 |
| 92. | Ac-(PEG)7-βALWRALWRLWRSLWRLLWKA-NH2 | ADGN-106-PEG7 |
| 93. | Ac-(PEG)2-βALWRALWRLWRSLWRLLWKA-NH2 | ADGN-106-PEG2 |
| 94. | Ac-YIGSR-(G)4-ALWRALWRLWRSLWRLLWKA-NH2 | ADGN-106-Hydro-1 |
| 95. | Ac-GYVS-(G)4-ALWRALWRLWRSLWRLLWKA-NH2 | ADGN-106 hydro-2 |
| 96. | Ac-YIGSR-Ava-ALWRALWRLWRSLWRLLWKA-NH2<br>Ava is 5-amino pentanoic acid | ADGN-106-Hydro-3: |
| 97. | Ac-GYVS-Ava-ALWRALWRLWRSLWRLLWKA-NH2<br>Ava is 5-amino pentanoic acid | ADGN-106 hydro-4 |
| 98. | Ac-YIGSR-Aun-ALWRALWRLWRSLWRLLWKA-NH2<br>Aun is 11-amino-undecanoic acid | ADGN-106-Hydro-5 |
| 99. | Ac-GYVS-Aun-ALWRALWRLWRSLWRLLWKA-NH2<br>Aun is 11-amino-undecanoic acid | ADGN-106 hydro-6 |
| 100. | Stearyl-βA-ALWRALWRLWRSLWRLLWKA-NH2 | ADGN-106 Stearyl |
| 101. | Ac-YIGSR-Ava-KWRSALWRWRLWRVRSWSR-NH2<br>Ava is 5-amino pentanoic acid | ADGN-100-Hydro-3 |
| 102. | Ac-GYVS-AVa-KWRSALWRWRLWRVRSWSR-NH2<br>Ava is 5-amino pentanoic acid | ADGN-100 hydro-4 |
| 103. | Ac-YIGSR-Aun-KWRSALWRWRLWRVRSWSR-NH2<br>Aun is 11-amino-undecanoic acid | ADGN-100-Hydro-5 |
| 104. | Ac-GYVS-Aun-KWRSALWRWRLWRVRSWSR-NH2<br>Aun is 11-amino-undecanoic acid | ADGN-100 hydro-6 |
| 105. | Ac-YIGSR-βALWRALWRLWRSLWRLLWKA-NH2 | ADGN-106-Hydro |

| SEQUENCE LISTING | | |
|---|---|---|
| SEQ ID | Sequence | Annotations |
| 106. | Ac-YIGSR-βA-KWRSALWRWRLWRVRSWSR-NH2 | ADGN-100-Hydro |
| 107. | Ac-YIGSR-(PEG)2-βALWRALWRLWRSLWRLLWKA-NH2 | ADGN-106-HYPEG2 |
| 108. | Ac-YIGSR-(PEG)4-βALWRALWRLWRSLWRLLWKA-NH2 | ADGN-106-HYPEG4 |
| 109. | Ac-YIGSR-(PEG)7-βALWRALWRLWRSLWRLLWKA-NH2 | ADGN-106-HYPEG7 |
| 110. | Ac-YIGSR-(PEG)2-βA-KWRSALWRWRLWRVRSWSR-NH2 | ADGN-100-HYPEG2 |
| 111. | Ac-YIGSR-(PEG)4-βA-KWRSALWRWRLWRVRSWSR-NH2 | ADGN-100-HYPEG4 |
| 112. | Ac-YIGSR-(PEG)7-βA-KWRSALWRWRLWRVRSWSR-NH2 | ADGN-100-HYPEG7 |
| 113. | ASSLNIA-Ava-KWWERWWREWPRKRR | VEPEP-3C |
| 114. | LSSRLDA-Ava-KWWERWWREWPRKRR | VEPEP-3D |
| 115. | Ac-SYTSSTM-ava-KWWERWWREWPRKRR | VEPEP-3E |
| 116. | KSYDTY-ava-ALRWLRWASRWFSRWAWR | VEPEP-9A |
| 117. | Ac-CKRAVRWWLRWASRWFSRWAWWR | VEPEP-9B |
| 118. | beta-RWWLRWASRWFSRWAWR | VEPEP-9C |
| 119. | KSYDTYAAETRRWASRWFSRWAWWR | VEPEP-9D |
| 120. | KWWERWWREWPRKRR | VEPEP-9 |
| 121. | Ac-CARPARWRSAGWRWRLWRVRSWSR-NH2 | ADGN-101 |
| 122. | TGNYKALHPDHNGWRSALRWRLWRWSR-NH2 | ADGN-102 |
| 123. | Ac-TGNYKALHPDHNG-ava-WRSALRWRLWRWSR-NH2 | |
| 124. | Ac-KWRSA(GALNAC)LWRWRLWRVRSWSR-NH2 | ADGN-100 GALNAC |
| 125. | Ac-YIGSR-Ahx-KWRSALWRWRLWRVRSWSR-NH2 | ADGN-100 Hydro-7 |
| 126. | Ac-YIGSR-Ahx-KWRSALWRWRLWRVRSWSR-NH2 | ADGN-100-Hydro-7 |
| 127. | Ac-GYVS-Ahx-KWRSALWRWRLWRVRSWSR-NH2 | ADGN-100 hydro-8 |
| 128. | Ac-SYTSSTM-ava-KWRSALWRWRLWRVRSWSR-NH2 | |
| 129. | ALWIRA(GalNac)LWRLWRSLWRLLWKA-NH2 | ADGN-106 gaLnaC |
| 130. | Ac-YIGSR-Ahx-ALWRALWRLWRSLWRLLWKA-NHX | ADGN-106 hydro-7 |
| 131. | Ac-SYTSSTM-ava-βALWRALWRLWRSLWRLLWKA-NH2 | ADGN-106-TB |
| 132. | Ac-SYTSSTM-ava-βALWRALWRLWRSLWRLLWK-NH2 | |
| 133. | Ac-THRPPNWSPVWPRALWRLWRSLWRLRWKA-NH2 | ADGN-106-TC |
| 134. | Ac-CKTRRVPWRALWRLWRSLWRLLWKA-NH2 | ADGN-106-TD |
| 135. | Ac-YIGSR-Ahx-ALWRALWRLWRSLWRLLWKA-NH2 | ADGN-106-Hydro-7 |

| SEQUENCE LISTING | | |
|---|---|---|
| SEQ ID | Sequence | Annotations |
| 136. | Ac-GYVS-Ahx-ALWRALWRLWRSLWRLLWKA-NH2 | ADGN-106 hydro-8 |
| 137. | Ac-CKTRRVP-aya-WRALWRLWRSLWRLLWKA-NH2 | |
| 138. | Ac-THRPPNWSPV-ava-WRALWRLWRSLWRLRWK-NH2 | |
| 139. | Ac-CARPAR-ava-WRALWRLWRSLWRLLWK-NH2 | |
| 140. | XWXRLXXXXXX<br>X in position 1 is beta-A or S; X in positions 3, 9 and 10 are, independently from each other, W or F; X in position 6 is R if X in position 8 is S, and X in position 6 is S if X in position 8 is R; X in position 7 is L or none; X in position 11 is R or none, and X in position 7 is L if X in position 11 is none | VEPEP-4 |
| 141. | X₁WWRLSLRWW<br>X₁ is beta-A or S | VEPEP-4 |
| 142. | X₁WFRLSLRFWR<br>X₁ is beta-A or S | VEPEP-4 |
| 143. | X₁WWRLRSWFR<br>X₁ is beta-A or S | VEPEP-4 |
| 144. | X₁WFRLSLRFW<br>X₁ is beta-A or S | VEPEP-4 |
| 145. | RXWXRLWXRLR<br>X in position 2 is R or S; and X in positions 4 and 8 are, independently from each other, W or F | VEPEP-5 |
| 146. | X₁WWRLWWRLR<br>X₁ is beta-A or S | VEPEP-5 |
| 147. | X₁WFRLWFRLR<br>X₁ is beta-A or S | VEPEP-5 |
| 148. | X₁WFRLWWRLR<br>X₁ is beta-A or S | VEPEP-5 |
| 149. | XHD 1WWRLWFRLR<br>X₁ is beta-A or S | VEPEP-5 |
| 150. | X₁RWWRLWWRL<br>X₁ is beta-A or S | VEPEP-5 |
| 151. | X₁RSWFRLWFR<br>X₁ is beta-A or S | VEPEP-5 |
| 152. | SYTSSTM | Targeting sequence |
| 153. | CKTRRVP | Targeting sequence |
| 154. | THRPPNWSPV | Targeting sequence |
| 155. | TGNYKALHPDHNG | Targeting sequence |
| 156. | CARPAR | Targeting sequence |
| 157. | YIGSR | Targeting sequence |
| 158. | GYVS | Targeting sequence |
| 159. | ASSLNIA | Targeting sequence |

| SEQUENCE LISTING | | |
|---|---|---|
| SEQ ID | Sequence | Annotations |
| 160. | LSSRLDA | Targeting sequence |
| 161. | KSYDTY | Targeting sequence |
| 162. | CKRAV | Targeting sequence |
| 163. | PKKKRKV | NLS sequence |
| 164. | KRPAATKKAGQAKKKK | NLS sequence |
| 165. | PAAKRVKLD | NLS sequence |
| 166. | RQRRNELKRSP | NLS sequence |
| 167. | NQSSNFGPMKGGNFGGRSSGPYGGGGQYFAKPRNQGGY | NLS sequence |
| 168. | RMRIZFKNKGKDTAELRRRRVEVSVELRKAKKDEQILKRRNV | NLS sequence |
| 169. | VSRKRPRP | NLS sequence |
| 170. | PPKKARED | NLS sequence |
| 171. | PQPKKKPL | NLS sequence |
| 172. | SALIKKKKKMAP | NLS sequence |
| 173. | DRLRR | NLS sequence |
| 174. | PKQKKRK | NLS sequence |
| 175. | RKLKKKIKKL | NLS sequence |
| 176. | REKKKFLKRR | NLS sequence |
| 177. | KRKGDEVDGVDEVAKKKSKK | NLS sequence |
| 178. | RKCLQAGMNLEARKTKK | NLS sequence |
| 179. | 5'-GUUGGAGCUUGUGGCGUAGUU-3' | KRAS siRNA targeting G12C mutaton (sense) |
| 180. | 5'-CUACGCCACCAGCUCCAACUU-3' | KRAS siRNA targeting G12C mutation (anti-sense) |
| 181. | 5'-GATGAGGCTATTCATGATGATT-3' | Factor VIII siRNA (sense) |
| 182. | 5'-GAAGUGCAUACACCGAGACUU-3' | KRAS siRNA targeting Q61K mutation (sense) |
| 183. | 5'-GUCUCGGUGUAGCACUUCUU-3' | KRAS siRNA targeting Q61K mutation (anti-sense) |
| 184. | 5'-GUUGGAGCUGUUGGCGUAGUU-3' | KRAS siRNA targeting G12D mutation (sense) |
| 185. | 5'-CUACGCCAACAGCUCCAACUU-3' | KRAS siRNA targeting G12D mutation (anti-sense) |

The invention claimed is:

1. A cargo delivery complex for intracellular delivery of a cargo molecule comprising a) a first peptide comprising a first cell-penetrating peptide; b) a second peptide comprising a second cell-penetrating peptide; and c) a cargo molecule, wherein the second peptide comprises a polyethylene glycol (PEG) moiety that is covalently linked to the second cell-penetrating peptide, wherein the first peptide does not have a PEG moiety, wherein the first and the second cell-penetrating peptides are each independently an ADGN-100 peptide, and wherein the number of ethylene glycol units in the PEG moiety is two to ten ethylene glycol units.

2. The cargo delivery complex of claim 1, wherein the ADGN-100 peptide comprises an amino acid sequence selected from the group consisting of SEQ ID NOs: 53-70, 79, 80, 88-90, 101-104, 106, and 124-127.

3. The cargo delivery complex of claim 1, wherein the first and the second cell-penetrating peptide are the same.

4. The cargo delivery complex of claim 1, wherein the cargo molecule is selected from the group consisting of a nucleic acid, a virus, a polypeptide, a protein/nucleic complex, virus like particles, and a protein complex.

5. The cargo delivery complex of claim 1 wherein the cargo molecule is a nucleic acid selected from the group consisting of an siRNA, an miRNA, a shRNA, a gRNA, an mRNA, a DNA, a DNA, a DNA plasmid, an oligonucleotide and an analogue thereof.

6. The cargo delivery complex of claim 5, wherein the nucleic acid comprises an mRNA.

7. The cargo delivery complex of claim 6, wherein the nucleic acid comprises an mRNA and an RNAi, and wherein the mRNA encodes a therapeutic protein for treating a disease or condition, and wherein the RNAi targets an RNA, wherein expression of the RNA is associated with the disease or condition.

8. The cargo delivery complex of claim 1, wherein the PEG moiety is a linear PEG.

9. The cargo delivery complex of claim 1, wherein the PEG moiety is a branched PEG.

10. The cargo delivery complex of claim 1, wherein the first and/or second peptide further comprises one or more moieties selected from the group consisting of an acetyl group, a stearyl group, a fatty acid, a cholesterol, a nuclear localization signal, a nuclear export signal, an antibody or antibody fragment thereof, a peptide, a polysaccharide, and a targeting sequence, wherein the one or more moieties are covalently linked to the N-terminus of the first or the second cell-penetrating peptide, or the PEG moiety.

11. The cargo delivery complex of claim 10, wherein the one or more moieties are covalently linked to the N-terminus of the first cell-penetrating peptide, the second cell-penetrating peptide or the PEG moiety via a linker.

12. The cargo delivery complex of claim 10, wherein the one or more moieties comprise a targeting sequence.

13. The cargo delivery complex of claim 12, wherein the targeting sequence is selected from the group consisting of GY, YV, VS, SK, GYV, YVS, VSK, GYVS (SEQ ID NO: 158), YVSK (SEQ ID NO: 186), YI, IG, GS, SR, YIG, IGS, GSR, YIGS (SEQ ID NO: 187), IGSR (SEQ ID NO: 188), GYVSK (SEQ ID NO: 189), and YIGSR (SEQ ID NO: 157).

14. The cargo delivery complex of claim 1, wherein the first and/or second peptide further comprises one or more moieties selected from the group consisting of a cysteamide, a cysteine, a thiol, an amide, a nitrilotriacetic acid optionally substituted, a carboxyl, a linear or ramified $C_1$-$C_6$ alkyl optionally substituted, a primary or secondary amine, an osidic derivative, a lipid, a phospholipid, a fatty acid, a cholesterol, a nuclear localization signal, nuclear export signal, an antibody, a polysaccharide and a targeting sequence, wherein the one or more moieties are covalently linked to the C-terminus of the first cell-penetrating peptide, the second cell-penetrating peptide or the PEG moiety.

15. The cargo delivery complex of claim 14, wherein the one or more moieties are covalently linked to the C-terminus of the first cell-penetrating peptide, the second cell-penetrating peptide or the PEG moiety via a linker.

16. The cargo delivery complex of claim 1, wherein the first and/or second cell-penetrating peptide is a retro-inverso peptide.

17. A nanoparticle comprising a core comprising the cargo delivery complex of claim 1.

18. A pharmaceutical composition comprising the cargo delivery complex of claim 1 or a nanoparticle comprising a core comprising the cargo delivery complex, and a pharmaceutically acceptable carrier.

19. A method of preparing the cargo delivery complex of claim 1, comprising a) combining the first peptide and the second peptide, thereby forming a peptide mixture; b) combining the peptide mixture with the cargo, thereby forming the cargo delivery complex.

20. A method of delivering one or more cargo into a cell, comprising contacting the cell with the cargo delivery complex of claim 1 or a nanoparticle comprising a core comprising the cargo delivery complex, wherein the cargo delivery complex comprises one or more cargo.

21. A method of delivering one or more cargo into a tissue or organ of an individual, comprising administering into the individual an effective amount of the cargo delivery complex of claim 1 or a nanoparticle comprising a core comprising the delivery complex, wherein the tissue or organ is selected from the group consisting of liver, lung, kidney, brain, intestine, spleen, heart, muscle, and lymph node.

22. The cargo delivery complex of claim 6, wherein the mRNA encodes a therapeutic protein.

23. The cargo delivery complex of claim 22, wherein the therapeutic protein encodes a tumor suppressor gene or a variant thereof selected from the group consisting of TP53, BRCA1, PTEN, Retinoblastoma RB (or RBl), TP63, TP73, CDKN2A (INK4A), CDKN1B, CDKN1C, DLD/NP1, HEP-ACAM, SDHB, SDHD, SFRP1, TCF21, TIG1, MLH1, MSH2, MSH6, WT1, WT2, NF1, NF2N, VHL, KLF4, pVHL, APC, CD95, ST5, YPEL3, ST7, MADR2, BRCA2, Patched, TSC1, TSC2, PALB2, ST14, or VHL factor VIII, alpha 1 antitrypsin, frataxin, insulin, growth hormone (somatotropin), growth factors, hormones, dystrophin, insulin-like growth factor 1 (IGF1), factor IX, antithrombin III, protein C, β-gluco-cerebrosidase, alglucosidase-α, α-1-iduronidase, Iduronate-2-sulphatase, galsulphase, human α-galactosidase A, α-1-Proteinase inhibitor, lactase, pancreatic enzymes, adenosine deaminase, albumin, a CRISPR-associated nuclease, a Cas9, or recombinant forms thereof.

24. The cargo delivery complex of claim 5, wherein cargo comprises a guide RNA, and wherein the guide RNA is a KRAS gRNA.

25. The cargo delivery complex of claim 1, wherein the PEG moiety is conjugated to the N-terminus of the second cell-penetrating peptide.

* * * * *